(12) United States Patent
Elsing et al.

(10) Patent No.: US 11,492,632 B2
(45) Date of Patent: Nov. 8, 2022

(54) METHODS AND COMPOSITIONS FOR ACCELERATED TRAIT INTROGRESSION

(71) Applicant: PIONEER HI-BRED INTERNATIONAL, INC., Johnston, IA (US)

(72) Inventors: Michael T Elsing, Urbandale, IA (US); William James Gordon-Kamm, Urbandale, IA (US); Leandro Daniel Perugini, Urbandale, IA (US); Huaxun Ye, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 15/554,234

(22) PCT Filed: Mar. 16, 2016

(86) PCT No.: PCT/US2016/022621
§ 371 (c)(1),
(2) Date: Aug. 29, 2017

(87) PCT Pub. No.: WO2016/149352
PCT Pub. Date: Sep. 22, 2016

(65) Prior Publication Data
US 2018/0119162 A1 May 3, 2018

Related U.S. Application Data
(60) Provisional application No. 62/135,261, filed on Mar. 19, 2015.

(51) Int. Cl.
*C12N 15/82* (2006.01)
*A01H 1/04* (2006.01)

(52) U.S. Cl.
CPC ........... *C12N 15/8241* (2013.01); *A01H 1/04* (2013.01); *C12N 15/825* (2013.01); *C12N 15/8212* (2013.01); *C12N 15/8213* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 2009/0070891 A1* | 3/2009 | Foley | A01H 1/02 800/263 |
| 2011/0203012 A1* | 8/2011 | Dotson | C12N 15/8213 800/278 |
| 2013/0198888 A1 | 8/2013 | Falco et al. | |
| 2014/0283166 A1 | 9/2014 | Chomet et al. | |
| 2015/0059010 A1 | 2/2015 | Cigan et al. | |

FOREIGN PATENT DOCUMENTS

WO 2013019411 2/2013

OTHER PUBLICATIONS

Mohan, et al.; "Identification of quantitative trait loci associated with resistance to foliar diseases in sorghum [*Sorghum bicolor* (L.) Moench]"; Euphytica (2010)176(2):199-211.
The International Search Report and Written Opinion PCT/US2016/022621 dated May 25, 2016.

* cited by examiner

*Primary Examiner* — Brent T Page

(57) ABSTRACT

Compositions and methods are provided for the use of pollen-inhibitor genes and/or color marker genes in accelerated trait introgression. Compositions and methods are also provided for introducing a pollen-inhibitor gene and/or a color marker gene in close proximity to a trait locus of interest. Breeding methods and methods for selecting plants comprising a trait locus of interest in close proximity to at least one pollen-inhibitor gene and/or color marker gene are also disclosed. The methods and compositions employ at least one pollen-inhibitor gene and/or color marker gene to provide an effective system for accelerated trait introgression in the genome of a plant.

3 Claims, 26 Drawing Sheets
Specification includes a Sequence Listing.

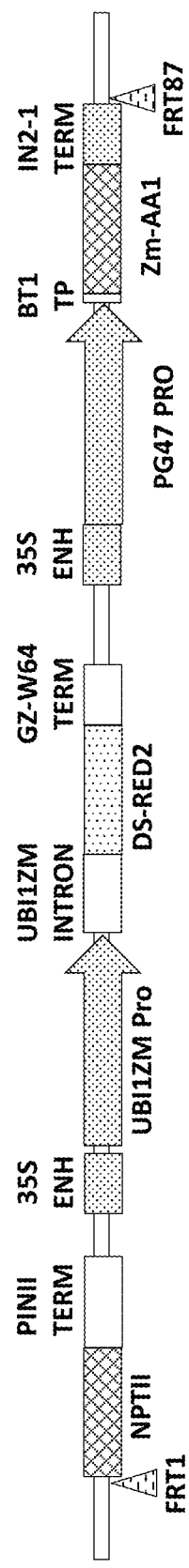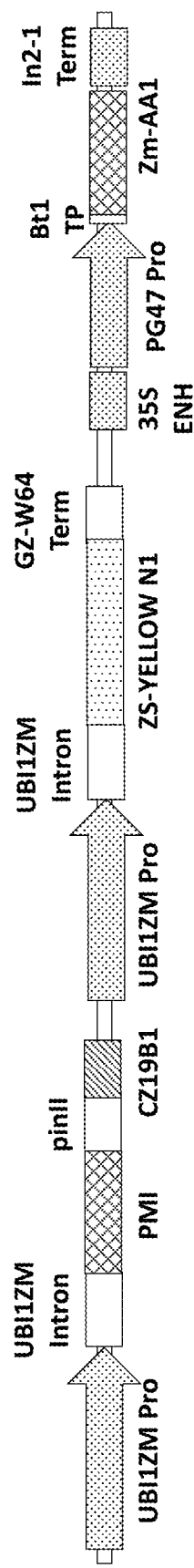

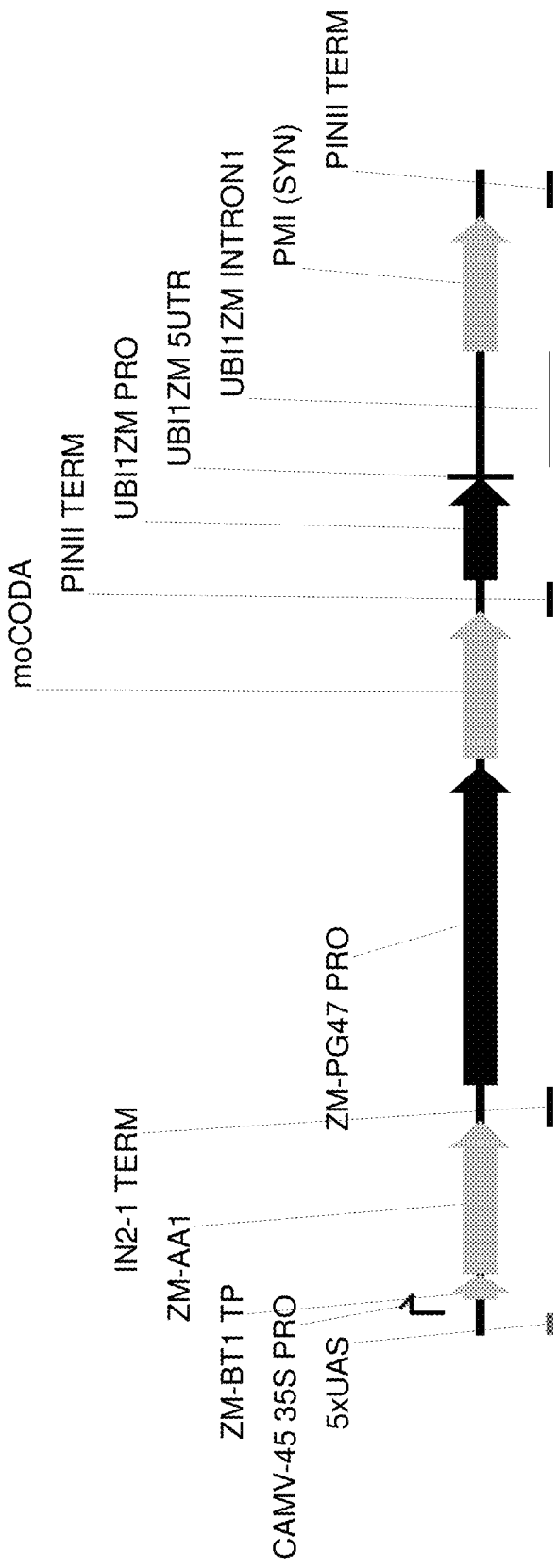

SEQUENCE LISTING

<160> NUMBER OF SEQ ID NOS: 122

<210> SEQ ID NO 1
<211> LENGTH: 48
<212> TYPE: DNA
<213> ORGANISM: Saccharomyces cerevisiae

<400> SEQUENCE: 1
gaagttccta ttccgaagtt cctattctct agaaagtata ggaacttc            48

<210> SEQ ID NO 2
<211> LENGTH: 48
<212> TYPE: DNA
<213> ORGANISM: Saccharomyces cerevisiae

<400> SEQUENCE: 2
gaagttccta ttccgaagtt cctattctcc agaaagtata ggaacttc            48

<210> SEQ ID NO 3
<211> LENGTH: 420
<212> TYPE: PRT
<213> ORGANISM: Zea mays

<400> SEQUENCE: 3

Ala Cys Gly Leu Val Gln Ala Gln Val Leu Phe Gln Gly Phe Asn Trp
1               5                   10                  15

Glu Ser Cys Lys Gln Gln Gly Gly Trp Tyr Asn Arg Leu Lys Ala Gln
            20                  25                  30

Val Asp Asp Ile Ala Lys Ala Gly Val Thr His Val Trp Leu Pro Pro
        35                  40                  45

Pro Ser His Ser Val Ser Pro Gln Gly Tyr Met Pro Gly Arg Leu Tyr
    50                  55                  60

Asp Leu Asp Ala Ser Lys Tyr Gly Thr Ala Ala Glu Leu Lys Ser Leu
65                  70                  75                  80

Ile Ala Ala Phe His Gly Arg Gly Val Gln Cys Val Ala Asp Ile Val
                85                  90                  95

Ile Asn His Arg Cys Ala Glu Lys Lys Asp Ala Arg Gly Val Tyr Cys
            100                 105                 110

Ile Phe Glu Gly Gly Thr Pro Asp Asp Arg Leu Asp Trp Gly Pro Gly
        115                 120                 125

Met Ile Cys Ser Asp Asp Thr Gln Tyr Ser Asp Gly Thr Gly His Arg
    130                 135                 140

Asp Thr Gly Glu Gly Phe Ala Ala Pro Asp Ile Asp His Leu Asn
145                 150                 155                 160

Pro Arg Val Gln Arg Glu Leu Ser Ala Trp Leu Asn Trp Leu Arg Ser
                165                 170                 175

Asp Ala Val Gly Phe Asp Gly Trp Arg Leu Asp Phe Ala Lys Gly Tyr
            180                 185                 190

Ser Pro Ala Val Ala Arg Met Tyr Val Glu Ser Thr Gly Pro Pro Ser
        195                 200                 205

Phe Val Val Ala Glu Ile Trp Asn Ser Leu Ser Tyr Ser Gly Asp Gly
    210                 215                 220

Lys Pro Ala Pro Asn Gln Asp Gln Cys Arg Gln Glu Leu Leu Asp Trp
225                 230                 235                 240

Thr Arg Ala Val Gly Gly Pro Ala Met Ala Phe Asp Phe Pro Thr Lys
                245                 250                 255

Gly Leu Leu Gln Ala Gly Val Gln Gly Glu Leu Trp Arg Leu Arg Asp

```
                    260                 265                 270
        Ser Ser Gly Asn Ala Ala Gly Leu Ile Gly Trp Ala Pro Glu Lys Ala
                275                 280                 285

Val Thr Phe Val Asp Asn His Asp Thr Gly Ser Thr Gln Lys Leu Trp
                290                 295                 300

Pro Phe Pro Ser Asp Lys Val Met Gln Gly Tyr Ala Tyr Ile Leu Thr
        305                 310                 315                 320

His Pro Gly Val Pro Cys Ile Phe Tyr Asp His Met Phe Asp Trp Asn
                        325                 330                 335

Leu Lys Gln Glu Ile Ser Thr Leu Ser Ala Ile Arg Ala Arg Asn Gly
                    340                 345                 350

Ile Arg Ala Gly Ser Lys Leu Arg Ile Leu Val Ala Asp Ala Asp Ala
                    355                 360                 365

Tyr Val Ala Val Val Asp Glu Lys Val Met Val Lys Ile Gly Thr Arg
                    370                 375                 380

Tyr Gly Val Ser Ser Val Val Pro Ser Asp Phe His Pro Ala Ala His
        385                 390                 395                 400

Gly Lys Asp Tyr Cys Val Trp Glu Lys Ala Ser Leu Arg Val Pro Ala
                        405                 410                 415

Gly Arg His Leu
                    420

<210> SEQ ID NO 4
<211> LENGTH: 1336
<212> TYPE: DNA
<213> ORGANISM: Zea mays

<400> SEQUENCE: 4
gcctgcggcc tggtccaggc acaagtcctc ttccaggggt ttaactggga gtcgtgcaag      60
cagcagggag gctggtacaa caggctcaag gcccaggtcg acgacatcgc caaggccggc     120
gtcacgcacg tctggctgcc tccaccctcg cactccgtct cgccacaagg ctacatgcca     180
ggccgcctat acgacctgga cgcgtccaag tacggcacgg cggcggagct caagtccctg     240
atagcggcgt tccacggcag gggcgtgcag tgcgtggcgg acatcgtcat caaccaccgg     300
tgcgcggaaa agaaggacgc cgcgcggcgtg tactgcatct tcgagggcgg gactcccgac     360
gaccgcctgg actggggccc cgggatgatc tgcagcgacg acacgcagta ctcggacggg     420
acggggcacc gcgacacggg cgaggggttc gcggcggcgc ccgacatcga ccacctcaac     480
ccgcgcgtgc agcgggagct ctccgcctgg ctcaactggc tcaggtccga cgccgtgggg     540
ttcgacggct ggcgcctcga cttcgccaag ggctactcgc cggccgtcgc cagaatgtac     600
gtggagagca cggggccgcc gagcttcgtc gtcgcggaga tatggaactc gctgagctac     660
agcggggacg gcaagccggc gcccaaccag gaccagtgcc ggcaggagct gctggactgg     720
acgcgggccg tcggcgggcc cgccatggcg ttcgacttcc ccaccaaggg cctgctgcag     780
gcgggcgtgc agggggagct gtggcggctg cgcgacagcc ccggcaacgc ggccggcctg     840
atcgggtggg cgcccgagaa ggccgtcacc ttcgtcgaca accatgacac cgggtcgacg     900
cagaagctct ggccgttccc atccgacaag gtcatgcagg gctacgccta catcctcacc     960
catccaggag tccctgcat tttctacgac cacatgttcg actggaacct gaagcaggag    1020
atatccacgc tgtctgccat cagggcgcgg aacggcatcc gcgccgggag caagctgcgg    1080
atcctcgtgg cggacgcgga cgcgtacgtg gccgtcgtcg acgagaaggt catggtgaag    1140
atcgggacaa ggtacggcgt gagcagcgtg gtcccgtcgg atttccaccc ggcggcgcac    1200
```

```
ggcaaggact actgcgtctg ggagaaagcg agcctccgcg tcccggcggg gcgccacctc    1260
tagcagctca gattgctcag tcttgtgctg cattgcaaac acagcagcac gacactgcat    1320
aacgtctttt ccttga                                                    1336
```

<210> SEQ ID NO 5
<211> LENGTH: 264
<212> TYPE: PRT
<213> ORGANISM: Escherichia coli

<400> SEQUENCE: 5

```
Met Val Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Asp Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 6
<211> LENGTH: 795
<212> TYPE: DNA
<213> ORGANISM: Escherichia coli

<400> SEQUENCE: 6

```
atggttgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
```

```
caggacgagg cagcgcggct atcgtggctg gccacgacgg gcgttccttg cgcagctgtg      240
ctcgacgttg tcactgaagc gggaagggac tggctgctat tgggcgaagt gccggggcag      300
gatctcctgt catctcacct tgctcctgcc gagaaagtat ccatcatggc tgatgcaatg      360
cggcggctgc atacgcttga tccggctacc tgcccattcg accaccaagc gaaacatcgc      420
atcgagcgag cacgtactcg gatggaagcc ggtcttgtcg atcaggatga tctggacgaa      480
gagcatcagg ggctcgcgcc agccgaactg ttcgccaggc tcaaggcgcg catgcccgac      540
ggcgatgatc tcgtcgtgac ccatggcgat gcctgcttgc cgaatatcat ggtggaaaat      600
ggccgctttt ctggattcat cgactgtggc cggctgggtg tggcggaccg ctatcaggac      660
atagcgttgg ctacccgtga tattgctgaa gagcttggcg gcgaatgggc tgaccgcttc      720
ctcgtgcttt acggtatcgc cgctcccgat tcgcagcgca tcgccttcta tcgccttctt      780
gacgagttct tctga                                                      795

<210> SEQ ID NO 7
<211> LENGTH: 203
<212> TYPE: DNA
<213> ORGANISM: Cauliflower Mosaic Virus

<400> SEQUENCE: 7
cgctgaaatc accagtctct ctctacaaat ctatctctct ctataataat gtgtgagtag       60
ttcccagata agggaattag ggttcttata gggtttcgct catgtgttga gcatataaga      120
aacccttagt atgtatttgt atttgtaaaa tacttctatc aataaaattt ctaattccta      180
aaaccaaaat ccagtggcga gct                                             203

<210> SEQ ID NO 8
<211> LENGTH: 310
<212> TYPE: DNA
<213> ORGANISM: Solanum tuberosum

<400> SEQUENCE: 8
ctagacttgt ccatcttctg gattggccaa cttaattaat gtatgaaata aaaggatgca       60
cacatagtga catgctaatc actataatgt gggcatcaaa gttgtgtgtt atgtgtaatt      120
actagttatc tgaataaaag agaaagagat catccatatt tcttatccta aatgaatgtc      180
acgtgtcttt ataattcttt gatgaaccag atgcatttca ttaaccaaat ccatatacat      240
ataaatatta atcatatata attaatatca attgggttag caaaacaaat ctagtctagg      300
tgtgttttgc                                                            310

<210> SEQ ID NO 9
<211> LENGTH: 850
<212> TYPE: DNA
<213> ORGANISM: Zea mays

<400> SEQUENCE: 9
gatctcgatg tgtagtctac gagaagggtt aaccgtctct tcgtgagaat aaccgtggcc       60
taaaaataag ccgatgagga taaataaaat gtggtggtac agtacttcaa gaggtttact      120
catcaagagg atgcttttcc gatgagctct agtagtacat cggacctcac atacctccat      180
tgtggtgaaa tattttgtgc tcatttagtg atgggtaaat tttgtttatg tcactctagg      240
ttttgacatt tcagttttgc cactcttagg ttttgacaaa taattccat tccgcggcaa       300 aagcaaaaca attttatttt acttttacca ctcttagctt tcacaatgta tcacaaatgc      360
```

-continued

```
cactctagaa attctgttta tgccacagaa tgtgaaaaaa acactcact tatttgaagc    420 caaggtgttc atggcatgga aatgtgacat aaagtaacgt tcgtgtataa gaaaaaattg    480
tactcctcgt aacaagagac ggaaacatca tgagacaatc gcgtttggaa ggctttgcat    540
cacctttgga tgatgcgcat gaatggagtc gtctgcttgc tagccttcgc ctaccgccca    600
ctgagtccgg gcggcaacta ccatcggcga acgacccagc tgacctctac cgaccggact    660
tgaatgcgct accttcgtca gcgacgatgg ccgcgtacgc tggcgacgtg ccccgcatg    720 catggcggca catggcgagc tcagaccgtg cgtggctggc tacaaatacg taccccgtga    780
gtgccctagc tagaaactta cacctgcaac tgcgagagcg agcgtgtgag tgtagccgat    840
agatccgccc                                                           850
```

<210> SEQ ID NO 10
<211> LENGTH: 233
<212> TYPE: PRT
<213> ORGANISM: Artificial Sequence
<220> FEATURE:
<223> OTHER INFORMATION: Sequence from Dictosoma species

<400> SEQUENCE: 10

```
Met Ser Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn
225                 230
```

<210> SEQ ID NO 11
<211> LENGTH: 702
<212> TYPE: DNA
<213> ORGANISM: Artificial Sequence
<220> FEATURE:

<223> OTHER INFORMATION: Sequence from Dictosoma species

<400> SEQUENCE: 11

| | | | | | |
|---|---|---|---|---|---|
| atgagcgagc | tgattaaaga | gaacatgcac | atgaagctgt | acatggaggg | gaccgtcgac | 60 |
| aaccaccact | tcaagtgcac | ctccgagggc | gagggtaagc | cgtatgaggg | cacgcagaca | 120 |
| atgaggatta | aagtggttga | gggcggccg | ctgccttcg | cattcgacat | cctcgccacc | 180 |
| agcttcctgt | acgggtccaa | gaccttcatc | aaccacaccc | agggcatccc | cgacttcttc | 240 |
| aaacagtcct | tcccggaggg | tttcacgtgg | gagagggtga | caacctacga | agatggcggc | 300 |
| gtgctgaccg | ccacgcagga | tacatctctc | caggacgggt | gcctgatcta | caacgtcaag | 360 |
| atcagggcg | tcaacttcac | gagcaacggc | ccggtcatgc | agaagaagac | gctcggctgg | 420 |
| gaagccttca | cggagacact | ctaccccgcc | gacggcgggc | tggaaggtag | gaacgacatg | 480 |
| gccctcaagc | tcgtgggcgg | cagccacctc | atcgccaaca | tcaaaaccac | ctacaggagc | 540 |
| aagaagcccg | ccaagaacct | gaagatgccc | ggcgtgtact | acgtcgacta | caggctcgag | 600 |
| agaattaagg | aggccaacaa | cgagacgtac | gtggagcagc | acgaggttgc | agttgccagg | 660 |
| tactgcgacc | tgccgagcaa | gctcggccac | aagctgaact | ag | | 702 |

<210> SEQ ID NO 12
<211> LENGTH: 476
<212> TYPE: DNA
<213> ORGANISM: Zea mays

<400> SEQUENCE: 12

| | | | | | |
|---|---|---|---|---|---|
| gaagaaacta | tgtgctgtag | tatagccgct | gcccgctggc | tagctagcta | gttgagtcat | 60 |
| ttagcggcga | tgattgagta | ataatgtgtc | acgcatcacc | atgcatgggt | ggcagtgtca | 120 |
| gtgtgagcaa | tgacctgaat | gaacaattga | atgaaaaga | aaaagtatt | gttccaaatt | 180 |
| aaacgtttta | accttttaat | aggtttatac | aataattgat | atatgttttc | tgtatatgtc | 240 |
| taatttgtta | tcatccattt | agatatagac | aaaaaaaatc | taagaactaa | acaaatgct | 300 |
| aatttgaaat | gaagggagta | tatattggga | taatgtcgat | gagatccctc | gtaatatcac | 360 |
| cgacatcaca | cgtgtccagt | taatgtatca | gtgatacgtg | tattcacatt | tgttgcgcgt | 420 |
| aggcgtaccc | aacaattttg | atcgactatc | agaaagtcaa | cggaagcgag | tcgacc | 476 |

<210> SEQ ID NO 13
<211> LENGTH: 2773
<212> TYPE: DNA
<213> ORGANISM: Zea mays

<400> SEQUENCE: 13

| | | | | | |
|---|---|---|---|---|---|
| aagcttgcat | gcctgcaggt | cgactctaga | ggatctgcac | cggacactgt | ctggtggcat | 60 |
| accagacagt | ccggtgtgcc | agatcagggc | acccttcggt | tcctttgctc | ctttgctttt | 120 |
| gaaccctaac | tttgatcgtt | tattggtttg | tgttgaacct | ttatgcacct | gtggaatata | 180 |
| taatctagaa | caaactagtt | agtccaatca | tttgtgttgg | gcattcaacc | accaaaatta | 240 |
| tttataggaa | aaggttaaac | cttatttccc | tttcaatctc | ccccttttg | gtgattgatg | 300 |
| ccaacacaaa | ccaagaaaaa | tatataagtg | cagaattgaa | ctagtttgca | taaggtaagt | 360 |
| gcataggtta | cttagaatta | aatcaattta | tactttact | tgatatgcat | ggttgctttc | 420 |
| ttttatttta | acatttttgga | ccacatttgc | accacttgtt | ttgtttttg | caaatctttt | 480 |
| tggaaattct | ttttcaaagt | cttttgcaaa | tagtcaaagg | tatatgaata | agattgtaag | 540 |
| aagcattttc | aagatttgaa | atttctcccc | ctgtttcaaa | tgcttttcct | ttgactaaac | 600 |

```
aaaactcccc ctgaataaaa ttctcctctt agctttcaag agggttttaa atagatatca    660
attggaaata tatttagatg ctaattttga aaatatacca attgaaaatc aacataccaa    720
tttgaaatta aacataccaa tttaaaaaat ttcaaaaagt ggtggtgcgg tccttttgct    780
ttgggcttaa tatttctccc cctttggcat taatcgccaa aaacggagac tttgtgagcc    840
atttatactt tctccccatt ggtaaatgaa atatgagtga agattatac caaatttgga     900
cagtgatgcg gagtgacggc gaaggataaa cgataccgtt agagtggagt ggaagccttg    960
tcttcgccga agactccatt tccctttcaa tctacgactt agcatagaaa tacacttgaa    1020
aacacattag tcgtagccac gaaagagata tgatcaaagg tatacaaatg agctatgtgt    1080
gtaatgtttc aatcaaagtt tcgagaatca agaatattta gctcattcct aagtttgcta    1140
aaggttttat catctaatgg tttggtaaag atatcgacta attgttcttt ggtgctaaca    1200
taagcaatct cgatatcacc cctttgttgg tgatccctca aaaagtgata ccgaatgtct    1260
atgtgcttag tgcggctgtg ttcaacggga ttatccgcca tgcagatagc actctcattg    1320
tcacatagga gagggacttt gctcaatttg tagccatagt ccctaaggtt ttgcctcatc    1380
caaagtaatt gcacacaaca atgtcctgcg gcaatatact tggcttcggc ggtagaaaga    1440
gctattgagt tttgtttctt tgaagtccaa gacaccaggg atctccctag aaactgacaa    1500
gtccctgatg tgctcttcct atcaatttta cacccctgccc aatcggcatc tgaatatcct   1560
attaaatcaa aggtggatcc cttggggtac caaagaccaa atttaggagt gtaaactaaa    1620
tatctcatga ttcttttcac ggccctaagg tgaacttcct taggatcggc ttggaatctt    1680
gcacacatgc atatagaaag catactatct ggtcgagatg cacataaata gagtaaagat    1740
cctatcatcg accggtatac cttttggtct acggatttac ctcccgtgtc gaggtcgaga    1800
tgcccattag ttcccatggg tgtcctgatg ggcttggcat ccttcattcc aaacttgttg    1860
agtatgtctt gaatgtactt tgtttggctg atgaaggtgc catctggag ttgcttgact     1920
tgaaatccta gaaaatattt caacttcccc atcatagaca tctcgaattt cggaatcatg    1980
atcctactaa actcttcaca agtagatttg ttagtagacc caaatataat atcatcaaca    2040
taaatttggc atacaaacaa aactttgaa atggttttag taaagagagt aggatcggct     2100
ttactgactc tgaagccatt agtgataaga aaatctctta ggcattcata ccatgctgtt    2160
ggggcttgct tgagcccata aagcgccttt gagagtttat aaacatggtt agggtactca    2220
ctatcttcaa agccgagagg ttgctcaaca tagacctatt caccccattt gatcacttt     2280
ttggtccttc aggatctaat agttatgtat aatttagagt ctcttgttta atggccagat    2340
atttctaatt aatctaagaa tttatgatat ttttttaattt tttatcatgt ctgatgagaa   2400
ttaacataaa ggctcaattg ggtcctgaat taataataga gtgaaaatta tccagaggc     2460
tctattagaa ccttcaatta gtaataccaa gatatatata agatagtaga gtatagttta    2520
aatgttggca ttgttcattc tttcttttgt tatttaattt atgctttcca cggtggttag    2580
tggttacttc tgaagggtcc aaataatgca tgaagagttt gaggacaaga agtctgccct    2640
aaaaatagcg atgcaaaggc atggtgtcca agccatacat atagcgcact aattttatca    2700
gcagaacaat ggtatttata ggtcctagtg cccaggcaac aagagacacg aataaagcat    2760
cgatcacgac acc                                                      2773
```

<210> SEQ ID NO 14
<211> LENGTH: 75
<212> TYPE: PRT

<213> ORGANISM: Zea mays

<400> SEQUENCE: 14

```
Met Ala Ala Thr Met Ala Val Thr Thr Met Val Thr Arg Ser Lys Glu
1               5                   10                  15

Ser Trp Ser Ser Leu Gln Val Pro Ala Val Ala Phe Pro Trp Lys Pro
            20                  25                  30

Arg Gly Gly Lys Thr Gly Gly Leu Glu Phe Pro Arg Arg Ala Met Phe
        35                  40                  45

Ala Ser Val Gly Leu Asn Val Cys Pro Gly Val Pro Ala Gly Arg Asp
    50                  55                  60

Pro Arg Glu Pro Asp Pro Lys Val Val Arg Ala
65                  70                  75
```

<210> SEQ ID NO 15
<211> LENGTH: 450
<212> TYPE: DNA
<213> ORGANISM: Zea mays

<400> SEQUENCE: 15

```
atggcggcga caatggcagt gacgacgatg gtgacgagga gcaaggagag ctggtcgtca    60
ttgcaggtcc cggcggtggc attcccttgg aagccacgag gtggcaagac cggcggcctc   120
gagttccctc gccgggcgat gttcgccagc gtcggcctca acgtgtgccc gggcgtcccg   180
gcggggcgcg acccgcggga gcccgatccc aaggtcgtcc gggcgatggc ggcgacaatg   240
gcagtgacga cgatggtgac gaggagcaag gagagctggt cgtcattgca ggtcccggcg   300
gtggcattcc cttggaagcc acgaggtggc aagaccggcg gcctcgagtt ccctcgccgg   360
gcgatgttcg ccagcgtcgg cctcaacgtg tgcccgggcg tcccggcggg gcgcgacccg   420
cgggagcccg atcccaaggt cgtccgggcg                                   450
```

<210> SEQ ID NO 16
<211> LENGTH: 348
<212> TYPE: DNA
<213> ORGANISM: Zea mays

<400> SEQUENCE: 16

```
gatctgacaa agcagcatta gtccgttgat cggtggaaga ccactcgtca gtgttgagtt    60
gaatgtttga tcaataaaat acggcaatgc tgtaagggtt gttttttatg ccattgataa   120
tacactgtac tgttcagttg ttgaactcta tttcttagcc atgccaagtg ctttcttat   180
tttgaataac attacagcaa aaagttgaaa gacaaaaaaa aaaaccccg aacagagtgc   240
tttgggtccc aagctacttt agactgtgtt cggcgttccc cctaaatttc tccccctata   300
tctcactcac ttgtcacatc agcgttctct ttcccctata tctccacg                348
```

<210> SEQ ID NO 17
<211> LENGTH: 391
<212> TYPE: PRT
<213> ORGANISM: Bacillus amyloliquefaciens

<400> SEQUENCE: 17

```
Met Gln Lys Leu Ile Asn Ser Val Gln Asn Tyr Ala Trp Gly Ser Lys
1               5                   10                  15

Thr Ala Leu Thr Glu Leu Tyr Gly Met Glu Asn Pro Ser Ser Gln Pro
            20                  25                  30

Met Ala Glu Leu Trp Met Gly Ala His Pro Lys Ser Ser Ser Arg Val
        35                  40                  45
```

Gln Asn Ala Ala Gly Asp Ile Val Ser Leu Arg Asp Val Ile Glu Ser
    50                  55                  60

Asp Lys Ser Thr Leu Leu Gly Glu Ala Val Ala Lys Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys His Asn Ser Glu Ile Gly Phe Ala Lys Glu
            100                 105                 110

Asn Ala Ala Gly Ile Pro Met Asp Ala Ala Glu Arg Asn Tyr Lys Asp
            115                 120                 125

Pro Asn His Lys Pro Glu Leu Val Phe Ala Leu Thr Pro Phe Leu Ala
130                 135                 140

Met Asn Ala Phe Arg Glu Phe Ser Glu Ile Val Ser Leu Leu Gln Pro
145                 150                 155                 160

Val Ala Gly Ala His Pro Ala Ile Ala His Phe Leu Gln Gln Pro Asp
                165                 170                 175

Ala Glu Arg Leu Ser Glu Leu Phe Ala Ser Leu Leu Asn Met Gln Gly
            180                 185                 190

Glu Glu Lys Ser Arg Ala Leu Ala Ile Leu Lys Ser Ala Leu Asp Ser
            195                 200                 205

Gln Gln Gly Glu Pro Trp Gln Thr Ile Arg Leu Ile Ser Glu Phe Tyr
210                 215                 220

Pro Glu Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
            275                 280                 285

Ala Asn Val Lys Phe Glu Ala Lys Pro Ala Asn Gln Leu Leu Thr Gln
290                 295                 300

Pro Val Lys Gln Gly Ala Glu Leu Asp Phe Pro Ile Pro Val Asp Asp
305                 310                 315                 320

Phe Ala Phe Ser Leu His Asp Leu Ser Asp Lys Glu Thr Thr Ile Ser
                325                 330                 335

Gln Gln Ser Ala Ala Ile Leu Phe Cys Val Glu Gly Asp Ala Thr Leu
            340                 345                 350

Trp Lys Gly Ser Gln Gln Leu Gln Leu Lys Pro Gly Glu Ser Ala Phe
            355                 360                 365

Ile Ala Ala Asn Glu Ser Pro Val Thr Val Lys Gly His Gly Arg Leu
370                 375                 380

Ala Arg Val Tyr Asn Lys Leu
385                 390

<210> SEQ ID NO 18
<211> LENGTH: 274
<212> TYPE: DNA
<213> ORGANISM: Bacillus amyloliquefaciens

<400> SEQUENCE: 18
atgaaaaaag cagtcattaa cggggaacaa atcagaagta tcagcgacct ccaccagaca      60
ttgaaaaagg agcttgccct tccggaatac tacggtgaaa acctggacgc tttatgggat     120

| | |
|---|---|
| tgtctgaccg gatgggtgga gtacccgctc gttttggaat ggaggcagtt tgaacaaagc | 180 |
| aagcagctga ctgaaaatgg cgccgagagt gtgcttcagg ttttccgtga agcgaaagcg | 240 |
| gaaggctgcg acatcaccat catactttct taac | 274 |

<210> SEQ ID NO 19
<211> LENGTH: 900
<212> TYPE: DNA
<213> ORGANISM: Zea mays

<400> SEQUENCE: 19

| | |
|---|---|
| ctgcagtgca gcgtgacccg gtcgtgcccc tctctagaga taatgagcat tgcatgtcta | 60 |
| agttataaaa aattaccaca tatttttttt gtcacacttg tttgaagtgc agtttatcta | 120 |
| tctttataca tatatttaaa ctttactcta cgaataatat aatctatagt actacaataa | 180 |
| tatcagtgtt ttagagaatc atataaatga acagttagac atggtctaaa ggacaattga | 240 |
| gtatttgac aacaggactc tacagtttta tcttttagt gtgcatgtgt tctccttttt | 300 |
| ttttgcaaat agcttcacct atataatact tcatccattt tattagtaca tccatttagg | 360 |
| gtttagggtt aatggttttt atagactaat tttttagta catctatttt attctatttt | 420 |
| agcctctaaa ttaagaaaac taaaactcta ttttagtttt tttatttaat aatttagata | 480 |
| taaaatagaa taaaataaag tgactaaaaa ttaaacaaat acccctttaag aaattaaaaa | 540 |
| aactaaggaa acatttttct tgtttcgagt agataatgcc agcctgttaa acgccgtcga | 600 |
| cgagtctaac ggacaccaac cagcgaacca gcagcgtcgc gtcgggccaa gcgaagcaga | 660 |
| cggcacggca tctctgtcgc tgcctctgga cccctctcga gagttccgct ccaccgttgg | 720 |
| acttgctccg ctgtcggcat ccagaaattg cgtggcggag cggcagacgt gagccggcac | 780 |
| ggcaggcggc ctcctcctcc tctcacggca ccggcagcta cggggggattc ctttcccacc | 840 |
| gctccttcgc tttcccttcc tcgcccgccg taataaatag acaccccctc cacaccctct | 900 |

<210> SEQ ID NO 20
<211> LENGTH: 1012
<212> TYPE: DNA
<213> ORGANISM: Zea mays

<400> SEQUENCE: 20

| | |
|---|---|
| gtacgccgct cgtcctcccc cccccccctc tctaccttct ctagatcggc gttccggtcc | 60 |
| atgcatggtt agggcccggt agttctactt ctgttcatgt ttgtgttaga tccgtgtttg | 120 |
| tgttagatcc gtgctgctag cgttcgtaca cggatgcgac ctgtacgtca gacacgttct | 180 |
| gattgctaac ttgccagtgt ttctctttgg ggaatcctgg gatggctcta gccgttccgc | 240 |
| agacgggatc gatttcatga tttttttttgt ttcgttgcat agggtttggt ttgccctttt | 300 |
| cctttatttc aatatatgcc gtgcacttgt ttgtcgggtc atcttttcat gctttttttt | 360 |
| gtcttggttg tgatgatgtg gtctggttgg gcggtcgttc tagatcggag tagaattctg | 420 |
| tttcaaacta cctggtggat ttattaattt tggatctgta tgtgtgtgcc atacatattc | 480 |
| atagttacga attgaagatg atggatggaa atatcgatct aggataggta tacatgttga | 540 |
| tgcgggtttt actgatgcat atacagagat gcttttttgtt cgcttggttg tgatgatgtg | 600 |
| gtgtggttgg gcggtcgttc attcgttcta gatcggagta gaatactgtt tcaaactacc | 660 |
| tggtgtattt attaattttg gaactgtatg tgtgtgtcat acatcttcat agttacgagt | 720 |
| ttaagatgga tggaaatatc gatctaggat aggtatacat gttgatgtgg gttttactga | 780 |
| tgcatataca tgatggcata tgcagcatct attcatatgc tctaaccttg agtacctatc | 840 |

```
tattataata aacaagtatg ttttataatt attttgatct tgatatactt ggatgatggc    900
atatgcagca gctatatgtg gattttttta gccctgcctt catacgctat ttatttgctt    960
ggtactgttt cttttgtcga tgctcaccct gttgtttggt gttacttctg ca           1012
```

```
<210> SEQ ID NO 21
<211> LENGTH: 224
<212> TYPE: PRT
<213> ORGANISM: Artificial Seqeunce
<220> FEATURE:
<223> OTHER INFORMATION: Sequence from Dictosoma species

<400> SEQUENCE: 21
```

```
Ala Ser Ser Glu Asn Val Ile Thr Glu Phe Met Arg Phe Lys Val Arg
 1               5                  10                  15

Met Glu Gly Thr Val Asn Gly His Glu Phe Ile Glu Gly Glu Gly
            20                  25                  30

Glu Gly Arg Pro Tyr Glu Gly His Asn Thr Val Lys Leu Lys Val Thr
        35                  40                  45

Lys Gly Gly Pro Leu Pro Phe Ala Trp Asp Ile Leu Ser Pro Gln Phe
    50                  55                  60

Gln Tyr Gly Ser Lys Val Tyr Val Lys His Pro Ala Asp Ile Pro Asp
65                  70                  75                  80

Tyr Lys Lys Leu Ser Phe Pro Glu Gly Phe Lys Trp Glu Arg Val Met
                85                  90                  95

Asn Phe Glu Asp Gly Gly Val Ala Thr Val Thr Gln Asp Ser Ser Leu
            100                 105                 110

Gln Asp Gly Cys Phe Ile Tyr Lys Val Lys Phe Ile Gly Val Asn Phe
        115                 120                 125

Pro Ser Asp Gly Pro Val Met Gln Lys Lys Thr Met Gly Trp Glu Ala
    130                 135                 140

Ser Thr Glu Arg Leu Tyr Pro Arg Asp Gly Val Leu Lys Gly Glu Thr
145                 150                 155                 160

His Lys Ala Leu Lys Leu Lys Asp Gly Gly His Tyr Leu Val Glu Phe
                165                 170                 175

Lys Ser Ile Tyr Met Ala Lys Lys Pro Val Gln Leu Pro Gly Tyr Tyr
            180                 185                 190

Tyr Val Asp Ala Lys Leu Asp Ile Thr Ser His Asn Glu Asp Tyr Thr
        195                 200                 205

Ile Val Glu Gln Tyr Glu Arg Thr Glu Gly Arg His His Leu Phe Leu
    210                 215                 220
```

```
<210> SEQ ID NO 22
<211> LENGTH: 678
<212> TYPE: DNA
<213> ORGANISM: Artificial sequence
<220> FEATURE:
<223> OTHER INFORMATION: Sequence from Dictosoma species

<400> SEQUENCE: 22
atggcctcct ccgagaacgt catcaccgag ttcatgcgct tcaaggtgcg catggagggc     60
accgtgaacg gccacgagtt cgagatcgag ggcgagggcg agggccgccc ctacgagggc    120
cacaacaccg tgaagctgaa ggtgaccaag ggcggccccc tgcccttcgc ctgggacatc    180
ctgtcccccc agttccagta cggctccaag gtgtacgtga agcaccccgc cgacatcccc    240
gactacaaga agctgtcctt ccccgagggc ttcaagtggg agcgcgtgat gaacttcgag    300
```

```
gacggcggcg tggcgaccgt gacccaggac tcctccctgc aggacggctg cttcatctac    360
aaggtgaagt tcatcggcgt gaacttcccc tccgacggcc ccgtgatgca agaagagacc    420
atgggctggg aggcctccac cgagcgcctg taccccgcg acggcgtgct gaagggcgag    480
acccacaagg ccctgaagct gaaggacggc ggccactacc tggtggagtt caagtccatc    540
tacatggcca agaagcccgt gcagctgccc ggctactact acgtggacgc caagctggac    600
atcacctccc acaacgagga ctacaccatc gtggagcagt acgagcgcac cgagggccgc    660
caccacctgt tcctgtag                                                  678

<210> SEQ ID NO 23
<211> LENGTH: 391
<212> TYPE: PRT
<213> ORGANISM: Escherichia coli

<400> SEQUENCE: 23

Met Gln Lys Leu Ile Asn Ser Val Gln Asn Tyr Ala Trp Gly Ser Lys
1               5                   10                  15

Thr Ala Leu Thr Glu Leu Tyr Gly Met Glu Asn Pro Ser Ser Gln Pro
            20                  25                  30

Met Ala Glu Leu Trp Met Gly Ala His Pro Lys Ser Ser Arg Val
        35                  40                  45

Gln Asn Ala Ala Gly Asp Ile Val Ser Leu Arg Asp Val Ile Glu Ser
    50                  55                  60

Asp Lys Ser Thr Leu Leu Gly Glu Ala Val Ala Lys Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys His Asn Ser Glu Ile Gly Phe Ala Lys Glu
            100                 105                 110

Asn Ala Ala Gly Ile Pro Met Asp Ala Ala Glu Arg Asn Tyr Lys Asp
        115                 120                 125

Pro Asn His Lys Pro Glu Leu Val Phe Ala Leu Thr Pro Phe Leu Ala
    130                 135                 140

Met Asn Ala Phe Arg Glu Phe Ser Glu Ile Val Ser Leu Leu Gln Pro
145                 150                 155                 160

Val Ala Gly Ala His Pro Ala Ile Ala His Phe Leu Gln Gln Pro Asp
                165                 170                 175

Ala Glu Arg Leu Ser Glu Leu Phe Ala Ser Leu Leu Asn Met Gln Gly
            180                 185                 190

Glu Glu Lys Ser Arg Ala Leu Ala Ile Leu Lys Ser Ala Leu Asp Ser
        195                 200                 205

Gln Gln Gly Glu Pro Trp Gln Thr Ile Arg Leu Ile Ser Glu Phe Tyr
    210                 215                 220

Pro Glu Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Glu Ala Lys Pro Ala Asn Gln Leu Leu Thr Gln
    290                 295                 300
```

```
Pro Val Lys Gln Gly Ala Glu Leu Asp Phe Pro Ile Pro Val Asp Asp
305                 310                 315                 320

Phe Ala Phe Ser Leu His Asp Leu Ser Asp Lys Glu Thr Thr Ile Ser
            325                 330                 335

Gln Gln Ser Ala Ala Ile Leu Phe Cys Val Glu Gly Asp Ala Thr Leu
        340                 345                 350

Trp Lys Gly Ser Gln Gln Leu Gln Leu Lys Pro Gly Glu Ser Ala Phe
            355                 360                 365

Ile Ala Ala Asn Glu Ser Pro Val Thr Val Lys Gly His Gly Arg Leu
        370                 375                 380

Ala Arg Val Tyr Asn Lys Leu
385                 390
```

<210> SEQ ID NO 24
<211> LENGTH: 1176
<212> TYPE: DNA
<213> ORGANISM: Escherichia coli

<400> SEQUENCE: 24

```
atgcagaagc tgatcaactc ggtccagaac tatgcctggg gctccaagac cgccctgacg      60
gaactctacg gcatggagaa cccgtcgtca caaccgatgg ccgagctgtg gatgggtgct     120
catccgaagt cctcttctcg cgtgcagaat gcagcaggtg acatcgtgtc gctgcgggat     180
gtgattgagt cagacaagtc cacccttctg ggtgaggctg tggccaagcg cttcggcgaa     240
ctcccattcc tcttcaaggt gctctgcgcc gcacagccgc tctcaatcca gtccaccccc     300
aacaagcata actccgagat cggattcgcc aaggagaatg cggctggcat cccgatggac     360
gccgctgaga gaaactacaa agacccgaat cacaagccgg agcttgtctt cgcactcacg     420
ccatttctcg ctatgaacgc atttcgcgag ttcagcgaga tcgtcagcct gctccagccg     480
gtggcgggtg ctcatccagc aatcgcgcat tcttgcagc agcctgatgc cgaaaggctc      540
agcgagctgt tcgcgtcccct tcttaacatg caggagagg agaagtcccg cgcacttgca     600
atactcaaga gcgcgctgga ctcacagcaa ggagagccgt ggcaaaccat acggctcatc     660
tccgagttct atcccgagga ctcaggactg ttctcgccgt gctgctcaa cgtggtcaag      720
ctgaaccccg agaggcgat gttcttgttc gccgaaactc cgcatgctta cctccaagga     780
gtcgctctgg aagtgatggc caattcggac aacgttcttc gggcaggatt gacgcccaag     840
tacatcgaca tcccggaact cgtggccaat gttaagtttg aagcgaagcc tgccaaccag     900
ctgcttacgc agcctgttaa gcagggagcc gaactggatt tccctattcc ggtgacgac      960
ttcgcattct ccctccacga cctctcagac aaggagacga ccatctctca gcaaagcgct    1020
gcgattctgt tctgcgtgga aggcgatgcg accctgtgga agggctcaca gcagcttcag    1080
ctgaagcctg gcgagtccgc cttcatcgcc gctaacgagt ctcccgtcac cgtgaaaggg    1140
catgggaggc tcgctcgggt ctacaacaag ctctag                              1176
```

<210> SEQ ID NO 25
<211> LENGTH: 157
<212> TYPE: PRT
<213> ORGANISM: Bacillus amyloliquefaciens

<400> SEQUENCE: 25

```
Met Met Lys Met Glu Gly Ile Ala Leu Lys Lys Arg Leu Ser Trp Ile
1               5                   10                  15

Ser Val Cys Leu Leu Val Leu Val Ser Ala Ala Gly Met Leu Phe Ser
            20                  25                  30
```

```
Thr Ala Ala Lys Thr Glu Thr Ser Ser His Lys Ala His Thr Glu Ala
            35                  40                  45

Gln Val Ile Asn Thr Phe Asp Gly Val Ala Asp Tyr Leu Gln Thr Tyr
        50                  55                  60

His Lys Leu Pro Asp Asn Tyr Ile Thr Lys Ser Glu Ala Gln Ala Leu
65                  70                  75                  80

Gly Trp Val Ala Ser Lys Gly Asn Leu Ala Asp Val Ala Pro Gly Lys
                85                  90                  95

Ser Ile Gly Gly Asp Ile Phe Ser Asn Arg Glu Gly Lys Leu Pro Gly
            100                 105                 110

Lys Ser Gly Arg Thr Trp Arg Glu Ala Asp Ile Asn Tyr Thr Ser Gly
            115                 120                 125

Phe Arg Asn Ser Asp Arg Ile Leu Tyr Ser Ser Asp Trp Leu Ile Tyr
        130                 135                 140

Lys Thr Thr Asp His Tyr Gln Thr Phe Thr Lys Ile Arg
145                 150                 155
```

```
<210> SEQ ID NO 26
<211> LENGTH: 533
<212> TYPE: DNA
<213> ORGANISM: Bacillus amyloliquefaciens

<400> SEQUENCE: 26
ctcatggcac aggttatcaa cacgtttgac ggggttgcgg attatcttca gacatatcat      60
aagctacctg ataattacat tacaaaatca gaagcacaag ccctcggctg ggtggcatca     120
aaagggaacc ttgcagacgt cgctccgggg aaaagcatcg gcggagacat cttctcaaac    180
agggaaggca aactcccgta agtttctgct tctacctttg atatatatat aataattatc    240
attaattagt agtaatataa tatttcaaat attttttca aaataaaaga atgtagtata     300
tagcaattgc ttttctgtag tttataagtg tgtatatttt aatttataac ttttctaata    360
tatgaccaaa acatggtgat gtgcaggggc aaaagcggac gaacatggcg tgaagcggat    420
attaactata catcaggctt cagaaattca gaccggattc tttactcagg cgactggctg    480
atttacaaaa caacggacca ttatcagacc tttacaaaaa tcagataact gca            533

<210> SEQ ID NO 27
<211> LENGTH: 482
<212> TYPE: DNA
<213> ORGANISM: Cauliflower Mosaic virus

<400> SEQUENCE: 27
catggagtca agattcaaa tagaggacct aacagaactc gccgtaaaga ctggcgaaca      60
gttcatacag agtctcttac gactcaatga caagaagaaa atcttcgtca acatggtgga    120
gcacgacacg cttgtctact ccaaaaatat caaagataca gtctcagaag accaaagggc    180
aattgagact ttcaacaaa gggtaatatc cggaaacctc ctcggattcc attgcccagc    240
tatctgtcac tttattgtga agatagtgga aaaggaaggt ggctcctaca atgccatca    300
ttgcgataaa ggaaaggcca tcgttgaaga tgcctctgcc gacagtggtc ccaaagatgg    360
acccccaccc acgaggagca tcgtggaaaa agaagacgtt ccaaccacgt cttcaaagca    420
agtggattga tgtgatatct ccactgacgt aagggatgac gcacaatccc actaagctga    480
cc                                                                    482

<210> SEQ ID NO 28
```

```
<211> LENGTH: 147
<212> TYPE: PRT
<213> ORGANISM: Bacillus licheniformis

<400> SEQUENCE: 28

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Cys Met Tyr
            20                  25                  30

Glu Thr Asp Leu Leu Arg Gly Ala Phe His Leu Gly Phe Tyr Gly
        35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 29
<211> LENGTH: 444
<212> TYPE: PRT
<213> ORGANISM: Bacillus licheniformis

<400> SEQUENCE: 29

Ala Thr Gly Gly Cys Gly Ala Thr Cys Gly Ala Gly Thr Cys Ala
1               5                   10                  15

Ala Gly Cys Cys Ala Ala Thr Cys Ala Ala Cys Gly Cys Gly Ala
            20                  25                  30

Gly Gly Ala Thr Ala Cys Cys Thr Ala Cys Gly Ala Cys Thr Cys
        35                  40                  45

Cys Gly Cys Cys Ala Cys Ala Gly Gly Thr Thr Thr Thr Gly Cys
50                  55                  60

Gly Cys Cys Cys Gly Ala Ala Cys Cys Ala Ala Cys Cys Gly Ala Thr
65                  70                  75                  80

Ala Gly Ala Ala Gly Thr Gly Thr Gly Cys Ala Thr Gly Thr Ala Cys
                85                  90                  95

Gly Ala Gly Ala Cys Cys Gly Ala Thr Cys Thr Thr Cys Thr Cys
            100                 105                 110

Gly Cys Gly Gly Ala Gly Cys Gly Thr Thr Cys Cys Ala Cys Thr
        115                 120                 125

Thr Gly Gly Cys Gly Gly Cys Thr Thr Cys Thr Ala Thr Gly Gly Cys
130                 135                 140

Gly Gly Cys Ala Ala Gly Cys Thr Gly Ala Thr Ala Ala Gly Cys Gly
145                 150                 155                 160

Thr Cys Gly Cys Gly Ala Gly Cys Thr Thr Cys Cys Ala Cys Cys Ala
                165                 170                 175

Gly Gly Cys Ala Gly Ala Gly Cys Ala Cys Ala Gly Cys Gly Ala Gly
                180                 185                 190
```

Cys Thr Cys Cys Ala Ala Gly Gly Cys Ala Ala Ala Ala Gly Cys
        195                 200                 205

Ala Gly Thr Ala Cys Cys Ala Ala Cys Thr Gly Cys Gly Cys Gly
    210                 215                 220

Cys Gly Thr Thr Gly Cys Gly Ala Cys Cys Thr Cys Gly Ala Gly
225                 230                 235                 240

Gly Gly Ala Thr Ala Thr Cys Gly Cys Gly Ala Cys Cys Ala Gly Ala
                245                 250                 255

Ala Gly Gly Cys Thr Gly Gly Cys Ala Gly Cys Ala Gly Cys Cys Thr
        260                 265                 270

Thr Gly Thr Gly Ala Ala Gly Cys Ala Cys Gly Cys Cys Gly Ala Ala
        275                 280                 285

Gly Ala Gly Ala Thr Ala Cys Thr Cys Ala Gly Ala Ala Gly Ala
        290                 295                 300

Gly Ala Gly Gly Cys Gly Cys Cys Gly Ala Cys Ala Thr Gly Cys Thr
305                 310                 315                 320

Thr Thr Gly Gly Thr Gly Cys Ala Ala Cys Gly Cys Cys Ala Gly Gly
                325                 330                 335

Ala Cys Gly Ala Gly Cys Gly Cys Ala Ala Gly Cys Gly Gly Cys Thr
        340                 345                 350

Ala Cys Thr Ala Cys Gly Ala Ala Ala Ala Gly Cys Thr Thr Gly Gly
        355                 360                 365

Cys Thr Thr Cys Ala Gly Cys Gly Ala Gly Cys Ala Ala Gly Gly Ala
        370                 375                 380

Gly Ala Gly Gly Thr Cys Thr Cys Gly Ala Ala Ala Cys Gly Cys
385                 390                 395                 400

Cys Thr Cys Cys Cys Gly Cys Ala Gly Gly Cys Cys Cys Gly Cys Ala
        405                 410                 415

Cys Ala Thr Cys Cys Thr Cys Ala Thr Gly Thr Ala Thr Ala Ala Gly
        420                 425                 430

Cys Gly Cys Cys Thr Thr Ala Cys Gly Thr Ala Gly
        435                 440

<210> SEQ ID NO 30
<211> LENGTH: 1089
<212> TYPE: DNA
<213> ORGANISM: Arabidopsis thaliana

<400> SEQUENCE: 30
tttttgtgat ctgatgataa gtggttggtt cgtgtctcat gcacttggga ggtgatctat    60
ttcacctggt gtagtttgtg tttccgtcag ttggaaaaac ttatccctat cgatttcgtt   120
ttcattttct gcttttcttt tatgtacctt cgtttgggct tgtaacgggc ctttgtattt   180
caactctcaa taataatcca agtgcatgtt aaacaatttg tcatctgttt cggctttgat   240
atactactgg tgaagatggg ccgtactact gcatcacaac gaaaataat aataagatga    300 aaaacttgaa gtggaaaaaa aaaaaaactt gaatgttcac tactactcat tgaccataat   360
gtttaacata catagctcaa tagtattttt gtgaatatgg caacacaaac agtccaaaac   420
aattgtctct tactatacca aaccaagggc gccgcttgtt tgccactctt tgtgtgcaat   480
agtgtgatta ccacatctcc acattcaata tattccctga attatctgac gattttgatg   540
gctcactgtt ttcccaagtc ttgaattgtc ttctgtgcgc cagtcaaatg catatgtgtt   600
gagtttatct tttaaatatc aagctttgt ttttaactt tgtttgtaac caaaaactca    660

```
cagtaggagt ttgatcacat aattttatgt ttgcctttgc aatttctagt gagtctttga    720
ttaaaagctt gaaagaaaaa tgcagccaag cttaccaagt aagttatgtg tattaaccag    780
aggaagagag aatcttgcaa aatttcaaca acacaaaaa gaagtattac tacgattggt    840
ggagaaagaa aacgattcca aatcttgaac tgttgttgta aaagcatagc agaaagtggg    900
agacaaccga aatagaaatg actataactt aatttaatgt tatcattata atttcttcta    960
gcaaatattt agaaagtaaa tatcacatca acctttaatg taattaagct ttctcttttt    1020
gattcatgtg agatgaaaag aaaaaaaaga agagaaaagt gtagaaaaca catcatttct    1080
aagctgaag                                                            1089

<210> SEQ ID NO 31
<211> LENGTH: 745
<212> TYPE: DNA
<213> ORGANISM: Zea mays

<400> SEQUENCE: 31
ttcttatgtg cttctagtct ccaaatgtgg ttgatagtta ttttgctcta agatcaacag    60
taatgaagta taaatcatcg ttgtggtgtg ctactcggtt aattgagcat aacacacac    120 aaacatgacg aggatggtat aatctccaaa aatgtgtact tgttaggtg ggaccctata    180 gccttgatta atgtgctatg ttaggcatgc ctggaaacgt gtgacgcata tgttttgtga    240
acctgttgat attatatgtg cttttatatt accatatttt attaaaatac taatatttat    300
tactagtaag atataacatt ctatctagct taaaaactaa ccataaatat tccataataa    360
ctagatttac caaactaata tactaaatat acataataaa tacaaaatta acaagacaat    420
aatcaatatt tatgagctta atatatttag acattatggt tggtcgacga taatcatgct    480
aacttttcgt aattgcttga ttgaaatatg cttagaataa tgcctctttg ttctacatgg    540 caaatagga ccattatggt gtaacaccct gggaaccaca acaccccga atgctacta     600 aactacacaa ctaaccttca tatataaat ttcgacagca tctcctttga aaatttgcat    660
agacgtggaa gcaacagagt ataaacagat atcatgataa gaaaacatac tagacattaa    720
taatctgcta gaaatgggaa gaatc                                         745

<210> SEQ ID NO 32
<211> LENGTH: 1682
<212> TYPE: DNA
<213> ORGANISM: Oryza sativa

<400> SEQUENCE: 32
atccctcagc cgccttttcac tatcttttt gcccgagtca ttgtcatgtg aaccttggca    60
tgtataatcg gtgaattgcg tcgatttttcc tcttataggt gggccaatga atccgtgtga    120
tcgcgtctga ttggctagag atatgtttct tccttgttgg atgtattttc atacataatc    180
atatgcatac aaatatttca ttcacttta tagaaatggt cagtaataaa ccctatcact    240
atgtctggtg tttcattta tttgctttta aacgaaaatt gacttcctga ttcaatattt    300
aaggatcgtc aacggtgtgc agttactaaa ttctggtttg taggaactat agtaaactat    360
tcaagtcttc acttattgtg cactcacctc tcgccacatc accacagatg ttattcacgt    420
cttaaatttg aactacacat catattgaca caatattttt tttaaataag cgattaaaac    480
ctagcctcta tgtcaacaat ggtgtacata accagcgaag tttagggagt aaaaaacatc    540
gccttacaca aagttcgctt taaaaataa agagtaaatt ttactttgga ccacccttca    600
accaatgttt cactttagaa cgagtaattt tattattgtc actttggacc accctcaaat    660
```

```
ctttttttcca tctacatcca atttatcatg tcaaagaaat ggtctacata cagctaagga      720
gatttatcga cgaatagtag ctagcatact cgaggtcatt catatgcttg agaagagagt      780
cgggatagtc caaaataaaa caaaggtaag attacctggt caaaagtgaa aacatcagtt      840
aaaaggtggt ataaagtaaa atatcggtaa taaaaggtgg cccaaagtga aatttactct      900
tttctactat tataaaaatt gaggatgttt tgtcggtac tttgatacgt catttttgta       960
tgaattggtt tttaagttta ttcgcttttg gaaatgcata tctgtatttg agtcgggttt     1020
taagttcgtt tgcttttgta aatacagagg gatttgtata agaaatatct ttaaaaaaac     1080
ccatatgcta atttgacata atttttgaga aaaatatata ttcaggcgaa ttctcacaat     1140
gaacaataat aagattaaaa tagctttccc ccgttgcagc gcatgggtat ttttctagt      1200 aaaaataaaa gataaactta gactcaaaac atttacaaaa acaacccta aagttcctaa      1260 agcccaaagt gctatccacg atccatagca agcccagccc aacccaaccc aacccaaccc     1320
accccagtcc agccaactgg acaatagtct ccacaccccc ccactatcac cgtgagttgt     1380
ccgcacgcac cgcacgtctc gcagccaaaa aaaaaaaag aagaaaaaa agaaaaaga       1440 aaaaacagca ggtgggtccg ggtcgtgggg gccggaaacg cgaggaggat cgcgagccag     1500
cgacgaggcc ggccctccct ccgcttccaa agaaacgccc cccatcgcca ctatatacat     1560 accccccct ctcctcccat ccccccaacc ctaccaccac caccaccacc acctccacct      1620 cctccccct cgctgccgga cgacgagctc ctcccccctc cccctccgcc gccgccgcgc      1680
cg                                                                   1682

<210> SEQ ID NO 33
<211> LENGTH: 462
<212> TYPE: DNA
<213> ORGANISM: Oryza sativa

<400> SEQUENCE: 33
gtaaccaccc cgcccctctc ctctttcttt ctccgttttt ttttccgtc tcggtctcga       60 tctttggcct tggtagtttg ggtgggcgag aggcggcttc gtgcgcgccc agatcggtgc     120
gcgggagggg cgggatctcg cggctggggc tctcgccggc gtggatcagg cccggatctc     180
gcggggaatg gggctctcgg atgtagatct gcgatccgcc gttgttgggg gagatgatgg     240
ggggtttaaa atttccgcca tgctaaacaa gatcaggaag agggggaaaag ggcactatgg     300 tttatatttt tatatatttc tgctgcttcg tcaggcttag atgtgctaga tctttctttc     360
ttctttttgt gggtagaatt tgaatccctc agcattgttc atcggtagtt tttcttttca     420
tgatttgtga caaatgcagc ctcgtgcgga gctttttgt ag                         462

<210> SEQ ID NO 34
<211> LENGTH: 183
<212> TYPE: PRT
<213> ORGANISM: Streptomyces viridochromogenes

<400> SEQUENCE: 34

Met Ser Pro Glu Arg Arg Pro Val Glu Ile Arg Pro Ala Thr Ala Ala
1               5                   10                  15

Asp Met Ala Ala Val Cys Asp Ile Val Asn His Tyr Ile Glu Thr Ser
            20                  25                  30

Thr Val Asn Phe Arg Thr Glu Pro Gln Thr Pro Gln Glu Trp Ile Asp
        35                  40                  45

Asp Leu Glu Arg Leu Gln Asp Arg Tyr Pro Trp Leu Val Ala Glu Val
```

Glu Gly Val Val Ala Gly Ile Ala Tyr Ala Gly Pro Trp Lys Ala Arg
65                  70                  75                  80

Asn Ala Tyr Asp Trp Thr Val Glu Ser Thr Val Tyr Val Ser His Arg
            85                  90                  95

His Gln Arg Leu Gly Leu Gly Ser Thr Leu Tyr Thr His Leu Leu Lys
        100                 105                 110

Ser Met Glu Ala Gln Gly Phe Lys Ser Val Val Ala Val Ile Gly Leu
            115                 120                 125

Pro Asn Asp Pro Ser Val Arg Leu His Glu Ala Leu Gly Tyr Thr Ala
        130                 135                 140

Arg Gly Thr Leu Arg Ala Ala Gly Tyr Lys His Gly Gly Trp His Asp
145                 150                 155                 160

Val Gly Phe Trp Gln Arg Asp Phe Glu Leu Pro Ala Pro Pro Arg Pro
                165                 170                 175

Val Arg Pro Val Thr Gln Ile
            180

<210> SEQ ID NO 35
<211> LENGTH: 552
<212> TYPE: DNA
<213> ORGANISM: Streptomyces viridochromogenes

<400> SEQUENCE: 35 atgtccccccg agcgccgccc cgtcgagatc cgcccggcca ccgccgccga catggccgcc    60
gtgtgcgaca tcgtgaacca ctacatcgag acctccaccg tgaacttccg caccgagccg   120
cagaccccgc aggagtggat cgacgacctg agcgcctcc aggaccgcta cccgtggctc    180
gtggccgagg tggagggcgt ggtggccggc atcgcctacg ccggcccgtg gaaggcccgc   240
aacgcctacg actggaccgt ggagtccacc gtgtacgtgt cccaccgcca ccagcgcctc   300
ggcctcggct ccaccctcta cacccacctc ctcaagagca tggaggccca gggcttcaag   360
tccgtggtgg ccgtgatcgg cctcccgaac gacccgtccg tgcgcctcca cgaggccctc   420
ggctacaccg cccgcggcac cctgcgcgcc gccggctaca agcacggcgg ctggcacgac   480
gtcggcttct ggcagcgcga cttcgagctg ccggccccgc cgcgcccggt gcgcccggtg   540
acgcagatct ga                                                       552

<210> SEQ ID NO 36
<211> LENGTH: 231
<212> TYPE: PRT
<213> ORGANISM: Artificial sequence
<220> FEATURE:
<223> OTHER INFORMATION: Sequence from Zoanthus species

<400> SEQUENCE: 36

Met Ala His Ser Lys His Gly Leu Lys Glu Glu Met Thr Met Lys Tyr
1               5                   10                  15

His Met Glu Gly Cys Val Asn Gly His Lys Phe Val Ile Thr Gly Glu
            20                  25                  30

Gly Ile Gly Tyr Pro Phe Lys Gly Lys Gln Thr Ile Asn Leu Cys Val
        35                  40                  45

Ile Glu Gly Gly Pro Leu Pro Phe Ser Glu Asp Ile Leu Ser Ala Gly
    50                  55                  60

Phe Lys Tyr Gly Asp Arg Ile Phe Thr Glu Tyr Pro Gln Asp Ile Val
65                  70                  75                  80

```
Asp Tyr Phe Lys Asn Ser Cys Pro Ala Gly Tyr Thr Trp Gly Arg Ser
            85                  90                  95

Phe Leu Phe Glu Asp Gly Ala Val Cys Ile Cys Asn Val Asp Ile Thr
            100                 105                 110

Val Ser Val Lys Glu Asn Cys Ile Tyr His Lys Ser Ile Phe Asn Gly
            115                 120                 125

Val Asn Phe Pro Ala Asp Gly Pro Val Met Lys Met Thr Thr Asn
            130                 135                 140

Trp Glu Ala Ser Cys Glu Lys Ile Met Pro Val Pro Lys Gln Gly Ile
145                 150                 155                 160

Leu Lys Gly Asp Val Ser Met Tyr Leu Leu Lys Asp Gly Gly Arg
                165                 170                 175

Tyr Arg Cys Gln Phe Asp Thr Val Tyr Lys Ala Lys Ser Val Pro Ser
            180                 185                 190

Lys Met Pro Glu Trp His Phe Ile Gln His Lys Leu Leu Arg Glu Asp
            195                 200                 205

Arg Ser Asp Ala Lys Asn Gln Lys Trp Gln Leu Thr Glu His Ala Ile
    210                 215                 220

Ala Phe Pro Ser Ala Leu Ala
225                 230

<210> SEQ ID NO 37
<211> LENGTH: 696
<212> TYPE: DNA
<213> ORGANISM: Artificial sequence
<220> FEATURE:
<223> OTHER INFORMATION: Sequence from Zoanthus species

<400> SEQUENCE: 37
atggcccaca gcaagcacgg cctgaaggag gagatgacca tgaagtacca catggagggc      60
tgcgtgaacg gccacaagtt cgtgatcacc ggcgagggca tcggctaccc cttcaagggc     120
aagcagacca tcaacctgtg cgtgatcgag ggcggccccc tgcccttcag cgaggacatc     180
ctgagcgccg gcttcaagta cggcgaccgg atcttcaccg agtaccccca ggacatcgtg     240
gactacttca gaacagctg ccccgccggc tacacctggg gccggagctt cctgttcgag     300
gacggcgccg tgtgcatctg taacgtggac atcaccgtga gcgtgaagga gaactgcatc     360
taccacaaga gcatcttcaa cggcgtgaac ttccccgccg acggccccgt gatgaagaag     420
atgaccacca actgggaggc cagctgcgag aagatcatgc ccgtgcctaa gcagggcatc     480
ctgaagggcg acgtgagcat gtacctgctg ctgaaggacg gcggccggta ccggtgccag     540
ttcgacaccg tgtacaaggc caagagcgtg cccagcaaga tgcccgagtg gcacttcatc     600
cagcacaagc tgctgcggga ggaccggagc gacgccaaga accagaagtg gcagctgacc     660
gagcacgcca tcgccttccc cagcgccctg gcctga                               696

<210> SEQ ID NO 38
<211> LENGTH: 207
<212> TYPE: PRT
<213> ORGANISM: Escherichia coli

<400> SEQUENCE: 38

Met Ala Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
```

```
        35                  40                  45

Arg Ala Leu Leu Asp Ala Leu Ala Ile Glu Met Leu Asp Arg His His
    50                  55                  60
Thr His Phe Cys Pro Leu Glu Gly Glu Ser Trp Gln Asp Phe Leu Arg
65                  70                  75                  80
Asn Asn Ala Lys Ser Phe Arg Cys Ala Leu Leu Ser His Arg Asp Gly
                85                  90                  95
Ala Lys Val His Leu Gly Thr Arg Pro Thr Glu Lys Gln Tyr Glu Thr
            100                 105                 110
Leu Glu Asn Gln Leu Ala Phe Leu Cys Gln Gln Gly Phe Ser Leu Glu
        115                 120                 125
Asn Ala Leu Tyr Ala Leu Ser Ala Val Gly His Phe Thr Leu Gly Cys
    130                 135                 140
Val Leu Glu Asp Gln Glu His Gln Val Ala Lys Glu Glu Arg Glu Thr
145                 150                 155                 160
Pro Thr Thr Asp Ser Met Pro Pro Leu Leu Arg Gln Ala Ile Glu Leu
                165                 170                 175
Phe Asp His Gln Gly Ala Glu Pro Ala Phe Leu Phe Gly Leu Glu Leu
            180                 185                 190
Ile Ile Cys Gly Leu Glu Lys Gln Leu Lys Cys Glu Ser Gly Ser
        195                 200                 205
```

<210> SEQ ID NO 39
<211> LENGTH: 624
<212> TYPE: DNA
<213> ORGANISM: Escherichia coli

<400> SEQUENCE: 39

```
atggccagac tcgacaagag caaggtgatc aacagcgcac tggagctgct gaacgaggtc     60
ggaatcgaag gcctcacaac ccgtaaactc gcccagaagc tcggggtaga gcagcctaca    120
ttgtattggc acgtcaagaa caagcgggct ttgctagacg ccctcgccat tgagatgctc    180
gataggcacc atacccactt ctgccctttg gaaggggaaa gctggcaaga cttcttgagg    240
aacaacgcta agagcttcag atgtgctttg ctcagtcacc gtgatggagc caaggtccac    300
ctaggtacac ggcctacgga gaagcagtat gaaactctcg agaaccagct cgccttcctg    360
tgccaacaag gtttctccct tgagaatgcc ctctacgcac tctccgctgt agggcacttc    420
actctgggtt gcgtattgga agatcaagag caccaagtcg ctaaggagga gagggaaaca    480
cctactactg atagtatgcc gccactgctc cgacaagcta tcgagctctt cgatcaccaa    540
ggtgcagagc cagccttcct gttcggcctt gaattgatca tatgcggatt ggagaagcag    600
ctgaagtgtg aaagtgggtc ttaa                                           624
```

<210> SEQ ID NO 40
<211> LENGTH: 19
<212> TYPE: DNA
<213> ORGANISM: Escherichia coli

<400> SEQUENCE: 40

```
actctatcag tgatagagt                                                  19
```

<210> SEQ ID NO 41
<211> LENGTH: 34
<212> TYPE: DNA
<213> ORGANISM: Artificial Sequence
<220> FEATURE:
<223> OTHER INFORMATION: LOX-FAS

```
<400> SEQUENCE: 41
acaacttcgt atataccttt ctatacgaag ttgt                          34

<210> SEQ ID NO 42
<211> LENGTH: 34
<212> TYPE: DNA
<213> ORGANISM: artificial sequence
<220> FEATURE:
<223> OTHER INFORMATION: LOX-2272

<400> SEQUENCE: 42
ataacttcgt ataggatacc ttatacgaag ttat                          34

<210> SEQ ID NO 43
<211> LENGTH: 9810
<212> TYPE: DNA
<213> ORGANISM: artificial sequence
<220> FEATURE:
<223> OTHER INFORMATION: PHP70154

<400> SEQUENCE: 43
agcgtcagac cccgtagaaa agatcaaagg atcttcttga gatcctttt tttctgcgcgt    60 aatctgctgc ttgcaaacaa aaaaaccacc gctaccagcg gtggtttgtt tgccggatca   120
agagctacca actctttttc cgaaggtaac tggcttcagc agagcgcaga taccaaatac   180
tgtccttcta gtgtagccgt agttaggcca ccacttcaag aactctgtag caccgcctac   240
atacctcgct ctgctaatcc tgttaccagt ggctgctgcc agtggcgata gtcgtgtct    300 taccggggttg gactcaagac gatagttacc ggataaggcg cagcggtcgg gctgaacggg   360
gggttcgtgc acacagccca gcttggagcg aacgacctac accgaactga gatacctaca   420
gcgtgagcta tgagaaagcg ccacgcttcc cgaagggaga aaggcggaca ggtatccggt   480
aagcggcagg gtcggaacag gagagcgcac gagggagctt ccaggggaa acgcctggta    540 tctttatagt cctgtcgggt ttcgccacct ctgacttgag cgtcgatttt tgtgatgctc   600 gtcaggggg cggagcctat ggaaaaacgc cagcaacgcg gccttttac ggttcctggc     660 cttttgctgg cctttttgctc acatgttctt tcctgcgtta tccctgatt ctgtggataa   720 ccgtattacc gcctttgagt gagctgatac cgagcggata acaatttcac acaggaaaca   780
gctatgacca tgattacgcc aagctatcaa cttttgtatag aaagttgaa gcttcgctga   840 aatcaccagt ctctctctac aaatctatct ctctctataa taatgtgtga gtagttccca   900
gataagggaa ttagggttct tatagggttt cgctcatgtg ttgagcatat aagaaaccct   960
tagtatgtat ttgtatttgt aaaatacttc tatcaataaa atttctaatt cctaaaacca  1020
aaatccagtg gcgagctgct agcgaagttc ctattccgaa gttcctattc tctagaaagt  1080
ataggaactt cagatccacc ggctagagga tccaccatgg ttgaacaaga tggattgcac  1140
gcaggttctc cggccgcttg gtggagagg ctattcggct atgactggc acaacagaca    1200 atcggctgct ctgatgccgc cgtgttccgg ctgtcagcgc aggggcgccc ggttcttttt  1260
gtcaagaccg acctgtccgg tgccctgaat gaactgcagg acgaggcagc gcggctatcg  1320
tggctggcca cgacgggcgt tccttgcgca gctgtgctcg acgttgtcac tgaagcggga  1380
agggactggc tgctattggg cgaagtgccg gggcaggatc tcctgtcatc tcaccttgct  1440
cctgccgaga aagtatccat catggctgat gcaatgcggc ggctgcatac gcttgatccg  1500
gctacctgcc cattcgacca ccaagcgaaa catcgcatcg agcgagcacg tactcggatg  1560
```

```
gaagccggtc ttgtcgatca ggatgatctg gacgaagagc atcaggggct cgcgccagcc    1620
gaactgttcg ccaggctcaa ggcgcgcatg cccgacggcg atgatctcgt cgtgacccat    1680
ggcgatgcct gcttgccgaa tatcatggtg aaaatggcc gcttttctgg attcatcgac     1740
tgtggccggc tgggtgtggc ggaccgctat caggacatag cgttggctac ccgtgatatt    1800
gctgaagagc ttggcggcga atgggctgac cgcttcctcg tgctttacgg tatcgccgct    1860
cccgattcgc agcgcatcgc cttctatcgc cttcttgacg agttcttctg aggatccacc    1920
atggttaacc tagacttgtc catcttctgg attggccaac ttaattaatg tatgaaataa    1980
aaggatgcac acatagtgac atgctaatca ctataatgtg ggcatcaaag ttgtgtgtta    2040
tgtgtaatta ctagttatct gaataaaaga gaaagagatc atccatattt cttatcctaa    2100
atgaatgtca cgtgtcttta taattctttg atgaaccaga tgcatttcat taaccaaatc    2160
catatacata taaatattaa tcatatataa ttaatatcaa ttgggttagc aaaacaaatc    2220
tagtctaggt gtgttttgcg aatgcggccg ggtaccgagc tcgaattcgg cccaagtttg    2280
tacaaaaaag caggctccgg ccagaatggc ccggaccgaa gctggccgct ctagaactag    2340
tggatctcga tgtgtagtct acgagaaggg ttaaccgtct cttcgtgaga ataaccgtgg    2400
cctaaaaata agccgatgag gataaataaa atgtggtggt acagtacttc aagaggttta    2460
ctcatcaaga ggatgctttt ccgatgagct ctagtagtac atcggacctc acatacctcc    2520
attgtggtga atattttgt gctcatttag tgatgggtaa attttgttta tgtcactcta     2580
ggttttgaca tttcagtttt gccactctta ggttttgaca ataatttcc attccgcggc     2640
aaaagcaaaa caatttttatt ttacttttac cactcttagc tttcacaatg tatcacaaat   2700
gccactctag aaattctgtt tatgccacag aatgtgaaaa aaacactca cttatttgaa     2760
gccaaggtgt tcatggcatg gaaatgtgac ataaagtaac gttcgtgtat aagaaaaaat    2820
tgtactcctc gtaacaagag acggaaacat catgagacaa tcgcgtttgg aaggctttgc    2880
atcacctttg gatgatgcgc atgaatggag tcgtctgctt gctagccttc gcctaccgcc    2940
cactgagtcc gggcggcaac taccatcggc gaacgaccca gctgacctct accgaccgga    3000
cttgaatgcg ctaccttcgt cagcgacgat ggccgcgtac gctggcgacg tgccccgca     3060
tgcatggcgg cacatggcga gctcagaccg tgcgtggctg gctacaaata cgtacccgt     3120
gagtgcccta gctagaaact tacacctgca actgcgagag cgagcgtgtg agtgtagccg    3180
atagatccgc ccatgagcga gctgattaaa gagaacatgc acatgaagct gtacatggag    3240
gggaccgtcg acaaccacca cttcaagtgc acctccgagg gcgagggtaa gccgtatgag    3300
ggcacgcaga caatgaggat taaagtggtt gagggcgggc gctgcctttt cgcattcgac    3360
atcctcgcca ccagcttcct gtacgggtcc aagaccttca tcaaccacac ccagggcatc    3420
cccgacttct tcaaacagtc cttcccggag ggtttcacgt gggagagggt gacaacctac    3480
gaagatggcg gcgtgctgac cgccacgcag gatacatctc tccaggacgg gtgcctgatc    3540
tacaacgtca agatcaggg cgtcaacttc acgagcaacg gcccggtcat gcagaagaag    3600
acgctcggct gggaagcctt cacggagaca ctctaccccg ccgacggcgg gctggaaggt   3660
aggaacgaca tggccctcaa gctcgtgggc ggcagccacc tcatcgccaa catcaaaacc    3720
acctacagga gcaagaagcc cgccaagaac ctgaagatgc ccggcgtgta ctacgtcgac    3780
tacaggctcg agagaattaa ggaggccaac aacgagacgt acgtggagca gcacgaggtt    3840
gcagttgcca ggtactgcga cctgccgagc aagctcggcc acaagctgaa ctagggatct    3900
cgatagggat ctgttaacga tccccggcgg tgtcccccac tgaagaaact atgtgctgta    3960
```

```
gtatagccgc tgcccgctgg ctagctagct agttgagtca tttagcggcg atgattgagt    4020
aataatgtgt cacgcatcac catgcatggg tggcagtgtc agtgtgagca atgacctgaa    4080
tgaacaattg aaatgaaaag aaaaaagtat tgttccaaat taaacgtttt aaccttttaa    4140
taggtttata caataattga tatatgtttt ctgtatatgt ctaatttgtt atcatccatt    4200
tagatataga caaaaaaaat ctaagaacta aaacaaatgc taatttgaaa tgaagggagt    4260
atatattggg ataatgtcga tgagatccct cgtaatatca ccgacatcac acgtgtccag    4320
ttaatgtatc agtgatacgt gtattcacat tgttgcgcg taggcgtacc caacaatttt     4380
gatcgactat cagaaagtca acggaagcga gtcgacctcg agggggggcc ccggccgaag    4440
cttgcatgcc tgcaggtcga ctctagagga tctgcaccgg acactgtctg gtggcatacc    4500
agacagtccg gtgtgccaga tcagggcacc cttcggttcc tttgctcctt tgcttttgaa    4560
ccctaacttt gatcgtttat tggtttgtgt tgaacctta tgcacctgtg aatatataa     4620 tctagaacaa actagttagt ccaatcattt gtgttgggca ttcaaccacc aaaattattt    4680
ataggaaaag gttaaacctt atttcccttt caatctcccc cttttggtg attgatgcca    4740 acacaaacca aagaaaatat ataagtgcag aattgaacta gtttgcataa ggtaagtgca    4800
taggttactt agaattaaat caatttatac ttttacttga tatgcatggt tgctttcttt    4860
tattttaaca ttttggacca catttgcacc acttgttttg ttttttgcaa atcttttttgg   4920 aaattctttt tcaaagtctt ttgcaaatag tcaaaggtat atgaataaga ttgtaagaag    4980
cattttcaag atttgaaatt ctcccctg tttcaaatgc ttttcctttg actaaacaaa     5040 actcccctg aataaaattc tcctcttagc tttcaagagg gttttaaata gatatcaatt    5100
ggaaatatat ttagatgcta attttgaaaa tataccaatt gaaatcaac ataccaattt     5160 gaaattaaac ataccaattt aaaaaatttc aaaaagtggt ggtgcggtcc ttttgctttg    5220
ggcttaatat ttctccccct ttggcattaa tcgccaaaaa cggagacttt gtgagccatt    5280
tatactttct ccccattggt aaatgaaata tgagtgaaag attataccaa atttggacag    5340
tgatgcggag tgacggcgaa ggataaacga taccgttaga gtggagtgga agccttgtct    5400
tcgccgaaga ctccatttcc ctttcaatct acgacttagc atagaaatac acttgaaaac    5460
acattagtcg tagccacgaa agagatatga tcaaaggtat acaaatgagc tatgtgtgta    5520
atgtttcaat caaagtttcg agaatcaaga atatttagct cattcctaag tttgctaaag    5580
gttttatcat ctaatggttt ggtaaagata tcgactaatt gttctttggt gctaacataa    5640
gcaatctcga tatcacccct ttgttggtga tccctcaaaa agtgataccg aatgtctatg    5700
tgcttagtgc ggctgtgttc aacgggatta tccgccatgc agatagcact ctcattgtca    5760
cataggagag ggactttgct caatttgtag ccatagtccc taaggttttg cctcatccaa    5820
agtaattgca cacaacaatg tcctgcggca atatacttgg cttcggcggt agaaagagct    5880
attgagtttt gttctcttga agtccaagac accaggatc tccctagaaa ctgacaagtc     5940
cctgatgtgc tcttcctatc aattttacac cctgcccaat cggcatctga atatcctatt    6000
aaatcaaagg tggatccctt ggggtaccaa atttaaggag tgtaaactaa atatctcatg    6060
attcttttca cggccctaag gtgaacttcc ttaggatcgg cttggaatct tgcacacatg    6120
catatagaaa gcatagctat ctggtcgaga tgcacataaa tagagtaaag atcctatcat    6180
cgaccggtat acctttggt cgtacggatt tacctcccgt gtcgaggtcg agatgcccat    6240
tagttcccat gggtgtacct gatgggcttg gcatccttca ttccaaactt gttgagtatg    6300
```

```
tcttgaatgt actttgtttg gctgatgaag gtgccatctt ggagttgctt gacttgaaat    6360
cctagaaaat atttcaactt ccccatcata gacatctcga atttcggaat catgatccta    6420
ctaaactctt cacaagtaga tttgttagta gacccaaata taatatcatc aacataaatt    6480
tggcatacaa acaaaacttt tgaaatggtt ttagtaaaga gagtaggatc ggctttactg    6540
actctgaagc cattagtgat aagaaaatct cttaggcatt cataccatgc tgttggggct    6600
tgcttgagcc cataaagcgc cttttgagagt ttataaacat ggttagggta ctcactatct    6660
tcaaagccga gaggttgctc aacatagacc tattcacccc atttgatcac ttttttggtc    6720
cttcaggatc taatagttat gtataattta gagtctcttg tttaatggcc agatatttct    6780
aattaatcta agaatttatg atatttttta attttttatc atgtctgatg agaattaaca    6840
taaaggctca attgggtcct gaattaataa tagagtgaaa attaatccag aggctctatt    6900
agaaccttca attagtaata ccaagatata tataagatag tagagtatag tttaaatgtt    6960
ggcattgttc attcttttctt ttgttatttta atttatgctt tccacggtgg ttagtggtta    7020
cttctgaagg gtccaaataa tgcatgaaga gtttgaggac aagaagtctg ccctaaaaat    7080
agcgatgcaa aggcatggtg tccaagccat acatatagcg cactaatttt atcagcagaa    7140
caatggtatt tataggtcct agtgcccagg caacaagaga cacgaataaa gcatcgatca    7200
cgacaccaga tctcatggca caggttatca acacgtttga cggggttgcg gattatcttc    7260
agacatatca taagctacct gataattaca ttacaaaatc agaagcacaa gccctcggct    7320
gggtggcatc aaaagggaac cttgcagacg tcgctccggg gaaaagcatc ggcggagaca    7380
tcttctcaaa cagggaaggc aaactcccgt aagtttctgc ttctaccttt gatatatata    7440
taataattat cattaattag tagtaatata atatttcaaa tatttttttc aaaataaaag    7500
aatgtagtat atagcaattg cttttctgta gtttataagt gtgtatattt taatttataa    7560
cttttctaat atatgaccaa aacatggtga tgtgcagggg caaaagcgga cgaacatggc    7620
gtgaagcgga tattaactat acatcaggct tcagaaattc agaccggatt ctttactcag    7680
gcgactggct gatttacaaa acaacggacc attatcagac ctttacaaaa atcagataac    7740
tgcagctaga cttgtccatc ttctggattg gccaacttaa ttaatgtatg aaataaaagg    7800
atgcacacat agtgacatgc taatcactat aatgtgggca tcaaagttgt gtgttatgtg    7860
taattactag ttatctgaat aaaagagaaa gagatcatcc atatttctta tcctaaatga    7920
atgtcacgtg tcttttataat tcttttgatga accagatgca tttcattaac caaatccata    7980
tacatataaa tattaatcat atataattaa tatcaattgg gttagcaaaa caaatctagg    8040
gtcacccggt ccgggcctag aaggccgatc tcccgggcac ccagctttct tgtacaaagt    8100
ggccgttaac ggatcccggt gaagttccta ttccgaagtt cctattctcc agaaagtata    8160
ggaacttcac tagagcttgc ggccgccccg ggcaacttta ttatacatag ttgataattc    8220
actggccgtc gttttacaac gtcgtgactg gaaaaccct ggcgttaccc aacttaatcg    8280
ccttgcagca catccccctt cgccagctg gcgtaatagc gaagaggccc gcaccgatcg    8340
cccttcccaa cagttgcgca gcctgaatgg cgaatggcgc ctgatgcggt attttctcct    8400
tacgcatctg tgcggtattt cacaccgcat atggtgcact ctcagtacaa tctgctctga    8460
tgccgcatag ttaagccagc cccgacaccc gccaacaccc gctgacgcgc cctgacgggc    8520
ttgtctgctc ccggcatccg cttacagaca agctgtgacc gtctccggga gctgcatgtg    8580
tcagaggttt tcaccgtcat caccgaaacg cgcgagacga aagggcctcg tgatacgcct    8640
atttttatag gttaatgtca tgataataat ggtttcttag acgtcaggtg gcacttttcg    8700
```

```
gggaaatgtg cgcggaaccc ctatttgttt attttctaa atacattcaa atatgtatcc    8760
gctcatgaga caataaccct gataaatgct tcaataatat tgaaaaagga agagtatgag    8820
tattcaacat ttccgtgtcg cccttattcc cttttttgcg gcattttgcc ttcctgtttt    8880
tgctcaccca gaaacgctgg tgaaagtaaa agatgctgaa gatcagttgg gtgcacgagt    8940
gggttacatc gaactggatc tcaacagcgg taagatcctt gagagttttc gccccgaaga    9000
acgttttcca atgatgagca cttttaaagt tctgctatgt ggcgcggtat tatcccgtat    9060
tgacgccggg caagagcaac tcggtcgccg catacactat tctcagaatg acttggttga    9120
gtactcacca gtcacagaaa agcatcttac ggatggcatg acagtaagag aattatgcag    9180
tgctgccata accatgagtg ataacactgc ggccaactta cttctgacaa cgatcggagg    9240
accgaaggag ctaaccgctt ttttgcacaa catgggggat catgtaactc gccttgatcg    9300
ttgggaaccg gagctgaatg aagccatacc aaacgacgag cgtgacacca cgatgcctgt    9360
agcaatggca acaacgttgc gcaaactatt aactggcgaa ctacttactc tagcttcccg    9420
gcaacaatta atagactgga tggaggcgga taaagttgca ggaccacttc tgcgctcggc    9480
ccttccggct ggctggttta ttgctgataa atctggagcc ggtgagcgtg gtctcgcgg    9540 tatcattgca gcactggggc cagatggtaa gccctcccgt atcgtagtta tctacacgac    9600
ggggagtcag gcaactatgg atgaacgaaa tagacagatc gctgagatag gtgcctcact    9660
gattaagcat tggtaactgt cagaccaagt ttactcatat atactttaga ttgatttaaa    9720
acttcatttt taatttaaaa ggatctaggt gaagatcctt tttgataatc tcatgaccaa    9780
aatcccttaa cgtgagtttt cgttccactg                                    9810

<210> SEQ ID NO 44
<211> LENGTH: 8485
<212> TYPE: DNA
<213> ORGANISM: artificial sequence
<220> FEATURE:
<223> OTHER INFORMATION: FRT1-FRT87 from PHP69519

<400> SEQUENCE: 44
gaagttccta ttccgaagtt cctattctct agaaagtata ggaacttcag atccaccggc     60
tagaggatcc accatggttg aacaagatgg attgcacgca ggttctccgg ccgcttgggt    120
ggagaggcta ttcggctatg actgggcaca acagacaatc ggctgctctg atgccgccgt    180
gttccggctg tcagcgcagg ggcgcccggt tctttttgtc aagaccgacc tgtccggtgc    240
cctgaatgaa ctgcaggacg aggcagcgcg gctatcgtgg ctggccacga cgggcgttcc    300
ttgcgcagct gtgctcgacg ttgtcactga agcgggaagg gactggctgc tattgggcga    360
agtgccgggg caggatctcc tgtcatctca ccttgctcct gccgagaaag tatccatcat    420
ggctgatgca atgcggcggc tgcatacgct tgatccggct acctgcccat tcgaccacca    480
agcgaaacat cgcatcgagc gagcacgtac tcggatggaa gccggtcttg tcgatcagga    540
tgatctggac gaagagcatc aggggctcgc gccagccgaa ctgttcgcca ggctcaaggc    600
gcgcatgccc gacggcgatg atctcgtcgt gacccatggc gatgcctgct tgccgaatat    660
catggtggaa aatggccgct tttctggatt catcgactgt ggccggctgg gtgtggcgga    720
ccgctatcag gacatagcgt tggctacccg tgatattgct gaagagcttg gcggcgaatg    780
ggctgaccgc ttcctcgtgc tttacggtat cgccgctccc gattcgcagc gcatcgcctt    840
ctatcgcctt cttgacgagt tcttctgagg atccaccatg gttaacctag acttgtccat    900
```

```
cttctggatt ggccaactta attaatgtat gaaataaaag gatgcacaca tagtgacatg    960
ctaatcacta taatgtgggc atcaaagttg tgtgttatgt gtaattacta gttatctgaa   1020
taaaagagaa agagatcatc catatttctt atcctaaatg aatgtcacgt gtctttataa   1080
ttctttgatg aaccagatgc atttcattaa ccaaatccat atacatataa atattaatca   1140
tatataatta atatcaattg ggttagcaaa acaaatctag tctaggtgtg ttttgcgaat   1200
tgcggccggg taccgagctc gaattcggcc caagtttgta caaaaaagca ggctccggcc   1260
agaatggccc ggaccgaagc tggccgctct agaactaggt aagtgactag ggtcacatcg   1320
aattgggatc taggagcttg taggagcttc taggagcttg catgcgcggg ccgcgaggtc   1380
atcacatcaa tccacttgct ttgaagacgt ggttggaacg tcttcttttt ccacgatgct   1440
cctcgtgggt gggggtccat ctttgggacc actgtcggca gaggcatctt caacgatggc   1500
ctttccttta tcgcaatgat ggcatttgta ggagccacct tccttttcca ctatcttcac   1560
aataaagtga cagatagctg ggcaatggaa tccgaggagg tttccggata ttacccttt g  1620
ttgaaaagtc tcaattgccc tttggtcttc tgagactgta tctttgatat ttttggagta   1680
gacaagcgtg tcgtgctcca ccatgttgac gaagattttc ttcttgtcat tgagtcgtaa   1740
gagactctgt atgaactgtt cgccagtctt tacggcgagt tctgttaggt cctctatttg   1800
aatctttgac tccatggacg tatcgataa gctagcttga tatcacatca atccacttgc    1860
tttgaagacg tggttggaac gtcttctttt tccacgatgc tcctcgtggg tggggtccat   1920
tctttgggac cactgtcggc agaggcatct tcaacgatgg cctttccttt atcgcaatga   1980
tggcatttgt aggagccacc ttccttttcc actatcttca ataaagtg acagatagct     2040
gggcaatgga atccgaggag gtttccggat attaccttt gttgaaaagt ctcaattgcc    2100
ctttggtctt ctgagactgt atctttgata ttttggagt agacaagcgt gtcgtgctcc    2160
accatgttga cgaagatttt cttcttgtca ttgagtcgta agagactctg tatgaactgt   2220
tcgccagtct ttacggcgag ttctgttagg cctctatttt gaatctttga ctccatgatc   2280
gaattatcac atcaatccac ttgctttgaa gacgtggttg gaacgtcttc tttttccacg   2340
atgctcctcg tgggtggggg tccatctttg ggaccactgt cggcagaggc atcttcaacg   2400
atggcctttc ctttatcgca atgatggcat tgtaggagc caccttcctt ttccactatc    2460
ttcacaataa agtgacagat agctgggcaa tggaatccga ggaggtttcc ggatattacc   2520
ctttgttgaa aagtctcaat gcccttt gg tcttctgaga ctgtatcttt gattttttg    2580
gagtagacaa gcgtgtcgtg ctccaccatg ttgacgaaga ttttcttctt gtcattgagt   2640
cgtaagagac tctgtatgaa ctgttcgcca gtctttacgg cgagttctgt taggtcctct   2700
atttgaatct tgactccat gggaattcct gcagccgcag tgcagcgtga cccggtcgtg    2760
ccctctcta gagataatga gcattgcatg tctaagttat aaaaaattac cacatatttt    2820
ttttgtcaca cttgtttgaa gtgcagttta tctatcttta tacatatatt taaactttac   2880
tctacgaata atataatcta tagtactaca ataaatatcag tgttttagag aatcatataa   2940
atgaacagtt agacatggtc taaaggacaa ttgagtattt tgacaacagg actctacagt   3000
tttatctttt tagtgtgcat gtgttctcct ttttttttgc aaatagcttc acctatataa   3060
tacttcatcc atttttattag tacatccatt tagggtttag ggttaatggt ttttatagac   3120
taattttttt agtacatcta ttttattcta tttagcctc taaattaaga aaactaaaac    3180
tctattttag tttttttatt taataattta gatataaaat agaataaaat aaagtgacta   3240
aaaattaaac aaatacccct taagaaatta aaaaaactaa ggaaacattt tcttgtttc    3300
```

```
gagtagataa tgccagcctg ttaaacgccg tcgacgagtc taacggacac caaccagcga    3360
accagcagcg tcgcgtcggg ccaagcgaag cagacggcac ggcatctctg tcgctgcctc    3420
tggacccctc tcgagagttc cgctccaccg ttggacttgc tccgctgtcg gcatccagaa    3480
attgcgtggc ggagcggcag acgtgagccg gcacggcagg cggcctcctc ctcctctcac    3540
ggcaccggca gctacggggg attcctttcc caccgctcct tcgctttccc ttcctcgccc    3600
gccgtaataa atagacaccc cctccacacc ctctttcccc aacctcgtgt tgttcggagc    3660
gcacacacac acaaccagat ctcccccaaa tccacccgtc ggcacctccg cttcaaggta    3720
cgccgctcgt cctcccccc ccccctctct accttctcta gatcggcgtt ccggtccatg    3780
gttagggccc ggtagttcta cttctgttca tgtttgtgtt agatccgtgt ttgtgttaga    3840
tccgtgctgc tagcgttcgt acacggatgc gacctgtacg tcagacacgt tctgattgct    3900
aacttgccag tgtttctctt tggggaatcc tgggatggct ctagccgttc cgcagacggg    3960
atcgatttca tgattttttt tgtttcgttg catagggttt ggtttgccct tttccttat    4020 ttcaatatat gccgtgcact tgtttgtcgg gtcatctttt catgctttt tttgtcttgg    4080 ttgtgatgat gtggtctggt tgggcggtcg ttctagatcg gagtagaatt ctgtttcaaa    4140
ctacctggtg gatttattaa ttttggatct gtatgtgtgt gccatacata ttcatagtta    4200
cgaattgaag atgatggatg gaaatatcga tctaggatag gtacatgt tgatgcgggt     4260 tttactgatg catatacaga gatgcttttt gttcgcttgg ttgtgatgat gtggtgtggt    4320
tgggcggtcg ttcattcgtt ctagatcgga gtagaatact gtttcaaact acctggtgta    4380
tttattaatt ttggaactgt atgtgtgtgt catacatctt catagttacg agtttaagat    4440
ggatggaaat atcgatctag ataggtata catgttgatg tgggttttac tgatgcatat     4500
acatgatggc atatgcagca tctattcata tgctctaacc ttgagtacct atctattata    4560
ataaacaagt atgttttata attattttga tcttgatata cttggatgat ggcatatgca    4620
gcagctatat gtggattttt ttagccctgc cttcatacgc tatttatttg cttggtactg    4680
tttcttttgt cgatgctcac cctgttgttt ggtgttactt ctgcagacta gtatggcgat    4740
cgaggtcaag ccaatcaacg ccgaggatac ctacgacctc cgccacaggg ttttgcgccc    4800
gaaccaaccg atagaagtgt gcatgtacga gaccgatctt cttcgcggag cgttccacct    4860
tggcggcttc tatggcggca agctgataag cgtcgcgagc ttccaccagg cagagcacag    4920
cgagctccaa ggcaaaaagc agtaccaact gcgcggcgtt gcgaccctcg agggatatcg    4980
cgaccagaag gctggcagca gccttgtgaa gcacgccgaa gagatactca ggaagagagg    5040
cgccgacatg ctttggtgca acgccaggac gagcgcaagc ggctactacg aaaagcttgg    5100
cttcagcgag caaggagagg tcttcgaaac gcctcccgca ggcccgcaca tcctcatgta    5160
taagcgcctt acgtagggat ccgttttttgt gatctgatga taagtggttg gttcgtgtct    5220
catgcacttg ggaggtgatc tatttcacct ggtgtagttt tgtttccgt cagttggaaa     5280 aacttatccc tatcgatttc gttttcattt tctgcttttc ttttatgtac cttcgtttgg    5340
gcttgtaacg ggccttttgta tttcaactct caataataat ccaagtgcat gttaaacaat    5400
ttgtcatctg tttcggcttt gatatactac tggtgaagat gggccgtact actgcatcac    5460
aacgaaaaat aataataaga tgaaaaactt gaagtggaaa aaaaaaaaa cttgaatgtt     5520 cactactact cattgaccat aatgtttaac atacatagct caatagtatt tttgtgaata    5580
tggcaacaca aacagtccaa aacaattgtc tcttactata ccaaaccaag ggcgccgctt    5640
```

```
gtttgccact ctttgtgtgc aatagtgtga ttaccacatc tccacattca atatattccc   5700
tgaattatct gacgattttg atggctcact gttttcccaa gtcttgaatt gtcttctgtg   5760
cgccagtcaa atgcatatgt gttgagttta tcttttaaat atcaagcttt tgtttttaac   5820
ttttgtttgt aaccaaaaac tcacagtagg agtttgatca cataatttta tgtttgcctt   5880
tgcaatttct agtgagtctt tgattaaaag cttgaaaaga aaatgcagcc aagcttacca   5940
agtaagttat gtgtattaac cagaggaaga gagaatcttg caaaatttca acaaacacaa   6000
aaagaagtat tactacgatt ggtggagaaa gaaaacgatt ccaaatcttg aactgttgtt   6060
gtaaaagcat agcagaaagt gggagacaac cgaaatagaa atgactataa cttaatttaa   6120
tgttatcatt ataatttctt ctagcaaata tttagaaagt aaatatcaca tcaacccttta  6180 atgtaattaa gctttctctt tttgattcat gtgagatgaa aagaaaaaaa agaagagaaa   6240
agtgtagaaa acacatcatt tctaagctga agcctagtgg atctcgatgt gtagtctacg   6300
agaagggtta accgtctctt cgtgagaata accgtggcct aaaaataagc cgatgaggat   6360
aaataaaatg tggtggtaca gtacttcaag aggtttactc atcaagagga tgcttttccg   6420
atgagctcta gtagtacatc ggacctcaca tacctccatt gtggtgaaat attttgtgct   6480
catttagtga tgggtaaatt ttgttttatgt cactctaggt tttgacattt cagttttgcc   6540
actcttaggt tttgacaaat aatttccatt ccgcggcaaa agcaaaacaa ttttatttta   6600
cttttaccac tcttagcttt cacaatgtat cacaaatgcc actctagaaa ttctgtttat   6660
gccacagaat gtgaaaaaaa acactcactt atttgaagcc aaggtgttca tggcatggaa   6720
atgtgacata aagtaacgtt cgtgtataag aaaaaattgt actcctcgta acaagagacg   6780
gaaacatcat gagacaatcg cgtttggaag gctttgcatc acctttggat gatgcgcatg   6840
aatggagtcg tctgcttgct agccttcgcc taccgcccac tgagtccggg cggcaactac   6900
catcggcgaa cgacccagct gacctctacc gaccggactt gaatgcgcta ccttcgtcag   6960
cgacgatggc cgcgtacgct ggcgacgtgc ccccgcatgc atggcggcac atggcgagct   7020
cagaccgtgc gtggctggct acaaatacgt accccgtgag tgccctagct agaaacttac   7080
acctgcaact gcgagagcga gcgtgtgagt gtagccgata gatccgccca tggcctcctc   7140
cgagaacgtc atcaccgagt tcatgcgctt caaggtgcgc atggagggca ccgtgaacgg   7200
ccacgagttc gagatcgagg gcgagggcga gggccgcccc tacgagggcc acaacaccgt   7260
gaagctgaag gtgaccaagg gcggccccct gcccttcgcc tgggacatcc tgtcccccca   7320
gttccagtac ggctccaagg tgtacgtgaa gcaccccgcc gacatccccg actacaagaa   7380
gctgtccttc cccgagggct tcaagtggga gcgcgtgatg aacttcgagg acggcggcgt   7440
ggcgaccgtg acccaggact cctccctgca ggacggctgc ttcatctaca aggtgaagtt   7500
catcggcgtg aacttcccct ccgacggccc cgtgatgcag aagaagacca tgggctggga   7560
ggcctccacc gagcgcctgt accccgcga cggcgtgctg aagggcgaga cccacaaggc   7620
cctgaagctg aaggacggcg gccactacct ggtggagttc aagtccatct acatggccaa   7680
gaagcccgtg cagctgcccg gctactacta cgtggacgcc aagctggaca tcacctccca   7740
caacgaggac tacaccatcg tggagcagta cgagcgcacc gagggccgcc accacctgtt   7800
cctgtaggga tctcgatagg gatctgttaa cgatcccgg cggtgtcccc cactgaagaa   7860
actatgtgct gtagtatagc cgctgccgc tggctagcta gctagttgag tcatttagcg   7920
gcgatgattg agtaataatg tgtcacgcat caccatgcat gggtggcagt gtcagtgtga   7980
gcaatgacct gaatgaacaa ttgaaatgaa aagaaaaaag tattgttcca aattaaacgt   8040
```

| | | | | |
|---|---|---|---|---|
| tttaacctttt | taataggtttt | atacaataat | tgatatatgt | tttctgtata tgtctaatttt | 8100 |
| gttatcatcc | atttagatat | agacaaaaaa | aatctaagaa | ctaaaacaaa tgctaatttg | 8160 |
| aaatgaaggg | agtatatatt | gggataatgt | cgatgagatc | cctcgtaata tcaccgacat | 8220 |
| cacacgtgtc | cagttaatgt | atcagtgata | cgtgtattca | catttgttgc gcgtaggcgt | 8280 |
| acccaacaat | tttgatcgac | tatcagaaag | tcaacggaag | cgagtcgacc tcgaggggg | 8340 |
| gccccggccg | aagcttggtc | acccggtccg | ggcctagaag | gccgatctcc cgggcaccca | 8400 |
| gctttcttgt | acaaagtggc | cgttaacgga | tcccggtgaa | gttcctattc cgaagttcct | 8460 |
| attctccaga | aagtatagga | acttc | | | 8485 |

<210> SEQ ID NO 45
<211> LENGTH: 3602
<212> TYPE: DNA
<213> ORGANISM: artificial sequence
<220> FEATURE:
<223> OTHER INFORMATION: UBI PRO-FLPm-pinII

<400> SEQUENCE: 45

| | | | | | |
|---|---|---|---|---|---|
| ctgcagtgca | gcgtgacccg | gtcgtgcccc | tctctagaga | taatgagcat tgcatgtcta | 60 |
| agttataaaa | aattaccaca | tatttttttt | gtcacacttg | tttgaagtgc agtttatcta | 120 |
| tctttataca | tatatttaaa | ctttactcta | cgaataatat | aatctatagt actacaataa | 180 |
| tatcagtgtt | ttagagaatc | atataaatga | acagttagac | atggtctaaa ggacaattga | 240 |
| gtattttgac | aacaggactc | tacagtttta | tcttttagt | gtgcatgtgt tctccttttt | 300 |
| ttttgcaaat | agcttcacct | atataatact | tcatccattt | tattagtaca tccatttagg | 360 |
| gtttagggtt | aatggttttt | atagactaat | tttttagta | catctatttt attctatttt | 420 |
| agcctctaaa | ttaagaaaac | taaaactcta | ttttagtttt | tttatttaat aatttagata | 480 |
| taaaatagaa | taaaataaag | tgactaaaaa | ttaaacaaat | acccctttaag aaattaaaaa | 540 |
| aactaaggaa | acatttttct | tgtttcgagt | agataatgcc | agcctgttaa acgccgtcga | 600 |
| cgagtctaac | ggacaccaac | cagcgaacca | gcagcgtcgc | gtcgggccaa gcgaagcaga | 660 |
| cggcacggca | tctctgtcgc | tgcctctgga | cccctctcga | gagttccgct ccaccgttgg | 720 |
| acttgctccg | ctgtcggcat | ccagaaattg | cgtggcggag | cggcagacgt gagccggcac | 780 |
| ggcaggcggc | ctcctcctcc | tctcacggca | cggcagctac | gggggattcc tttcccaccg | 840 |
| ctccttcgct | ttcccttcct | cgcccgccgt | aataaataga | caccccctcc acaccctctt | 900 |
| tccccaacct | cgtgttgttc | ggagcgcaca | cacacacaac | cagatctccc ccaaatccac | 960 |
| ccgtcggcac | ctccgcttca | aggtacgccg | ctcgtcctcc | ccccccccc ctctctacct | 1020 |
| tctctagatc | ggcgttccgg | tccatggtta | gggcccggta | gttctacttc tgttcatgtt | 1080 |
| tgtgttagat | ccgtgtttgt | gttagatccg | tgctgctagc | gttcgtacac ggatgcgacc | 1140 |
| tgtacgtcag | acacgttctg | attgctaact | tgccagtgtt | tctctttggg gaatcctggg | 1200 |
| atggctctag | ccgttccgca | gacgggatcg | atttcatgat | ttttttttgtt tcgttgcata | 1260 |
| gggtttggtt | tgcccttttc | ctttatttca | atatatgccg | tgcacttgtt tgtcgggtca | 1320 |
| tcttttcatg | cttttttttg | tcttggttgt | gatgatgtgg | tctggttggg cggtcgttct | 1380 |
| agatcggagt | agaattctgt | ttcaaactac | ctggtggatt | tattaatttt ggatctgtat | 1440 |
| gtgtgtgcca | tacatattca | tagttacgaa | ttgaagatga | tggatggaaa tatcgatcta | 1500 |
| ggataggtat | acatgttgat | gcgggttttta | ctgatgcata | tacagagatg ctttttgttc | 1560 |

| | | |
|---|---|---|
| gcttggttgt gatgatgtgg tgtggttggg cggtcgttca ttcgttctag atcggagtag | 1620 |
| aatactgttt caaactacct ggtgtattta ttaattttgg aactgtatgt gtgtgtcata | 1680 |
| catcttcata gttacgagtt taagatggat ggaaatatcg atctaggata ggtatacatg | 1740 |
| ttgatgtggg ttttactgat gcatatacat gatggcatat gcagcatcta ttcatatgct | 1800 |
| ctaaccttga gtacctatct attataataa acaagtatgt tttataatta ttttgatctt | 1860 |
| gatatacttg gatgatggca tatgcagcag ctatatgtgg atttttttag ccctgccttc | 1920 |
| atacgctatt tatttgcttg gtactgtttc ttttgtcgat gctcaccctg ttgtttggtg | 1980 |
| ttacttctgc aggtcgactc tagaggatcc aacaatgccc cagttcgaca tcctctgcaa | 2040 |
| gaccccccc aagtgctcg tgaggcagtt cgtggagagg ttcgagaggc cctccggcga | 2100 |
| gaagatcgcc ctctgcgccg ccgagctcac ctacctctgc tggatgatca cccacaacgg | 2160 |
| caccgccatt aagagggcca ccttcatgtc atacaacacc atcatctcca actccctctc | 2220 |
| cttcgacatc gtgaacaagt ccctccagtt caaatacaag acccagaagg ccaccatcct | 2280 |
| cgaggcctcc ctcaagaagc tcatccccgc ctgggagttc accatcatcc cctactacgg | 2340 |
| ccagaagcac cagtccgaca tcaccgacat cgtgtcatcc ctccagcttc agttcgagtc | 2400 |
| ctccgaggag gctgacaagg gcaactccca ctccaagaag atgctgaagg ccctcctctc | 2460 |
| cgagggcgag tccatctggg agatcaccga agatcctc aactccttcg agtacacctc | 2520 |
| caggttcact aagaccaaga ccctctacca gttcctcttc ctcgccacct tcatcaactg | 2580 |
| cggcaggttc tcagacatca agaacgtgga ccccaagtcc ttcaagctcg tgcagaacaa | 2640 |
| gtacctcggc gtgatcatcc agtgcctcgt gaccgagacc aagacctccg tgtccaggca | 2700 |
| catctacttc ttctccgctc gcggcaggat cgaccccctc gtgtacctcg acgagttcct | 2760 |
| caggaactca gagcccgtgc tcaagagggt gaacaggacc ggcaactcct cctccaacaa | 2820 |
| gcaggagtac cagctcctca aggacaacct cgtgaggtcc tacaacaagg ccctcaagaa | 2880 |
| gaacgccccc tactccatct tcgccatcaa gaacggcccc aagtcccaca tcggtaggca | 2940 |
| cctcatgacc tccttcctct caatgaaggg cctcaccgag ctcaccaacg tggtgggcaa | 3000 |
| ctggtccgac aagagggcct ccgccgtggc caggaccacc tacacccacc agatcaccgc | 3060 |
| catccccgac cactacttcg ccctcgtgtc aaggtactac gcctacgacc ccatctccaa | 3120 |
| ggagatgatc gccctcaagg acgagactaa ccccatcgag gagtggcagc acatcgagca | 3180 |
| gctcaagggc tccgccgagg gctccatcag gtaccccgcc tggaacggca tcatctccca | 3240 |
| ggaggtgctc gactacctct cctcctacat caacaggagg atctgagtta acctagactt | 3300 |
| gtccatcttc tggattggcc aacttaatta atgtatgaaa taaaggatg cacacatagt | 3360 |
| gacatgctaa tcactataat gtgggcatca aagttgtgtg ttatgtgtaa ttactagtta | 3420 |
| tctgaataaa agagaaagag atcatccata tttcttatcc taaatgaatg tcacgtgtct | 3480 |
| ttataattct tgatgaacc agatgcattt cattaaccaa atccatatac atataaatat | 3540 |
| taatcatata taattaatat caattgggtt agcaaaacaa atctagtcta ggtgtgtttt | 3600 |
| gc | 3602 |

<210> SEQ ID NO 46
<211> LENGTH: 9305
<212> TYPE: DNA
<213> ORGANISM: artificial sequence
<220> FEATURE:
<223> OTHER INFORMATION: FRT1-FRT87 fragment from PHP68884

<400> SEQUENCE: 46

-continued

```
gaagttccta ttccgaagtt cctattctct agaaagtata ggaacttcag atccaccggc    60
tagaggatcc accatggttg aacaagatgg attgcacgca ggttctccgg ccgcttgggt   120
ggagaggcta ttcggctatg actgggcaca acagacaatc ggctgctctg atgccgccgt   180
gttccggctg tcagcgcagg ggcgcccggt tcttttttgtc aagaccgacc tgtccggtgc   240
cctgaatgaa ctgcaggacg aggcagcgcg gctatcgtgg ctggccacga cgggcgttcc   300
ttgcgcagct gtgctcgacg ttgtcactga agcgggaagg gactggctgc tattgggcga   360
agtgccgggg caggatctcc tgtcatctca ccttgctcct gccgagaaag tatccatcat   420
ggctgatgca atgcggcggc tgcatacgct tgatccggct acctgcccat tcgaccacca   480
agcgaaacat cgcatcgagc gagcacgtac tcggatggaa gccggtcttg tcgatcagga   540
tgatctggac gaagagcatc aggggctcgc gccagccgaa ctgttcgcca ggctcaaggc   600
gcgcatgccc gacggcgatg atctcgtcgt gacccatggc gatgcctgct tgccgaatat   660
catggtggaa aatggccgct tttctggatt catcgactgt ggccggctgg gtgtggcgga   720
ccgctatcag gacatagcgt tggctacccg tgatattgct gaagagcttg gcggcgaatg   780
ggctgaccgc ttcctcgtgc tttacggtat cgccgctccc gattcgcagc gcatcgcctt   840
ctatcgcctt cttgacgagt tcttctgagg atccaccatg gttaacctag acttgtccat   900
cttctggatt ggccaactta attaatgtat gaaataaaag gatgcacaca tagtgacatg   960
ctaatcacta taatgtgggc atcaaagttg tgtgttatgt gtaattacta gttatctgaa  1020
taaaagagaa agagatcatc catatttctt atcctaaatg aatgtcacgt gtctttataa  1080
ttctttgatg aaccagatgc atttcattaa ccaaatccat atacatataa atattaatca  1140
tatataatta atatcaattg ggttagcaaa acaaatctag tctaggtgtg ttttgcgaat  1200
gcggccgggt accgagctcg aattcggccc aagtttgtac aaaaaagcag gctccggcca  1260
gaatggcccg gaccgaagct ggccgctcta gaactaggca tggagtcaaa gattcaaata  1320
gaggacctaa cagaactcgc cgtaaagact ggcgaacagt tcatacagag tctcttacga  1380
ctcaatgaca agaagaaaat cttcgtcaac atggtggagc acgacacgct tgtctactcc  1440
aaaaatatca agatacagt ctcagaagac caaagggcaa ttgagacttt tcaacaaagg  1500
gtaatatccg gaaacctcct cggattccat tgcccagcta tctgtcactt tattgtgaag  1560
atagtggaaa aggaaggtgg ctcctacaaa tgccatcatt gcgataaagg aaaggccatc  1620
gttgaagatg cctctgccga cagtggtccc aaagatggac ccccacccac gaggagcatc  1680
gtggaaaaag aagacgttcc aaccacgtct tcaaagcaag tggattgatg tgatatctcc  1740
actgacgtaa gggatgacgc acaatcccac taagctgacc tagtggatct cgatgtgtag  1800
tctacgagaa gggttaaccg tctcttcgtg agaataaccg tggcctaaaa ataagccgat  1860
gaggataaat aaaatgtggt ggtacagtac ttcaagaggt ttactcatca agaggatgct  1920
tttccgatga gctctagtag tacatcggac ctcacatacc tccattgtgg tgaaatattt  1980
tgtgctcatt tagtgatggg taaattttgt ttatgtcact ctaggttttg acatttcagt  2040
tttgccactc ttaggttttg acaaataatt tccattccgc ggcaaaagca aaacaatttt  2100
attttacttt taccactctt agctttcaca atgtatcaca aatgccactc tagaaattct  2160
gtttatgcca cagaatgtga aaaaaaacac tcacttattt gaagccaagg tgttcatggc  2220
atggaaatgt gacataaagt aacgttcgtg tataagaaaa aattgtactc ctcgtaacaa  2280
gagacggaaa catcatgaga caatcgcgtt tggaaggctt tgcatcacct ttggatgatg  2340
```

```
cgcatgaatg gagtcgtctg cttgctagcc ttcgcctacc gcccactgag tccgggcggc    2400
aactaccatc ggcgaacgac ccagctgacc tctaccgacc ggacttgaat gcgctacctt    2460
cgtcagcgac gatggccgcg tacgctggcg acgtgccccc gcatgcatgg cggcacatgg    2520
cgagctcaga ccgtgcgtgg ctggctacaa atacgtaccc cgtgagtgcc ctagctagaa    2580
acttacacct gcaactgcga gagcgagcgt gtgagtgtag ccgatagatc cgcccatgag    2640
cgagctgatt aaagagaaca tgcacatgaa gctgtacatg gaggggaccg tcgacaacca    2700
ccacttcaag tgcacctccg agggcgaggg taagccgtat gagggcacgc agacaatgag    2760
gattaaagtg gttgagggcg ggccgctgcc tttcgcattc gacatcctcg ccaccagctt    2820
cctgtacggg tccaagacct tcatcaacca cacccagggc atccccgact tcttcaaaca    2880
gtccttcccg agggtttca cgtgggagag ggtgacaacc tacgaagatg gcggcgtgct    2940
gaccgccacg caggatacat ctctccagga cgggtgcctg atctacaacg tcaagatcag    3000
gggcgtcaac ttcacgagca acggcccggt catgcagaag aagacgctcg gctgggaagc    3060
cttcacggag acactctacc ccgccgacgg cgggctggaa ggtaggaacg acatggccct    3120
caagctcgtg ggcggcagcc acctcatcgc caacatcaaa accacctaca ggagcaagaa    3180
gcccgccaag aacctgaaga tgcccggcgt gtactacgtc gactacaggc tcgagagaat    3240
taaggaggcc aacaacgaga cgtacgtgga gcagcacgag gttgcagttg ccaggtactg    3300
cgacctgcca agcaagctcg gccacaagct gaactaggga tctcgatagg gatctgttaa    3360
cgatccccgg cggtgtcccc cactgaagaa actatgtgct gtagtatagc cgctgcccgc    3420
tggctagcta gctagttgag tcatttagcg gcgatgattg agtaataatg tgtcacgcat    3480
caccatgcat gggtggcagt gtcagtgtga gcaatgacct gaatgaacaa ttgaaatgaa    3540 agaaaaaag tattgttcca aattaaacgt tttaaccttt taataggttt atacaataat    3600
tgatatatgt tttctgtata tgtctaattt gttatcatcc atttagatat agacaaaaaa    3660
aatctaagaa ctaaacaaa tgctaatttg aaatgaaggg agtatatatt gggataatgt    3720
cgatgagatc cctcgtaata tcaccgacat cacacgtgtc cagttaatgt atcagtgata    3780
cgtgtattca catttgttgc gcgtaggcgt acccaacaat tttgatcgac tatcagaaag    3840
tcaacggaag cgagtcgacc tcgaggcatg gagtcaaaga ttcaaataga ggacctaaca    3900
gaactcgccg taaagactgg cgaacagttc atacagagtc tcttacgact caatgacaag    3960
aagaaaatct tcgtcaacat ggtggagcac gacacgcttg tctactccaa aaatatcaaa    4020
gatacagtct cagaagacca aagggcaatt gagactttc aacaaagggt aatatccgga    4080
aacctcctcg gattccattg cccagctatc tgtcacttta ttgtgaagat agtggaaaag    4140
gaaggtggct cctacaaatg ccatcattgc gataaaggaa aggccatcgt tgaagatgcc    4200
tctgccgaca gtggtcccaa agatggaccc ccacccacga ggagcatcgt ggaaaaagaa    4260
gacgttccaa ccacgtcttc aaagcaagtg gattgatgtg atatctccac tgacgtaagg    4320
gatgacgcac aatcccacta agctgaccgg gcccggccga agcttgcatg cctgcaggtc    4380
gactctagag gatctgcacc ggacactgtc tggtggcata ccagacagtc cggtgtgcca    4440
gatcagggca ccccttcggtt cctttgctcc tttgcttttg aaccctaact ttgatcgttt    4500
attggtttgt gttgaacctt tatgcacctg tggaatatat aatctagaac aaactagtta    4560
gtccaatcat ttgtgttggg cattcaacca ccaaaattat ttataggaaa aggttaaacc    4620
ttatttccct ttcaatctcc cccttttttgg tgattgatgc caacacaaac caaagaaaat    4680
atataagtgc agaattgaac tagtttgcat aaggtaagtg cataggttac ttagaattaa    4740
```

```
atcaatttat actttractt gatatgcatg gttgctttct tttattttaa cattttggac    4800
cacatttgca ccacttgttt tgttttttgc aaatctttt  ggaaattctt tttcaaagtc    4860
ttttgcaaat agtcaaaggt atatgaataa gattgtaaga agcattttca agatttgaaa    4920
tttctccccc tgtttcaaat gcttttcctt tgactaaaca aaactccccc tgaataaaat    4980
tctcctctta gctttcaaga gggttttaaa tagatatcaa ttggaaatat atttagatgc    5040
taattttgaa aatataccaa ttgaaaatca acataccaat ttgaaattaa acataccaat    5100
ttaaaaaatt tcaaaaagtg gtggtgcggt ccttttgctt tgggcttaat atttctcccc    5160
ctttggcatt aatcgccaaa aacggagact ttgtgagcca tttatacttt ctccccattg    5220
gtaaatgaaa tatgagtgaa agattatacc aaatttggac agtgatgcgg agtgacggcg    5280
aaggataaac gataccgtta gagtggagtg aagccttgt  cttcgccgaa gactccattt    5340
cccttcaat  ctacgactta gcatagaaat acacttgaaa acacattagt cgtagccacg    5400
aaagagatat gatcaaaggt atacaaatga gctatgtgtg taatgtttca atcaaagttt    5460
cgagaatcaa gaatatttag ctcattccta agtttgctaa aggttttatc atctaatggt    5520
ttggtaaaga tatcgactaa ttgttctttg gtgctaacat aagcaatctc gatatcaccc    5580
ctttgttggt gatccctcaa aaagtgatac cgaatgtcta tgtgcttagt gcggctgtgt    5640
tcaacgggat tatccgccat gcagatagca ctctcattgt cacataggag agggactttg    5700
ctcaatttgt agccatagtc cctaaggttt tgcctcatcc aaagtaattg cacacaacaa    5760
tgtcctgcgg caatatactt ggcttcggcg gtagaaagag ctattgagtt ttgtttcttt    5820
gaagtccaag acaccaggga tctccctaga aactgacaag tccctgatgt gctcttccta    5880
tcaatttac  accctgccca atcggcatct gaatatccta ttaaatcaaa ggtggatccc    5940
ttggggtacc aaagaccaaa tttaggagtg taaactaaat atctcatgat tcttttcacg    6000
gccctaaggt gaacttcctt aggatcggct tggaatcttg cacacatgca tatagaaagc    6060
atactatctg gtcgagatgc acataaatag agtaaagatc ctatcatcga ccggtatacc    6120
ttttggtcta cggatttacc tcccgtgtcg aggtcgagat gcccattagt tcccatgggt    6180
gtcctgatgg gcttggcatc cttcattcca aacttgttga gtatgtcttg aatgtacttt    6240
gtttggctga tgaaggtgcc atcttggagt tgcttgactt gaaatcctag aaaatatttc    6300
aacttccca  tcatagacat ctcgaatttc ggaatcatga tcctactaaa ctcttcacaa    6360
gtagatttgt tagtagaccc aaatataata tcatcaacat aaatttggca tacaaacaaa    6420
acttttgaaa tggttttagt aaagagagta ggatcggctt tactgactct gaagccatta    6480
gtgataagaa aatctcttag gcattcatac catgctgttg gggcttgctt gagcccataa    6540
agcgcctttg agagtttata aacatggtta gggtactcac tatcttcaaa gccgagaggt    6600
tgctcaacat agacctattc accccatttg atcactttt  tggtccttca ggatctaata    6660
gttatgtata atttagagtc tcttgtttaa tggccagata tttctaatta atctaagaat    6720
ttatgatatt ttttaatttt ttatcatgtc tgatgagaat taacataaag gctcaattgg    6780
gtcctgaatt aataatagag tgaaaattaa tccagaggct ctattagaac cttcaattag    6840
taataccaag atatatataa gatagtagag tatagtttaa atgttggcat tgttcattct    6900
ttcttttgtt atttaattta tgctttccac ggtggttagt ggttacttct gaagggtcca    6960
aataatgcat gaagagtttg aggacaagaa gtctgcccta aaaatagcga tgcaaaggca    7020
tggtgtccaa gccatacata tagcgcacta attttatcag cagaacaatg gtatttatag    7080
```

```
gtcctagtgc ccaggcaaca agagacacga ataaagcatc gatcacgaca ccatggcggc    7140
gacaatggca gtgacgacga tggtgacgag gagcaaggag agctggtcgt cattgcaggt    7200
cccggcggtg gcattccctt ggaagccacg aggtggcaag accggcggcc tcgagttccc    7260
tcgccgggcg atgttcgcca gcgtcggcct caacgtgtgc ccgggcgtcc ggcggggcg     7320 cgacccgcgg gagcccgatc ccaaggtcgt ccggcggcc tgcggcctgg tccaggcaca     7380
agtcctcttc caggggttta actgggagtc gtgcaagcag cagggaggct ggtacaacag    7440
gctcaaggcc caggtcgacg acatcgccaa ggccggcgtc acgcacgtct ggctgcctcc    7500
accctcgcac tccgtctcgc acaaggcta catgccaggc cgcctatacg acctggacgc     7560
gtccaagtac ggcacggcgg cggagctcaa gtccctgata gcggcgttcc acggcagggg    7620
cgtgcagtgc gtggcggaca tcgtcatcaa ccaccggtgc gcggaaaaga aggacgcgcg    7680
cggcgtgtac tgcatcttcg agggcgggac tcccgacgac cgcctggact ggggccccgg    7740
gatgatctgc agcgacgaca cgcagtactc ggacgggacg gggcaccgcg acacgggcga    7800
ggggttcgcg gcggcgcccg acatcgacca cctcaacccg cgcgtgcagc gggagctctc    7860
cgcctggctc aactggctca ggtccgacgc cgtgggggttc gacggctggc gcctcgactt    7920
cgccaagggc tactcgccgg ccgtcgccag aatgtacgtg gagagcacgg ggccgccgag    7980
cttcgtcgtc gcggagatat ggaactcgct gagctacagc ggggacggca agccggcgcc    8040
caaccaggac cagtgccggc aggagctgct ggactgacg cgggccgtcg gcgggcccgc     8100
catggcgttc gacttcccca ccaagggcct gctgcaggcg ggcgtgcagg gggagctgtg    8160
gcggctgcgc gacagctccg gcaacgcggc cggcctgatc gggtgggcgc ccgagaaggc    8220
cgtcaccttc gtcgacaacc atgacaccgg gtcgacgcag aagctctggc cgttcccatc    8280
cgacaaggtc atgcagggct acgcctacat cctcacccat ccaggagtcc cctgcatttt    8340
ctacgaccac atgttcgact ggaacctgaa gcaggagata tccacgctgt ctgccatcag    8400
ggcgcggaac ggcatccgcg ccgggagcaa gctgcggatc ctcgtggcgg acgcggacgc    8460
gtacgtggcc gtcgtcgacg agaaggtcat ggtgaagatc gggacaaggt acggcgtgag    8520
cagcgtggtc ccgtcggatt tccacccggc ggcgcacggc aaggactact gcgtctggga    8580
gaaagcgagc ctccgcgtcc cggcggggcg ccacctctag cagctcagat tgctcagtct    8640
tgtgctgcat tgcaaacaca gcagcacgac actgcataac gtcttttcct tgagatctga    8700
caaagcagca ttagtccgtt gatcggtgga agaccactcg tcagtgttga gttgaatgtt    8760
tgatcaataa aatacggcaa tgctgtaagg gttgttttttt atgccattga taatacactg    8820
tactgttcag ttgttgaact ctatttctta gccatgccaa gtgcttttct tattttgaat    8880
aacattacag caaaaagttg aaagacaaaa aaaaaaccc ccgaacagag tgctttgggt     8940
cccaagctac tttagactgt gttcggcgtt cccctaaat ttctccccct atatctcact     9000
cacttgtcac atcagcgttc tctttccct atatctccac gtcgacgcgg ccgctctaga     9060
actagtggat cccccgggct gcaggaattc ctcgagaccg tacgtgcgcg cgaatgcatc    9120
cagatcttcc ctctagtcaa ggccttaagc gcgcgttcga acgcgcggtt aagcttggtc    9180
acccggtccg ggcctagaag gccgatctcc cgggcaccca gctttcttgt acaaagtggc    9240
cgttaacgga tcccggtgaa gttcctattc cgaagttcct attctccaga aagtatagga    9300
acttc                                                               9305
```

<210> SEQ ID NO 47
<211> LENGTH: 8962

<212> TYPE: DNA
<213> ORGANISM: artificial sequence
<220> FEATURE:
<223> OTHER INFORMATION: T-DNA from PHP66566

<400> SEQUENCE: 47

```
gtttacccgc caatatatcc tgtcaaacac tgatagttta aactgaaggc gggaaacgac      60
aatctgatca tgagcggaga attaagggag tcacgttatg accccgccg atgacgcggg     120
acaagccgtt ttacgtttgg aactgacaga accgcaacgt tgaaggagcc actcagcaag    180
ctggtacgat tgtaatacga ctcactatag ggcgaattga gcgctgttta aacgctcttc    240
aactggaaga gcggttacgc tgtttaaacg ctcttcaact ggaagagcgg ttactaccgg    300
ttcactagct agctgctaag gttaccagag ctggtcacct tgtccacca acttattaag     360
tatctagttg aagacacgtt cttcttcacg taagaagaca ctcagtagtc ttcggccaga    420
atggcctctt gattcagcgg gcctagaagg ccggatcact gactagctaa tttaaatcct    480
gataaggacc cggcggaccg aagctggccg ctctagaact aggctgcagt gcagcgtgac    540
ccggtcgtgc ccctctctag agataatgag cattgcatgt ctaagttata aaaaattacc    600
acatattttt tttgtcacac ttgtttgaag tgcagtttat ctatctttat acatatattt    660
aaactttact ctacgaataa tataatctat agtactacaa taatatcagt gttttagaga    720
atcatataaa tgaacagtta gacatggtct aaaggacaat tgagtatttt gacaacagga    780
ctctacagtt ttatctttt agtgtgcatg tgttctcctt tttttttgca aatagcttca     840
cctatataat acttcatcca ttttattagt acatccattt agggtttagg gttaatggtt    900
tttatagact aatttttta gtacatctat tttattctat tttagcctct aaattaagaa     960
aactaaaact ctattttagt tttttattt aataatttag atataaaata gaataaaata    1020
aagtgactaa aaattaaaca aatacccttt aagaaattaa aaaaactaag gaaacatttt    1080
tcttgtttcg agtagataat gccagcctgt taaacgccgt cgacgagtct aacggacacc    1140
aaccagcgaa ccagcagcgt cgcgtcgggc caagcgaagc agacggcacg gcatctctgt    1200
cgctgcctct ggaccctct cgagagttcc gctccaccgt tggacttgct ccgctgtcgg    1260
catccagaaa ttgcgtggcg gagcggcaga cgtgagccgg cacggcaggc ggcctcctcc    1320
tcctctcacg gcaccggcag ctacggggga ttccttccc accgctcctt cgctttccct    1380
tcctcgcccg ccgtaataaa tagacacccc ctccacaccc tctttcccca acctcgtgtt    1440
gttcggagcg cacacacaca caaccagatc tcccccaaat ccaccgtcg gcacctccgc    1500
ttcaaggtac gccgctcgtc ctccccccc ccctctcta ccttctctag atcggcgttc      1560
cggtccatgc atggttaggg cccggtagtt ctacttctgt tcatgtttgt gttagatccg    1620
tgtttgtgtt agatccgtgc tgctagcgtt cgtacacgga tgcgacctgt acgtcagaca    1680
cgttctgatt gctaacttgc cagtgttct cttgggaa tcctgggatg gctctagccg       1740
ttccgcagac gggatcgatt tcatgatttt ttttgtttcg ttgcataggg tttggtttgc    1800
cctttccctt tatttcaata tatgccgtgc acttgtttgt cgggtcatct tttcatgctt    1860
ttttttgtct tggttgtgat gatgtggtct ggttgggcgg tcgttctaga tcggagtaga    1920
attctgtttc aaactacctg gtggatttat taatttgga tctgtatgtg tgtgccatac     1980
atattcatag ttacgaattg aagatgatgg atggaaatat cgatctagga taggtataca    2040
tgttgatgcg ggttttactg atgcatatac agagatgctt tttgttcgct tggttgtgat    2100
gatgtggtgt ggttgggcgg tcgttcattc gttctagatc ggagtagaat actgtttcaa    2160
```

```
actacctggt gtatttatta attttggaac tgtatgtgtg tgtcatacat cttcatagtt    2220
acgagtttaa gatggatgga aatatcgatc taggataggt atacatgttg atgtgggttt    2280
tactgatgca tatacatgat ggcatatgca gcatctattc atatgctcta accttgagta    2340
cctatctatt ataataaaca agtatgtttt ataattattt tgatcttgat atacttggat    2400
gatggcatat gcagcagcta tatgtggatt tttttagccc tgccttcata cgctatttat    2460
ttgcttggta ctgtttcttt tgtcgatgct caccctgttg tttggtgtta cttctgcagg    2520
tcgactctag aggatccagc gagagcccag gatgaaaaaa gcagtcatta acggggaaca    2580
aatcagaagt atcagcgacc tccaccagac attgaaaaag gagcttgccc ttccggaata    2640
ctacggtgaa aacctggacg ctttatggga ttgtctgacc ggatgggtgg agtacccgct    2700
cgttttggaa tggaggcagt ttgaacaaag caagcagctg actgaaaatg cgccgagag    2760 tgtgcttcag gttttccgtg aagcgaaagc ggaaggctgc gacatcacca tcatactttc    2820
ttaactgcag ctagacttgt ccatcttctg gattggccaa cttaattaat gtatgaaata    2880
aaaggatgca cacatagtga catgctaatc actataatgt gggcatcaaa gttgtgtgtt    2940
atgtgtaatt actagttatc tgaataaaag agaaagagat catccatatt tcttatccta    3000
aatgaatgtc acgtgtcttt ataattcttt gatgaaccag atgcatttca ttaaccaaat    3060
ccatatacat ataaatatta atcatatata attaatatca attgggttag caaaacaaat    3120
ccctagtgga tctcgatgtg tagtctacga aagggttaa ccgtctcttc gtgagaataa    3180
ccgtggccta aaaataagcc gatgaggata aataaaatgt ggtggtacag tacttcaaga    3240
ggtttactca tcaagaggat gcttttccga tgagctctag tagtacatcg acctcacat    3300 acctccattg tggtgaaata ttttgtgctc atttagtgat gggtaaattt tgtttatgtc    3360
actctaggtt ttgacatttc agttttgcca ctcttaggtt ttgacaaata atttccattc    3420
cgcggcaaaa gcaaaacaat tttattttac ttttaccact cttagctttc acaatgtatc    3480
acaaatgcca ctctagaaat tctgtttatg ccacagaatg tgaaaaaaaa cactcactta    3540
tttgaagcca aggtgttcat ggcatggaaa tgtgacataa agtaacgttc gtgtataaga    3600
aaaaattgta ctcctcgtaa caagagacgg aaacatcatg agacaatcgc gtttggaagg    3660 cttttgcatca cctttggatg atgcgcatga atggagtcgt ctgcttgcta gccttcgcct    3720
accgcccact gagtccgggc ggcaactacc atcggcgaac gacccagctg acctctaccg    3780
accggacttg aatgcgctac cttcgtcagc gacgatggcc gcgtacgctg gcgacgtgcc    3840
cccgcatgca tggcggcaca tggcgagctc agaccgtgcg tggctggcta caaatacgta    3900
ccccgtgagt gccctagcta gaaacttaca cctgcaactg cgagagcgag cgtgtgagtg    3960
tagccgatag atccgcccat ggcctcctcc gagaacgtca tcaccgagtt catgcgcttc    4020
aaggtgcgca tggagggcac cgtgaacggc cacgagttcg agatcgaggg cgagggcgag    4080
ggcgccccct acgagggcca acaccgtg aagctgaagg tgaccaaggg cggccccctg    4140
cccttcgcct gggacatcct gtccccccag ttccagtacg gctccaaggt gtacgtgaag    4200
caccccgccg acatccccga ctacaagaag ctgtccttcc ccgagggctt caagtgggag    4260
cgcgtgatga cttcgagga cggcggcgtg gcgaccgtga cccaggactc ctccctgcag    4320
gacggctgct tcatctacaa ggtgaagttc atcggcgtga acttcccctc cgacggcccc    4380
gtgatgcaga agaagaccat gggctgggag gcctccaccg agcgcctgta ccccgcgac    4440 ggcgtgctga gggcgagac ccacaaggcc ctgaagctga aggacggcgg ccactacctg    4500
gtggagttca gtccatctta catggccaag aagcccgtgc agctgcccgg ctactactac    4560
```

```
gtggacgcca agctggacat cacctcccac aacgaggact acaccatcgt ggagcagtac    4620
gagcgcaccg agggccgcca ccacctgttc ctgtagggat ctcgataggg atctgttaac    4680
gatccccggc ggtgtccccc actgaagaaa ctatgtgctg tagtatagcc gctgcccgct    4740
ggctagctag ctagttgagt catttagcgg cgatgattga gtaataatgt gtcacgcatc    4800
accatgcatg ggtggcagtg tcagtgtgag caatgacctg aatgaacaat tgaaatgaaa    4860
agaaaaaagt attgttccaa attaaacgtt ttaaccttt aataggttta tacaataatt     4920
gatatatgtt ttctgtatat gtctaatttg ttatcatcca tttagatata gacaaaaaaa    4980
atctaagaac taaaacaaat gctaatttga aatgaaggga gtatatattg ggataatgtc    5040
gatgagatcc ctcgtaatat caccgacatc acacgtgtcc agttaatgta tcagtgatac    5100
gtgtattcac atttgttgcg cgtaggcgta cccaacaatt ttgatcgact atcagaaagt    5160
caacggaagc gagtcgacct cgagggggg ccccggccga agcttgcatg cctgcagtgc     5220
agcgtgaccc ggtcgtgccc ctctctagag ataatgagca ttgcatgtct aagttataaa    5280
aaattaccac atattttttt tgtcacactt gtttgaagtg cagtttatct atctttatac    5340
atatatttaa actttactct acgaataata taatctatag tactacaata atatcagtgt    5400
tttagagaat catataaatg aacagttaga catggtctaa aggacaattg agtattttga    5460
caacaggact ctacagtttt atctttttag tgtgcatgtg ttctcctttt tttttgcaaa    5520
tagcttcacc tatataatac ttcatccatt ttattagtac atccatttag ggtttagggt    5580
taatggtttt tatagactaa tttttttagt acatctattt tattctattt tagcctctaa    5640
attaagaaaa ctaaaactct attttagttt ttttatttaa taatttagat ataaaataga    5700
ataaaataaa gtgactaaaa attaaacaaa tacccttaa gaaattaaaa aaactaagga     5760
aacatttttc ttgtttcgag tagataatgc cagcctgtta aacgccgtcg acgagtctaa    5820
cggacaccaa ccagcgaacc agcagcgtcg cgtcgggcca agcgaagcag acggcacggc    5880
atctctgtcg ctgcctctgg accctctcg agagttccgc tccaccgttg gacttgctcc     5940
gctgtcggca tccagaaatt gcgtggcgga gcggcagacg tgagccggca cggcaggcgg    6000
cctcctcctc ctctcacggc accggcagct acggggatt cctttcccac cgctccttcg     6060 cttcccttc ctcgcccgcc gtaataaata gacaccccct ccacaccctc tttcccaac      6120 ctcgtgttgt tcggagcgca cacacacaca accagatctc ccccaaatcc acccgtcggc    6180
acctccgctt caaggtacgc cgctcgtcct ccccccccc cctctctacc ttctctagat     6240
cggcgttccg gtccatgcat ggttagggcc cggtagttct acttctgttc atgtttgtgt    6300
tagatccgtg tttgtgttag atccgtgctg ctagcgttcg tacacggatg cgacctgtac    6360
gtcagacacg ttctgattgc taacttgcca gtgtttctct ttggggaatc ctgggatggc    6420
tctagccgtt ccgcagacgg gatcgatttc atgattttt ttgtttcgtt gcatagggtt     6480
tggtttgccc ttttccttta tttcaatata tgccgtgcac ttgttgtcg ggtcatcttt     6540 tcatgctttt ttttgtcttg gttgtgatga tgtggtctgg ttgggcggtc gttctagatc    6600
ggagtagaat tctgtttcaa actacctggt ggatttatta attttggatc tgtatgtgtg    6660
tgccatacat attcatagtt acgaattgaa gatgatggat ggaaatatcg atctaggata    6720
ggtatacatg ttgatgcggg ttttactgat gcatatacag agatgctttt tgttcgcttg    6780
gttgtgatga tgtggtgtgg ttgggcggtc gttcattcgt tctagatcgg agtagaatac    6840
tgtttcaaac tacctggtgt atttattaat tttggaactg tatgtgtgtg tcatacatct    6900
```

| | | | | | |
|---|---|---|---|---|---|
| tcatagttac | gagtttaaga | tggatggaaa | tatcgatcta | ggataggtat | acatgttgat | 6960 |
| gtgggttttta | ctgatgcata | tacatgatgg | catatgcagc | atctattcat | atgctctaac | 7020 |
| cttgagtacc | tatctattat | aataaacaag | tatgtttttat | aattattttg | atcttgatat | 7080 |
| acttggatga | tggcatatgc | agcagctata | tgtggatttt | tttagccctg | ccttcatacg | 7140 |
| ctatttattt | gcttggtact | gtttcttttg | tcgatgctca | ccctgttgtt | tggtgttact | 7200 |
| tctgcaggtc | gactctagag | gatccatgca | gaagctgatc | aactcggtcc | agaactatgc | 7260 |
| ctggggctcc | aagaccgccc | tgacggaact | ctacggcatg | gagaacccgt | cgtcacaacc | 7320 |
| gatggccgag | ctgtggatgg | tgctcatcc | gaagtcctct | tctcgcgtgc | agaatgcagc | 7380 |
| aggtgacatc | gtgtcgctgc | gggatgtgat | tgagtcagac | aagtccaccc | ttctgggtga | 7440 |
| ggctgtggcc | aagcgcttcg | gcgaactccc | attcctcttc | aaggtgctct | cgccgcaca | 7500 |
| gccgctctca | atccaagtcc | accccaacaa | gcataactcc | gagatcggat | tcgccaagga | 7560 |
| gaatgcggct | ggcatcccga | tggacgccgc | tgagagaaac | tacaaagacc | cgaatcacaa | 7620 |
| gccggagctt | gtcttcgcac | tcacgccatt | tctcgctatg | aacgcatttc | gcgagttcag | 7680 |
| cgagatcgtc | agcctgctcc | agccggtggc | gggtgctcat | ccagcaatcg | cgcatttctt | 7740 |
| gcagcagcct | gatgccgaaa | ggctcagcga | gctgttcgcg | tcccttctta | acatgcaggg | 7800 |
| agaggagaag | tcccgcgcac | ttgcaatact | caagagcgcg | ctggactcac | agcaaggaga | 7860 |
| gccgtggcaa | accatacggc | tcatctccga | gttctatccc | gaggactcag | gactgttctc | 7920 |
| gccgttgctg | ctcaacgtgg | tcaagctgaa | ccccggagag | gcgatgttct | tgttcgccga | 7980 |
| aactccgcat | gcttacctcc | aaggagtcgc | tctggaagtg | atggccaatt | cggacaacgt | 8040 |
| tcttcgggca | ggattgacgc | ccaagtacat | cgacatcccg | gaactcgtgg | ccaatgttaa | 8100 |
| gtttgaagcg | aagcctgcca | accagctgct | tacgcagcct | gttaagcagg | gagccgaact | 8160 |
| ggatttccct | attccggtgg | acgacttcgc | attctccctc | cacgacctct | cagacaagga | 8220 |
| gacgaccatc | tctcagcaaa | gcgctgcgat | tctgttctgc | gtggaaggcg | atgcgaccct | 8280 |
| gtggaagggc | tcacagcagc | ttcagctgaa | gcctggcgag | tccgccttca | tcgccgctaa | 8340 |
| cgagtctccc | gtcaccgtga | aagggcatgg | gaggctcgct | cgggtctaca | acaagctcta | 8400 |
| ggagcttact | gaaaaaatta | acatctcttg | ctaagatcca | tggatattcg | aacgcgtagg | 8460 |
| taccacatgg | ttaacctaga | cttgtccatc | ttctggattg | gccaacttaa | ttaatgtatg | 8520 |
| aaataaaagg | atgcacacat | agtgacatgc | taatcactat | aatgtgggca | tcaaagttgt | 8580 |
| gtgttatgtg | taattactag | ttatctgaat | aaaagagaaa | gagatcatcc | atatttctta | 8640 |
| tcctaaatga | atgtcacgtg | tctttataat | tctttgatga | accagatgca | tttcattaac | 8700 |
| caaatccata | tacatataaa | tattaatcat | atataattaa | tatcaattgg | gttagcaaaa | 8760 |
| caaatctagt | ctaggtgtgt | tttgcgaatg | cggcctgtac | cgagctcgaa | ttcattccga | 8820 |
| ttaatcgtgg | cctcttgctc | ttcaggatga | agagctatgt | ttaaacgtgc | aagcgctact | 8880 |
| agacaattca | gtacattaaa | aacgtccgca | atgtgttatt | aagttgtcta | agcgtcaatt | 8940 |
| tgtttacacc | acaatatatc | ct | | | | 8962 |

<210> SEQ ID NO 48
<211> LENGTH: 9807
<212> TYPE: DNA
<213> ORGANISM: artificial sequence
<220> FEATURE:
<223> OTHER INFORMATION: PHP71464

<400> SEQUENCE: 48

```
agcgtcagac cccgtagaaa agatcaaagg atcttcttga gatccttttt ttctgcgcgt      60
aatctgctgc ttgcaaacaa aaaaccacc gctaccagcg gtggtttgtt tgccggatca     120
agagctacca actcttttc cgaaggtaac tggcttcagc agagcgcaga taccaaatac     180
tgtccttcta gtgtagccgt agttaggcca ccacttcaag aactctgtag caccgcctac     240
atacctcgct ctgctaatcc tgttaccagt ggctgctgcc agtggcgata agtcgtgtct     300
taccgggttg gactcaagac gatagttacc ggataaggcg cagcggtcgg gctgaacggg     360
gggttcgtgc acacagccca gcttggagcg aacgacctac accgaactga gatacctaca     420
gcgtgagcta tgagaaagcg ccacgcttcc cgaagggaga aaggcggaca ggtatccggt     480
aagcggcagg gtcggaacag gagagcgcac gagggagctt ccaggggaa acgcctggta     540 tctttatagt cctgtcgggt ttcgccacct ctgacttgag cgtcgatttt tgtgatgctc     600
gtcagggggg cggagcctat ggaaaaacgc cagcaacgcg gccttttac ggttcctggc     660 cttttgctgg ccttttgctc acatgttctt cctgcgtta tcccctgatt ctgtggataa     720
ccgtattacc gcctttgagt gagctgatac cgagcggata acaatttcac acaggaaaca     780
gctatgacca tgattacgcc aagctatcaa ctttgtatag aaaagttgaa gcttcgctga     840
aatcaccagt ctctctctac aaatctatct ctctctataa taatgtgtga gtagttccca     900
gataagggaa ttagggttct tatagggttt cgctcatgtg ttgagcatat aagaaaccct     960
tagtatgtat ttgtatttgt aaaatacttc tatcaataaa atttctaatt cctaaaacca    1020
aaatccagtg gcgagctgct agcgaagttc ctattccgaa gttcctattc tctagaaagt    1080
ataggaactt cagatccacc ggctagagga tccaccatgg ttgaacaaga tggattgcac    1140
gcaggttctc cggccgcttg ggtggagagg ctattcggct atgactgggc acaacagaca    1200
atcggctgct ctgatgccgc cgtgttccgg ctgtcagcgc agggggccc ggttctttttt   1260 gtcaagaccg acctgtccgg tgccctgaat gaactgcagg acgaggcagc gcggctatcg    1320
tggctggcca cgacgggcgt tccttgcgca gctgtgctcg acgttgtcac tgaagcggga    1380
agggactggc tgctattggg cgaagtgccg gggcaggatc tcctgtcatc tcaccttgct    1440
cctgccgaga aagtatccat catggctgat gcaatgcggc ggctgcatac gcttgatccg    1500
gctacctgcc cattcgacca ccaagcgaaa catcgcatcg agcgagcacg tactcggatg    1560
gaagccggtc ttgtcgatca ggatgatctg gacgaagagc atcaggggct cgcgccagcc    1620
gaactgttcg ccaggctcaa ggcgcgcatg cccgacggcg atgatctcgt cgtgacccat    1680
ggcgatgcct gcttgccgaa tatcatggtg gaaaatggcc gcttttctgg attcatcgac    1740
tgtggccggc tgggtgtggc ggaccgctat caggacatag cgttggctac ccgtgatatt    1800
gctgaagagc ttggcggcga atgggctgac cgcttcctcg tgctttacgg tatcgccgct    1860
cccgattcgc agcgcatcgc cttctatcgc cttcttgacg agttcttctg aggatccacc    1920
atggttaacc tagacttgtc catcttctgg attggccaac ttaattaatg tatgaaataa    1980
aaggatgcac acatagtgac atgctaatca ctataatgtg gcatcaaag ttgtgtgtta     2040 tgtgtaatta ctagttatct gaataaaaga gaaagagatc atccatattt cttatcctaa    2100
atgaatgtca cgtgtcttta taattctttg atgaaccaga tgcatttcat taccaaatc     2160 catatacata taaatattaa tcatatataa ttaatatcaa ttgggttagc aaaacaaatc    2220
tagtctaggt gtgttttgcg aatgcggccg ggtaccgagc tcgaattcgg cccaagtttg    2280
tacaaaaaag caggctccgg ccagaatggc ccggaccgaa gctggccgct ctagaactag    2340
```

```
tggatctcga tgtgtagtct acgagaaggg ttaaccgtct cttcgtgaga ataaccgtgg    2400
cctaaaaata agccgatgag gataaataaa atgtggtggt acagtacttc aagaggttta    2460
ctcatcaaga ggatgctttt ccgatgagct ctagtagtac atcggacctc acatacctcc    2520
attgtggtga aatattttgt gctcatttag tgatgggtaa attttgttta tgtcactcta    2580
ggttttgaca tttcagtttt gccactctta ggttttgaca ataatttcc attccgcggc     2640 aaaagcaaaa caattttatt ttacttttac cactcttagc tttcacaatg tatcacaaat    2700
gccactctag aaattctgtt tatgccacag aatgtgaaaa aaacactca cttatttgaa     2760 gccaaggtgt tcatggcatg gaaatgtgac ataaagtaac gttcgtgtat aagaaaaaat    2820
tgtactcctc gtaacaagag acggaaacat catgagacaa tcgcgtttgg aaggctttgc    2880
atcacctttg gatgatgcgc atgaatggag tcgtctgctt gctagccttc gcctaccgcc    2940
cactgagtcc gggcggcaac taccatcggc gaacgaccca gctgacctct accgaccgga    3000
cttgaatgcg ctaccttcgt cagcgacgat ggccgcgtac gctggcgacg tgccccgca    3060 tgcatggcgg cacatggcga gctcagaccg tgcgtggctg gctacaaata cgtacccgt     3120 gagtgcccta gctagaaact tacacctgca actgcgagag cgagcgtgtg agtgtagccg    3180
atagatccgc ccatggccca cagcaagcac ggcctgaagg aggagatgac catgaagtac    3240
cacatggagg gctgcgtgaa cggccacaag ttcgtgatca ccggcgaggg catcggctac    3300
cccttcaagg gcaagcagac catcaacctg tgcgtgatcg agggcggccc cctgcccttc    3360
agcgaggaca tcctgagcgc cggcttcaag tacggcgacc ggatcttcac cgagtacccc    3420
caggacatcg tggactactt caagaacagc tgccccgccg gctacacctg ggccggagc     3480 ttcctgttcg aggacggcgc cgtgtgcatc tgtaacgtgg acatcaccgt gagcgtgaag    3540
gagaactgca tctaccacaa gagcatcttc aacggcgtga acttcccgc cgacggcccc     3600 gtgatgaaga agatgaccac caactgggag gccagctgcg agaagatcat gcccgtgcct    3660
aagcagggca tcctgaaggg cgacgtgagc atgtacctgc tgctgaagga cggcggccgg    3720
taccggtgcc agttcgacac cgtgtacaag gccaagagcg tgcccagcaa gatgcccgag    3780
tggcacttca tccagcacaa gctgctgcgg gaggaccgga cgacgccaa gaaccagaag     3840 tggcagctga ccgagcacgc catcgccttc cccagcgccc tggcctgagg atctcgatag    3900
ggatctgtta acgatccccg gcggtgtccc ccactgaaga aactatgtgc tgtagtatag    3960
ccgctgcccg ctggctagct agctagttga gtcatttagc ggcgatgatt gagtaataat    4020
gtgtcacgca tcaccatgca tgggtggcag tgtcagtgtg agcaatgacc tgaatgaaca    4080
attgaaatga aagaaaaaa gtattgttcc aaattaaacg ttttaaccttt ttaataggtt     4140 tatacaataa ttgatatatg ttttctgtat atgtctaatt tgttatcatc catttagata    4200
tagacaaaaa aaatctaaga actaaaacaa atgctaattt gaaatgaagg gagtatatat    4260
tgggataatg tcgatgagat ccctcgtaat atcaccgaca tcacacgtgt ccagttaatg    4320
tatcagtgat acgtgtattc acatttgttg cgcgtaggcg tacccaacaa ttttgatcga    4380
ctatcagaaa gtcaacggaa gcgagtcgac ctcgaggggg ggccccggcc gaagcttgca    4440
tgcctgcagg tcgactctag aggatctgca ccggacactg tctggtggca taccagacag    4500
tccggtgtgc cagatcaggg caccttcgg ttcctttgct cctttgcttt tgaaccctaa      4560
ctttgatcgt ttattggttt tgttgaacc tttatgcacc tgtggaatat ataatctaga     4620
acaaactagt tagtccaatc atttgtgttg ggcattcaac caccaaaatt atttatagga    4680
aaaggttaaa ccttatttcc ctttcaatct cccccttttt ggtgattgat gccaacacaa    4740
```

```
accaaagaaa atatataagt gcagaattga actagtttgc ataaggtaag tgcataggtt    4800
acttagaatt aaatcaattt atacttttac ttgatatgca tggttgcttt cttttatttt    4860
aacattttgg accacatttg caccacttgt tttgtttttt gcaaatcttt ttggaaattc    4920
tttttcaaag tcttttgcaa atagtcaaag gtatatgaat aagattgtaa gaagcatttt    4980
caagatttga aatttctccc cctgtttcaa atgcttttcc tttgactaaa caaaactccc    5040
cctgaataaa attctcctct tagctttcaa gagggtttta aatagatatc aattggaaat    5100
atatttagat gctaattttg aaaatatacc aattgaaaat caacatacca atttgaaatt    5160
aaacatacca atttaaaaaa tttcaaaaag tggtggtgcg gtccttttgc tttgggctta    5220
atatttctcc cccttttggca ttaatcgcca aaaacggaga ctttgtgagc catttatact    5280
ttctccccat tggtaaatga aatatgagtg aaagattata ccaaatttgg acagtgatgc    5340
ggagtgacgg cgaaggataa acgataccgt tagagtggag tggaagcctt gtcttcgccg    5400
aagactccat ttccctttca atctacgact tagcatagaa atacacttga aaacacatta    5460
gtcgtagcca cgaaagagat atgatcaaag gtatacaaat gagctatgtg tgtaatgttt    5520
caatcaaagt ttcgagaatc aagaatattt agctcattcc taagtttgct aaaggtttta    5580
tcatctaatg gtttggtaaa gatatcgact aattgttctt tggtgctaac ataagcaatc    5640
tcgatatcac ccctttgttg gtgatccctc aaaaagtgat accgaatgtc tatgtgctta    5700
gtgcggctgt gttcaacggg attatccgcc atgcagatag cactctcatt gtcacatagg    5760
agagggactt tgctcaattt gtagccatag tccctaaggt tttgcctcat ccaaagtaat    5820
tgcacacaac aatgtcctgc ggcaatatac ttggcttcgg cggtagaaag agctattgag    5880
ttttgtttct ttgaagtcca agacaccagg gatctcccta gaaactgaca agtccctgat    5940
gtgctcttcc tatcaatttt acaccctgcc caatcggcat ctgaatatcc tattaaatca    6000
aaggtggatc ccttggggta ccaaagacca aatttaggag tgtaaactaa atatctcatg    6060
attcttttca cggccctaag gtgaacttcc ttaggatcgg cttggaatct tgcacacatg    6120
catatagaaa gcatactatc tggtcgagat gcacataaat agagtaaaga tcctatcatc    6180
gaccggtata ccttttggtc tacgatttta cctcccgtgt cgaggtcgag atgcccatta    6240
gttcccatgg gtgtcctgat gggcttggca tccttcattc caaacttgtt gagtatgtct    6300
tgaatgtact ttgtttggct gatgaaggtg ccatcttgga gttgcttgac ttgaaatcct    6360
agaaaatatt tcaacttccc catcatagac atctcgaatt tcggaatcat gatcctacta    6420
aactcttcac aagtagattt gttagtagac ccaaatataa tatcatcaac ataaatttgg    6480
catacaaaca aaacttttga aatggtttta gtaaagagag taggatcggc tttactgact    6540
ctgaagccat tagtgataag aaaatctctt aggcattcat accatgctgt tggggcttgc    6600
ttgagcccat aaagcgcctt tgagagttta taaacatggt tagggtactc actatcttca    6660
aagccgagag gttgctcaac atagacctat tcaccccatt tgatcacttt tttggtcctt    6720
caggatctaa tagttatgta taatttagag tctcttgttt aatggccaga tatttctaat    6780
taatctaaga atttatgata tttttttaatt ttttatcatg tctgatgaga attaacataa    6840
aggctcaatt gggtcctgaa ttaataatag agtgaaaatt aatccagagg ctctattaga    6900
accttcaatt agtaatacca agatatatat aagatagtag agtatagttt aaatgttggc    6960
attgttcatt ctttctttg ttatttaatt tatgctttcc acggtggtta gtggttactt    7020
ctgaagggtc caaataatgc atgaagagtt tgaggacaag aagtctgccc taaaaatagc    7080
```

```
gatgcaaagg catggtgtcc aagccataca tatagcgcac taattttatc agcagaacaa    7140
tggtatttat aggtcctagt gcccaggcaa caagagacac gaataaagca tcgatcacga    7200
caccagatct catggcacag gttatcaaca cgtttgacgg ggttgcggat tatcttcaga    7260
catatcataa gctacctgat aattacatta caaaatcaga agcacaagcc ctcggctggg    7320
tggcatcaaa agggaacctt gcagacgtcg ctccggggaa aagcatcggc ggagacatct    7380
tctcaaacag ggaaggcaaa ctcccgtaag tttctgcttc tacctttgat atatatataa    7440
taattatcat taattagtag taatataata tttcaaatat ttttttcaaa ataaaagaat    7500
gtagtatata gcaattgctt ttctgtagtt tataagtgtg tatattttaa tttataactt    7560
ttctaatata tgaccaaaac atggtgatgt gcaggggcaa aagcggacga acatggcgtg    7620
aagcggatat taactataca tcaggcttca gaaattcaga ccggattctt tactcaggcg    7680
actggctgat ttacaaaaca acggaccatt atcagacctt tacaaaaatc agataactgc    7740
agctagactt gtccatcttc tggattggcc aacttaatta atgtatgaaa taaaaggatg    7800
cacacatagt gacatgctaa tcactataat gtgggcatca aagttgtgtg ttatgtgtaa    7860
ttactagtta tctgaataaa agagaaagag atcatcccata tttcttatcc taaatgaatg    7920
tcacgtgtct ttataattct ttgatgaacc agatgcattt cattaaccaa atccatatac    7980
atataaatat taatcatata taattaatat caattgggtt agcaaaacaa atctagggtc    8040
acccggtccg ggcctagaag gccgatctcc cgggcaccca gctttcttgt acaaagtggc    8100
cgttaacgga tcccggtgaa gttcctattc cgaagttcct attctccaga aagtatagga    8160
acttcactag agcttgcggc cgccccgggc aactttatta tacatagttg ataattcact    8220
ggccgtcgtt ttacaacgtc gtgactggga aaaccctggc gttacccaac ttaatcgcct    8280
tgcagcacat ccccctttcg ccagctggcg taatagcgaa gaggcccgca ccgatcgccc    8340
ttcccaacag ttgcgcagcc tgaatggcga atggcgcctg atgcggtatt ttctccttac    8400
gcatctgtgc ggtatttcac accgcatatg gtgcactctc agtacaatct gctctgatgc    8460
cgcatagtta agccagcccc gacacccgcc aacacccgct gacgcgccct gacgggcttg    8520
tctgctcccg gcatccgctt acagacaagc tgtgaccgtc tccgggagct gcatgtgtca    8580
gaggttttca ccgtcatcac cgaaacgcgc gagacgaaag gcctcgtga tacgcctatt    8640 tttataggtt aatgtcatga taataatggt ttcttagacg tcaggtggca cttttcgggg    8700
aaatgtgcgc ggaaccccta tttgtttatt tttctaaata cattcaaata tgtatccgct    8760
catgagacaa taaccctgat aaatgcttca ataatattga aaaggaaga gtatgagtat    8820 tcaacatttc cgtgtcgccc ttattccctt ttttgcggca ttttgccttc ctgtttttgc    8880
tcacccagaa acgctggtga agtaaaaga tgctgaagat cagttgggtg cacgagtggg    8940
ttacatcgaa ctggatctca acagcggtaa gatccttgag agttttcgcc ccgaagaacg    9000
ttttccaatg atgagcactt taaagttct gctatgtggc gcggtattat cccgtattga    9060
cgccgggcaa gagcaactcg gtcgccgcat acactattct cagaatgact tggttgagta    9120
ctcaccagtc acagaaaagc atcttacgga tggcatgaca gtaagagaat tatgcagtgc    9180
tgccataacc atgagtgata acactgcggc caacttactt ctgacaacga tcggaggacc    9240
gaaggagcta accgcttttt tgcacaacat gggggatcat gtaactcgcc ttgatcgttg    9300
ggaaccggag ctgaatgaag ccataccaaa cgacgagcgt gacaccacga tgcctgtagc    9360
aatggcaaca acgttgcgca aactattaac tggcgaacta cttactctag cttcccggca    9420
acaattaata gactggatgg aggcggataa agttgcagga ccacttctgc gctcggccct    9480
```

```
tccggctggc tggtttattg ctgataaatc tggagccggt gagcgtgggt ctcgcggtat    9540
cattgcagca ctggggccag atggtaagcc ctcccgtatc gtagttatct acacgacggg    9600
gagtcaggca actatggatg aacgaaatag acagatcgct gagataggtg cctcactgat    9660
taagcattgg taactgtcag accaagttta ctcatatata ctttagattg atttaaaact    9720
tcatttttaa tttaaaagga tctaggtgaa gatccttttt gataatctca tgaccaaaat    9780
cccttaacgt gagttttcgt tccactg                                        9807

<210> SEQ ID NO 49
<211> LENGTH: 2085
<212> TYPE: DNA
<213> ORGANISM: artificial sequence
<220> FEATURE:
<223> OTHER INFORMATION: dpzm03g014880.1.1_Promoter glycosyltransferase

<400> SEQUENCE: 49
agatgacagg ggtgttgtgt tgaagggatg gcgatcgacg actgttaatc gtgttttctg      60 cttttggct agggtttgtg attcctctga gtttgaacat catatgttgt gttgctgtca     120
tctcgagttt gtgttcgtgg tgatactatc aaactggaaa ttgtaccacg cggctgaaag    180
cacctaccgc tgacaggcag aagccatgca cgaatagatt ccaacatgga aaatgtaaaa    240
gtcgatgttt agagatgcac ataatgtgag acttctaaac taattttata ctccctccag    300
tcttcagata ctcgatattt tgaacatgat cttatataga aaacgtaata cattgatctg    360
ttcactattc actaatttat acatgtgtta agcattaaag tgctcgcagt tcacacaata    420
ttatgctatt gttaattta ttttggttc catttatttc ttaaaaggat ttttcttact    480
actataacat gtaaaactat tgtatctatc ctgcaccatg ggaggtgatt tttgttattt    540
acgttatttt ctactccctg tgttcctggt cactttggct tttctatagt ataatattcc    600
aaacttgtga gtatttcgag tatttattgg ggtagtgtaa agtttatatg catacttcct    660
gtatatagag gttgatgcta tttatctaat gatagtggta aggcttagct aatagtatga    720
tttgtgtacg gtgagttgca tccgttcaca attctctttc tcacatgctt ctcttccttt    780
gattttggat atgccattaa gtacaagaac aaacaccatt tactgctcaa atagaaaaca    840
tcatctaact atcaaatttc tgcttcaata aaattcacct acaacgtata tgtgttcact    900
cgactgatta tccagaagtc atgatgtttc ggcgattttg aattttgtg agaattgtac    960 accagaattt ttgacgcctt acctggatgg aatcgtgaat aaattacttg ttcttcttca   1020
ggcacgcaat tacttgtgtt gaattaggtt tcaggttgct tcaaatatat ttgttatcat   1080
gtttagtaaa caatgctaat tgctcatgtt catattctag aatggcaagc aaatggtgca   1140
cggagagcat tgacagctct agcgtcagta gcagattcat cacaggcgtt gttcacttgg   1200
gagttttatg catagtgaat ctctgttatt gtgcatcatg gcctcatggg gttgtcgtat   1260
tgttattgcg ctttctaact tactcataat aacaacttta tatatcattt acattgtttt   1320
ttgtttgtct atctgatcat aagtttgtag caataacttt tttgtttgtc catttacatg   1380
gggcagcagg ctgctgcgct cttgggagag cagcccgtct accacgccgt acaacgttcc   1440
attggctgcg gggccaccat gcccctagtg gcgctgcccg acaaggaggc tgggtatttg   1500
ggggattatc agcgaagcat catgactccc gacgaagcag gggctgcgac cagcgcgctg   1560
gacgttgctg gggccgcctg atggtggcga cggctgctgt ctggggcag cagcagagct   1620 catgatcgtc gagaccttttg ataccagatt ggtaggagcc acgttcctta taatgacgat   1680
```

| | |
|---|---:|
| atgtttccgt tgcaacgcac gggcatccac ctagtaacct atatgtgtgg ggttttctcc | 1740 |
| tcctaggttt agctctccaa actagcctga aaaaagaaa aacacacccg gagaaaaaaa | 1800 |
| aaagcaccca aatttgactc gcgaaatgca tgccgtttaa tttgatccga gcccacagtc | 1860 |
| tctcctcggg cccaccgcgt ccgaccggcg cgcacgggca tccacctagt aacctatatg | 1920 |
| tgtggggttt tctcctccta ggtttagctc tccaaactag cctgaaaaaa agaaaaacac | 1980 |
| acccggagaa aaaaaaagc acccaaattt gactcgcgaa atgcatgccg tttaatttga | 2040 |
| tccgagccca cagtctctcc tcgggcccac cgcgtccgac cggcg | 2085 |

<210> SEQ ID NO 50
<211> LENGTH: 6270
<212> TYPE: DNA
<213> ORGANISM: artificial sequence
<220> FEATURE:
<223> OTHER INFORMATION: PHP5096

<400> SEQUENCE: 50

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgccaa gcttgcatgc ctgcagtgca | 420 |
| gcgtgacccg gtcgtgcccc tctctagaga taatgagcat tgcatgtcta agttataaaa | 480 |
| aattaccaca tatttttttt gtcacacttg tttgaagtgc agtttatcta tctttataca | 540 |
| tatatttaaa ctttactcta cgaataatat aatctatagt actacaataa tatcagtgtt | 600 |
| ttagagaatc atataaatga acagttagac atggtctaaa ggacaattga gtattttgac | 660 |
| aacaggactc tacagtttta tcttttttagt gtgcatgtgt tctcctttttt ttttgcaaat | 720 |
| agcttcacct atataatact tcatccattt tattagtaca tccatttagg gtttagggtt | 780 |
| aatggttttt atagactaat ttttttagta catctatttt attctatttt agcctctaaa | 840 |
| ttaagaaaac taaaactcta ttttagtttt tttatttaat aatttagata taaaatagaa | 900 |
| taaaataaag tgactaaaaa ttaaacaaat acccttaag aaattaaaaa aactaaggaa | 960 |
| acatttttct tgtttcgagt agataatgcc agcctgttaa acgccgtcga cgagtctaac | 1020 |
| ggacaccaac cagcgaacca gcagcgtcgc gtcgggccaa gcgaagcaga cggcacggca | 1080 |
| tctctgtcgc tgcctctgga cccctctcga gagttccgct ccaccgttgg acttgctccg | 1140 |
| ctgtcggcat ccagaaattg cgtggcggag cggcagacgt gagccggcac ggcaggcggc | 1200 |
| ctcctcctcc tctcacggca cggcagctac gggggattcc tttcccaccg ctccttcgct | 1260 |
| ttcccttcct cgcccgccgt aataaataga caccccctcc acccctcttt ccccaacct | 1320 |
| cgtgttgttc ggagcgcaca cacacaac cagatctccc ccaaatccac ccgtcggcac | 1380 |
| ctccgcttca aggtacgccg ctcgtcctcc cccccccccc ctctctacct tctctagatc | 1440 |
| ggcgttccgg tccatggtta gggcccggta gttctacttc tgttcatgtt tgtgttagat | 1500 |
| ccgtgtttgt gttagatccg tgctgctagc gttcgtacac ggatgcgacc tgtacgtcag | 1560 |
| acacgttctg attgctaact tgccagtgtt tctctttggg gaatcctggg atggctctag | 1620 |
| ccgttccgca gacgggatcg atttcatgat ttttttttgtt tcgttgcata gggtttggtt | 1680 |

```
tgcccttttc ctttatttca atatatgccg tgcacttgtt tgtcgggtca tcttttcatg    1740
cttttttttg tcttggttgt gatgatgtgg tctggttggg cggtcgttct agatcggagt    1800
agaattctgt ttcaaactac ctggtggatt tattaatttt ggatctgtat gtgtgtgcca    1860
tacatattca tagttacgaa ttgaagatga tggatggaaa tatcgatcta ggataggtat    1920
acatgttgat gcgggtttta ctgatgcata tacagagatg cttttttgttc gcttggttgt   1980 gatgatgtgg tgtggttggg cggtcgttca ttcgttctag atcggagtag aatactgttt    2040
caaactacct ggtgtattta ttaattttgg aactgtatgt gtgtgtcata catcttcata    2100
gttacgagtt taagatggat ggaaatatcg atcaggata ggtatacatg ttgatgtggg     2160
ttttactgat gcatatacat gatggcatat gcagcatcta ttcatatgct ctaaccttga    2220
gtacctatct attataataa acaagtatgt tttataatta ttttgatctt gatatacttg    2280
gatgatggca tatgcagcag ctatatgtgg attttttttag ccctgccttc atacgctatt   2340
tatttgcttg gtactgtttc ttttgtcgat gctcaccctg ttgtttggtg ttacttctgc    2400
aggtcgactc tagaggatcc aacaatgccc cagttcgaca tcctctgcaa gaccccccc     2460 aaggtgctcg tgaggcagtt cgtggagagg ttcgagaggc cctccggcga aagatcgcc     2520 ctctgcgccg ccgagctcac ctacctctgc tggatgatca cccacaacgg caccgccatt    2580
aagagggcca ccttcatgtc atacaacacc atcatctcca actccctctc cttcgacatc    2640
gtgaacaagt ccctccagtt caaatacaag acccagaagg ccaccatcct cgaggcctcc    2700
ctcaagaagc tcatccccgc ctgggagttc accatcatcc cctactacgg ccagaagcac    2760
cagtccgaca tcaccgacat cgtgtcatcc ctccagcttc agttcgagtc ctccgaggag    2820
gctgacaagg gcaactccca ctccaagaag atgctgaagg ccctcctctc cgagggcgag    2880
tccatctggg agatcaccga aagatcctc aactccttcg agtacacctc caggttcact    2940
aagaccaaga ccctctacca gttcctcttc ctcgccacct tcatcaactg cggcaggttc    3000
tcagacatca agaacgtgga ccccaagtcc ttcaagctcg tgcagaacaa gtacctcggc    3060
gtgatcatcc agtgcctcgt gaccgagacc aagacctccg tgtccaggca catctacttc    3120
ttctccgctc gcggcaggat cgaccccctc gtgtacctcg acgagttcct caggaactca    3180
gagcccgtgc tcaagagggt gaacaggacc ggcaactcct cctccaacaa gcaggagtac    3240
cagctcctca aggacaacct cgtgaggtcc tacaacaagg ccctcaagaa gaacgccccc    3300
tactccatct tcgccatcaa gaacggcccc aagtcccaca tcggtaggca cctcatgacc    3360
tccttcctct caatgaaggg cctcaccgag ctcaccaacg tggtgggcaa ctggtccgac    3420
aagagggcct ccgccgtggc caggaccacc tacacccacc agatcaccgc catccccgac    3480
cactacttcg ccctcgtgtc aaggtactac gcctacgacc ccatctccaa ggagatgatc    3540
gccctcaagg acgagactaa ccccatcgag gagtggcagc acatcgagca gctcaagggc    3600
tccgccgagg gctccatcag gtaccccgcc tggaacggca tcatcccca ggaggtgctc     3660 gactacctct cctcctacat caacaggagg atctgagtta acctagactt gtccatcttc    3720
tggattggcc aacttaatta atgtatgaaa taaaaggatg cacacatagt gacatgctaa    3780
tcactataat gtgggcatca aagttgtgtg ttatgtgtaa ttactagtta tctgaataaa    3840
agagaaagag atcatccata tttcttatcc taaatgaatg tcacgtgtct ttataattct    3900
ttgatgaacc agatgcattt cattaaccaa atccatatac atataaatat taatcatata    3960
taattaatat caattgggtt agcaaaacaa atctagtcta ggtgtgtttt gcgaattgcg    4020
```

```
gccgcgatct ggggaattcg taatcatggt catagctgtt tcctgtgtga aattgttatc    4080
cgctcacaat tccacacaac atacgagccg aagcataaa gtgtaaagcc tggggtgcct     4140
aatgagtgag ctaactcaca ttaattgcgt tgcgctcact gcccgctttc cagtcgggaa    4200
acctgtcgtg ccagctgcat taatgaatcg gccaacgcgc ggggagaggc ggtttgcgta    4260
ttgggcgctc ttccgcttcc tcgctcactg actcgctgcg ctcggtcgtt cggctgcggc    4320
gagcggtatc agctcactca aaggcggtaa tacggttatc cacagaatca ggggataacg    4380
caggaaagaa catgtgagca aaaggccagc aaaaggccag gaaccgtaaa aaggccgcgt    4440
tgctggcgtt tttccatagg ctccgccccc ctgacgagca tcacaaaaat cgacgctcaa    4500
gtcagaggtg gcgaaacccg acaggactat aaagatacca ggcgtttccc cctggaagct    4560
ccctcgtgcg ctctcctgtt ccgaccctgc cgcttaccgg atacctgtcc gcctttctcc    4620
cttcgggaag cgtggcgctt tctcatagct cacgctgtag gtatctcagt tcggtgtagg    4680
tcgttcgctc caagctgggc tgtgtgcacg aaccccccgt tcagcccgac cgctgcgcct    4740
tatccggtaa ctatcgtctt gagtccaacc cggtaagaca cgacttatcg ccactggcag    4800
cagccactgg taacaggatt agcagagcga ggtatgtagg cggtgctaca gagttcttga    4860
agtggtggcc taactacggc tacactagaa ggacagtatt tggtatctgc gctctgctga    4920
agccagttac cttcggaaaa agagttggta gctcttgatc cggcaaacaa accaccgctg    4980
gtagcggtgg ttttttgtt tgcaagcagc agattacgcg cagaaaaaa ggatctcaag     5040
aagatccttt gatcttttct acggggtctg acgctcagtg gaacgaaaac tcacgttaag    5100
ggatttggt catgagatta tcaaaaagga tcttcaccta gatcctttta aattaaaaat    5160
gaagttttaa atcaatctaa agtatatatg agtaaacttg gtctgacagt taccaatgct    5220
taatcagtga ggcacctatc tcagcgatct gtctatttcg ttcatccata gttgcctgac    5280
tccccgtcgt gtagataact acgatacggg agggcttacc atctggcccc agtgctgcaa    5340
tgataccgcg agacccacgc tcaccggctc cagatttatc agcaataaac cagccagccg    5400
aagggccga gcgcagaagt ggtcctgcaa ctttatccgc ctccatccag tctattaatt    5460
gttgccggga agctagagta agtagttcgc cagttaatag tttgcgcaac gttgttgcca    5520
ttgctacagg catcgtggtg tcacgctcgt cgtttggtat ggcttcattc agctccggtt    5580
cccaacgatc aaggcgagtt acatgatccc ccatgttgtg caaaaaagcg gttagctcct    5640
tcggtcctcc gatcgttgtc agaagtaagt tggccgcagt gttatcactc atggttatgg    5700
cagcactgca taattctctt actgtcatgc catccgtaag atgcttttct gtgactggtg    5760
agtactcaac caagtcattc tgagaatagt gtatgcggcg accgagttgc tcttgcccgg    5820
cgtcaatacg ggataatacc gcgccacata gcagaacttt aaaagtgctc atcattggaa    5880
aacgttcttc ggggcgaaaa ctctcaagga tcttaccgct gttgagatcc agttcgatgt    5940
aacccactcg tgcacccaac tgatcttcag catcttttac tttcaccagc gtttctgggt    6000
gagcaaaaac aggaaggcaa aatgccgcaa aaagggaat aagggcgaca cggaaatgtt    6060
gaatactcat actcttcctt tttcaatatt attgaagcat ttatcagggt tattgtctca    6120
tgagcggata catatttgaa tgtatttaga aaaataaaca ataggggtt ccgcgcacat    6180
ttccccgaaa agtgccacct gacgtctaag aaaccattat tatcatgaca ttaacctata    6240
aaaataggcg tatcacgagg ccctttcgtc                                     6270
```

<210> SEQ ID NO 51
<211> LENGTH: 8986

<212> TYPE: DNA
<213> ORGANISM: artificial sequence
<220> FEATURE:
<223> OTHER INFORMATION: PHP01

<400> SEQUENCE: 51

```
gtttacccgc caatatatcc tgtcaaacac tgatagttta aactgaaggc gggaaacgac      60
aatctgatca tgagcggaga attaagggag tcacgttatg accccgccg atgacgcggg      120
acaagccgtt ttacgtttgg aactgacaga accgcaacgt tgaaggagcc actcagcaag     180
ctggtacgat tgtaatacga ctcactatag ggcgaattga gcgctgttta aacgctcttc     240
aactggaaga gcggttacta ccggttaagt gactagggtc acgtgaccct agtcacttag     300
gttatgatat cacatcaatc cacttgcttt gaagacgtgg ttggaacgtc ttcttttcc      360
acgatgctcc tcgtgggtgg gggtccatct ttgggaccac tgtcggcaga ggcatcttca     420
acgatggcct ttcctttatc gcaatgatgg catttgtagg agccaccttc cttttccact     480
atcttcacaa taaagtgaca gatagctggg caatggaatc cgaggaggtt tccggatatt     540
accctttgtt gaaaagtctc aattgccctt tggtcttctg agactgtatc tttgatattt     600
ttggagtaga caagcgtgtc gtgctccacc atgttgacga agattttctt cttgtcattg     660
agtcgtaaga gactctgtat gaactgttcg ccagtcttta cggcgagttc tgttaggtcc     720
tctatttgaa tctttgactc catgatcgaa ccagaaagct tgcatgcctg caggtcgact     780
ctagaggatc tgcaccggac actgtctggt ggcataccag acagtccggt gtgccagatc     840
agggcaccct tcggttcctt tgctcctttg cttttgaacc ctaactttga tcgtttattg     900
gtttgtgttg aacctttatg cacctgtgga atatataatc tagaacaaac tagttagtcc     960
aatcatttgt gttgggcatt caaccaccaa aattatttat aggaaaaggt taaaccttat    1020
ttccctttca atctccccct ttttggtgat tgatgccaac acaaaccaaa gaaaatatat    1080
aagtgcagaa ttgaactagt ttgcataagg taagtgcata ggttacttag aattaaatca    1140
atttatactt ttacttgata tgcatggttg ctttcttttta ttttaacatt ttggaccaca    1200
tttgcaccac ttgttttgtt tttgcaaat cttttttggaa attcttttc aaagtctttt     1260
gcaaatagtc aaaggtatat gaataagatt gtaagaagca ttttcaagat ttgaaatttc    1320
tccccctgtt tcaaatgctt ttcctttgac taaacaaaac tcccctgaa taaaattctc     1380
ctcttagctt tcaagagggt tttaaataga tatcaattgg aaatatattt agatgctaat    1440
tttgaaaata taccaattga aaatcaacat accaatttga aattaaacat accaatttaa    1500
aaaatttcaa aaagtggtgg tgcggtcctt ttgcttggg cttaatatttt ctcccccttt    1560
ggcattaatc gccaaaaacg gagactttgt gagccattta actttctcc ccattggtaa     1620
atgaaatatg agtgaaagat tataccaaat ttggacagtg atgcggagtg acggcgaagg    1680
ataaacgata ccgttagagt ggagtggaag ccttgtcttc gccgaagact ccatttccct    1740
ttcaatctac gacttagcat agaaatacac ttgaaaacac attagtcgta gccacgaaag    1800
agatatgatc aaaggtatac aaatgagcta tgtgtgtaat gtttcaatca aagtttcgag    1860
aatcaagaat atttagctca ttcctaagtt tgctaaaggt tttatcatct aatggtttgg    1920
taaagatatc gactaattgt tctttggtgc aacataagc aatctcgata tcacccctt     1980
gttggtgatc cctcaaaaag tgataccgaa tgtctatgtg cttagtgcgg ctgtgttcaa    2040
cgggattatc cgccatgcag atagcactct cattgtcaca taggagaggg actttgctca    2100
atttgtagcc atagtcccta aggttttgcc tcatccaaag taattgcaca caacaatgtc    2160
```

```
ctgcggcaat atacttggct tcggcggtag aaagagctat tgagttttgt ttctttgaag    2220
tccaagacac cagggatctc cctagaaact gacaagtccc tgatgtgctc ttcctatcaa    2280
ttttacaccc tgcccaatcg gcatctgaat atcctattaa atcaaaggtg gatcccttgg    2340
ggtaccaaag accaaattta ggagtgtaaa ctaaatatct catgattctt ttcacggccc    2400
taaggtgaac ttccttagga tcggcttgga atcttgcaca catgcatata gaaagcatac    2460
tatctggtcg agatgcacat aaatagagta aagatcctat catcgaccgg tatacctttt    2520
ggtctacgga tttacctccc gtgtcgaggt cgagatgccc attagttccc atgggtgtcc    2580
tgatgggctt ggcatccttc attccaaact tgttgagtat gtcttgaatg tactttgttt    2640
ggctgatgaa ggtgccatct ggagttgct tgacttgaaa tcctagaaaa tatttcaact     2700
tccccatcat agacatctcg aatttcggaa tcatgatcct actaaactct tcacaagtag    2760
atttgttagt agacccaaat ataatatcat caacataaat ttggcataca aacaaaactt    2820
ttgaaatggt tttagtaaag agagtaggat cggctttact gactctgaag ccattagtga    2880
taagaaaatc tcttaggcat tcataccatg ctgttgggc ttgcttgagc ccataaagcg     2940
cctttgagag tttataaaca tggttagggt actcactatc ttcaaagccg agaggttgct    3000
caacatagac ctattcaccc catttgatca ctttttggt ccttcaggat ctaatagtta     3060
tgtataattt agagtctctt gtttaatggc cagatatttc taattaatct aagaatttat    3120
gatatttttt aattttttat catgtctgat gagaattaac ataaaggctc aattgggtcc    3180
tgaattaata atagagtgaa aattaatcca gaggctctat tagaaccttc aattagtaat    3240
accaagatat atataagata gtagagtata gtttaaatgt tggcattgtt cattctttct    3300
tttgttattt aatttatgct ttccacggtg gttagtggtt acttctgaag ggtccaaata    3360
atgcatgaag agtttgagga caagaagtct gccctaaaaa tagcgatgca aaggcatggt    3420
gtccaagcca tacatatagc gcactaattt tatcagcaga acaatggtat ttataggtcc    3480
tagtgcccag gcaacaagag acacgaataa agcatcgatc acgacaccat ggccagactc    3540
gacaagagca aggtgatcaa cagcgcactg gagctgctga acgaggtcgg aatcgaaggc    3600
ctcacaaccc gtaaactcgc ccagaagctc ggggtagagc agcctacatt gtattggcac    3660
gtcaagaaca agcgggcttt gctagacgcc ctcgccattg agatgctcga taggcaccat    3720
acccacttct gcccttttgga aggggaaagc tggcaagact tcttgaggaa caacgctaag    3780
agcttcagat gtgctttgct cagtcaccgt gatggagcca aggtccacct aggtacacgg    3840
cctacggaga agcagtatga aactctcgag aaccagctcg ccttcctgtg ccaacaaggt    3900
ttctcccttg agaatgccct ctacgcactc tccgctgtag ggcacttcac tctgggttgc    3960
gtattggaag atcaagagca ccaagtcgct aaggaggaga gggaaacacc tactactgat    4020
agtatgccgc cactgctccg acaagctatc gagctcttcg atcaccaagg tgcagagcca    4080
gccttcctgt tcggccttga attgatcata tgcggattgg agaagcagct gaagtgtgaa    4140
agtgggtctt aacacatcgt tctgaaggcc gaaagtgggt cttaatgata gctgcagaag    4200
gtacctcagc cgtcaacagc cagggtgatt agagcccag catgcaaaat gatcacctgg     4260
tcgctcatcc ttgactaaag catggctcgg cggtcgctgt ttacctatat ccctatagta    4320
ggtactcctg tacataaagc ctgaaaaaat gggttcagtt gtttatcgaa ctctgccaaa    4380
tttgcttttg catataatgt aaaattcagc tagctctgct aagctcctcg cttcagttcg    4440
acagaactgc aattgatatt gatgttatgg aaattgatat tggaacaatc agcaatatta    4500
tgcttatatt catttcttgg gcgtgctcta ctctgtgccg atgatatcat ccgatgggtt    4560
```

```
ttgtacttct tacttatgaa gtgaacgata ataggttgcc tggtcccagt tctcagcttg   4620
atgttatgat aatcatatgt gatttcagtt ctttgtctgg cattggtctg tttttgtgtc   4680
tgtgtctgtg ggctgtggct ctgtgtgttg ataactcgag cttgattgca tcagtgaact   4740
gcgacttaca acagcagaca gagtgttagc agcaggaag gagaatagag aaattaggga    4800
gtaaagagaa catagttgcc tttcagagga cagcttagca agataacaaa attatgttct   4860
ctccttttaa ggattacaga ggcatagcct cagcgacgcg cgtgctagcg gatccagtta   4920
tcatcatcgt gttgggcttc ctgggcctgg cctgcctagc aggcctgtcg acagcttcag   4980
aaggggaact cgttggcgga ttgtccacag tagcacgtac tatatgcaga aaaagtcctt   5040
atgtctctct tatcattagc ctattaatca tattaattca gtccacatag gaccgaattt    5100
ataacttaac aatcttttag tttcctgagc aatatcgtta aatcaaaaca tattcttgta   5160
ccaaattttg ctatcaacgg ttcaacgctg gtgcagcgtg acccggtcgt gccctctct    5220 agagataatg agcattgcat gtctaagtta taaaaaatta ccacatattt tttttgtcac   5280
acttgtttga agtgcagttt atctatcttt atacatatat ttaaacttta ctctacgaat   5340
aatataatct atagtactac aataatatca gtgttttaga gaatcatata aatgaacagt   5400
tagacatggt ctaaaggaca attgagtatt ttgacaacag gactctacag ttttatcttt   5460
ttagtgtgca tgtgttctcc tttttttttg caaatagctt cacctatata atacttcatc   5520
cattttatta gtacatccat ttagggttta gggttaatgg tttttataga ctaattttt    5580 tagtacatct attttattct attttagcct ctaaattaag aaaactaaaa ctctatttta   5640 gttttttat ttaataattt agatataaaa tagaataaaa taaagtgact aaaaattaaa    5700 caaatacccct ttaagaaatt aaaaaaacta aggaaacatt tttcttgttt cgagtagata  5760
atgccagcct gttaaacgcc gtcgacgagt ctaacggaca ccaaccagcg aaccagcagc   5820
gtcgcgtcgg gccaagcgaa gcagacggca cggcatctct gtcgctgcct ctggaccct    5880 ctcgagagtt ccgctccacc gttggacttg ctccgctgtc ggcatccaga aattgcgtgg   5940
cggagcggca gacgtgagcc ggcacggcag gcggcctcct cctcctctca cggcaccggc   6000
agctacgggg gattcctttc ccaccgctcc ttcgctttcc cttcctcgcc cgccgtaata   6060
aatagacacc ccctccacac cctctttccc caacctcgtg ttgttcggag cgcacacaca   6120
cacaaccaga tctcccccaa atccaccccgt cggcacctcc gcttcaaggt acgccgctcg  6180 tcctccccccc cccccctctc taccttctct agatcggcgt tccggtccat gcatggttag   6240
ggcccggtag ttctacttct gttcatgttt gtgttagatc cgtgtttgtg ttagatccgt   6300
gctgctagcg ttcgtacacg gatgcgacct gtacgtcaga cacgttctga ttgctaactt   6360
gccagtgttt ctctttgggg aatcctggga tggctctagc cgttccgcag acgggatcga   6420
tttcatgatt tttttttgttt cgttgcatag ggtttggttt gccctttttcc tttatttcaa  6480 tatatgccgt gcacttgttt gtcgggtcat cttttcatgc tttttttttgt cttggttgtg   6540 atgatgtggt ctggttgggc ggtcgttcta gatcggagta gaattctgtt tcaaactacc   6600
tggtggattt attaattttg gatctgtatg tgtgtgccat acatattcat agttacgaat    6660
tgaagatgat ggatggaaat atcgatctag gataggtata catgttgatg cgggttttac   6720
tgatgcatat acagagatgc ttttttgttcg cttggttgtg atgatgtggt gtggttgggc   6780
ggtcgttcat tcgttctaga tcggagtaga atactgtttc aaactacctg gtgtatttat   6840
taattttgga actgtatgtg tgtgtcatac atcttcatag ttacgagttt aagatggatg   6900
```

```
gaaatatcga tctaggatag gtatacatgt tgatgtgggt tttactgatg catatacatg    6960
atggcatatg cagcatctat tcatatgctc taaccttgag tacctatcta ttataataaa    7020
caagtatgtt ttataattat tttgatcttg atatacttgg atgatggcat atgcagcagc    7080
tatatgtgga ttttttttagc cctgccttca tacgctattt atttgcttgg tactgtttct    7140
tttgtcgatg ctcaccctgt tgtttggtgt tacttctgca ggtcgacttt aacttagcct    7200
aggatccatg caaaaactca ttaactcagt gcaaaactat gcctggggca gcaaaacggc    7260
gttgactgaa ctttatggta tggaaaatcc gtccagccag ccgatggccg agctgtggat    7320
gggcgcacat ccgaaaagca gttcacgagt gcagaatgcc gccggagata tcgtttcact    7380
gcgtgatgtg attgagagtg ataaatcgac tctgctcgga gaggccgttg ccaaacgctt    7440
tggcgaactg cctttcctgt tcaaagtatt atgcgcagca cagccactct ccattcaggt    7500
tcatccaaac aaacacaatt ctgaaatcgg ttttgccaaa gaaaatgccg caggtatccc    7560
gatggatgcc gccgagcgta actataaaga tcctaaccac aagccggagc tggttttttgc    7620
gctgacgcct ttccttgcga tgaacgcgtt tcgtgaattt ccgagatttg tctccctact    7680
ccagccggtc gcaggtgcac atccggcgat tgctcacttt ttacaacagc ctgatgccga    7740
acgtttaagc gaactgttcg ccagcctgtt gaatatgcag ggtgaagaaa atcccgcgc    7800
gctggcgatt ttaaaatcgg ccctcgatag ccagcagggt gaaccgtggc aaacgattcg    7860
tttaattct gaatttttacc cggaagacag cggtctgttc tccccgctat tgctgaatgt    7920
ggtgaaattg aaccctggcg aagcgatgtt cctgttcgct gaaacaccgc acgcttacct    7980
gcaaggcgtg cgctggaag tgatggcaaa ctccgataac gtgctgcgtg cgggtctgac    8040
gcctaaatac attgatattc cggaactggt tgccaatgtg aaattcgaag ccaaaccggc    8100
taaccagttg ttgacccagc cggtgaaaca aggtgcagaa ctggacttcc cgattccagt    8160
ggatgatttt gccttctcgc tgcatgacct tagtgataaa gaaaccacca ttagccagca    8220
gagtgccgcc attttgttct gcgtcgaagg cgatgcaacg ttgtggaaag ttctcagca    8280
gttacagctt aaaccgggtg aatcagcgtt tattgccgcc aacgaatcac cggtgactgt    8340
caaaggccac ggccgtttag cgcgcgttta caacaagctg taaatcacta gcgaacgcgt    8400
aggtaccaca tggttaacct agacttgtcc atcttctgga ttggccaact taattaatgt    8460
atgaaataaa aggatgcaca catagtgaca tgctaatcac tataatgtgg gcatcaaagt    8520
tgtgtgttat gtgtaattac tagttatctg aataaaagag aaagagatca tccatatttc    8580
ttatcctaaa tgaatgtcac gtgtctttat aattctttga tgaaccagat gcatttcatt    8640
aaccaaatcc atatacatat aaatattaat catatataat taatatcaat tgggttagca    8700
aaacaaatct agtctaggtg tgttttgcga atgcggccgc caccgcggtg gagctcgaat    8760
tccggtccga agctggccga taagtgacta gggtcacgtg accctagtca cttaggtacc    8820
gagctcgaat tcattccgat taatcgtggc ctcttgctct tcaggatgaa gagctatgtt    8880
taaacgtgca agcgctacta gacaattcag tacattaaaa acgtccgcaa tgtgttatta    8940
agttgtctaa gcgtcaattt gtttacacca caatatatcc tgccac                    8986
```

<210> SEQ ID NO 52
<211> LENGTH: 9304
<212> TYPE: DNA
<213> ORGANISM: artificial sequence
<220> FEATURE:
<223> OTHER INFORMATION: PHP02

<400> SEQUENCE: 52

| | |
|---|---:|
| agaagttcct attccgaagt tcctattctc tagaaagtat aggaacttca gatccaccgg | 60 |
| ctagaggatc caccatggtt gaacaagatg gattgcacgc aggttctccg gccgcttggg | 120 |
| tggagaggct attcggctat gactgggcac aacagacaat cggctgctct gatgccgccg | 180 |
| tgttccggct gtcagcgcag gggcgcccgg ttcttttgt caagaccgac ctgtccggtg | 240 |
| ccctgaatga actgcaggac gaggcagcgc ggctatcgtg gctggccacg acgggcgttc | 300 |
| cttgcgcagc tgtgctcgac gttgtcactg aagcgggaag ggactggctg ctattgggcg | 360 |
| aagtgccggg gcaggatctc ctgtcatctc accttgctcc tgccgagaaa gtatccatca | 420 |
| tggctgatgc aatgcggcgg ctgcatacgc ttgatccggc tacctgccca ttcgaccacc | 480 |
| aagcgaaaca tcgcatcgag cgagcacgta ctcggatgga agccggtctt gtcgatcagg | 540 |
| atgatctgga cgaagagcat caggggctcg cgccagccga actgttcgcc aggctcaagg | 600 |
| cgcgcatgcc cgacggcgat gatctcgtcg tgacccatgg cgatgcctgc ttgccgaata | 660 |
| tcatggtgga aaatggccgc ttttctggat tcatcgactg tggccggctg ggtgtggcgg | 720 |
| accgctatca ggacatagcg ttggctaccc gtgatattgc tgaagagctt ggcggcgaat | 780 |
| gggctgaccg cttcctcgtg ctttacggta tcgccgctcc cgattcgcag cgcatcgcct | 840 |
| tctatcgcct tcttgacgag ttcttctgag gatccaccat ggttaaccta gacttgtcca | 900 |
| tcttctggat tggccaactt aattaatgta tgaaataaaa ggatgcacac atagtgacat | 960 |
| gctaatcact ataatgtggg catcaaagtt gtgtgttatg tgtaattact agttatctga | 1020 |
| ataaaagaga aagagatcat ccatatttct tatcctaaat gaatgtcacg tgtctttata | 1080 |
| attctttgat gaaccagatg catttcatta accaaatcca tatacatata aatattaatc | 1140 |
| atatataatt aatatcaatt gggttagcaa aacaaatcta gtctaggtgt gttttgcgaa | 1200 |
| tgcggccggg taccgagctc gaattcggcc caagtttgta caaaaaagca ggctccggcc | 1260 |
| agaatggccc ggaccgaagc tggccgctct agaactaggc atggagtcaa agattcaaat | 1320 |
| agaggaccta acagaactcg ccgtaaagac tggcgaacag ttcatacaga gtctcttacg | 1380 |
| actcaatgac aagaagaaaa tcttcgtcaa catggtggag cacgacacgc ttgtctactc | 1440 |
| caaaaatatc aaagatacag tctcagaaga ccaaggggca attgagactt ttcaacaaag | 1500 |
| ggtaatatcc ggaaacctcc tcggattcca ttgcccagct atctgtcact ttattgtgaa | 1560 |
| gatagtggaa aaggaaggtg gctcctacaa atgccatcat tgcgataaag gaaaggccat | 1620 |
| cgttgaagat gcctctgccg acagtggtcc caaagatgga cccccaccca cgaggagcat | 1680 |
| cgtggaaaaa gaagacgttc caaccacgtc ttcaaagcaa gtggattgat gtgatatctc | 1740 |
| cactgacgta agggatgacg cacaatccca ctaagctgac ctagtggatc tcgatgtgta | 1800 |
| gtctacgaga agggttaacc gtctcttcgt gagaataacc gtggcctaaa ataagccga | 1860 |
| tgaggataaa taaatgtggt ggtacagta cttcaagagg tttactcatc aagaggatgc | 1920 |
| ttttccgatg agctctagta gtacatcgga cctcacatac ctccattgtg gtgaaatatt | 1980 |
| ttgtgctcat ttagtgatgg gtaaattttg tttatgtcac tctaggtttt gacatttcag | 2040 |
| ttttgccact cttaggtttt gacaaataat ttccattccg cggcaaaagc aaaacaattt | 2100 |
| tattttactt ttaccactct tagctttcac aatgtatcac aaatgccact ctagaaattc | 2160 |
| tgtttatgcc acagaatgtg aaaaaaaaca ctcacttatt tgaagccaag gtgttcatgg | 2220 |
| catggaaatg tgcataaaag taacgttcgt gtataagaaa aaattgtact cctcgtaaca | 2280 |
| agagacggaa acatcatgag acaatcgcgt ttggaaggct ttgcatcacc tttggatgat | 2340 |

```
gcgcatgaat ggagtcgtct gcttgctagc cttcgcctac cgcccactga gtccgggcgg    2400
caactaccat cggcgaacga cccagctgac ctctaccgac cggacttgaa tgcgctacct    2460
tcgtcagcga cgatggccgc gtacgctggc gacgtgcccc cgcatgcatg gcggcacatg    2520
gcgagctcag accgtgcgtg gctggctaca aatacgtacc ccgtgagtgc cctagctaga    2580
aacttacacc tgcaactgcg agagcgagcg tgtgagtgta gccgatagat ccgcccgcct    2640
cctccgagaa cgtcatcacc gagttcatgc gcttcaaggt gcgcatggag ggcaccgtga    2700
acggccacga gttcgagatc gagggcgagg gcgagggccg ccctacgag ggccacaaca     2760 ccgtgaagct gaaggtgacc aagggcggcc ccctgccctt cgcctgggac atcctgtccc    2820
cccagttcca gtacggctcc aaggtgtacg tgaagcaccc cgccgacatc cccgactaca    2880
agaagctgtc cttccccgag ggcttcaagt gggagcgcgt gatgaacttc gaggacggcg    2940
gcgtggcgac cgtgacccag gactcctccc tgcaggacgg ctgcttcatc tacaaggtga    3000
agttcatcgg cgtgaacttc ccctccgacg gccccgtgat gcagaagaag accatgggct    3060
gggaggcctc caccgagcgc ctgtaccccc gcgacgcgt gctgaagggc gagacccaca     3120
aggccctgaa gctgaaggac ggcggccact acctggtgga gttcaagtcc atctacatgg    3180
ccaagaagcc cgtgcagctg cccggctact actacgtgga cgccaagctg gacatcacct    3240
cccacaacga ggactacacc atcgtggagc agtacgagcg caccgagggc cgccaccacc    3300
tgttcctgta gtgaagaaac tatgtgctgt agtatagccg ctgcccgctg gctagctagc    3360
tagttgagtc atttagcggc gatgattgag taataatgtg tcacgcatca ccatgcatgg    3420
gtggcagtgt cagtgtgagc aatgaccgta atgaacaatt gaaatgaaaa gaaaaagta    3480 ttgttccaaa ttaaacgttt taaccttta ataggttat caataattg atatatgttt       3540 tctgtatatg tctaatttgt tatcatccat ttagatatag acaaaaaaaa tctaagaact    3600
aaaacaaatg ctaatttgaa atgaagggag tatatattgg gataatgtcg atgagatccc    3660
tcgtaatatc accgacatca cacgtgtcca gttaatgtat cagtgatacg tgtattcaca    3720
tttgttgcgc gtaggcgtac ccaacaattt tgatcgacta tcagaaagtc aacggaagcg    3780
agtcgacctc gaggcatgga gtcaaagatt caaatagagg acctaacaga actcgccgta    3840
aagactggcg aacagttcat acagagtctc ttacgactca atgacaagaa gaaaatcttc    3900
gtcaacatgg tggagcacga cacgcttgtc tactccaaaa atatcaaaga tacagtctca    3960
gaagaccaaa gggcaattga acttttcaa caaagggtaa tatccggaaa cctcctcgga    4020
ttccattgcc cagctatctg tcactttatt gtgaagatag tggaaaagga aggtggctcc    4080
tacaaatgcc atcattgcga taaggaaag gccatcgttg aagatgcctc tgccgacagt     4140
ggtcccaaag atggacccc acccacgagg agcatcgtgg aaaaagaaga cgttccaacc    4200
acgtcttcaa agcaagtgga ttgatgtgat atctccactg acgtaaggga tgacgcacaa    4260
tcccactaag ctgaccttcg gagaagcttg catgcctgca ggtcgactct agaggatctg    4320
caccggacac tgtctggtgg cataccagac agtccggtgt gccagatcag ggcaccttc     4380 ggttcctttg ctcctttgct tttgaaccct aactttgatc gtttattggt ttgtgttgaa    4440
cctttatgca cctgtggaat atataatcta gaacaaacta gttagtccaa tcatttgtgt    4500
tgggcattca accaccaaaa ttatttatag gaaaaggtta aaccttattt cccttttcaat   4560 ctccccettt ttggtgattg atgccaacac aaaccaaaga aaatatataa gtgcagaatt    4620
gaactagttt gcataaggta agtgcatagg ttacttagaa ttaaatcaat ttatactttt    4680
acttgatatg catggttgct ttcttttatt ttaacatttt ggaccacatt tgcaccactt    4740
```

```
gttttgttttt ttgcaaatct ttttggaaat tcttttcaa agtcttttgc aaatagtcaa      4800
aggtatatga ataagattgt aagaagcatt ttcaagattt gaaatttctc ccctgtttc       4860 aaatgctttt cctttgacta aacaaaactc ccctgaata aaattctcct cttagctttc       4920
aagagggttt taaatagata tcaattggaa atatatttag atgctaattt tgaaaatata     4980
ccaattgaaa atcaacatac caatttgaaa ttaaacatac caatttaaaa aatttcaaaa     5040
agtggtggtg cggtccttt gctttgggct taatatttct ccccctttgg cattaatcgc      5100
caaaaacgga gactttgtga gccatttata ctttctcccc attggtaaat gaaatatgag      5160
tgaaagatta taccaaattt ggacagtgat gcggagtgac ggcgaaggat aaacgatacc      5220
gttagagtgg agtggaagcc ttgtcttcgc cgaagactcc atttcccttt caatctacga     5280
cttagcatag aaatacactt gaaaacacat tagtcgtagc cacgaaagag atatgatcaa      5340
aggtatacaa atgagctatg tgtgtaatgt ttcaatcaaa gtttcgagaa tcaagaatat     5400
ttagctcatt cctaagtttg ctaaaggttt tatcatctaa tggtttggta aagatatcga      5460
ctaattgttc tttggtgcta acataagcaa tctcgatatc cccctttgt tggtgatccc      5520 tcaaaaagtg ataccgaatg tctatgtgct tagtgcggct gtgttcaacg ggattatccg      5580
ccatgcagat agcactctca ttgtcacata ggagagggac tttgctcaat ttgtagccat      5640
agtccctaag gttttgcctc atccaaagta attgcacaca acaatgtcct gcggcaatat      5700
acttggcttc ggcggtagaa agagctattg agttttgttt ctttgaagtc caagacacca      5760
gggatctccc tagaaactga caagtccctg atgtgctctt cctatcaatt ttacaccctg     5820
cccaatcggc atctgaatat cctattaaat caaaggtgga tcccttgggg taccaaagac      5880
caaatttagg agtgtaaact aaatatctca tgattctttt cacggcccta aggtgaactt      5940
ccttaggatc ggcttggaat cttgcacaca tgcatataga aagcatacta tctggtcgag     6000
atgcacataa atagagtaaa gatcctatca tcgaccggta tacctttggg tctacggatt      6060
tacctcccgt gtcgaggtcg agatgcccat tagttcccat gggtgtcctg atgggcttgg      6120
catccttcat tccaaacttg ttgagtatgt cttgaatgta ctttgtttgg ctgatgaagg      6180
tgccatcttg gagttgcttg acttgaaatc ctagaaaata tttcaacttc cccatcatag     6240
acatctcgaa tttcggaatc atgatcctac taaactcttc acaagtagat tgttagtag     6300 acccaaatat aatatcatca acataaattt ggcatacaaa caaaacttt gaatggtttt     6360 tagtaaagag agtaggatcg gctttactga ctctgaagcc attagtgata agaaaatctc     6420
ttaggcattc ataccatgct gttggggctt gcttgagccc ataaagcgcc tttgagagtt     6480
tataaacatg gttagggtac tcactatctt caaagccgag aggttgctca acatagacct      6540 attcaccccca tttgatcact ttttggtcc ttcaggatct aatagttatg tataatttag      6600
agtctcttgt ttaatggcca gatatttcta attaatctaa gaatttatga tatttttaa      6660 tttttatca tgtctgatga gaattaacat aaaggctcaa ttgggtcctg aattaataat      6720
agagtgaaaa ttaatccaga ggctctatta gaaccttcaa ttagtaatac caagatatat      6780
ataagatagt agagtatagt ttaaatgttg gcattgttca ttctttcttt tgttatttaa      6840
tttatgcttt ccacggtggt tagtggttac ttctgaaggg tccaaataat gcatgaagag      6900
tttgaggaca agaagtctgc cctaaaaata gcgatgcaaa ggcatggtgt ccaagccata      6960
catatagcgc actaattta tcagcagaac aatggtattt ataggtccta gtgcccaggc      7020
aacaagagac acgaataaag catcgatcac gacaccgaga ctctatcagt gatagagtgt     7080
```

```
atataagact ctatcagtga tagagtgaac tctatcagtg atagagttat ggcggcgaca    7140
atggcagtga cgacgatggt gacgaggagc aaggagagct ggtcgtcatt gcaggtcccg    7200
gcggtggcat tcccttggaa gccacgaggt ggcaagaccg gcggcctcga gttccctcgc    7260
cgggcgatgt tcgccagcgt cggcctcaac gtgtgcccgg gcgtcccggc ggggcgcgac    7320
ccgcgggagc ccgatcccaa ggtcgtccgg gcggcctgcg gcctggtcca ggcacaagtc    7380
ctcttccagg ggtttaactg ggagtcgtgc aagcagcagg gaggctggta caacaggctc    7440
aaggcccagg tcgacgacat cgccaaggcc ggcgtcacgc acgtctggct gcctccaccc    7500
tcgcactccg tctcgccaca aggctacatg ccaggccgcc tatacgacct ggacgcgtcc    7560
aagtacggca cggcggcgga gctcaagtcc ctgatagcgg cgttccacgg caggggcgtg    7620
cagtgcgtgg cggacatcgt catcaaccac cggtgcgcgg aaaagaagga cgcgcgcggc    7680
gtgtactgca tcttcgaggg cgggactccc gacgaccgcc tggactgggg ccccgggatg    7740
atctgcagcg acgacacgca gtactcggac gggacggggc accgcgacac gggcgagggg    7800
ttcgcggcgg cgcccgacat cgaccacctc aacccgcgcg tgcagcggga gctctccgcc    7860
tggctcaact ggctcaggtc cgacgccgtg gggttcgacg gctggcgcct cgacttcgcc    7920
aagggctact cgccggccgt cgccagaatg tacgtggaga gcacggggcc gccgagcttc    7980
gtcgtcgcgg agatatggaa ctcgctgagc tacagcgggg acggcaagcc ggcgcccaac    8040
caggaccagt gccggcagga gctgctggac tggacgcggg ccgtcggcgg gcccgccatg    8100
gcgttcgact tccccaccaa gggcctgctg caggcgggcg tgcagggggga gctgtggcgg    8160
ctgcgcgaca gctccggcaa cgcggccggc ctgatcgggt gggcgcccga gaaggccgtc    8220
accttcgtcg acaaccatga caccgggtcg acgcagaagc tctggccgtt cccatccgac    8280
aaggtcatgc agggctacgc ctacatcctc acccatccag gagtcccctg cattttctac    8340
gaccacatgt tcgactggaa cctgaagcag gagatatcca cgctgtctgc catcagggcg    8400
cggaacggca tccgcgccgg gagcaagctg cggatcctcg tggcggacgc ggacgcgtac    8460
gtggccgtcg tcgacgagaa ggtcatggtg aagatcggga caaggtacgg cgtgagcagc    8520
gtggtcccgt cggatttcca cccggcgcg cacggcaagg actactgcgt ctgggagaaa    8580
gcgagcctcc gcgtcccggc ggggcgccac ctctagcagc tcagattgct cagtcttgtg    8640
ctgcattgca aacacagcag cacgacactg cataacgtct tttccttgag atctgacaaa    8700
gcagcattag tccgttgatc ggtggaagac cactcgtcag tgttgagttg aatgtttgat    8760
caataaaata cggcaatgct gtaagggttg ttttttatgc cattgataat acactgtact    8820
gttcagttgt tgaactctat ttcttagcca tgccaagtgc ttttcttatt ttgaataaca    8880
ttacagcaaa aagttgaaag acaaaaaaaa aaacccccga acagagtgct ttgggtccca    8940
agctacttta gactgtgttc ggcgttcccc ctaaatttct cccctatat ctcactcact    9000
tgtcacatca gcgttctctt tccccctatat ctccacgtcg acgcggccgc tctagaacta    9060
gtggatcccc cgggctgcag gaattcctcg agaccgtacg tgcgcgcgaa tgcatccaga    9120
tcttccctct agtcaaggcc ttaagcgcgc gttcgaacgc gcggttaagc ttggtcaccc    9180
ggtccgggcc tagaaggccg atctcccggg cacccagctt tcttgtacaa agtggccgtt    9240
aacggatccc ggtgaagttc ctattccgaa gttcctattc tccagaaagt ataggaactt    9300
cgat                                                                9304
```

<210> SEQ ID NO 53
<211> LENGTH: 9325

<212> TYPE: DNA
<213> ORGANISM: artificial sequence
<220> FEATURE:
<223> OTHER INFORMATION: PHP03

<400> SEQUENCE: 53

```
agaagttcct attccgaagt tcctattctc tagaaagtat aggaacttca gatccaccgg      60
ctagaggatc caccatggtt gaacaagatg gattgcacgc aggttctccg gccgcttggg     120
tggagaggct attcggctat gactgggcac aacagacaat cggctgctct gatgccgccg     180
tgttccggct gtcagcgcag ggcgcccgg ttcttttttgt caagaccgac ctgtccggtg     240
ccctgaatga actgcaggac gaggcagcgc ggctatcgtg gctggccacg acgggcgttc     300
cttgcgcagc tgtgctcgac gttgtcactg aagcgggaag ggactggctg ctattgggcg     360
aagtgccggg gcaggatctc ctgtcatctc accttgctcc tgccgagaaa gtatccatca     420
tggctgatgc aatgcggcgg ctgcatacgc ttgatccggc tacctgccca ttcgaccacc     480
aagcgaaaca tcgcatcgag cgagcacgta ctcggatgga agccggtctt gtcgatcagg     540
atgatctgga cgaagagcat caggggctcg cgccagccga actgttcgcc aggctcaagg     600
cgcgcatgcc cgacggcgat gatctcgtcg tgacccatgg cgatgcctgc ttgccgaata     660
tcatggtgga aaatggccgc ttttctggat tcatcgactg tggccggctg ggtgtggcgg     720
accgctatca ggacatagcg ttggctaccc gtgatattgc tgaagagctt ggcggcgaat     780
gggctgaccg cttcctcgtg ctttacggta tcgccgctcc cgattcgcag cgcatcgcct     840
tctatcgcct tcttgacgag ttcttctgag gatccaccat ggttaaccta gacttgtcca     900
tcttctggat tggccaactt aattaatgta tgaaataaaa ggatgcacac atagtgacat     960
gctaatcact ataatgtggg catcaaagtt gtgtgttatg tgtaattact agttatctga    1020
ataaaagaga aagagatcat ccatatttct tatcctaaat gaatgtcacg tgtctttata    1080
attctttgat gaaccagatg catttcatta accaaatcca tatacatata aatattaatc    1140
atatataatt aatatcaatt gggttagcaa acaaatctag tctaggtgt gttttgcgaa     1200
tgcggccggg taccgagctc gaattcggcc caagtttgta caaaaaagca ggctccggcc    1260
agaatggccc ggaccgaagc tggccgctct agaactaggc atggagtcaa agattcaaat    1320
agaggaccta acagaactcg ccgtaaagac tggcgaacag ttcatacaga gtctcttacg    1380
actcaatgac aagaagaaaa tcttcgtcaa catggtggag cacgacacgc ttgtctactc    1440
caaaaatatc aaagatacag tctcagaaga ccaaagggca attgagactt tcaacaaag    1500
ggtaatatcc ggaaacctcc tcggattcca ttgcccagct atctgtcact ttattgtgaa    1560
gatagtggaa aaggaaggtg gctcctacaa atgccatcat tgcgataaag gaaaggccat    1620
cgttgaagat gcctctgccg acagtggtcc caaagatgga cccccaccca cgaggagcat    1680
cgtggaaaaa gaagacgttc caaccacgtc ttcaaagcaa gtggattgat gtgatatctc    1740
cactgacgta agggatgacg cacaatccca ctaagctgac ctagtggatc tcgatgtgta    1800
gtctacgaga agggttaacc gtctcttcgt gagaataacc gtggcctaaa aataagccga    1860
tgaggataaa taaatgtggg tggtacagta cttcaagagg tttactcatc aagaggatgc    1920
ttttccgatg agctctagta gtacatcgga cctcacatac ctccattgtg gtgaaatatt    1980
ttgtgctcat ttagtgatgg gtaaattttg tttatgtcac tctaggtttt gacatttcag    2040
ttttgccact cttaggtttt gacaaataat ttccattccg cggcaaaagc aaaacaattt    2100
tattttactt ttaccactct tagctttcac aatgtatcac aaatgccact ctagaaattc    2160
```

```
tgtttatgcc acagaatgtg aaaaaaaaca ctcacttatt tgaagccaag gtgttcatgg    2220
catggaaatg tgacataaag taacgttcgt gtataagaaa aaattgtact cctcgtaaca    2280
agagacggaa acatcatgag acaatcgcgt ttggaaggct ttgcatcacc tttggatgat    2340
gcgcatgaat ggagtcgtct gcttgctagc cttcgcctac cgcccactga gtccgggcgg    2400
caactaccat cggcgaacga cccagctgac ctctaccgac cggacttgaa tgcgctacct    2460
tcgtcagcga cgatggccgc gtacgctggc gacgtgcccc cgcatgcatg gcggcacatg    2520
gcgagctcag accgtgcgtg gctggctaca aatacgtacc ccgtgagtgc cctagctaga    2580
aacttacacc tgcaactgcg agagcgagcg tgtgagtgta gccgatagat ccgcccatgg    2640
cccacagcaa gcacggcctg aaggaggaga tgaccatgaa gtaccacatg gagggctgcg    2700
tgaacggcca aagttcgtg atcaccggca agggcatcgg ctaccccttc aagggcaagc    2760
agaccatcaa cctgtgcgtg atcgagggcg gcccctgcc cttcagcgag gacatcctga    2820
gcgccggctt caagtacggc gaccggatct tcaccgagta ccccaggac atcgtggact    2880 acttcaagaa cagctgcccc gccggctaca cctgggccg gagcttcctg ttcgaggacg    2940
gcgccgtgtg catctgtaac gtggacatca ccgtgagcgt gaaggagaac tgcatctacc    3000
acaagagcat cttcaacggc gtgaacttcc ccgccgacgg ccccgtgatg aagaagatga    3060
ccaccaactg ggaggccagc tgcgagaaga tcatgcccgt gcctaagcag gcatcctga    3120 agggcgacgt gagcatgtac ctgctgctga aggacggcgg ccggtaccgg tgccagttcg    3180
acaccgtgta caaggccaag agcgtgccca gcaagatgcc cgagtggcac ttcatccagc    3240
acaagctgct gcgggaggac cggagcgacg ccaagaacca gaagtggcag ctgaccgagc    3300
acgccatcgc cttccccagc gccctggcct gatgaagaaa ctatgtgctg tagtatagcc    3360
gctgcccgct ggctagctag ctagttgagt catttagcgg cgatgattga gtaataatgt    3420
gtcacgcatc accatgcatg ggtggcagtg tcagtgtgag caatgacctg aatgaacaat    3480
tgaaatgaaa agaaaaaagt attgttccaa attaaacgtt ttaaccttttt aataggttta    3540 tacaataatt gatatatgtt ttctgtatat gtctaatttg ttatcatcca tttagatata    3600
gacaaaaaaa atctaagaac taaaacaaat gctaatttga aatgaaggga gtatatattg    3660
ggataatgtc gatgagatcc ctcgtaatat caccgacatc acacgtgtcc agttaatgta    3720
tcagtgatac gtgtattcac atttgttgcg cgtaggcgta cccaacaatt ttgatcgact    3780
atcagaaagt caacggaagc gagtcgacct cgaggcatgg agtcaaagat tcaaatagag    3840
gacctaacag aactcgccgt aaagactggc gaacagttca tacagagtct cttacgactc    3900
aatgacaaga agaaaatctt cgtcaacatg gtggagcacg acacgcttgt ctactccaaa    3960
aatatcaaag atacagtctc agaagaccaa agggcaattg actttttca acaaagggta    4020 atatccggaa acctcctcgg attccattgc ccagctatct gtcactttat tgtgaagata    4080
gtggaaaagg aaggtggctc ctacaaatgc catcattgcg ataaaggaaa ggccatcgtt    4140
gaagatgcct ctgccgacag tggtcccaaa gatggacccc cacccacgag gagcatcgtg    4200
gaaaaagaag acgttccaac cacgtcttca aagcaagtgg attgatgtga tatctccact    4260
gacgtaaggg atgacgcaca atcccactaa gctgacttc ggagaagctt gcatgcctgc    4320
aggtcgactc tagaggatct gcaccggaca ctgtctggtg gcataccaga cagtccggtg    4380
tgccagatca gggcacccctt cggttccttt gctcctttgc ttttgaaccc taactttgat    4440
cgtttattgg tttgtgttga acctttatgc acctgtggaa tatataatct agaacaaact    4500
agttagtcca atcatttgtg ttgggcattc aaccaccaaa attatttata ggaaaaggtt    4560
```

```
aaaccttatt tcccttttcaa tctcccccctt tttggtgatt gatgccaaca caaaccaaag    4620
aaaatatata agtgcagaat tgaactagtt tgcataaggt aagtgcatag gttacttaga    4680
attaaatcaa tttatacttt tacttgatat gcatggttgc tttcttttat tttaacattt    4740
tggaccacat ttgcaccact tgttttgttt ttgcaaatc tttttggaaa ttcttttca    4800 aagtcttttg caaatagtca aaggtatatg aataagattg taagaagcat tttcaagatt    4860
tgaaatttct ccccctgttt caaatgcttt tcctttgact aaacaaaact cccctgaat    4920 aaaattctcc tcttagcttt caagagggtt ttaaatagat atcaattgga aatatattta    4980
gatgctaatt ttgaaaatat accaattgaa atcaacata ccaatttgaa attaaacata    5040
ccaatttaaa aaatttcaaa agtggtggt gcggtccttt tgctttgggc ttaatatttc    5100
tccccctttg gcattaatcg ccaaaaacgg agactttgtg agccatttat acttctccc    5160 cattggtaaa tgaaatatga gtgaaagatt ataccaaatt tggacagtga tgcggagtga    5220
cggcgaagga taaacgatac cgttagagtg gagtggaagc cttgtcttcg ccgaagactc    5280 catttcccctt tcaatctacg acttagcata gaaatacact tgaaaacaca ttagtcgtag    5340
ccacgaaaga gatatgatca aaggtataca aatgagctat gtgtgtaatg tttcaatcaa    5400
agtttcgaga atcaagaata tttagctcat tcctaagttt gctaaaggtt ttatcatcta    5460
atggtttggt aaagatatcg actaattgtt ctttggtgct aacataagca atctcgatat    5520 caccccctttg ttggtgatcc ctcaaaaagt gataccgaat gtctatgtgc ttagtgcggc    5580
tgtgttcaac gggattatcc gccatgcaga tagcactctc attgtcacat aggagaggga    5640
ctttgctcaa tttgtagcca tagtccctaa ggttttgcct catccaaagt aattgcacac    5700
aacaatgtcc tgcggcaata tacttggctt cggcggtaga aagagctatt gagttttgtt    5760
tctttgaagt ccaagacacc agggatctcc ctagaaactg acaagtccct gatgtgctct    5820
tcctatcaat tttacaccct gcccaatcgg catctgaata tcctattaaa tcaaaggtgg    5880
atcccttggg gtaccaaaga ccaaatttag gagtgtaaac taaatatctc atgattcttt    5940
tcacggccct aaggtgaact tccttaggat cggcttggaa tcttgcacac atgcatatag    6000
aaagcatact atctggtcga gatgcacata aatagagtaa agatcctatc atcgaccggt    6060
ataccttttg gtctacggat ttacctcccg tgtcgaggtc gagatgccca ttagttccca    6120
tgggtgtcct gatgggcttg gcatccttca ttccaaactt gttgagtatg tcttgaatgt    6180
actttgtttg gctgatgaag gtgccatctt ggagttgctt gacttgaaat cctagaaaat    6240
atttcaactt ccccatcata gacatctcga atttcggaat catgatccta ctaaactctt    6300
cacaagtaga tttgttagta gacccaaata taatatcatc aacataaatt tggcatacaa    6360
acaaaacttt tgaaatggtt ttagtaaaga gagtaggatc ggcttactg actctgaagc    6420 cattagtgat aagaaaatct cttaggcatt cataccatgc tgttggggct tgcttgagcc    6480
cataaagcgc ctttgagagt ttataaacat ggttagggta ctcactatct tcaaagccga    6540
gaggttgctc aacatagacc tattcacccc atttgatcac ttttttggtc cttcaggatc    6600
taatagttat gtataattta gagtctcttg tttaatggcc agatatttct aattaatcta    6660
agaatttatg atatttttta atttttatc atgtctgatg agaattaaca taaaggctca    6720
attgggtcct gaattaataa tagagtgaaa attaatccag aggctctatt agaaccttca    6780
attagtaata ccaagatata tataagatag tagagtatag tttaaatgtt ggcattgttc    6840
attcttctct ttgttatttta atttatgctt tccacggtgg ttagtggtta cttctgaagg    6900
```

```
gtccaaataa tgcatgaaga gtttgaggac aagaagtctg ccctaaaaat agcgatgcaa      6960
aggcatggtg tccaagccat acatatagcg cactaatttt atcagcagaa caatggtatt      7020
tataggtcct agtgcccagg caacaagaga cacgaataaa gcatcgatca cgacaccgag      7080
actctatcag tgatagagtg tatataagac tctatcagtg atagagtgaa ctctatcagt      7140
gatagagtta tggcggcgac aatggcagtg acgacgatgg tgacgaggag caaggagagc      7200
tggtcgtcat tgcaggtccc ggcggtggca ttcccttgga agccacgagg tgcaagacc      7260 ggcggcctcg agttccctcg ccgggcgatg ttcgccagcg tcggcctcaa cgtgtgcccg      7320
ggcgtcccgg cggggcgcga cccgcgggag cccgatccca aggtcgtccg gcggcctgc      7380 ggcctggtcc aggcacaagt cctcttccag gggtttaact gggagtcgtg caagcagcag      7440
ggaggctggt acaacaggct caaggcccag gtcgacgaca tcgccaaggc cggcgtcacg      7500
cacgtctggc tgcctccacc ctcgcactcc gtctcgccac aaggctacat gccaggccgc      7560
ctatacgacc tggacgcgtc caagtacggc acggcggcgg agctcaagtc cctgatagcg      7620
gcgttccacg gcaggggcgt gcagtgcgtg gcggacatcg tcatcaacca ccggtgcgcg      7680
gaaaagaagg acgcgcgcgg cgtgtactgc atcttcgagg gcgggactcc cgacgaccgc      7740
ctggactggg gcccggggat gatctgcagc gacgacacga agtactcgga cgggacgggg      7800
caccgcgaca cgggcgaggg gttcgcggcg gcgcccgaca tcgaccacct caacccgcgc      7860
gtgcagcggg agctctccgc ctggctcaac tggctcaggt ccgacgccgt ggggttcgac      7920
ggctggcgcc tcgacttcgc caagggctac tcgccggccg tcgccagaat gtacgtggag      7980
agcacggggc cgccgagctt cgtcgtcgcg gagatatgga actcgctgag ctacagcggg      8040
gacggcaagc cggcgcccaa ccaggaccag tgccggcagg agctgctgga ctggacgcgg      8100
gccgtcggcg ggcccgccat ggcgttcgac ttccccacca agggcctgct gcaggcgggc      8160
gtgcaggggg agctgtggcg gctgcgcgac agctccggca acgggccggg cctgatcggg      8220
tgggcgcccg agaaggccgt caccttcgtc gacaaccatg acaccgggtc gacgcagaag      8280
ctctggccgt tcccatccga caaggtcatg cagggctacg cctacatcct cacccatcca      8340 ggagtccccct gcattttcta cgaccacatg ttcgactgga acctgaagca ggagatatcc      8400
acgctgtctg ccatcagggc gcggaacggc atccgcgccg ggagcaagct gcggatcctc      8460
gtggcggacg cggacgcgta cgtggccgtc gtcgacgaga aggtcatggt gaagatcggg      8520
acaaggtacg gcgtgagcag cgtggtcccg tcggatttcc acccggcggc gcacggcaag      8580
gactactgcg tctgggagaa agcgagcctc cgcgtcccgg cggggcgcca cctctagcag      8640
ctcagattgc tcagtcttgt gctgcattgc aaacacagca gcacgacact gcataacgtc      8700 tttttccttga gatctgacaa agcagcatta gtccgttgat cggtggaaga ccactcgtca      8760
gtgttgagtt gaatgtttga tcaataaaat acggcaatgc tgtaagggtt gttttttatg      8820
ccattgataa tacactgtac tgttcagttg ttgaactcta tttcttagcc atgccaagtg      8880
cttttcttat tttgaataac attacagcaa aaagttgaaa gacaaaaaaa aaaaccccg      8940 aacagagtgc tttgggtccc aagctacttt agactgtgtt cggcgttccc cctaaatttc      9000 tcccccctata tctcactcac ttgtcacatc agcgttctct ttcccctata tctccacgtc      9060
gacgcggccg ctctagaact agtggatccc ccgggctgca ggaattcctc gagaccgtac      9120
gtgcgcgcga atgcatccag atcttccctc tagtcaaggc cttaagcgcg cgttcgaacg      9180
cgcggttaag cttggtcacc cggtccgggc ctagaaggcc gatctcccgg gcacccagct      9240
ttcttgtaca aagtggccgt taacggatcc cggtgaagtt cctattccga agttcctatt      9300
```
ctccagaaag tataggaact tcgat 9325

<210> SEQ ID NO 54
<211> LENGTH: 6755
<212> TYPE: DNA
<213> ORGANISM: artificial sequence
<220> FEATURE:
<223> OTHER INFORMATION: PHP04

<400> SEQUENCE: 54

| | | | | | |
|---|---|---|---|---|---|
| gaagttccta | ttccgaagtt | cctattctct | agaaagtata | ggaacttcag | atccaccggc | 60 |
| tagaggatcc | accatggttg | aacaagatgg | attgcacgca | ggttctccgg | ccgcttgggt | 120 |
| ggagaggcta | ttcggctatg | actgggcaca | acagacaatc | ggctgctctg | atgccgccgt | 180 |
| gttccggctg | tcagcgcagg | ggcgcccggt | tcttttttgtc | aagaccgacc | tgtccggtgc | 240 |
| cctgaatgaa | ctgcaggacg | aggcagcgcg | gctatcgtgg | ctggccacga | cgggcgttcc | 300 |
| ttgcgcagct | gtgctcgacg | ttgtcactga | agcgggaagg | gactggctgc | tattgggcga | 360 |
| agtgccgggg | caggatctcc | tgtcatctca | ccttgctcct | gccgagaaag | tatccatcat | 420 |
| ggctgatgca | atgcggcggc | tgcatacgct | tgatccggct | acctgcccat | tcgaccacca | 480 |
| agcgaaacat | cgcatcgagc | gagcacgtac | tcggatggaa | gccggtcttg | tcgatcagga | 540 |
| tgatctggac | gaagagcatc | aggggctcgc | gccagccgaa | ctgttcgcca | ggctcaaggc | 600 |
| gcgcatgccc | gacggcgatg | atctcgtcgt | gacccatggc | gatgcctgct | tgccgaatat | 660 |
| catggtggaa | aatggccgct | tttctggatt | catcgactgt | ggccggctgg | gtgtggcgga | 720 |
| ccgctatcag | gacatagcgt | tggctacccg | tgatattgct | gaagagcttg | gcggcgaatg | 780 |
| ggctgaccgc | ttcctcgtgc | tttacggtat | cgccgctccc | gattcgcagc | gcatcgcctt | 840 |
| ctatcgcctt | cttgacgagt | tcttctgagg | atccaccatg | gttaacctag | acttgtccat | 900 |
| cttctggatt | ggccaactta | attaatgtat | gaaataaaag | gatgcacaca | tagtgacatg | 960 |
| ctaatcacta | taatgtgggc | atcaaagttg | tgtgttatgt | gtaattacta | gttatctgaa | 1020 |
| taaaagagaa | agagatcatc | catatttctt | atcctaaatg | aatgtcacgt | gtctttataa | 1080 |
| ttctttgatg | aaccagatgc | atttcattaa | ccaaatccat | acatataa | atattaatca | 1140 |
| tatataatta | atatcaattg | ggttagcaaa | acaaatctag | tctaggtgtg | ttttgcgaat | 1200 |
| gcggccgggt | accgagctcg | aattcggccc | aagtttgtac | aaaaaagcag | gctccggcca | 1260 |
| gaatggcccg | gaccgaagct | ggccgctcta | gaactagtgg | atctcgatgt | gtagtctacg | 1320 |
| agaagggtta | accgtctctt | cgtgagaata | accgtggcct | aaaaataagc | cgatgaggat | 1380 |
| aaataaaatg | tggtggtaca | gtacttcaag | aggtttactc | atcaagagga | tgcttttccg | 1440 |
| atgagctcta | gtagtacatc | ggacctcaca | tacctccatt | gtggtgaaat | attttgtgct | 1500 |
| catttagtga | tgggtaaatt | tgttttatgt | cactctaggt | tttgacattt | cagttttgcc | 1560 |
| actcttaggt | tttgacaaat | aatttccatt | ccgcggcaaa | agcaaaacaa | ttttatttta | 1620 |
| cttttaccac | tcttagcttt | cacaatgtat | cacaaatgcc | actctagaaa | ttctgtttat | 1680 |
| gccacagaat | gtgaaaaaaa | acactcactt | atttgaagcc | aaggtgttca | tggcatggaa | 1740 |
| atgtgacata | aagtaacgtt | cgtgtataag | aaaaaattgt | actcctcgta | acaagagacg | 1800 |
| gaaacatcat | gagacaatcg | cgtttggaag | gctttgcatc | acctttggat | gatgcgcatg | 1860 |
| aatggagtcg | tctgcttgct | agccttcgcc | taccgcccac | tgagtccggg | cggcaactac | 1920 |
| catcggcgaa | cgacccagct | gacctctacc | gaccggactt | gaatgcgcta | ccttcgtcag | 1980 |

```
cgacgatggc cgcgtacgct ggcgacgtgc ccccgcatgc atggcggcac atggcgagct    2040
cagaccgtgc gtggctggct acaaatacgt accccgtgag tgccctagct agaaacttac    2100
acctgcaact gcgagagcga gcgtgtgagt gtagccgata gatccgcccg gatcgcctcc    2160
tccgagaacg tcatcaccga gttcatgcgc ttcaaggtgc gcatggaggg caccgtgaac    2220
ggccacgagt tcgagatcga gggcgagggc gagggccgcc cctacgaggg ccacaacacc    2280
gtgaagctga aggtgaccaa gggcggcccc ctgcccttcg cctgggacat cctgtccccc    2340
cagttccagt acggctccaa ggtgtacgtg aagcaccccg ccgacatccc cgactacaag    2400
aagctgtcct tccccgaggg cttcaagtgg gagcgcgtga tgaacttcga ggacggcggc    2460
gtggcgaccg tgacccagga ctcctccctg caggacggct gcttcatcta caaggtgaag    2520
ttcatcggcg tgaacttccc ctccgacggc cccgtgatgc agaagaagac catgggctgg    2580
gaggcctcca ccgagcgcct gtaccccgcc gacggcgtgc tgaagggcga gacccacaag    2640
gccctgaagc tgaaggacgg cggccactac ctggtggagt tcaagtccat ctacatggcc    2700
aagaagcccg tgcagctgcc cggctactac tacgtggacg ccaagctgga catcacctcc    2760
cacaacgagg actacaccat cgtggagcag tacgagcgca ccgagggccg ccaccacctg    2820
ttcctgtagc cccactgaag aaactatgtg ctgtagtata gccgctgccc gctggctagc    2880
tagctagttg agtcatttag cggcgatgat tgagtaataa tgtgtcacgc atcaccatgc    2940
atgggtggca gtgtcagtgt gagcaatgac ctgaatgaac aattgaaatg aaaagaaaaa    3000
agtattgttc caaattaaac gttttaacct tttaataggt ttatacaata attgatatat    3060
gttttctgta tatgtctaat ttgttatcat ccatttagat atagacaaaa aaaatctaag    3120
aactaaaaca aatgctaatt tgaaatgaag ggagtatata ttgggataat gtcgatgaga    3180
tccctcgtaa tatcaccgac atcacacgtg tccagttaat gtatcagtga tacgtgtatt    3240
cacatttgtt gcgcgtaggc gtacccaaca attttgatcg actatcagaa agtcaacgga    3300
agcgagtcga cctcgagggg gggccccggc cgaagcttgc atgcctgcag gtcgactcta    3360
gaggatctgc accggacact gtctggtggc ataccagaca gtccggtgtg ccagatcagg    3420
gcacccttcg gttcctttgc tccttttgct ttgaacccta actttgatcg tttattggtt    3480
tgtgttgaac ctttatgcac ctgtggaata tataatctag aacaaactag ttagtccaat    3540
catttgtgtt gggcattcaa ccaccaaaat tatttatagg aaaaggttaa acctatttc     3600 cctttcaatc tccccctttt tggtgattga tgccaacaca aaccaaagaa aatatataag    3660
tgcagaattg aactagtttg cataaggtaa gtgcataggt tacttagaat taaatcaatt    3720
tatactttta cttgatatgc atggttgctt tcttttattt taacattttg gaccacattt    3780
gcaccacttg ttttgttttt tgcaaatctt tttggaaatt cttttttcaaa gtcttttgca    3840 aatagtcaaa ggtatatgaa taagattgta agaagcattt tcaagatttg aaatttctcc    3900
ccctgtttca aatgcttttc ctttgactaa acaaaactcc ccctgaataa aattctcctc    3960
ttagctttca agagggtttt aaatagatat caattggaaa tatatttaga tgctaatttt    4020
gaaaatatac caattgaaaa tcaacatacc aatttgaaat taaacatacc aatttaaaaa    4080
atttcaaaaa gtggtggtgc ggtccttttg ctttgggctt aatatttctc cccctttggc    4140
attaatcgcc aaaaacggag actttgtgag ccatttatac tttctcccca ttggtaaatg    4200
aaatatgagt gaaagattat accaaatttg acagtgatg cggagtgacg gcgaaggata    4260
aacgataccg ttagagtgga gtggaagcct tgtcttcgcc gaagactcca tttccctttc    4320
aatctacgac ttagcataga aatacacttg aaaacacatt agtcgtagcc acgaaagaga    4380
```

```
tatgatcaaa ggtatacaaa tgagctatgt gtgtaatgtt tcaatcaaag tttcgagaat     4440
caagaatatt tagctcattc ctaagtttgc taaaggtttt atcatctaat ggtttggtaa     4500
agatatcgac taattgttct ttggtgctaa cataagcaat ctcgatatca ccctttgtt      4560 ggtgatccct caaaaagtga taccgaatgt ctatgtgctt agtgcggctg tgttcaacgg     4620
gattatccgc catgcagata gcactctcat tgtcacatag gagagggact ttgctcaatt    4680
tgtagccata gtccctaagg ttttgcctca tccaaagtaa ttgcacacaa caatgtcctg    4740
cggcaatata cttggcttcg gcggtagaaa gagctattga gttttgtttc tttgaagtcc    4800
aagacaccag ggatctccct agaaactgac aagtccctga tgtgctcttc ctatcaattt    4860
tacaccctgc ccaatcggca tctgaatatc ctattaaatc aaaggtggat cccttggggt    4920
accaaagacc aaatttagga gtgtaaacta aatatctcat gattcttttc acggccctaa    4980
ggtgaacttc cttaggatcg gcttggaatc ttgcacacat gcatatagaa agcatactat    5040
ctggtcgaga tgcacataaa tagagtaaag atcctatcat cgaccggtat accttttggt    5100
ctacggattt acctcccgtg tcgaggtcga gatgcccatt agttcccatg ggtgtcctga    5160
tgggcttggc atccttcatt ccaaacttgt tgagtatgtc ttgaatgtac tttgtttggc    5220
tgatgaaggt gccatcttgg agttgcttga cttgaaatcc tagaaaatat ttcaacttcc    5280
ccatcataga catctcgaat ttcggaatca tgatcctact aaactcttca caagtagatt    5340
tgttagtaga cccaaatata atatcatcaa cataaatttg gcatacaaac aaaacttttg    5400
aaatggtttt agtaaagaga gtaggatcgg ctttactgac tctgaagcca ttagtgataa    5460
gaaaatctct taggcattca taccatgctg ttggggcttg cttgagccca taaagcgcct    5520
ttgagagttt ataaacatgg ttagggtact cactatcttc aaagccgaga ggttgctcaa    5580
catagaccta ttcaccccat ttgatcactt ttttggtcct tcaggatcta atagttatgt    5640
ataatttaga gtctcttgtt taatggccag atatttctaa ttaatctaag aatttatgat    5700
attttttaat tttttatcat gtctgatgag aattaacata aaggctcaat tgggtcctga    5760
attaataata gagtgaaaat taatccagag gctctattag aaccttcaat tagtaatacc    5820
aagatatata taagatagta gagtatagtt taaatgttgg cattgttcat tctttctttt    5880
gttatttaat ttatgctttc cacggtggtt agtggttact tctgaagggt ccaaataatg    5940
catgaagagt ttgaggacaa gaagtctgcc ctaaaaatag cgatgcaaag gcatggtgtc    6000
caagccatac atatagcgca ctaatttat cagcagaaca atggtattta taggtcctag    6060
tgcccaggca acaagagaca cgaataaagc atcgatcacg acaccagaat gatcaagatc    6120
gccacccgca agtacctcgg caagcagaac gtgtacgaca tcggcgtgga gagggaccac    6180
aacttcgcgc tgaagaacgg gttcatcgcc agcaactgcg accaaccaag aaccatcgac    6240
atgaaagcca gaggaggcaa aagactcgag agagtcccag aaacaatcat gaacgaagtc    6300
ctcggaagac tcagcaccat actcacatag tgctagactt gtccatcttc tggattggcc    6360
aacttaatta atgtatgaaa taaaaggatg cacacatagt gacatgctaa tcactataat    6420
gtgggcatca aagttgtgtg ttatgtgtaa ttactagtta tctgaataaa agagaaagag    6480
atcatccata tttcttatcc taaatgaatg tcacgtgtct ttataattct ttgatgaacc    6540
agatgcattt cattaaccaa atccatatac atataaatat taatcatata taattaatat    6600
caattgggtt agcaaaacaa atctagggtc acccggtccg ggcctagaag gccgatctcc    6660
cgggcaccca gctttcttgt acaaagtggc cgttaacgga tcccggtgaa gttcctattc    6720
```
cgaagttcct attctccaga aagtatagga acttc                                    6755

<210> SEQ ID NO 55
<211> LENGTH: 7250
<212> TYPE: DNA
<213> ORGANISM: artificial sequence
<220> FEATURE:
<223> OTHER INFORMATION: PHP05

<400> SEQUENCE: 55

```
gaagttccta ttccgaagtt cctattctct agaaagtata ggaacttcag atccaccggc      60
tagaggatcc accatggttg aacaagatgg attgcacgca ggttctccgg ccgcttgggt     120
ggagaggcta ttcggctatg actgggcaca acagacaatc ggctgctctg atgccgccgt     180
gttccggctg tcagcgcagg ggcgcccggt tctttttgtc aagaccgacc tgtccggtgc     240
cctgaatgaa ctgcaggacg aggcagcgcg gctatcgtgg ctggccacga cgggcgttcc     300
ttgcgcagct gtgctcgacg ttgtcactga agcgggaagg gactggctgc tattgggcga     360
agtgccgggg caggatctcc tgtcatctca ccttgctcct gccgagaaag tatccatcat     420
ggctgatgca atgcggcggc tgcatacgct tgatccggct acctgcccat tcgaccacca     480
agcgaaacat cgcatcgagc gagcacgtac tcggatggaa gccggtcttg tcgatcagga     540
tgatctggac gaagagcatc aggggctcgc gccagccgaa ctgttcgcca ggctcaaggc     600
gcgcatgccc gacggcgatg atctcgtcgt gacccatggc gatgcctgct tgccgaatat     660
catggtggaa aatggccgct tttctggatt catcgactgt ggccggctgg gtgtggcgga     720
ccgctatcag gacatagcgt tggctacccg tgatattgct gaagagcttg gcggcgaatg     780
ggctgaccgc ttcctcgtgc tttacggtat cgccgctccc gattcgcagc gcatcgcctt     840
ctatcgcctt cttgacgagt tcttctgagg atccaccatg gttaacctag acttgtccat     900
cttctggatt ggccaactta attaatgtat gaaataaaag gatgcacaca tagtgacatg     960
ctaatcacta taatgtgggc atcaaagttg tgtgttatgt gtaattacta gttatctgaa    1020
taaaagagaa agagatcatc catatttctt atcctaaatg aatgtcacgt gtctttataa    1080
ttctttgatg aaccagatgc atttcattaa ccaaatccat atacatataa atattaatca    1140
tatataatta atatcaattg ggttagcaaa acaaatctag tctaggtgtg ttttgcgaat    1200
gcggccgggt accgagctcg aattcggccc aagtttgtac aaaaaagcag ctccggccca    1260
gaatggcccg gaccgaagct ggccgctcta gaactagtgg atctcgatgt gtagtctacg    1320
agaagggtta accgtctctt cgtgagaata accgtggcct aaaaataagc cgatgaggat    1380
aaataaaatg tggtggtaca gtacttcaag aggtttactc atcaagagga tgcttttccg    1440
atgagctcta gtagtacatc ggacctcaca tacctccatt gtggtgaaat attttgtgct    1500
catttagtga tgggtaaatt tgtttatgt cactctaggt tttgacattt cagttttgcc    1560
actcttaggt tttgacaaat aatttccatt ccgcggcaaa agcaaaacaa ttttattta     1620
cttttaccac tcttagcttt cacaatgtat cacaaatgcc actctagaaa ttctgtttat    1680
gccacagaat gtgaaaaaaa acactcactt atttgaagcc aaggtgttca tggcatggaa    1740
atgtgacata aagtaacgtt cgtgtataag aaaaaattgt actcctcgta acaagagacg    1800
gaaacatcat gagacaatcg cgtttggaag ctttgcatc acctttggat gatgcgcatg     1860
aatggagtcg tctgcttgct agccttcgcc taccgcccac tgagtccggg cggcaactac    1920
catcggcgaa cgacccagct gacctctacc gaccggactt gaatgcgcta ccttcgtcag    1980
cgacgatggc cgcgtacgct ggcgacgtgc ccccgcatgc atggcggcac atggcgagct    2040
```

```
cagaccgtgc gtggctggct acaaatacgt accccgtgag tgccctagct agaaacttac    2100
acctgcaact gcgagagcga gcgtgtgagt gtagccgata gatccgccca tggcccacag    2160
caagcacggc ctgaaggagg agatgaccat gaagtaccac atggagggct gcgtgaacgg    2220
ccacaagttc gtgatcaccg gcgagggcat cggctacccc ttcaagggca agcagaccat    2280
caacctgtgc gtgatcgagg gcggccccct gcccttcagc gaggacatcc tgagcgccgg    2340
cttcaagtac ggcgaccgga tcttcaccga gtaccccag gacatcgtgg actacttcaa     2400
gaacagctgc cccgccggct acacctgggg ccggagcttc ctgttcgagg acggcgccgt    2460
gtgcatctgt aacgtggaca tcaccgtgag cgtgaaggag aactgcatct accacaagag    2520
catcttcaac ggcgtgaact tccccgccga cggccccgtg atgaagaaga tgaccaccaa    2580
ctgggaggcc agctgcgaga agatcatgcc cgtgcctaag cagggcatcc tgaagggcga    2640
cgtgagcatg tacctgctgc tgaaggacgg cggccggtac cggtgccagt tcgacaccgt    2700
gtacaaggcc aagagcgtgc ccagcaagat gcccgagtgg cacttcatcc agcacaagct    2760
gctgcgggag gaccggagcg acgccaagaa ccagaagtgg cagctgaccg agcacgccat    2820
cgccttcccc agcgccctgg cctgaggatc tcgatagga tctgttaacg atccccggcg     2880
gtgtccccca ctgaagaaac tatgtgctgt agtatagccg ctgcccgctg gctagctagc    2940
tagttgagtc atttagcggc gatgattgag taataatgtg tcacgcatca ccatgcatgg    3000
gtggcagtgt cagtgtgagc aatgacctga atgaacaatt gaaatgaaaa gaaaaaagta    3060
ttgttccaaa ttaaacgttt taacctttta ataggtttat acaataattg atatatgttt    3120
tctgtatatg tctaatttgt tatcatccat ttagatatag acaaaaaaaa tctaagaact    3180
aaaacaaatg ctaatttgaa atgaagggag tatatattgg gataatgtcg atgagatccc    3240
tcgtaatatc accgacatca cacgtgtcca gttaatgtat cagtgatacg tgtattcaca    3300
tttgttgcgc gtaggcgtac ccaacaattt tgatcgacta tcagaaagtc aacggaagcg    3360
agtcgacctc gagggggggc ccggccgaa gcttgcatgc ctgcaggtcg actctagagg      3420
atctgcaccg gacactgtct ggtggcatac cagacagtcc ggtgtgccag atcagggcac    3480
ccttcggttc ctttgctcct ttgcttttga accctaactt tgatcgttta ttggtttgtg    3540
ttgaaccttt atgcacctgt ggaatatata atctagaaca aactagttag tccaatcatt    3600
tgtgttgggc attcaaccac caaaattatt tataggaaaa ggttaaacct tatttccctt    3660
tcaatctccc ccttttggt gattgatgcc aacacaaacc aaagaaaata tataagtgca     3720
gaattgaact agtttgcata aggtaagtgc ataggttact tagaattaaa tcaatttata    3780
cttttacttg atatgcatgg ttgctttctt ttatttaac attttggacc acatttgcac     3840
cacttgtttt gttttttgca aatcttttg gaaattcttt ttcaaagtct tttgcaaata     3900
gtcaaaggta tatgaataag attgtaagaa gcattttcaa gatttgaaat ttctccccct    3960
gtttcaaatg cttttccttt gactaaacaa aactcccct gaataaaatt ctcctcttag     4020
cttttcaagag ggttttaaat agatatcaat tggaaatata tttagatgct aatttttgaaa  4080
atataccaat tgaaaatcaa cataccaatt tgaaattaaa cataccaatt taaaaaattt    4140
caaaaagtgg tggtgcggtc cttttgcttt gggcttaata tttctccccc tttggcatta    4200
atcgccaaaa acggagactt tgtgagccat ttatactttc tccccattgg taaatgaaat    4260
atgagtgaaa gattatacca aatttggaca gtgatgcgga gtgacggcga aggataaacg    4320
ataccgttag agtggagtgg aagccttgtc ttcgccgaag actccatttc cctttcaatc    4380
```

```
tacgacttag catagaaata cacttgaaaa cacattagtc gtagccacga aagagatatg    4440
atcaaaggta tacaaatgag ctatgtgtgt aatgtttcaa tcaaagtttc gagaatcaag    4500
aatatttagc tcattcctaa gtttgctaaa ggttttatca tctaatggtt tggtaaagat    4560
atcgactaat tgttctttgg tgctaacata agcaatctcg atatcacccc tttgttggtg    4620
atccctcaaa aagtgatacc gaatgtctat gtgcttagtg cggctgtgtt caacgggatt    4680
atccgccatg cagatagcac tctcattgtc acataggaga gggactttgc tcaatttgta    4740
gccatagtcc ctaaggtttt gcctcatcca agtaattgc acacaacaat gtcctgcggc      4800
aatatacttg gcttcggcgg tagaaagagc tattgagttt tgtttctttg aagtccaaga    4860
caccagggat ctccctagaa actgacaagt ccctgatgtg ctcttcctat caattttaca    4920
ccctgcccaa tcggcatctg aatatcctat taaatcaaag gtggatccct ggggtacca      4980 aagaccaaat ttaggagtgt aaactaaata tctcatgatt cttttcacgg ccctaaggtg    5040
aacttcctta ggatcggctt ggaatcttgc acacatgcat atagaaagca tactatctgg    5100
tcgagatgca cataaataga gtaaagatcc tatcatcgac cggtataccct tttggtctac    5160 ggatttacct cccgtgtcga ggtcgagatg cccattagtt cccatgggtg tcctgatggg    5220
cttggcatcc ttcattccaa acttgttgag tatgtcttga atgtactttg tttggctgat    5280
gaaggtgcca tcttggagtt gcttgacttg aaatcctaga aaatatttca acttccccat    5340
catagacatc tcgaatttcg gaatcatgat cctactaaac tcttcacaag tagatttgtt    5400
agtagaccca aatataatat catcaacata aatttggcat acaaacaaaa cttttgaaat    5460
ggttttagta aagagagtag gatcggcttt actgactctg aagccattag tgataagaaa    5520
atctcttagg cattcatacc atgctgttgg ggcttgcttg agcccataaa gcgcctttga    5580
gagtttataa acatggttag ggtactcact atccttcaaag ccgagaggtt gctcaacata    5640
gacctattca ccccatttga tcacttttt ggtccttcag gatctaatag ttatgtataa      5700
tttagagtct cttgtttaat ggccagatat ttctaattaa tctaagaatt tatgatatttt    5760 tttaattttt tatcatgtct gatgagaatt aacataaagg ctcaattggg tcctgaatta    5820
ataatagagt gaaaattaat ccagaggctc tattagaacc ttcaattagt aataccaaga    5880
tatatataag atagtagagt atagtttaaa tgttggcatt gttcattctt tcttttgtta    5940
tttaatttat gctttccacg gtggttagtg gttacttctg aagggtccaa ataatgcatg    6000
aagagtttga ggacaagaag tctgccctaa aaatagcgat gcaaaggcat ggtgtccaag    6060
ccatacatat agcgcactaa ttttatcagc agaacaatgg tatttatagg tcctagtgcc    6120
caggcaacaa gagacacgaa taaagcatcg atcacgacac cagaatgctc aagtaccagc    6180
tcaagaacga gaacggctgg atgcacagga gactcgtcag gaggaaaagc gacatggaga    6240
gaggcgaaat ctggctcgtc agcctcgatc ctacagctgg tcacgaacaa cagggcacca    6300
gacccgtcct catcgtcaca ccagccgcct tcaaccgcgt caccgagactc ccagtcgtcg    6360 tcccagtcac aagcggcggc aacttcgcca gaacagccgg cttcgccgtc agcctcgacg    6420
gagtcggaat caggacaaca ggcgtcgtca ggtgcctttc tttcggaact gagatcctta    6480
ccgttgagta cggaccactt cctattggta agatcgtttc tgaggaaatt aactgctcag    6540
tgtactctgt tgatccagaa ggaagagttt acactcaggc tatcgcacaa tggcacgata    6600
ggggtgaaca agaggttctc gagtacgagc ttgaagatgg atccgttatt cgtgctacct    6660
ctgaccatag attcttgact acagattatc agcttctcgc tatcgaggaa atctttgcta    6720
ggcaacttga tctccttact ttggagaaca tcaagcagac agaagaggct cttgacaacc    6780
```

| | |
|---|---|
| acagacttcc attcccttg ctcgatgctg gaaccatcaa gtgaatgcta gacttgtcca | 6840 |
| tcttctggat tggccaactt aattaatgta tgaaataaaa ggatgcacac atagtgacat | 6900 |
| gctaatcact ataatgtggg catcaaagtt gtgtgttatg tgtaattact agttatctga | 6960 |
| ataaaagaga aagagatcat ccatatttct tatcctaaat gaatgtcacg tgtctttata | 7020 |
| attctttgat gaaccagatg catttcatta accaaatcca tatacatata aatattaatc | 7080 |
| atatataatt aatatcaatt gggttagcaa aacaaatcta gggtcacccg gtccgggcct | 7140 |
| agaaggccga tctcccgggc acccagcttt cttgtacaaa gtggccgtta acggatcccg | 7200 |
| gtgaagttcc tattccgaag ttcctattct ccagaaagta taggaacttc | 7250 |

<210> SEQ ID NO 56
<211> LENGTH: 25
<212> TYPE: DNA
<213> ORGANISM: artificial sequence
<220> FEATURE:
<223> OTHER INFORMATION: RB

<400> SEQUENCE: 56

| | |
|---|---|
| gtttacccgc caatatatcc tgtca | 25 |

<210> SEQ ID NO 57
<211> LENGTH: 26
<212> TYPE: DNA
<213> ORGANISM: artificial sequence
<220> FEATURE:
<223> OTHER INFORMATION: LB

<400> SEQUENCE: 57

| | |
|---|---|
| gtttacacca caatatatcc tgccac | 26 |

<210> SEQ ID NO 58
<211> LENGTH: 34
<212> TYPE: DNA
<213> ORGANISM: artificial sequence
<220> FEATURE:
<223> OTHER INFORMATION: LOXP

<400> SEQUENCE: 58

| | |
|---|---|
| ataacttcgt atagcataca ttatacgaag ttat | 34 |

<210> SEQ ID NO 59
<211> LENGTH: 1176
<212> TYPE: DNA
<213> ORGANISM: Escherichia coli

<400> SEQUENCE: 59

| | |
|---|---|
| atgcagaagc tgatcaactc ggtccagaac tatgcctggg gctccaagac cgccctgacg | 60 |
| gaactctacg gcatggagaa cccgtcgtca caaccgatgg ccgagctgtg gatgggtgct | 120 |
| catccgaagt cctcttctcg cgtgcagaat gcagcaggtg acatcgtgtc gctgcgggat | 180 |
| gtgattgagt cagacaagtc caccttctg ggtgaggctg tggccaagcg cttcggcgaa | 240 |
| ctcccattcc tcttcaaggt gctctgcgcc gcacagccgc tctcaatcca agtccacccc | 300 |
| aacaagcata actccgagat cggattcgcc aaggagaatg cggctggcat cccgatggac | 360 |
| gccgctgaga gaaactacaa agacccgaat cacaagccgg agcttgtctt cgcactcacg | 420 |
| ccatttctcg ctatgaacgc atttcgcgag ttcagcgaga tcgtcagcct gctccagccg | 480 |
| gtggcgggtg ctcatccagc aatcgcgcat ttcttgcagc agcctgatgc cgaaaggctc | 540 |

```
agcgagctgt tcgcgtccct tcttaacatg cagggagagg agaagtcccg cgcacttgca    600
atactcaaga gcgcgctgga ctcacagcaa ggagagccgt ggcaaaccat acggctcatc    660
tccgagttct atcccgagga ctcaggactg ttctcgccgt tgctgctcaa cgtggtcaag    720
ctgaaccccg gagaggcgat gttcttgttc gccgaaactc cgcatgctta cctccaagga    780
gtcgctctgg aagtgatggc caattcggac aacgttcttc gggcaggatt gacgcccaag    840
tacatcgaca tcccggaact cgtggccaat gttaagtttg aagcgaagcc tgccaaccag    900
ctgcttacgc agcctgttaa gcagggagcc gaactggatt ccctattcc ggtggacgac     960 ttcgcattct ccctccacga cctctcagac aaggagacga ccatctctca gcaaagcgct   1020
gcgattctgt tctgcgtgga aggcgatgcg accctgtgga agggctcaca gcagcttcag   1080
ctgaagcctg gcgagtccgc cttcatcgcc gctaacgagt ctcccgtcac cgtgaagggg   1140
catgggaggc tcgctcgggt ctacaacaag ctctag                             1176
```

<210> SEQ ID NO 60
<211> LENGTH: 391
<212> TYPE: PRT
<213> ORGANISM: Escherichia coli

<400> SEQUENCE: 60

```
Met Gln Lys Leu Ile Asn Ser Val Gln Asn Tyr Ala Trp Gly Ser Lys
1               5                   10                  15

Thr Ala Leu Thr Glu Leu Tyr Gly Met Glu Asn Pro Ser Ser Gln Pro
                20                  25                  30

Met Ala Glu Leu Trp Met Gly Ala His Pro Lys Ser Ser Ser Arg Val
            35                  40                  45

Gln Asn Ala Ala Gly Asp Ile Val Ser Leu Arg Asp Val Ile Glu Ser
        50                  55                  60

Asp Lys Ser Thr Leu Leu Gly Glu Ala Val Ala Lys Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys His Asn Ser Glu Ile Gly Phe Ala Lys Glu
            100                 105                 110

Asn Ala Ala Gly Ile Pro Met Asp Ala Ala Glu Arg Asn Tyr Lys Asp
        115                 120                 125

Pro Asn His Lys Pro Glu Leu Val Phe Ala Leu Thr Pro Phe Leu Ala
130                 135                 140

Met Asn Ala Phe Arg Glu Phe Ser Glu Ile Val Ser Leu Leu Gln Pro
145                 150                 155                 160

Val Ala Gly Ala His Pro Ala Ile Ala His Phe Leu Gln Gln Pro Asp
                165                 170                 175

Ala Glu Arg Leu Ser Glu Leu Phe Ala Ser Leu Leu Asn Met Gln Gly
            180                 185                 190

Glu Glu Lys Ser Arg Ala Leu Ala Ile Leu Lys Ser Ala Leu Asp Ser
        195                 200                 205

Gln Gln Gly Glu Pro Trp Gln Thr Ile Arg Leu Ile Ser Glu Phe Tyr
    210                 215                 220

Pro Glu Asp Ser Gly Leu Phe Ser Pro Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
```

```
            260                 265                 270
Leu Arg Ala Gly Leu Thr Pro Lys Tyr Ile Asp Ile Pro Glu Leu Val
            275                 280                 285

Ala Asn Val Lys Phe Glu Ala Lys Pro Ala Asn Gln Leu Leu Thr Gln
            290                 295                 300

Pro Val Lys Gln Gly Ala Glu Leu Asp Phe Pro Ile Pro Val Asp Asp
305                 310                 315                 320

Phe Ala Phe Ser Leu His Asp Leu Ser Asp Lys Glu Thr Thr Ile Ser
                325                 330                 335

Gln Gln Ser Ala Ala Ile Leu Phe Cys Val Glu Gly Asp Ala Thr Leu
            340                 345                 350

Trp Lys Gly Ser Gln Gln Leu Gln Leu Lys Pro Gly Glu Ser Ala Phe
            355                 360                 365

Ile Ala Ala Asn Glu Ser Pro Val Thr Val Lys Gly His Gly Arg Leu
            370                 375                 380

Ala Arg Val Tyr Asn Lys Leu
385                 390

<210> SEQ ID NO 61
<211> LENGTH: 34
<212> TYPE: DNA
<213> ORGANISM: artificial sequence
<220> FEATURE:
<223> OTHER INFORMATION: ALL STOPS

<400> SEQUENCE: 61
taagtgacta gggtcacgtg accctagtca ctta                               34

<210> SEQ ID NO 62
<211> LENGTH: 980
<212> TYPE: DNA
<213> ORGANISM: Sorghum bicolor

<400> SEQUENCE: 62
gccgtcaaca gccagggtga ttagagcccc agcatgcaaa atgatcacct ggtcgctcat     60
ccttgactaa agcatggctc ggcggtcgct gtttacctat atccctatag taggtactcc    120
tgtacataaa gcctgaaaaa atgggttcag ttgtttatcg aactctgcca aatttgcttt    180
tgcatataat gtaaaattca gctagctctg ctaagctcct cgcttcagtt cgacagaact    240
gcaattgata ttgatgttat ggaaattgat attggaacaa tcagcaatat tatgcttata    300
ttcatttctt gggcgtgctc tactctgtgc cgatgatatc atccgatggg ttttgtactt    360
cttacttatg aagtgaacga ataggttg cctggtccca gttctcagct tgatgttatg     420
ataatcatat gtgatttcag ttctttgtct ggcattggtc tgtttttgtg tctgtgtctg    480
tgggctgtgg ctctgtgtgt tgataactcg agcttgattg catcagtgaa ctgcgactta    540
caacagcaga cagagtgtta gcagcaggga aggagaatag agaaattagg gagtaaagag    600
aacatagttg cctttcagag gacagcttag caagataaca aaattatgtt ctctcctttt    660
aaggattaca gaggcatagc ctcagcgacg cgcgtgctag cggatccagt tatcatcatc    720
gtgttgggct tcctgggcct ggcctgccta gcaggcctgt cgacagcttc agaaggggaa    780
ctcgttggcg gattgtccac agtagcacgt actatatgca gaaaaagtcc ttatgtctct    840
cttatcatta gcctattaat catattaatt cagtccacat aggaccgaat ttataactta    900
acaatctttt agtttcctga gcaatatcgt taaatcaaaa catattcttg taccaaattt    960
tgctatcaac ggttcaacgc                                               980
```

<210> SEQ ID NO 63
<211> LENGTH: 108
<212> TYPE: DNA
<213> ORGANISM: Nostoc punctiforme

<400> SEQUENCE: 63

```
atgatcaaga tcgccacccg caagtacctc ggcaagcaga acgtgtacga catcggcgtg      60
gagagggacc acaacttcgc gctgaagaac gggttcatcg ccagcaac                 108
```

<210> SEQ ID NO 64
<211> LENGTH: 36
<212> TYPE: PRT
<213> ORGANISM: Nostoc punctiforme

<400> SEQUENCE: 64

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn
        35

<210> SEQ ID NO 65
<211> LENGTH: 373
<212> TYPE: DNA
<213> ORGANISM: Nostoc punctiforme

<400> SEQUENCE: 65

```
tgcctttctt tcggaactga gatccttacc gttgagtacg gaccacttcc tattggtaag      60
atcgtttctg aggaaattaa ctgctcagtg tactctgttg atccagaagg aagagtttac     120
actcaggcta tcgcacaatg gcacgatagg ggtgaacaag aggttctcga gtacgagctt     180
gaagatggat ccgttattcg tgctacctct gaccatagat tcttgactac agattatcag     240
cttctcgcta tcgaggaaat ctttgctagg caacttgatc tccttacttt ggagaacatc     300
aagcagacag aagaggctct tgacaaccac agacttccat tcccttttgct cgatgctgga     360
accatcaagt gaa                                                        373
```

<210> SEQ ID NO 66
<211> LENGTH: 123
<212> TYPE: PRT
<213> ORGANISM: Nostoc punctiforme

<400> SEQUENCE: 66

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu

```
                    100                 105                 110
Pro Phe Pro Leu Leu Asp Ala Gly Thr Ile Lys
            115                 120

<210> SEQ ID NO 67
<211> LENGTH: 288
<212> TYPE: DNA
<213> ORGANISM: Escherichia coli

<400> SEQUENCE: 67
atgctcaagt accagctcaa gaacgagaac ggctggatgc acaggagact cgtcaggagg    60
aaaagcgaca tggagagagg cgaaatctgg ctcgtcagcc tcgatcctac agctggtcac   120
gaacaacagg gcaccagacc cgtcctcatc gtcacaccag ccgccttcaa ccgcgtcacc   180
agactcccag tcgtcgtccc agtcacaagc ggcggcaact cgccagaaac agccggcttc   240
gccgtcagcc tcgacggagt cggaatcagg acaacaggcg tcgtcagg              288

<210> SEQ ID NO 68
<211> LENGTH: 96
<212> TYPE: PRT
<213> ORGANISM: Escherichia coli

<400> SEQUENCE: 68

Met Leu Lys Tyr Gln Leu Lys Asn Glu Asn Gly Trp Met His Arg Arg
1               5                   10                  15

Leu Val Arg Arg Lys Ser Asp Met Glu Arg Gly Glu Ile Trp Leu Val
            20                  25                  30

Ser Leu Asp Pro Thr Ala Gly His Glu Gln Gln Gly Thr Arg Pro Val
        35                  40                  45

Leu Ile Val Thr Pro Ala Ala Phe Asn Arg Val Thr Arg Leu Pro Val
    50                  55                  60

Val Val Pro Val Thr Ser Gly Gly Asn Phe Ala Arg Thr Ala Gly Phe
65                  70                  75                  80

Ala Val Ser Leu Asp Gly Val Gly Ile Arg Thr Thr Gly Val Val Arg
                85                  90                  95

<210> SEQ ID NO 69
<211> LENGTH: 114
<212> TYPE: DNA
<213> ORGANISM: Escherichia coli

<400> SEQUENCE: 69
tgcgaccaac caagaaccat cgacatgaaa gccagaggag caaaagact cgagagagtc     60 ccagaaacaa tcatgaacga agtcctcgga agactcagca ccatactcac atag         114

<210> SEQ ID NO 70
<211> LENGTH: 37
<212> TYPE: PRT
<213> ORGANISM: Escherichia coli

<400> SEQUENCE: 70

Cys Asp Gln Pro Arg Thr Ile Asp Met Lys Ala Arg Gly Gly Lys Arg
1               5                   10                  15

Leu Glu Arg Val Pro Glu Thr Ile Met Asn Glu Val Leu Gly Arg Leu
            20                  25                  30

Ser Thr Ile Leu Thr
        35
```

<210> SEQ ID NO 71
<211> LENGTH: 690
<212> TYPE: DNA
<213> ORGANISM: Anemonia majano

<400> SEQUENCE: 71

```
atggccctgt ccaacaagtt catcggcgac gacatgaaga tgacgtacca catggacggg      60
tgcgtcaacg gccactactt caccgtcaag ggcgaagggt ccggtaagcc atacgagggc     120
acgcagacct ccacattcaa ggtcacgatg gctaacggtg gtccgctggc cttctcattc     180
gatatcctga gcaccgtctt catgtacggg aacaggtgct tcacggcgta cccgacctca     240
atgccagact acttcaagca ggccttcccg gacggcatgt cgtacgagag gaccttcacc     300
tacgaggacg gtggcgtggc gactgcttcg tgggagatct ccctcaaggg caactgcttc     360
gaacacaagt cgacgttcca cggcgtgaat ttcccagcgg acgggccagt catggcaaag     420
aagacgactg gctgggaccc gagcttcgag aagatgacgg tctgcgacgg catcctcaag     480
ggcgacgtta cggctttcct catgctgcag ggcggaggga attataggtg ccagttccac     540
accagctaca agacgaagaa gccggtcacg atgccgccga accacgtcgt cgagcacagg     600
atagcgagga ccgaccttga caagggcggc aactcggtgc agctcactga gcacgccgtc     660
gcacacatca cgtcagtcgt gccgttctag                                     690
```

<210> SEQ ID NO 72
<211> LENGTH: 229
<212> TYPE: PRT
<213> ORGANISM: Anemonia majano

<400> SEQUENCE: 72

Met Ala Leu Ser Asn Lys Phe Ile Gly Asp Asp Met Lys Met Thr Tyr
1               5                   10                  15

His Met Asp Gly Cys Val Asn Gly His Tyr Phe Thr Val Lys Gly Glu
            20                  25                  30

Gly Ser Gly Lys Pro Tyr Glu Gly Thr Gln Thr Ser Thr Phe Lys Val
        35                  40                  45

Thr Met Ala Asn Gly Gly Pro Leu Ala Phe Ser Phe Asp Ile Leu Ser
    50                  55                  60

Thr Val Phe Met Tyr Gly Asn Arg Cys Phe Thr Ala Tyr Pro Thr Ser
65                  70                  75                  80

Met Pro Asp Tyr Phe Lys Gln Ala Phe Pro Asp Gly Met Ser Tyr Glu
                85                  90                  95

Arg Thr Phe Thr Tyr Glu Asp Gly Gly Val Ala Thr Ala Ser Trp Glu
            100                 105                 110

Ile Ser Leu Lys Gly Asn Cys Phe Glu His Lys Ser Thr Phe His Gly
        115                 120                 125

Val Asn Phe Pro Ala Asp Gly Pro Val Met Ala Lys Lys Thr Thr Gly
    130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Asn Tyr Arg
                165                 170                 175

Cys Gln Phe His Thr Ser Tyr Lys Thr Lys Lys Pro Val Thr Met Pro
            180                 185                 190

Pro Asn His Val Val Glu His Arg Ile Ala Arg Thr Asp Leu Asp Lys
        195                 200                 205

Gly Gly Asn Ser Val Gln Leu Thr Glu His Ala Val Ala His Ile Thr

Ser Val Val Pro Phe
225

<210> SEQ ID NO 73
<211> LENGTH: 2102
<212> TYPE: DNA
<213> ORGANISM: artificial sequence
<220> FEATURE:
<223> OTHER INFORMATION: LTP2 PRO-AMCYAN-GZW64A TERM

<400> SEQUENCE: 73

```
ctctagaact agtggatctc gatgtgtagt ctacgagaag ggttaaccgt ctcttcgtga      60
gaataaccgt ggcctaaaaa taagccgatg aggataaata aaatgtggtg gtacagtact     120
tcaagaggtt tactcatcaa gaggatgctt ttccgatgag ctctagtagt acatcggacc     180
tcacatacct ccattgtggt gaaatatttt gtgctcattt agtgatgggt aaattttgtt     240
tatgtcactc taggttttga catttcagtt ttgccactct taggttttga caaataattt     300
ccattccgcg gcaaaagcaa acaattttta ttttactttt accactctta gctttcacaa     360
tgtatcacaa atgccactct agaaattctg tttatgccac agaatgtgaa aaaaaacact     420
cacttatttg aagccaaggt gttcatggca tggaaatgtg acataaagta acgttcgtgt     480
ataagaaaaa attgtactcc tcgtaacaag agacggaaac atcatgagac aatcgcgttt     540
ggaaggcttt gcatcacctt tggatgatgc gcatgaatgg agtcgtctgc ttgctagcct     600
tcgcctaccg cccactgagt ccgggcggca actaccatcg gcgaacgacc cagctgacct     660
ctaccgaccg gacttgaatg cgctaccttc gtcagcgacg atggccgcgt acgctggcga     720
cgtgccccg catgcatggc ggcacatggc gagctcagac cgtgcgtggc tggctacaaa     780
tacgtacccc gtgagtgccc tagctagaaa cttacacctg caactgcgag agcgagcgtg     840
tgagtgtagc cgagtagatc ccccgggctg aaggtcgact ctagaggatc caccggtcgc     900
caccatggcc ctgtccaaca gttcatcgg cgacgacatg aagatgacgt accacatgga     960
cgggtgcgtc aacggccact acttcaccgt caagggcgaa gggtccggta agccatacga    1020
gggcacgcag acctccacat tcaaggtcac gatggctaac ggtggtccgc tggccttctc    1080
attcgatatc ctgagcaccg tcttcatgta cgggaacagg tgcttcacgg cgtacccgac    1140
ctcaatgcca gactacttca gcaggcctt ccccggacggc atgtcgtacg agaggacctt    1200
cacctacgag gacggtggcg tggcgactgc ttcgtgggag atctccctca agggcaactg    1260
cttcgaacac aagtcgacgt tccacggcgt gaatttccca gcggacgggc cagtcatggc    1320
aaagaagacg actggctggg acccgagctt cgagaagatg acggtctgcg acggcatcct    1380
caagggcgac gttacggctt ttctcatgct gcagggcgga gggaattata ggtgccagtt    1440
ccacaccagc tacaagacga agaagccggt cacgatgccg ccgaaccacg tcgtcgagca    1500
caggatagcg aggaccgacc ttgacaaggg cggcaactcg gtgcagctca ctgagcacgc    1560
cgtcgcacac atcacgtcag tcgtgccgtt ctagttcgaa ggtaccgtta acgaagaaac    1620
tatgtgctgt agtatagccg ctgcccgctg gctaggtagc tagttgagtc atttagcggc    1680
gatgattgag taataatgtg tcacgcatca ccatgcatgg gtggcagtgt cagtgtgagc    1740
aatgacctga atgaacaatt gaaatgaaaa gaaaaaagta ttgttccaaa ttaaacgttt    1800
taacctttta ataggtttat acaataattg atatatgttt tctgtatatg tctaatttgt    1860
tatcatccat ttagatatag acaaaaaaaa tctaagaact aaaacaaatg ctaatttgaa    1920
```

-continued

| | |
|---|---|
| atgaaggag tatatattgg ataatgtcg atgagatccc tcgtaatatc accgacatca | 1980 |
| cacgtgtcca gttaatgtat cagtgatacg tgtattcaca tttgttgcgc gtaggcgtac | 2040 |
| ccaacaattt tgatcgacta tcagaaagtc aacggaagcg agtcgacctc gagggggggc | 2100 |
| cc | 2102 |

```
<210> SEQ ID NO 74
<211> LENGTH: 3042
<212> TYPE: DNA
<213> ORGANISM: artificial sequence
<220> FEATURE:
<223> OTHER INFORMATION: UBI1ZM PRO-UBI1ZM INTRON-AMCYAN-PINII TERM

<400> SEQUENCE: 74
```

| | |
|---|---|
| ctgcagtgca gcgtgacccg gtcgtgcccc tctctagaga taatgagcat tgcatgtcta | 60 |
| agttataaaa aattaccaca tattttttt gtcacacttg tttgaagtgc agtttatcta | 120 |
| tctttataca tatatttaaa ctttactcta cgaataatat aatctatagt actacaataa | 180 |
| tatcagtgtt ttagagaatc atataaatga acagttagac atggtctaaa ggacaattga | 240 |
| gtattttgac aacaggactc tacagtttta tcttttagt gtgcatgtgt tctccttttt | 300 |
| ttttgcaaat agcttcacct atataatact tcatccattt tattagtaca tccatttagg | 360 |
| gtttagggtt aatggttttt atagactaat ttttttagta catctatttt attctatttt | 420 |
| agcctctaaa ttaagaaaac taaaactcta ttttagtttt tttatttaat aatttagata | 480 |
| taaaatagaa taaaataaag tgactaaaaa ttaaacaaat acccctttaag aaattaaaaa | 540 |
| aactaaggaa acatttttct tgtttcgagt agataatgcc agcctgttaa acgccgtcga | 600 |
| cgagtctaac ggacaccaac cagcgaacca gcagcgtcgc gtcgggccaa gcgaagcaga | 660 |
| cggcacggca tctctgtcgc tgcctctgga cccctctcga gagttccgct ccaccgttgg | 720 |
| acttgctccg ctgtcggcat ccagaaattg cgtggcggag cggcagacgt gagccggcac | 780 |
| ggcaggcggc ctcctcctcc tctcacggca cggcagctac gggggattcc tttcccaccg | 840 |
| ctccttcgct ttcccttcct cgcccgccgt aataaataga caccccctcc cacccctctt | 900 |
| tccccaacct cgtgttgttc ggagcgcaca cacacacaac cagatctccc ccaaatccac | 960 |
| ccgtcggcac ctccgcttca aggtacgccg ctcgtcctcc cccccccccc ctctctacct | 1020 |
| tctctagatc ggcgttccgg tccatggtta gggcccggta gttctacttc tgttcatgtt | 1080 |
| tgtgttagat ccgtgtttgt gttagatccg tgctgctagc gttcgtacac ggatgcgacc | 1140 |
| tgtacgtcag acacgttctg attgctaact tgccagtgtt tctctttggg gaatcctggg | 1200 |
| atggctctag ccgttccgca gacgggatcg atttcatgat ttttttttgtt tcgttgcata | 1260 |
| gggtttggtt tgccctttt ctttatttca atatatgccg tgcacttgtt tgtcgggtca | 1320 |
| tcttttcatg cttttttttg tcttggttgt gatgatgtgg tctggttggg cggtcgttct | 1380 |
| agatcggagt agaattctgt ttcaaactac ctggtggatt tattaatttt ggatctgtat | 1440 |
| gtgtgtgcca tacatattca tagttacgaa ttgaagatga tggatggaaa tatcgatcta | 1500 |
| ggataggtat acatgttgat gcgggttta ctgatgcata tacagagatg cttttttgttc | 1560 |
| gcttggttgt gatgatgtgg tgtggttggg cggtcgttca ttcgttctag atcggagtag | 1620 |
| aatactgttt caaactacct ggtgtatttta ttaattttgg aactgtatgt gtgtgtcata | 1680 |
| catcttcata gttacgagtt taagatggat ggaaatatcg atctaggata ggtatacatg | 1740 |
| ttgatgtggg ttttactgat gcatatacat gatggcatat gcagcatcta ttcatatgct | 1800 |
| ctaaccttga gtacctatct attataataa acaagtatgt tttataatta ttttgatctt | 1860 |

| | | | |
|---|---|---|---|
| gatatacttg | gatgatggca | tatgcagcag | ctatatgtgg attttttttag ccctgccttc | 1920 |
| atacgctatt | tatttgcttg | gtactgtttc | ttttgtcgat gctcaccctg ttgtttggtg | 1980 |
| ttacttctgc | aggtcgactc | tagaggatcc | accggtcgcc accatggccc tgtccaacaa | 2040 |
| gttcatcggc | gacgacatga | agatgaccta | ccacatggac ggctgcgtga acggccacta | 2100 |
| cttcaccgtg | aagggcgagg | gcagcggcaa | gcccctacgag ggcacccaga cctccaccttt | 2160 |
| caaggtgacc | atggccaacg | gcggccccct | ggccttctcc ttcgacatcc tgtccaccgt | 2220 |
| gttcatgtac | ggcaaccgct | gcttcaccgc | ctaccccacc agcatgcccg actacttcaa | 2280 |
| gcaggccttc | cccgacggca | tgtcctacga | gagaaccttc acctacgagg acggcggcgt | 2340 |
| ggccaccgcc | agctgggaga | tcagcctgaa | gggcaactgc ttcgagcaca gtccaccttt | 2400 |
| ccacggcgtg | aacttccccg | ccgacggccc | cgtgatggcc aagaagacca ccggctggga | 2460 |
| ccccctccttc | gagaagatga | ccgtgtgcga | cggcatcttg aagggcgacg tgaccgcctt | 2520 |
| cctgatgctg | cagggcggcg | gcaactacag | atgccagttc cacacctcct acaagaccaa | 2580 |
| gaagcccgtg | accatgcccc | ccaaccacgt | ggtggagcac cgcatcgcca gaaccgacct | 2640 |
| ggacaagggc | ggcaacagcg | tgcagctgac | cgagcacgcc gtggcccaca tcacctccgt | 2700 |
| ggtgccttc | tgaagcggcc | gcaacctaga | cttgtccatc ttctggattg gccaacttaa | 2760 |
| ttaatgtatg | aaataaaagg | atgcacacat | agtgacatgc taatcactat aatgtgggca | 2820 |
| tcaaagttgt | gtgttatgtg | taattactag | ttatctgaat aaaagagaaa gagatcatcc | 2880 |
| atatttctta | tcctaaatga | atgtcacgtg | tctttataat tctttgatga accagatgca | 2940 |
| tttcattaac | caaatccata | tacatataaa | tattaatcat atataattaa tatcaattgg | 3000 |
| gttagcaaaa | caaatctagt | ctaggtgtgt | tttgcgaatt cg | 3042 |

<210> SEQ ID NO 75
<211> LENGTH: 2272
<212> TYPE: DNA
<213> ORGANISM: artificial sequence
<220> FEATURE:
<223> OTHER INFORMATION: RAB17 PRO-MOCRE-PINII TERM

<400> SEQUENCE: 75

| | | | |
|---|---|---|---|
| ctatagtatt | ttaaaattgc | attaacaaac | atgtcctaat tggtactcct gagatactat | 60 |
| accctcctgt | tttaaaatag | ttggcattat | cgaattatca ttttacttt taatgttttc | 120 |
| tcttcttta | atatattta | tgaattttaa | tgtattttaa aatgttatgc agttcgctct | 180 |
| ggactttct | gctgcgccta | cacttgggtg | tactgggcct aaattcagcc tgaccgaccg | 240 |
| cctgcattga | ataatggatg | agcaccggta | aaatccgcgt acccaacttt cgagaagaac | 300 |
| cgagacgtgg | cgggccgggc | caccgacgca | cggcaccagc gactgcacac gtcccgccgg | 360 |
| cgtacgtgta | cgtgctgttc | cctcactggc | cgcccaatcc actcatgcat gcccacgtac | 420 |
| accccctgccg | tggcgcgccc | agatcctaat | cctttcgccg ttctgcactt ctgctgccta | 480 |
| taaatggcgg | catcgaccgt | cacctgcttc | accaccggcg agccacatcg agaacacgat | 540 |
| cgagcacaca | agcacgaaga | ctcgtttagg | agaaaccaca aaccaccaag ccgtgcaagc | 600 |
| accaagcttg | gtcacccggt | ccgggcctag | aaggccagct tcaagtttgt acaaaaaagc | 660 |
| aggcttcgaa | ggagatagaa | ccgatccacc | atgtccaacc tgctcacggt tcaccagaac | 720 |
| cttccggctc | ttccagtgga | cgcgacgtcc | gatgaagtca ggaagaacct catggacatg | 780 |
| ttccgcgaca | ggcaagcgtt | cagcgagcac | acctggaaga tgctgctctc cgtctgccgc | 840 |

| | |
|---|---|
| tcctgggctg catggtgcaa gctgaacaac aggaagtggt tccccgctga gcccgaggac | 900 |
| gtgagggatt accttctgta cctgcaagcg cgaggtttgt ttctgcttct acctttgata | 960 |
| tatatataat aattatcatt aattagtagt aatataatat ttcaaatatt tttttcaaaa | 1020 |
| taaaagaatg tagtatatag caattgcttt tctgtagttt ataagtgtgt atattttaat | 1080 |
| ttataacttt tctaatatat gaccaaaaca tggtgatgcc taggtctggc agtgaagacc | 1140 |
| atccagcaac accttggaca actgaacatg cttcacaggc gctccggcct cccgcgcccc | 1200 |
| agcgactcga acgccgtgag cctcgtcatg cgccgcatca ggaaggaaaa cgtcgatgcc | 1260 |
| ggcgaaaggg caaagcaggc cctcgcgttc gagaggaccg atttcgacca ggtccgcagc | 1320 |
| ctgatggaga acagcgacag gtgccaggac attaggaacc tggcgttcct cggaattgca | 1380 |
| tacaacacgc tcctcaggat cgcggaaatt gcccgcattc gcgtgaagga cattagccgc | 1440 |
| accgacggcg gcaggatgct tatccacatt ggcaggacca agacgctcgt tccaccgca | 1500 |
| ggcgtcgaaa aggccctcag cctcggagtg accaagctcg tcgaacgctg gatctccgtg | 1560 |
| tccggcgtcg cggacgaccc aaacaactac ctcttctgcc gcgtccgcaa gaacggggtg | 1620 |
| gctgcccta cgccaccag ccaactcagc acgagggcct tggaaggtat tttcgaggcc | 1680 |
| acccaccgcc tgatctacgg cgcgaaggat gacagcggtc aacgctacct cgcatggtcc | 1740 |
| gggcactccg cccgcgttgg agctgctagg gacatggccc gcgccggtgt ttccatcccc | 1800 |
| gaaatcatgc aggcgggtgg atggacgaac gtgaacattg tcatgaacta cattcgcaac | 1860 |
| cttgacagcg agacgggcgc aatggttcgc ctcctggaag atggtgactg agctagaccc | 1920 |
| agctttcttg tacaaagtgg ccgttaacgg atccagactt gtccatcttc tggattggcc | 1980 |
| aacttaatta atgtatgaaa taaaaggatg cacacatagt gacatgctaa tcactataat | 2040 |
| gtgggcatca aagttgtgtg ttatgtgtaa ttactagtta tctgaataaa agagaaagag | 2100 |
| atcatccata tttcttatcc taaatgaatg tcacgtgtct ttataattct ttgatgaacc | 2160 |
| agatgcattt cattaaccaa atccatatac atataaaatat taatcatata taattaatat | 2220 |
| caattgggtt agcaaaacaa atctagtcta ggtgtgtttt gcgaattgcg gc | 2272 |

<210> SEQ ID NO 76
<211> LENGTH: 10435
<212> TYPE: DNA
<213> ORGANISM: artificial sequence
<220> FEATURE:
<223> OTHER INFORMATION: PHP06

<400> SEQUENCE: 76

| | |
|---|---|
| acctggcgga agttcctatt ccgaagttcc tattctctag aaagtatagg aacttcagat | 60 |
| ccaccggcta gaggatccac catggttgaa caagatggat tgcacgcagg ttctccggcc | 120 |
| gcttgggtgg agaggctatt cggctatgac tgggcacaac agacaatcgg ctgctctgat | 180 |
| gccgccgtgt tccggctgtc agcgcagggg cgcccggttc ttttttgtcaa gaccgacctg | 240 |
| tccggtgccc tgaatgaact gcaggacgag gcagcgcggc tatcgtggct ggccacgacg | 300 |
| ggcgttcctt gcgcagctgt gctcgacgtt gtcactgaag cgggaaggga ctggctgcta | 360 |
| ttgggcgaag tgccggggca ggatctcctg tcatctcacc ttgctcctgc cgagaaagta | 420 |
| tccatcatgg ctgatgcaat gcggcggctg catacgcttg atccggctac ctgcccattc | 480 |
| gaccaccaag cgaaacatcg catcgagcga cacgtactc ggatggaagc cggtcttgtc | 540 |
| gatcaggatg atctggacga agagcatcag gggctcgcgc cagccgaact gttcgccagg | 600 |
| ctcaaggcgc gcatgcccga cggcgatgat ctcgtcgtga cccatggcga tgcctgcttg | 660 |

-continued

| | |
|---|---|
| ccgaatatca tggtggaaaa tggccgcttt tctggattca tcgactgtgg ccggctgggt | 720 |
| gtggcggacc gctatcagga catagcgttg gctacccgtg atattgctga agagcttggc | 780 |
| ggcgaatggg ctgaccgctt cctcgtgctt tacggtatcg ccgctcccga ttcgcagcgc | 840 |
| atcgccttct atcgccttct tgacgagttc ttctgaggat ccaccatggt taacctagac | 900 |
| ttgtccatct tctggattgg ccaacttaat taatgtatga aataaaagga tgcacacata | 960 |
| gtgacatgct aatcactata atgtgggcat caaagttgtg tgttatgtgt aattactagt | 1020 |
| tatctgaata aaagagaaag agatcatcca tatttcttat cctaaatgaa tgtcacgtgt | 1080 |
| ctttataatt ctttgatgaa ccagatgcat ttcattaacc aaatccatat acatataaat | 1140 |
| attaatcata taaattaat atcaattggg ttagcaaaac aaatctagtc taggtgtgtt | 1200 |
| ttgcgaatgc ggccgggtac cgagctcgaa ttcggcccaa gtttgtacaa aaaagcaggc | 1260 |
| tccggccaga atggcccgga ccgaagctgg ccgctctaga actaggcatg gagtcaaaga | 1320 |
| ttcaaataga ggacctaaca gaactcgccg taaagactgg cgaacagttc atacagagtc | 1380 |
| tcttacgact caatgacaag aagaaaatct tcgtcaacat ggtggagcac gacacgcttg | 1440 |
| tctactccaa aaatatcaaa gatacagtct cagaagacca agggcaatt gagactttc | 1500 |
| aacaaagggt aatatccgga aacctcctcg gattccattg cccagctatc tgtcacttta | 1560 |
| ttgtgaagat agtggaaaag gaaggtggct cctacaaatg ccatcattgc gataaaggaa | 1620 |
| aggccatcgt tgaagatgcc tctgccgaca gtggtcccaa agatggaccc ccacccacga | 1680 |
| ggagcatcgt ggaaaaagaa gacgttccaa ccacgtcttc aaagcaagtg gattgatgtg | 1740 |
| atatctccac tgacgtaagg gatgacgcac aatcccacta agctgaccta gtggcagtgc | 1800 |
| agcgtgaccc ggtcgtgccc ctctctagag ataatgagca ttgcatgtct aagttataaa | 1860 |
| aaattaccac atatttttt tgtcacactt gtttgaagtg cagtttatct atctttatac | 1920 |
| atatatttaa actttactct acgaataata taatctatag tactacaata atatcagtgt | 1980 |
| tttagagaat catataaatg aacagttaga catggtctaa aggacaattg agtattttga | 2040 |
| caacaggact ctacagtttt atcttttag tgtgcatgtg ttctcctttt tttttgcaaa | 2100 |
| tagcttcacc tatataatac ttcatccatt ttattagtac atccatttag ggtttagggt | 2160 |
| taatggtttt tatagactaa tttttttagt acatctattt tattctattt tagcctctaa | 2220 |
| attaagaaaa ctaaaactct atttagtttt ttttatttaa taatttagat ataaaataga | 2280 |
| ataaaataaa gtgactaaaa attaaacaaa taccctttaa gaaattaaaa aaactaagga | 2340 |
| aacattttc ttgtttcgag tagataatgc cagcctgtta aacgccgtcg acgagtctaa | 2400 |
| cggacaccaa ccagcgaacc agcagcgtcg cgtcgggcca agcgaagcag acggcacggc | 2460 |
| atctctgtcg ctgcctctgg acccctctcg agagttccgc tccaccgttg acttgctcc | 2520 |
| gctgtcggca tccagaaatt gcgtggcgga gcggcagacg tgagccggca cggcaggcgg | 2580 |
| cctcctcctc ctctcacggc accggcagct acggggatt cctttcccac cgctccttcg | 2640 |
| cttcccttc ctcgcccgcc gtaataaata gacacccct ccacaccctc tttccccaac | 2700 |
| ctcgtgttgt tcggagcgca cacacacaca accagatctc ccccaaatcc acccgtcggc | 2760 |
| acctccgctt caaggtacgc cgctcgtcct cccccccccc cctctctacc ttctctagat | 2820 |
| cggcgttccg gtccatggtt agggccggt agttctactt ctgttcatgt ttgtgttaga | 2880 |
| tccgtgtttg tgttagatcc gtgctgctag cgttcgtaca cggatgcgac ctgtacgtca | 2940 |
| gacacgttct gattgctaac ttgccagtgt ttctctttgg ggaatcctgg gatggctcta | 3000 |

```
gccgttccgc agacgggatc gatttcatga ttttttttgt ttcgttgcat agggtttggt    3060
ttgccctttt cctttatttc aatatatgcc gtgcacttgt ttgtcgggtc atcttttcat    3120 gcttttttt gtcttggttg tgatgatgtg gtctggttgg gcggtcgttc tagatcggag     3180
tagaattctg tttcaaacta cctggtggat ttattaattt tggatctgta tgtgtgtgcc    3240
atacatattc atagttacga attgaagatg atggatggaa atatcgatct aggataggta    3300
tacatgttga tgcgggtttt actgatgcat atacagagat gcttttgtt cgcttggttg     3360 tgatgatgtg gtgtggttgg gcggtcgttc attcgttcta gatcggagta gaatactgtt    3420
tcaaactacc tggtgtattt attaattttg gaactgtatg tgtgtgtcat acatcttcat    3480
agttacgagt ttaagatgga tggaaatatc gatctaggat aggtatacat gttgatgtgg    3540
gttttactga tgcatataca tgatggcata tgcagcatct attcatatgc tctaaccttg    3600
agtacctatc tattataata aacaagtatg ttttataatt attttgatct tgatatactt    3660
ggatgatggc atatgcagca gctatatgtg gatttttta gccctgcctt catacgctat     3720
ttatttgctt ggtactgttt cttttgtcga tgctcaccct gttgtttggt gttacttctg    3780
caggcctcct ccgagaacgt catcaccgag ttcatgcgct tcaaggtgcg catggagggc    3840
accgtgaacg gccacgagtt cgagatcgag ggcgagggcg agggccgccc ctacgagggc    3900
cacaacaccg tgaagctgaa ggtgaccaag ggcggccccc tgcccttcgc ctgggacatc    3960
ctgtcccccc agttccagta cggctccaag gtgtacgtga agcaccccgc cgacatcccc    4020
gactacaaga gctgtccctt ccccgagggc ttcaagtggg agcgcgtgat gaacttcgag    4080
gacggcggcg tggcgaccgt gacccaggac tcctccctgc aggacggctg cttcatctac    4140
aaggtgaagt tcatcggcgt gaacttcccc tccgacggcc ccgtgatgca gaagaagacc    4200
atgggctggg aggcctccac cgagcgcctg taccccgcg acggcgtgct gaagggcgag     4260
acccacaagg ccctgaagct gaaggacggc ggccactacc tggtggagtt caagtccatc    4320
tacatggcca gaagcccgt gcagctgccc ggctactact acgtggacgc caagctggac     4380
atcacctccc acaacgagga ctacaccatc gtggagcagt acgagcgcac cgagggccgc    4440
caccacctgt tcctgtaggg atctcgatag ggatctgtta acgatccccg gcggtgtccc    4500
ccactgaaga aactatgtgc tgtagtatag ccgctgcccg ctggctagct agctagttga    4560
gtcatttagc ggcgatgatt gagtaataat gtgtcacgca tcaccatgca tgggtggcag    4620
tgtcagtgtg agcaatgacc tgaatgaaca attgaaatga aagaaaaaa gtattgttcc     4680 aaattaaacg tttaacctt ttaataggtt tatacaataa ttgatatatg ttttctgtat     4740
atgtctaatt tgttatcatc catttagata tagacaaaaa aaatctaaga actaaaacaa    4800
atgctaattt gaaatgaagg gagtatatat tgggataatg tcgatgagat ccctcgtaat    4860
atcaccgaca tcacacgtgt ccagttaatg tatcagtgat acgtgtattc acatttgttg    4920
cgcgtaggcg tacccaacaa ttttgatcga ctatcagaaa gtcaacggaa gcgagtcgac    4980
ctcgaggcat ggagtcaaag attcaaatag aggacctaac agaactcgcc gtaaagactg    5040
gcgaacagtt catacagagt ctcttacgac tcaatgacaa gaagaaaatc ttcgtcaaca    5100
tggtggagca cgacacgctt gtctactcca aaaatatcaa agatacagtc tcagaagacc    5160
aaagggcaat tgagactttt caacaagggg taatatccgg aaacctcctc ggattccatt    5220
gcccagctat ctgtcacttt attgtgaaga tagtggaaaa ggaaggtggc tcctacaaat    5280
gccatcattg cgataaagga aaggccatcg ttgaagatgc ctctgccgac agtggtccca    5340
aagatggacc cccacccacg aggagcatcg tggaaaaaga agacgttcca accacgtctt    5400
```

```
caaagcaagt ggattgatgt gatatctcca ctgacgtaag ggatgacgca caatcccact    5460
aagctgaccg ggcccggccg aagcttgcat gcctgcaggt cgactctaga ggatctgcac    5520
cggacactgt ctggtggcat accagacagt ccggtgtgcc agatcagggc acccttcggt    5580
tcctttgctc ctttgctttt gaaccctaac tttgatcgtt tattggtttg tgttgaacct    5640
ttatgcacct gtggaatata taatctagaa caaactagtt agtccaatca tttgtgttgg    5700
gcattcaacc accaaaatta tttataggaa aaggttaaac cttatttccc tttcaatctc    5760
cccctttttg gtgattgatg ccaacacaaa ccaaagaaaa tatataagtg cagaattgaa    5820
ctagtttgca taaggtaagt gcataggtta cttagaatta aatcaattta tacttttact    5880
tgatatgcat ggttgctttc ttttatttta acattttgga ccacatttgc accacttgtt    5940
ttgttttttg caaatctttt tggaaattct ttttcaaagt cttttgcaaa tagtcaaagg    6000
tatatgaata agattgtaag aagcattttc aagatttgaa atttctcccc ctgtttcaaa    6060
tgcttttcct ttgactaaac aaaactcccc ctgaataaaa ttctcctctt agctttcaag    6120
agggttttaa atagatatca attggaaata tatttagatg ctaattttga aaatatacca    6180
attgaaaatc aacataccaa tttgaaatta aacataccaa tttaaaaaat ttcaaaaagt    6240
ggtggtgcgg tccttttgct ttgggcttaa tatttctccc cctttggcat taatcgccaa    6300
aaacggagac tttgtgagcc atttatactt tctcccatt ggtaaatgaa atatgagtga    6360
aagattatac caaatttgga cagtgatgcg gagtgacggc gaaggataaa cgataccgtt    6420
agagtggagt ggaagccttg tcttcgccga agactccatt tcccttccaa tctacgactt    6480
agcatagaaa tacacttgaa aacacattag tcgtagccac gaaagagata tgatcaaagg    6540
tatacaaatg agctatgtgt gtaatgtttc aatcaaagtt tcgagaatca agaatattta    6600
gctcattcct aagtttgcta aaggttttat catctaatgg tttggtaaag atatcgacta    6660
attgttcttt ggtgctaaca taagcaatct cgatatcacc cctttgttgg tgatccctca    6720
aaaagtgata ccgaatgtct atgtgcttag tgcggctgtg ttcaacggga ttatccgcca    6780
tgcagatagc actctcattg tcacatagga gagggacttt gctcaatttg tagccatagt    6840
ccctaaggtt ttgcctcatc caaagtaatt gcacacaaca atgtcctgcg gcaatatact    6900
tggcttcggc ggtagaaaga gctattgagt tttgtttctt tgaagtccaa gacaccaggg    6960
atctccctag aaactgacaa gtccctgatg tgctcttcct atcaattta cacccctgccc    7020 aatcggcatc tgaatatcct attaaatcaa aggtggatcc cttggggtac caaagaccaa    7080
atttaggagt gtaaactaaa tatctcatga ttcttttcac ggccctaagg tgaacttcct    7140
taggatcggc ttggaatctt gcacacatgc atatagaaag catactatct ggtcgagatg    7200
cacataaata gagtaaagat cctatcatcg accggtatac cttttggtct acggatttac    7260
ctcccgtgtc gaggtcgaga tgcccattag ttcccatggg tgtcctgatg ggcttggcat    7320
ccttcattcc aaacttgttg agtatgtctt gaatgtactt tgtttggctg atgaaggtgc    7380
catcttggag ttgcttgact tgaaatccta gaaaatattt caacttcccc atcatagaca    7440
tctcgaattt cggaatcatg atcctactaa actcttcaca agtagatttg ttagtagacc    7500
caaatataat atcatcaaca taaatttggc atacaaacaa aacttttgaa atggttttag    7560
taaagagagt aggatcggct ttactgactc tgaagccatt agtgataaga aaatctctta    7620
ggcattcata ccatgctgtt ggggcttgct tgagcccata aagcgccttt gagagtttat    7680
aaacatggtt agggtactca ctatcttcaa agccgagagg ttgctcaaca tagacctatt    7740
```

-continued

```
caccccattt gatcactttt ttggtccttc aggatctaat agttatgtat aatttagagt    7800
ctcttgttta atggccagat atttctaatt aatctaagaa tttatgatat tttttaattt    7860
tttatcatgt ctgatgagaa ttaacataaa ggctcaattg ggtcctgaat taataataga    7920
gtgaaaatta atccagaggc tctattagaa ccttcaatta gtaataccaa gatatatata    7980
agatagtaga gtatagttta aatgttggca ttgttcattc tttcttttgt tatttaattt    8040
atgctttcca cggtggttag tggttacttc tgaagggtcc aaataatgca tgaagagttt    8100
gaggacaaga agtctgccct aaaaatagcg atgcaaaggc atggtgtcca agccatacat    8160
atagcgcact aattttatca gcagaacaat ggtatttata ggtcctagtg cccaggcaac    8220
aagagacacg aataaagcat cgatcacgac accatggcgg cgacaatggc agtgacgacg    8280
atggtgacga ggagcaagga gagctggtcg tcattgcagg tcccggcggt ggcattccct    8340
tggaagccac gaggtggcaa gaccggcggc ctcgagttcc ctcgccgggc gatgttcgcc    8400
agcgtcggcc tcaacgtgtg cccgggcgtc ccggcggggc gcgacccgcg ggagcccgat    8460
cccaaggtcg tccgggcggc ctgcggcctg gtccaggcac aagtcctctt ccaggggttt    8520
aactgggagt cgtgcaagca gcaggaggc tggtacaaca ggctcaaggc ccaggtcgac    8580
gacatcgcca aggccggcgt cacgcacgtc tggctgcctc caccctcgca ctccgtctcg    8640
ccacaaggct acatgccagg ccgcctatac gacctggacg cgtccaagta cggcacggcg    8700
gcggagctca agtccctgat agcggcgttc cacggcaggg gcgtgcagtg cgtggcggac    8760
atcgtcatca accaccggtg cgcggaaaag aaggacgcgc gcggcgtgta ctgcatcttc    8820
gagggcggga ctcccgacga ccgcctggac tggggccccg ggatgatctg cagcgacgac    8880
acgcagtact cggacgggac ggggcaccgc gacacgggcg aggggttcgc ggcggcgccc    8940
gacatcgacc acctcaaccc gcgcgtgcag cgggagctct ccgcctggct caactggctc    9000
aggtccgacg ccgtgggggtt cgacggctgg cgcctcgact tcgccaaggg ctactcgccg    9060
gccgtcgcca gaatgtacgt ggagagcacg gggccgccga gcttcgtcgt cgcggagata    9120
tggaactcgc tgagctacag cggggacggc aagccggcgc ccaaccagga ccagtgccgg    9180
caggagctgc tggactggac gcgggccgtc ggcgggcccg ccatggcgtt cgacttcccc    9240
accaagggcc tgctgcaggc gggcgtgcag ggggagctgt ggcggctgcg cgacagctcc    9300
ggcaacgcgg ccgccctgat cgggtgggcg cccgagaagg ccgtcacctt cgtcgacaac    9360
catgacaccg ggtcgacgca gaagctctgg ccgttcccat ccgacaaggt catgcagggc    9420
tacgcctaca tcctcaccca tccaggagtc ccctgcattt tctacgacca catgttcgac    9480
tggaacctga agcaggagat atccacgctg tctgccatca gggcgcggaa cggcatccgc    9540
gccgggagca agctgcggat cctcgtggcg gacgcggacg cgtacgtggc cgtcgtcgac    9600
gagaaggtca tggtgaagat cgggacaagg tacggcgtga gcagcgtggt cccgtcggat    9660
ttccacccgg cggcgcacgg caaggactac tgccgtctgg gagaaagcgag cctccgcgtc    9720
ccggcggggc gccacctcta gcagctcaga ttgctcagtc ttgtgctgca ttgcaaacac    9780
agcagcacga cactgcataa cgtcttttcc ttgagatctg acaaagcagc attagtccgt    9840
tgatcggtgg aagaccactc gtcagtgttg agttgaatgt ttgatcaata aaatacggca    9900
atgctgtaag ggttgttttt tatgccattg ataatacact gtactgttca gttgttgaac    9960
tctatttctt agccatgcca agtgcttttc ttattttgaa taacattaca gcaaaaagtt   10020
gaaagacaaa aaaaaaaacc cccgaacaga gtgctttggg tcccaagcta ctttagactg   10080
tgttcggcgt tcccccctaaa tttctccccc tatatctcac tcacttgtca catcagcgtt   10140
```

| | | |
|---|---|---|
| ctctttcccc tatatctcca cgtcgacgcg gccgctctag aactagtgga tcccccgggc | 10200 | |
| tgcaggaatt cctcgagacc gtacgtgcgc gcgaatgcat ccagatcttc cctctagtca | 10260 | |
| aggccttaag cgcgcgttcg aacgcgcggt taagcttggt cacccggtcc gggcctagaa | 10320 | |
| ggccgatctc ccgggcaccc agctttcttg tacaaagtgg ccgttaacgg atcccggtga | 10380 | |
| agttcctatt ccgaagttcc tattctccag aaagtatagg aacttcatta ccgat | 10435 | |

<210> SEQ ID NO 77
<211> LENGTH: 4682
<212> TYPE: DNA
<213> ORGANISM: artificial sequence
<220> FEATURE:
<223> OTHER INFORMATION: PG47 PRO-ZM-BT1 TP~ZM-AA1-IN2-1 TERM

<400> SEQUENCE: 77

| | | |
|---|---|---|
| aagcttgcat gcctgcaggt cgactctaga ggatctgcac cggacactgt ctggtggcat | 60 | |
| accagacagt ccggtgtgcc agatcagggc acccttcggt tcctttgctc ctttgctttt | 120 | |
| gaaccctaac tttgatcgtt tattggtttg tgttgaacct ttatgcacct gtggaatata | 180 | |
| taatctagaa caaactagtt agtccaatca tttgtgttgg gcattcaacc accaaaatta | 240 | |
| tttataggaa aaggttaaac cttatttccc tttcaatctc cccctttttg gtgattgatg | 300 | |
| ccaacacaaa ccaaagaaaa tatataagtg cagaattgaa ctagtttgca taaggtaagt | 360 | |
| gcataggtta cttagaatta aatcaatttt a tactttact tgatatgcat ggttgctttc | 420 | |
| ttttatttta acattttgga ccacatttgc accacttgtt ttgttttttg caaatctttt | 480 | |
| tggaaattct ttttcaaagt cttttgcaaa tagtcaaagg tatatgaata agattgtaag | 540 | |
| aagcattttc aagatttgaa atttctcccc ctgtttcaaa tgcttttcct ttgactaaac | 600 | |
| aaaactcccc ctgaataaaa ttctcctctt agctttcaag agggttttaa atagatatca | 660 | |
| attggaaata tatttagatg ctaattttga aaatatacca attgaaaatc aacataccaa | 720 | |
| tttgaaatta aacataccaa tttaaaaaat ttcaaaaagt ggtggtgcgg tccttttgct | 780 | |
| ttgggcttaa tatttctccc cctttggcat taatcgccaa aaacggagac tttgtgagcc | 840 | |
| atttatactt tctccccatt ggtaaatgaa atatgagtga agattatac caaatttgga | 900 | |
| cagtgatgcg gagtgacggc gaaggataaa cgataccgtt agagtggagt ggaagccttg | 960 | |
| tcttcgccga agactccatt tcccttttcaa tctacgactt agcatagaaa tacacttgaa | 1020 | |
| aacacattag tcgtagccac gaaagagata tgatcaaagg tatacaaatg agctatgtgt | 1080 | |
| gtaatgtttc aatcaaagtt tcgagaatca agaatatttta gctcattcct aagtttgcta | 1140 | |
| aaggttttat catctaatgg tttggtaaag atatcgacta attgttcttt ggtgctaaca | 1200 | |
| taagcaatct cgatatcacc cctttgttgg tgatccctca aaaagtgata ccgaatgtct | 1260 | |
| atgtgcttag tgcggctgtg ttcaacggga ttatccgcca tgcagatagc actctcattg | 1320 | |
| tcacatagga gagggacttt gctcaatttg tagccatagt ccctaaggtt ttgcctcatc | 1380 | |
| caaagtaatt gcacacaaca atgtcctgcg gcaatatact tggcttcggc ggtagaaaga | 1440 | |
| gctattgagt tttgtttctt tgaagtccaa gacaccaggg atctccctag aaactgacaa | 1500 | |
| gtccctgatg tgctcttcct atcaattta caccctgccc aatcggcatc tgaatatcct | 1560 | |
| attaaatcaa aggtggatcc cttggggtac caaagaccaa atttaggagt gtaaactaaa | 1620 | |
| tatctcatga ttcttttcac ggccctaagg tgaacttcct taggatcggc ttggaatctt | 1680 | |
| gcacacatgc atatagaaag catactatct ggtcgagatg cacataaata gagtaaagat | 1740 | |

```
cctatcatcg accggtatac cttttggtct acggatttac ctcccgtgtc gaggtcgaga    1800
tgcccattag ttcccatggg tgtcctgatg ggcttggcat ccttcattcc aaacttgttg    1860
agtatgtctt gaatgtactt tgtttggctg atgaaggtgc catcttggag ttgcttgact    1920
tgaaatccta gaaatatttt caacttcccc atcatagaca tctcgaattt cggaatcatg    1980
atcctactaa actcttcaca gtagatttg ttagtagacc caaatataat atcatcaaca     2040
taaatttggc atacaaacaa aacttttgaa atggttttag taaagagagt aggatcggct    2100
ttactgactc tgaagccatt agtgataaga aaatctctta ggcattcata ccatgctgtt    2160
ggggcttgct tgagcccata aagcgccttt gagagtttat aaacatggtt agggtactca    2220
ctatcttcaa agccgagagg ttgctcaaca tagaccatt cacccccattt gatcacttttt   2280 ttggtccttc aggatctaat agttatgtat aatttagagt ctcttgttta atggccagat    2340
atttctaatt aatctaagaa tttatgatat ttttttaattt tttatcatgt ctgatgagaa   2400
ttaacataaa ggctcaattg ggtcctgaat taataataga gtgaaaatta atccagaggc    2460
tctattagaa ccttcaatta gtaataccaa gatatatata agatagtaga gtatagttta   2520
aatgttggca ttgttcattc tttcttttgt tatttaattt atgctttcca cggtggttag    2580
tggttacttc tgaagggtcc aaataatgca tgaagagttt gaggacaaga agtctgccct    2640
aaaaatagcg atgcaaaggc atggtgtcca agccatacat atagcgcact aattttatca    2700
gcagaacaat ggtatttata ggtcctagtg cccaggcaac aagagacacg aataaagcat    2760
cgatcacgac accatggcgg cgacaatggc agtgacgacg atggtgacga ggagcaagga    2820
gagctggtcg tcattgcagg tcccggcggt ggcattccct tggaagccac gaggtggcaa    2880
gaccggcggc ctcgagttcc ctcgccgggc gatgttcgcc agcgtcggcc tcaacgtgtg    2940
cccgggcgtc ccggcgggc gcgacccgcg ggagcccgat cccaaggtcg tccgggcggc    3000
ctgcggcctg gtccaggcac aagtcctctt ccaggggttt aactgggagt cgtgcaagca    3060
gcagggaggc tggtacaaca ggctcaaggc ccaggtcgac gacatcgcca aggccggcgt    3120
cacgcacgtc tggctgcctc caccctcgca ctccgtctcg ccacaaggct acatgccagg    3180
ccgcctatac gacctggacg cgtccaagta cggcacggcg gcggagctca agtccctgat    3240
agcggcgttc cacggcaggg gcgtgcagtg cgtggcggac atcgtcatca accaccggtg    3300
cgcggaaaag aaggacgcgc gcggcgtgta ctgcatcttc gagggcggga ctcccgacga    3360
ccgcctggac tggggccccg ggatgatctg cagcgacgac acgcagtact cggacgggac    3420
ggggcaccgc gacacgggcg aggggttcgc ggcggcgccc gacatcgacc acctcaaccc    3480
gcgcgtgcag cgggagctct ccgcctggct caactggctc aggtccgacg ccgtggggtt    3540
cgacggctgg cgcctcgact tcgccaaggg ctactcgccg gccgtcgcca gaatgtacgt    3600
ggagagcacg gggccgccga gcttcgtcgt cgcggagata tggaactcgc tgagctacag    3660
cggggacgga aagccggcgc ccaaccagga ccagtgccgg caggagctgc tggactggac    3720
gcgggccgtc ggcgggcccg ccatggcgtt cgacttcccc accaagggcc tgctgcaggc    3780
gggcgtgcag ggggagctgt ggcggctgcg cgacagctcc ggcaacgcgg ccggcctgat    3840
cgggtgggcg cccgagaagg ccgtcacctt cgtcgacaac catgcacccg gtcgacgca    3900 gaagctctgg ccgttcccat ccgacaaggt catgcagggc tacgcctaca tcctcaccca    3960
tccaggagtc ccctgcattt tctacgacca catgttcgac tggaacctga gcaggagat    4020 atccacgctg tctgccatca gggcgcgaa cggcatccgc gccggagca agctgcggat    4080 cctcgtggcg gacgcggacg cgtacgtggc cgtcgtcgac gagaaggtca tggtgaagat    4140
```

-continued

```
cgggacaagg tacggcgtga gcagcgtggt cccgtcggat ttccacccgg cggcgcacgg    4200
caaggactac tgcgtctggg agaaagcgag cctccgcgtc ccggcggggc gccacctcta    4260
gcagctcaga ttgctcagtc ttgtgctgca ttgcaaacac agcagcacga cactgcataa    4320
cgtcttttcc ttgagatctg acaaagcagc attagtccgt tgatcggtgg aagaccactc    4380
gtcagtgttg agttgaatgt ttgatcaata aaatacggca atgctgtaag ggttgttttt    4440
tatgccattg ataatacact gtactgttca gttgttgaac tctatttctt agccatgcca    4500
agtgcttttc ttattttgaa taacattaca gcaaaaagtt gaaagacaaa aaaaaaaacc    4560
cccgaacaga gtgctttggg tcccaagcta ctttagactg tgttcggcgt tcccctaaa    4620 tttctccccc tatatctcac tcacttgtca catcagcgtt ctctttcccc tatatctcca    4680
cg                                                                   4682
```

<210> SEQ ID NO 78
<211> LENGTH: 3602
<212> TYPE: DNA
<213> ORGANISM: artificial sequence
<220> FEATURE:
<223> OTHER INFORMATION: PG47 PRO-BA-BARNASE-IN2-1 TERM

<400> SEQUENCE: 78

```
aagcttgcat gcctgcaggt cgactctaga ggatctgcac cggacactgt ctggtggcat      60
accagacagt ccggtgtgcc agatcagggc acccttcggt tcctttgctc ctttgctttt     120
gaaccctaac tttgatcgtt tattggtttg tgttgaacct ttatgcacct gtggaatata     180
taatctagaa caaactagtt agtccaatca tttgtgttgg gcattcaacc accaaaatta     240
tttataggaa aaggttaaac cttatttccc tttcaatctc cccctttttg gtgattgatg     300
ccaacacaaa ccaaagaaaa tatataagtg cagaattgaa ctagtttgca taaggtaagt     360
gcataggtta cttagaatta aatcaattta tacttttact tgatatgcat ggttgctttc     420 ttttattttta acattttgga ccacatttgc accacttgtt ttgttttttg caaatctttt    480
tggaaattct ttttcaaagt cttttgcaaa tagtcaaagg tatatgaata agattgtaag     540
aagcattttc aagatttgaa atttctcccc ctgtttcaaa tgcttttcct ttgactaaac     600
aaaactcccc ctgaataaaa ttctcctctt agctttcaag agggttttaa atagatatca     660
attggaaata tatttagatg ctaattttga aaatatacca attgaaaatc aacataccaa     720
tttgaaatta acataccaa tttaaaaaat tcaaaaagt ggtggtgcgg tccttttgct      780
ttgggcttaa tatttctccc cctttggcat taatcgccaa aaacggagac tttgtgagcc     840
atttatactt tctccccatt ggtaaatgaa atatgagtga agattatac caaatttgga     900 cagtgatgcg gagtgacggc gaaggataaa cgataccgtt agagtggagt ggaagccttg     960
tcttcgccga agactccatt tcccttccaa tctacgactt agcatagaaa tacacttgaa    1020
aacacattag tcgtagccac gaaagagata tgatcaaagg tatacaaatg agctatgtgt    1080
gtaatgtttc aatcaaagtt tcgagaatca agaatattta gctcattcct aagtttgcta    1140
aaggttttat catctaatgg tttggtaaag atatcgacta attgttcttt ggtgctaaca    1200
taagcaatct cgatatcacc cctttgttgg tgatccctca aaaagtgata ccgaatgtct    1260
atgtgcttag tgcggctgtg ttcaacggga ttatccgcca tgcagatagc actctcattg    1320
tcacatagga gagggacttt gctcaatttg tagccatagt ccctaaggtt ttgcctcatc    1380
caaagtaatt gcacacaaca atgtcctgcg gcaatatact tggcttcggc ggtagaaaga    1440
```

```
gctattgagt tttgtttctt tgaagtccaa gacaccaggg atctccctag aaactgacaa    1500
gtccctgatg tgctcttcct atcaatttta caccctgccc aatcggcatc tgaatatcct    1560
attaaatcaa aggtggatcc cttggggtac caaatttaag gagtgtaaac taaatatctc    1620
atgattcttt tcacggccct aaggtgaact tccttaggat cggcttggaa tcttgcacac    1680
atgcatatag aaagcatagc tatctggtcg agatgcacat aaatagagta aagatcctat    1740
catcgaccgg tataccttt ggtcgtacgg atttacctcc cgtgtcgagg tcgagatgcc     1800
cattagttcc catgggtgta cctgatgggc ttggcatcct tcattccaaa cttgttgagt    1860
atgtcttgaa tgtactttgt ttggctgatg aaggtgccat cttggagttg cttgacttga    1920
aatcctagaa aatatttcaa cttccccatc atagacatct cgaatttcgg aatcatgatc    1980
ctactaaact cttcacaagt agatttgtta gtagacccaa atataatatc atcaacataa    2040
atttggcata caaacaaaac ttttgaaatg gttttagtaa agagagtagg atcggcttta    2100
ctgactctga agccattagt gataagaaaa tctcttaggc attcatacca tgctgttggg    2160
gcttgcttga gcccataaag cgcctttgag agttataaa catggttagg gtactcacta     2220
tcttcaaagc cgagaggttg ctcaacatag acctattcac cccatttgat cacttttttg    2280
gtccttcagg atctaatagt tatgtataat ttagagtctc ttgtttaatg gccagatatt    2340
tctaattaat ctaagaattt atgatatttt ttaattttt atcatgtctg atgagaatta     2400
acataaaggc tcaattgggt cctgaattaa taatagagtg aaaattaatc cagaggctct    2460
attagaacct tcaattagta ataccaagat atataaga tagtagagta tagtttaaat      2520
gttggcattg ttcattcttt cttttgttat taatttatg ctttccacgg tggttagtgg     2580
ttacttctga agggtccaaa taatgcatga agagtttgag gacaagaagt ctgccctaaa    2640
aatagcgatg caaaggcatg gtgtccaagc catacatata gcgcactaat tttatcagca    2700
gaacaatggt atttataggt cctagtgccc aggcaacaag agacacgaat aaagcatcga    2760
tcacgacacc agatctcatg gcacaggtta tcaacacgtt tgacggggtt gcggattatc    2820
ttcagacata tcataagcta cctgataatt acattacaaa atcagaagca caagccctcg    2880
gctgggtggc atcaaaaggg aaccttgcag acgtcgctcc ggggaaaagc atcggcggag    2940
acatcttctc aaacagggaa ggcaaactcc cgtaagtttc tgcttctacc tttgatatat    3000
atataataat tatcattaat tagtagtaat ataatatttc aaatattttt ttcaaaataa    3060
aagaatgtag tatatagcaa ttgcttttct gtagtttata agtgtgtata ttttaattta    3120
taacttttct aatatatgac caaaacatgg tgatgtgcag gggcaaaagc ggacgaacat    3180
ggcgtgaagc ggatattaac tatacatcag gcttcagaaa ttcagaccgg attctttact    3240
caggcgactg gctgatttac aaaacaacgg accattatca gacctttaca aaaatcagat    3300
aactgcagct agacttgtcc atcttctgga ttggccaact taattaatgt atgaaataaa    3360
aggatgcaca catagtgaca tgctaatcac tataatgtgg gcatcaaagt tgtgtgttat    3420
gtgtaattac tagttatctg aataaaagag aaagagatca tccatatttc ttatcctaaa   3480
tgaatgtcac gtgtctttat aattctttga tgaaccagat gcatttcatt aaccaaatcc    3540
atatacatat aaatattaat catatataat taatatcaat tgggttagca aaacaaatct    3600
ag                                                                   3602
```

<210> SEQ ID NO 79
<211> LENGTH: 1188
<212> TYPE: DNA
<213> ORGANISM: Streptomyces griseolus

<400> SEQUENCE: 79

```
atgaccggaa ccatcccctt ccctcaggac cgcagttgtc cctaccaccc gccgacgaac      60
taccggccgc tgcgcgaatc cggtccgctc tcgcacgtca gcttctacaa cggccgcaag     120
gtctgggcgg tgaccgggca cgccgaggcg cggacgctgc tggtcgaccc ccgcctgtcg     180
tccgaccggc agaatccggc cttccccatc ccggtcgagc ggttcgaggc cgtccggcgg     240
gtgcgcactc ccttgatcgg cgtggacgat cccgagcaca acactcagcg ccgcatgctg     300
atccccagct tcagcgtcaa cggaccgccg cgctccgac cgcagatcca acagatcgtg      360
gacggcctcc tggaccggat gctggagcag ggcccacccg ccgagttggt ctccgcgttc     420
gcgctccccg tcccgtcgat ggtgatctgc tcgctgctcg gcgtcccgta cgcggaccac     480
gagttcttcg aggaccggtc gcgccgcatc ctccgcggag gcacggccga ggagagcgag     540
caggcccgac gcgaactgga gggataccct gcggatctga tggcccgcaa ggagacggat     600
ccgggtgacg gactgctcga cgagctgatc gccgagcggc tccgggccgg cacgctccaa     660
caccaggaac tggtccggct ggccatggtc ctgctggtcg ccgggcacga gaccaccgcc     720
aacatgatct ccctcggcac cttcgccctc ctcgaacacc ccgaccagtt ggcccagttg     780
aggtccgacg agagtctgat gccgggcgcg gtcgaggagt tgctgcggtt cttgtccata     840
gccgacggca tgctgcgggt cgcgaccgcc gacatcgaga tcgccgggca ccatccgc      900
accggcgacg gcgtggtgtt ctccacctcc ctgatcaacc gcgacgcgac ggcctacccg     960
tcaccggacg aactccatgt cgaccgttcg gcccgccacc acgtcgcgtt cggcttcggc    1020
atccaccagt gcctgggcca gaatctggcc cgcgccgagt tggagatcgc gctacgctcg    1080
ctgttccggc gagtgcccga cctgcgactc gccgtgccgg ctgccgaaat tcccttcaag    1140
ccgggggaaa ctctccaagg aatgatcgaa ctgccgctga tctggtag                1188
```

<210> SEQ ID NO 80
<211> LENGTH: 406
<212> TYPE: PRT
<213> ORGANISM: Streptomyces griseolus

<400> SEQUENCE: 80

```
Met Thr Asp Thr Ala Thr Thr Pro Gln Thr Thr Asp Ala Pro Ala Phe
1               5                   10                  15

Pro Ser Asn Arg Ser Cys Pro Tyr Gln Leu Pro Asp Gly Tyr Ala Gln
                20                  25                  30

Leu Arg Asp Thr Pro Gly Pro Leu His Arg Val Thr Leu Tyr Asp Gly
            35                  40                  45

Arg Gln Ala Trp Val Val Thr Lys His Glu Ala Ala Arg Lys Leu Leu
        50                  55                  60

Gly Asp Pro Arg Leu Ser Ser Asn Arg Thr Asp Asp Asn Phe Pro Ala
65                  70                  75                  80

Thr Ser Pro Arg Phe Glu Ala Val Arg Glu Ser Pro Gln Ala Phe Ile
                85                  90                  95

Gly Leu Asp Pro Pro Glu His Gly Thr Arg Arg Met Thr Ile Ser
                100                 105                 110

Glu Phe Thr Val Lys Arg Ile Lys Gly Met Arg Pro Glu Val Glu Glu
            115                 120                 125

Val Val His Gly Phe Leu Asp Glu Met Leu Ala Ala Gly Pro Thr Ala
        130                 135                 140

Asp Leu Val Ser Gln Phe Ala Leu Pro Val Pro Ser Met Val Ile Cys
```

```
                145                 150                 155                 160
Arg Leu Leu Gly Val Pro Tyr Ala Asp His Glu Phe Phe Gln Asp Ala
                165                 170                 175

Ser Lys Arg Leu Val Gln Ser Thr Asp Ala Gln Ser Ala Leu Thr Ala
                180                 185                 190

Arg Asn Asp Leu Ala Gly Tyr Leu Asp Gly Leu Ile Thr Gln Phe Gln
                195                 200                 205

Thr Glu Pro Gly Ala Gly Leu Val Gly Ala Leu Val Ala Asp Gln Leu
                210                 215                 220

Ala Asn Gly Glu Ile Asp Arg Glu Leu Ile Ser Thr Ala Met Leu
225                 230                 235                 240

Leu Leu Ile Ala Gly His Glu Thr Thr Ala Ser Met Thr Ser Leu Ser
                245                 250                 255

Val Ile Thr Leu Leu Asp His Pro Glu Gln Tyr Ala Ala Leu Arg Ala
                260                 265                 270

Asp Arg Ser Leu Val Pro Gly Ala Val Glu Glu Leu Leu Arg Tyr Leu
                275                 280                 285

Ala Ile Ala Asp Ile Ala Gly Gly Arg Val Ala Thr Ala Asp Ile Glu
                290                 295                 300

Val Glu Gly His Leu Ile Arg Ala Gly Glu Gly Val Ile Val Val Asn
305                 310                 315                 320

Ser Ile Ala Asn Arg Asp Gly Thr Val Tyr Glu Asp Pro Asp Ala Leu
                325                 330                 335

Asp Ile His Arg Ser Ala Arg His His Leu Ala Phe Gly Phe Gly Val
                340                 345                 350

His Gln Cys Leu Gly Gln Asn Leu Ala Arg Leu Glu Leu Glu Val Ile
                355                 360                 365

Leu Asn Ala Leu Met Asp Arg Val Pro Thr Leu Arg Leu Ala Val Pro
                370                 375                 380

Val Glu Gln Leu Val Leu Arg Pro Gly Thr Thr Ile Gln Gly Val Asn
385                 390                 395                 400

Glu Leu Pro Val Thr Trp
                405

<210> SEQ ID NO 81
<211> LENGTH: 1284
<212> TYPE: DNA
<213> ORGANISM: Escherichia coli

<400> SEQUENCE: 81
atgtcgaata acgctttaca acaattatt aacgcccggt taccaggcga agaggggctg        60
tggcagattc atctgcagga cggaaaaatc agcgccattg atgcgcaatc cggcgtgatg       120
cccataactg aaaacagcct ggatgccgaa caaggtttag ttataccgcc gtttgtggag       180
ccacatattc acctggacac cacgcaaacc gccggacaac cgaactggaa tcagtccggc       240
acgctgtttg aaggcattga acgctgggcc gagcgcaaag cgttattaac ccatgacgat       300
gtgaaacaac gcgcatggca aacgctgaaa tggcagattg ccaacggcat tcagcatgtg       360
cgtacccatg tcgatgtttc ggatgcaacg ctaactgcgc tgaaagcaat gctggaagtg       420
aagcaggaag tcgcgccgtg gattgatctg caaatcgtcg ccttccctca ggaagggatt       480
ttgtcgtatc ccaacggtga agcgttgctg gaagaggcgt tacgcttagg gcagatgta       540 gtgggggcga ttccgcattt tgaatttacc cgtgaatacg gcgtggagtc gctgcataaa       600
accttcgccc tggcgcaaaa atacgaccgt ctcatcgacg ttcactgtga tgagatcgat       660
```

```
gacgagcagt cgcgctttgt cgaaaccgtt gctgccctgg cgcaccatga aggcatgggc    720
gcgcgagtca ccgccagcca caccacggca atgcactcct ataacggggc gtatacctca    780
cgcctgttcc gcttgctgaa aatgtccggt attaactttg tcgccaaccc gctggtcaat    840
attcatctgc aaggacgttt cgatacgtat ccaaaacgtc gcggcatcac gcgcgttaaa    900
gagatgctgg agtccggcat taacgtctgc tttggtcacg atgatgtctt cgatccgtgg    960
tatccgctgg aacggcgaa tatgctgcaa gtgctgcata tggggctgca tgtttgccag   1020
ttgatgggct acgggcagat taacgatggc ctgaatttaa tcacccacca cagcgcaagg   1080
acgttgaatt tgcaggatta cggcattgcc gccggaaaca gcgccaacct gattatcctg   1140
ccggctgaaa atgggtttga tgcgctgcgc cgtcaggttc cggtacgtta ttcggtacgt   1200
ggcggcaagg tgattgccag cacacaaccg gcacaaacca ccgtatatct ggagcagcca   1260
gaagccatcg attacaaacg ttga                                          1284
```

<210> SEQ ID NO 82
<211> LENGTH: 427
<212> TYPE: PRT
<213> ORGANISM: Escherichia coli

<400> SEQUENCE: 82

```
Met Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
        35                  40                  45

Ala Glu Gln Gly Leu Val Ile Pro Pro Phe Val Glu Pro His Ile His
    50                  55                  60

Leu Asp Thr Thr Gln Thr Ala Gly Gln Pro Asn Trp Asn Gln Ser Gly
65                  70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
    130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
                165                 170                 175

Gly Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255
```

```
Ala Tyr Thr Ser Arg Leu Phe Arg Leu Leu Lys Met Ser Gly Ile Asn
                260                 265                 270

Phe Val Ala Asn Pro Leu Val Asn Ile His Leu Gln Gly Arg Phe Asp
            275                 280                 285

Thr Tyr Pro Lys Arg Arg Gly Ile Thr Arg Val Lys Glu Met Leu Glu
        290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
        355                 360                 365

Ile Ala Ala Gly Asn Ser Ala Asn Leu Ile Ile Leu Pro Ala Glu Asn
370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg
            420                 425

<210> SEQ ID NO 83
<211> LENGTH: 1645
<212> TYPE: DNA
<213> ORGANISM: artificial sequence
<220> FEATURE:
<223> OTHER INFORMATION: ZM-U6 POLIII CHR8 PRO-GT1 GUIDE RNA-ZM-U6
      POLIII CHR8 TERM

<400> SEQUENCE: 83
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat     180
gaatcctggc ttattccggt acaaccgaac aggccctgaa ggataccagt aatcgctgag     240
ctaaattggc atgctgtcag agtgtcagta ttgcagcaag gtagtgagat aaccggcatc     300
atggtgccag tttgatggca ccattagggt tagagatggt ggccatgggc gcatgtcctg     360
gccaactttg tatgatatat ggcagggtga ataggaaagt aaaattgtat tgtaaaaagg     420
gatttcttct gtttgttagc gcatgtacaa ggaatgcaag ttttgagcga gggggcatca     480
aagatctggc tgtgtttcca gctgtttttg ttagccccat cgaatccttg acataatgat     540
cccgcttaaa taagcaacct cgcttgtata gttccttgtg ctctaacaca cgatgatgat     600
aagtcgtaaa atagtggtgt ccaaagaatt tccaggccca gttgtaaaag ctaaatgct     660 attcgaattt ctactagcag taagtcgtgt ttagaaatta ttttttttata tacctttttt     720 ccttctatgt acagtaggac acagtgtcag cgccgcgttg acggagaata tttgcaaaaa     780
agtaaaagag aaagtcatag cggcgtatgt gccaaaaact tcgtcacaga gagggccata     840
agaaacatgg cccacggccc aatacgaagc accgcgacga agcccaaaca gcagtccgta     900
ggtggagcaa agcgctgggt aatacgcaaa cgttttgtcc caccttgact aatcacaaga     960
gtggagcgta cctataaaac cgagccgcaa gcaccgaatt ggcgcgccgt tcactgccgt    1020
ataggcaggt gcatcatgga ctcatggttt tagagctaga aatagcaagt taaaataagg    1080
```

-continued

```
ctagtccgtt atcaacttga aaaagtggca ccgagtcggt gctgttcact gccgtatagg    1140
cagcgctgta cggcgtggta gacgttttag agctagaaat agcaagttaa ataaggcta     1200 gtccgttatc aacttgaaaa agtggcaccg agtcggtgct gttcactgcc gtataggcag    1260
ccagcaacgt ccagcgcgcg ttttagagct agaaatagca agttaaaata aggctagtcc    1320
gttatcaact gaaaaagtg gcaccgagtc ggtgctgttc actgccgtat aggcaggggt    1380
gcccgtgcgt tgcaagtttt agagctagaa atagcaagtt aaaataaggc tagtccgtta    1440
tcaacttgaa aaagtggcac cgagtcggtg ctgttcactg ccgtataggc aggcatttcg    1500
cgagtcaaat ttgttttaga gctagaaata gcaagttaaa ataaggctag tccgttatca    1560
acttgaaaaa gtggcaccga gtcggtgctg ttcactgccg tataggcagg ttcactgccg    1620
tataggcagg cgatcgcttt ttttt                                          1645

<210> SEQ ID NO 84
<211> LENGTH: 4452
<212> TYPE: DNA
<213> ORGANISM: artificial sequence
<220> FEATURE:
<223> OTHER INFORMATION: moDCAS9 EXON1-STLS1 INTRON-moCAS9 EXON2

<400> SEQUENCE: 84
atggcaccga agaagaagcg caaggtgctg atcttcagc ttagactggg cggtggcggt       60
ggatccgaca agaagtacag catcggcctc gccatcggca ccaactcggt gggctgggcc     120
gtcatcacgg acgaatataa ggtcccgtcg aagaagttca aggtcctcgg caatacagac     180
cgccacagca tcaagaaaaa cttgatcggc gccctcctgt tcgatagcgg cgagaccgcg     240
gaggcgacca ggctcaagag gaccgccagg agacggtaca ctaggcgcaa gaacaggatc     300
tgctacctgc aggagatctt cagcaacgag atggcgaagg tggacgactc cttcttccac     360
cgcctggagg aatcattcct ggtggaggag acaagaagc atgagcggca cccaatcttc     420
ggcaacatcg tcgacgaggt aagtttctgc ttctaccttt gatatatata taataattat     480
cattaattag tagtaatata atatttcaaa tatttttttc aaaataaaag aatgtagtat     540
atagcaattg cttttctgta gtttataagt gtgtatattt taatttataa cttttctaat     600
atatgaccaa acatggtga tgtgcaggtg gcctaccacg agaagtaccc gacaatctac      660
cacctccgga gaaactggt ggacagcaca gacaaggcgg acctccggct catctacctt      720
gccctcgcgc atatgatcaa gttccgcggc cacttcctca tcgagggcga cctgaacccg     780
gacaactccg acgtggacaa gctgttcatc agctcgtgc agacgtacaa tcaactgttc      840
gaggagaacc ccataaacgc tagcggcgtg gacgccaagg ccatcctctc ggccaggctc     900
tcgaaatcaa gaaggctgga aaccttatcg cgcagttgc caggcgaaaa gaagaacggc      960
ctcttcggca accttattgc gctcagcctc ggcctgacgc gaacttcaa atcaaacttc     1020 gacctcgcgg aggacgccaa gctccagctc tcaaaggaca cctacgacga cgacctcgac    1080
aacctcctgg cccagatagg agaccagtac gcggacctct tcctcgccgc caagaacctc    1140
tccgacgcta tcctgctcag cgacatcctt cgggtcaaca ccgaaattac caaggcaccg    1200
ctgtccgcca gcatgattaa acgctacgac gagcaccatc aggacctcac gctgctcaag    1260
gcactcgtcc gccagcagct ccccgagaag tacaaggaga tcttcttcga ccaatcaaaa    1320
aacggctacg cggatatat cgacggcggt gccagccagg aagagttcta caagttcatc    1380
aaaccaatcc tggagaagat ggacggcacc gaggagttgc tggtcaagct caacagggag    1440
```

```
gacctcctca ggaagcagag gaccttcgac aacggctcca tcccgcatca gatccacctg   1500
ggcgaactgc atgccatcct gcggcgccag gaggacttct acccgttcct gaaggataac   1560
cgggagaaga tcgagaagat cttgacgttc cgcatcccat actacgtggg cccgctggct   1620
cgcggcaact cccggttcgc ctggatgacc cggaagtcgg aggagaccat cacaccctgg   1680
aactttgagg aggtggtcga taagggcgct agcgctcaga gcttcatcga gcgcatgacc   1740
aacttcgata aaaacctgcc caatgaaaaa gtcctcccca gcactcgct gctctacgag    1800 tacttcaccg tgtacaacga gctcaccaag gtcaaatacg tcaccgaggg catgcggaag   1860
ccggcgttcc tgagcggcga gcagaagaag gcgatagtgg acctcctctt caagaccaac   1920
aggaaggtga ccgtgaagca attaaaagag gactacttca gaaaatagga gtgcttcgac   1980
tccgtggaga tctcgggcgt ggaggatcgg ttcaacgcct cactcggcac gtatcacgac   2040
ctcctcaaga tcattaaaga caaggacttc ctcgacaacg aggagaacga ggacatcctc   2100
gaggacatcg tcctcaccct gaccctgttc gaggaccgcg aaatgatcga ggagaggctg   2160
aagacctacg cgcacctgtt cgacgacaag gtcatgaaac agctcaagag gcgccgctac   2220
actggttggg aaggctgtc ccgcaagctc attaatggca tcaggacaa gcagagcggc     2280 aagaccatcc tggacttcct caagtccgac gggttcgcca accgcaactt catgcagctc   2340
attcacgacg actcgctcac gttcaaggaa gacatccaga aggcacaggt gagcgggcag   2400
ggtgactccc tccacgaaca catcgccaac ctggccggct cgccggccat taaaaagggc   2460
atcctgcaga cggtcaaggt cgtcgacgag ctcgtgaagg tgatgggccg gcacaagccc   2520
gaaaatatcg tcatagagat ggccaggag aaccagacca cccaaaaagg gcagaagaac    2580
tcgcgcgagc ggatgaaacg gatcgaggag ggcattaaag agctcgggtc ccagatcctg   2640
aaggagcacc ccgtggaaaa tacccagctc cagaatgaaa agctctacct ctactacctg   2700
cagaacggcc gcgacatgta cgtggaccag gagctggaca ttaatcggct atcggactac   2760
gacgtcgacc ccatcgtgcc gcagtcgttc ctcaaggacg atagcatcga caacaaggtg   2820
ctcacccggt cggataaaaa tcggggcaag agcgacaacg tgcccagcga ggaggtcgtg   2880
aagaagatga aaaactactg gcgccagctc ctcaacgcga aactgatcac ccagcgcaag   2940
ttcgacaacc tgacgaaggc ggaacgcggt ggcttgagcg aactcgataa ggcgggcttc   3000
ataaaaaggc agctggtcga gacgcgccag atcacgaagc atgtcgccca gatcctggac   3060
agccgcatga atactaagta cgatgaaaac gacaagctga tccgggaggt gaaggtgatc   3120
acgctgaagt ccaagctcgt gtcggacttc cgcaaggact tccagttcta caaggtccgc   3180
gagatcaaca actaccacca cgcccacgac gcctacctga tgcggtggt cgggaccgcc    3240 ctgatcaaga agtacccgaa gctggagtcg gagttcgtgt acggcgacta caaggtctac   3300
gacgtgcgca aaatgatcgc caagtccgag caggagatcg gcaaggccac ggcaaaatac   3360
ttcttctact cgaacatcat gaacttcttc aagaccgaga tcaccctcgc gaacggcgag   3420
atccgcaagc gcccgctcat cgaaaccaac ggcgagacgg cgagatcgt ctgggataag    3480 ggccgggatt tcgcgacggt ccgcaaggtg ctctccatgc cgcaagtcaa tatcgtgaaa   3540
aagacggagg tccagacggg cgggttcagc aaggagtcca tcctcccgaa gcgcaactcc   3600
gacaagctca tcgcgaggaa gaaggattgg gacccgaaaa atatggcgg cttcgacagc    3660 ccgaccgtcg catacagcgt cctcgtcgtg gcgaaggtgg agaagggcaa gtcaaagaag   3720
ctcaagtccg tgaaggagct gctcgggatc acgattatgg agcggtcctc cttcgagaag   3780
aacccgatcg acttcctaga ggccaaggga tataaggagg tcaagaagga cctgattatt   3840
```

-continued

```
aaactgccga agtactcgct cttcgagctg gaaaacggcc gcaagaggat gctcgcctcc    3900
gcaggcgagt tgcagaaggg caacgagctc gccctcccga gcaaatacgt caatttcctg    3960
tacctcgcta gccactatga aaagctcaag ggcagcccgg aggacaacga gcagaagcag    4020
ctcttcgtgg agcagcacaa gcattacctg gacgagatca tcgagcagat cagcgagttc    4080
tcgaagcggg tgatcctcgc cgacgcgaac ctggacaagg tgctgtcggc atataacaag    4140
caccgcgaca aaccaatacg cgagcaggcc gaaaatatca tccacctctt caccctcacc    4200
aacctcggcg ctccggcagc cttcaagtac ttcgacacca cgattgaccg gaagcggtac    4260
acgagcacga aggaggtgct cgatgcgacg ctgatccacc agagcatcac agggctctat    4320
gaaacacgca tcgacctgag ccagctgggc ggagacggtg gcggtggatc cctggatctt    4380
cagcttagac tgggcaagag accacgggac cgccacgatg gcgagctggg aggccgcaag    4440
cgggcaaggt ag                                                        4452
```

<210> SEQ ID NO 85
<211> LENGTH: 1368
<212> TYPE: PRT
<213> ORGANISM: artificial sequence
<220> FEATURE:
<223> OTHER INFORMATION: DCAS9

<400> SEQUENCE: 85

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
```

-continued

```
                245                 250                 255
Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670
```

```
Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080
```

| Arg | Lys | Val | Leu | Ser | Met | Pro | Gln | Val | Asn | Ile | Val | Lys | Lys | Thr |
|---|---|---|---|---|---|---|---|---|---|---|---|---|---|---|
| 1085 | | | | | 1090 | | | | | 1095 | | | | |
| Glu | Val | Gln | Thr | Gly | Gly | Phe | Ser | Lys | Glu | Ser | Ile | Leu | Pro | Lys |
| 1100 | | | | | 1105 | | | | | 1110 | | | | |
| Arg | Asn | Ser | Asp | Lys | Leu | Ile | Ala | Arg | Lys | Lys | Asp | Trp | Asp | Pro |
| 1115 | | | | | 1120 | | | | | 1125 | | | | |
| Lys | Lys | Tyr | Gly | Gly | Phe | Asp | Ser | Pro | Thr | Val | Ala | Tyr | Ser | Val |
| 1130 | | | | | 1135 | | | | | 1140 | | | | |
| Leu | Val | Val | Ala | Lys | Val | Glu | Lys | Gly | Lys | Ser | Lys | Lys | Leu | Lys |
| 1145 | | | | | 1150 | | | | | 1155 | | | | |
| Ser | Val | Lys | Glu | Leu | Leu | Gly | Ile | Thr | Ile | Met | Glu | Arg | Ser | Ser |
| 1160 | | | | | 1165 | | | | | 1170 | | | | |
| Phe | Glu | Lys | Asn | Pro | Ile | Asp | Phe | Leu | Glu | Ala | Lys | Gly | Tyr | Lys |
| 1175 | | | | | 1180 | | | | | 1185 | | | | |
| Glu | Val | Lys | Lys | Asp | Leu | Ile | Ile | Lys | Leu | Pro | Lys | Tyr | Ser | Leu |
| 1190 | | | | | 1195 | | | | | 1200 | | | | |
| Phe | Glu | Leu | Glu | Asn | Gly | Arg | Lys | Arg | Met | Leu | Ala | Ser | Ala | Gly |
| 1205 | | | | | 1210 | | | | | 1215 | | | | |
| Glu | Leu | Gln | Lys | Gly | Asn | Glu | Leu | Ala | Leu | Pro | Ser | Lys | Tyr | Val |
| 1220 | | | | | 1225 | | | | | 1230 | | | | |
| Asn | Phe | Leu | Tyr | Leu | Ala | Ser | His | Tyr | Glu | Lys | Leu | Lys | Gly | Ser |
| 1235 | | | | | 1240 | | | | | 1245 | | | | |
| Pro | Glu | Asp | Asn | Glu | Gln | Lys | Gln | Leu | Phe | Val | Glu | Gln | His | Lys |
| 1250 | | | | | 1255 | | | | | 1260 | | | | |
| His | Tyr | Leu | Asp | Glu | Ile | Ile | Glu | Gln | Ile | Ser | Glu | Phe | Ser | Lys |
| 1265 | | | | | 1270 | | | | | 1275 | | | | |
| Arg | Val | Ile | Leu | Ala | Asp | Ala | Asn | Leu | Asp | Lys | Val | Leu | Ser | Ala |
| 1280 | | | | | 1285 | | | | | 1290 | | | | |
| Tyr | Asn | Lys | His | Arg | Asp | Lys | Pro | Ile | Arg | Glu | Gln | Ala | Glu | Asn |
| 1295 | | | | | 1300 | | | | | 1305 | | | | |
| Ile | Ile | His | Leu | Phe | Thr | Leu | Thr | Asn | Leu | Gly | Ala | Pro | Ala | Ala |
| 1310 | | | | | 1315 | | | | | 1320 | | | | |
| Phe | Lys | Tyr | Phe | Asp | Thr | Thr | Ile | Asp | Arg | Lys | Arg | Tyr | Thr | Ser |
| 1325 | | | | | 1330 | | | | | 1335 | | | | |
| Thr | Lys | Glu | Val | Leu | Asp | Ala | Thr | Leu | Ile | His | Gln | Ser | Ile | Thr |
| 1340 | | | | | 1345 | | | | | 1350 | | | | |
| Gly | Leu | Tyr | Glu | Thr | Arg | Ile | Asp | Leu | Ser | Gln | Leu | Gly | Gly | Asp |
| 1355 | | | | | 1360 | | | | | 1365 | | | | |

<210> SEQ ID NO 86
<211> LENGTH: 1000
<212> TYPE: DNA
<213> ORGANISM: artificial sequence
<220> FEATURE:
<223> OTHER INFORMATION: ZM-U6 POLIII CHR8 PRO

<400> SEQUENCE: 86

```
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat     180
gaatcctggc ttattccggt acaaccgaac aggccctgaa ggataccagt aatcgctgag     240
ctaaattggc atgctgtcag agtgtcagta ttgcagcaag gtagtgagat aaccggcatc     300
atggtgccag tttgatggca ccattagggt tagagatggt ggccatgggc gcatgtcctg     360
```

```
gccaactttg tatgatatat ggcagggtga ataggaaagt aaaattgtat tgtaaaaagg     420
gatttcttct gtttgttagc gcatgtacaa ggaatgcaag ttttgagcga ggggcatca      480
aagatctggc tgtgttttca gctgttttg ttagccccat cgaatccttg acataatgat      540
cccgcttaaa taagcaacct cgcttgtata gttccttgtg ctctaacaca cgatgatgat    600
aagtcgtaaa atagtggtgt ccaaagaatt tccaggccca gttgtaaaag ctaaaatgct     660
attcgaattt ctactagcag taagtcgtgt ttagaaatta ttttttttata taccttttt     720
ccttctatgt acagtaggac acagtgtcag cgccgcgttg acggagaata tttgcaaaaa     780
agtaaaagag aaagtcatag cggcgtatgt gccaaaaact tcgtcacaga gagggccata     840
agaaacatgg cccacggccc aatacgaagc accgcgacga agcccaaaca gcagtccgta     900
ggtggagcaa agcgctgggt aatacgcaaa cgttttgtcc caccttgact aatcacaaga    960
gtggagcgta ccttataaac cgagccgcaa gcaccgaatt                          1000
```

<210> SEQ ID NO 87
<211> LENGTH: 4452
<212> TYPE: DNA
<213> ORGANISM: artificial sequence
<220> FEATURE:
<223> OTHER INFORMATION: DCAS9-RP

<400> SEQUENCE: 87

```
atggcaccga agaagaagcg caaggtgctg gatcttcagc ttagactggg cggtggcggt     60
ggatccgaca agaagtacag catcggcctc gccatcggca ccaactcggt gggctgggcc    120
gtcatcacgg acgaatataa ggtcccgtcg aagaagttca aggtcctcgg caatacagac    180
cgccacagca tcaagaaaaa cttgatcggc gccctcctgt tcgatagcgg cgagaccgcg    240
gaggcgacca ggctcaagag gaccgccagg agacggtaca ctaggcgcaa gacaggatc     300
tgctacctgc aggagatctt cagcaacgag atggcgaagg tggacgactc cttcttccac    360
cgcctggagg aatcattcct ggtggaggag acaagaagc atgagcggca cccaatcttc      420
ggcaacatcg tcgacgaggt aagtttctgc ttctaccttt gatatatata taataattat    480
cattaattag tagtaatata atatttcaaa tatttttttc aaaataaaag aatgtagtat    540
atagcaattg cttttctgta gtttataagt gtgtatattt taatttataa cttttctaat    600
atatgaccaa acatggtga tgtgcaggtg gcctaccacg agaagtaccc gacaatctac     660
cacctccgga agaaactggt ggacagcaca gacaaggcgg acctccggct catctacctt    720
gccctcgcgc atatgatcaa gttccgcggc cacttcctca tcgagggcga cctgaacccg    780
gacaactccg acgtggacaa gctgttcatc cagctcgtgc agacgtacaa tcaactgttc    840
gaggagaacc ccataaacgc tagcggcgtg acgccaagg ccatcctctc ggccaggctc    900
tcgaaatcaa gaaggctgga gaaccttatc gcgcagttgc caggcgaaaa gaagaacggc    960
ctcttcggca accttattgc gctcagcctc ggcctgacgc cgaacttcaa atcaaacttc   1020
gacctcgcgg aggacgccaa gctccagctc tcaaaggaca cctacgacga cgacctcgac   1080
aacctcctgg cccagatagg agaccagtac gcggacctct tcctcgccgc caagaacctc   1140
tccgacgcta tcctgctcag cgacatcctt cgggtcaaca ccgaaattac caaggcaccg   1200
ctgtccgcca gcatgattaa acgctacgac gagcaccatc aggacctcac gctgctcaag   1260
gcactcgtcc gccagcagct ccccgagaag tacaaggaga tcttcttcga ccaatcaaaa   1320
aacggctacg cggatatat cgacggcggt gccagccagg aagagttcta caagttcatc   1380
aaaccaatcc tggagaagat ggacggcacc gaggagttgc tggtcaagct caacagggag   1440
```

```
gacctcctca ggaagcagag gaccttcgac aacggctcca tcccgcatca gatccacctg    1500
ggcgaactgc atgccatcct gcggcgccag gaggacttct acccgttcct gaaggataac    1560
cgggagaaga tcgagaagat cttgacgttc cgcatcccat actacgtggg cccgctggct    1620
cgcggcaact cccggttcgc ctggatgacc cggaagtcgg aggagaccat cacccctgg     1680
aactttgagg aggtggtcga tagggcgct agcgctcaga gcttcatcga gcgcatgacc     1740
aacttcgata aaaacctgcc caatgaaaaa gtcctcccca gcactcgct gctctacgag     1800
tacttcaccg tgtacaacga gctcaccaag gtcaaatacg tcaccgaggg catgcggaag    1860
ccggcgttcc tgagcggcga gcagaagaag gcgatagtgg acctcctctt caagaccaac    1920
aggaaggtga ccgtgaagca attaaaagag gactacttca gaaaatagag tgcttcgac    1980
tccgtggaga tctcgggcgt ggaggatcgg ttcaacgcct cactcggcac gtatcacgac    2040
ctcctcaaga tcattaaaga caaggacttc ctcgacaacg aggagaacga ggacatcctc    2100
gaggacatcg tcctcaccct gaccctgttc gaggaccgcg aaatgatcga ggagaggctg    2160
aagacctacg cgcacctgtt cgacgacaag gtcatgaaac agctcaagag gcgccgctac    2220
actggttggg gaaggctgtc ccgcaagctc attaatggca tcaggacaa gcagagcggc     2280
aagaccatcc tggacttcct caagtccgac gggttcgcca accgcaactt catgcagctc    2340
attcacgacg actcgctcac gttcaaggaa gacatccaga aggcacaggt gagcgggcag    2400
ggtgactccc tccacgaaca catcgccaac ctggccggct cgccggccat taaaaagggc    2460
atcctgcaga cggtcaaggt cgtcgacgag ctcgtgaagg tgatgggccg gcacaagccc    2520
gaaaatatcg tcatagagat ggccagggag aaccagacca cccaaaaagg gcagaagaac    2580
tcgcgcgagc ggatgaaacg gatcgaggag ggcattaaag agctcgggtc ccagatcctg    2640
aaggagcacc ccgtggaaaa tacccagctc cagaatgaaa agctctacct ctactacctg    2700
cagaacggcc gcgacatgta cgtggaccag gagctggaca ttaatcggct atcggactac    2760
gacgtcgacg ccatcgtgcc gcagtcgttc ctcaaggacg atagcatcga caacaaggtg    2820
ctcacccggt cggataaaaa tcggggcaag agcgacaacg tgcccagcga ggaggtcgtg    2880
aagaagatga aaaactactg cgccagctc ctcaacgcga aactgatcac ccagcgcaag     2940
ttcgacaacc tgacgaaggc ggaacgcggt ggcttgagcg aactcgataa ggcgggcttc    3000
ataaaaaggc agctggtcga gacgcgccag atcacgaagc atgtcgccca gatcctggac    3060
agccgcatga atactaagta cgatgaaaac gacaagctga tccgggaggt gaaggtgatc    3120
acgctgaagt ccaagctcgt gtcggacttc cgcaaggact tccagttcta caaggtccgc    3180
gagatcaaca actaccacca cgcccacgac gcctacctga atgcggtggt cgggaccgcc    3240
ctgatcaaga agtacccgaa gctggagtcg gagttcgtgt acggcgacta caaggtctac    3300
gacgtgcgca aaatgatcgc caagtccgag caggagatcg gcaaggccac ggcaaaatac    3360
ttcttctact cgaacatcat gaacttcttc aagaccgaga tcaccctcgc gaacggcgag    3420
atccgcaagc gcccgctcat cgaaaccaac ggcgagacgg gcgagatcgt ctgggataag    3480
ggccgggatt tcgcgacggt ccgcaaggtg ctctccatgc cgcaagtcaa tatcgtgaaa    3540
aagacggagg tccagacggg cggggttcagc aaggagtcca tcctcccgaa gcgcaactcc    3600
gacaagctca tcgcgaggaa gaaggattgg gacccgaaaa aatatggcgg cttcgacagc    3660
ccgaccgtcg catacagcgt cctcgtcgtg gcgaaggtgg agaagggcaa gtcaaagaag    3720
ctcaagtccg tgaaggagct gctcgggatc acgattatgg agcggtcctc cttcgagaag    3780
```

```
aacccgatcg acttcctaga ggccaaggga tataaggagg tcaagaagga cctgattatt    3840
aaactgccga agtactcgct cttcgagctg gaaaacggcc gcaagaggat gctcgcctcc    3900
gcaggcgagt tgcagaaggg caacgagctc gccctcccga gcaaatacgt caatttcctg    3960
tacctcgcta gccactatga aaagctcaag ggcagcccgg aggacaacga gcagaagcag    4020
ctcttcgtgg agcagcacaa gcattacctg gacgagatca tcgagcagat cagcgagttc    4080
tcgaagcggg tgatcctcgc cgacgcgaac ctggacaagg tgctgtcggc atataacaag    4140
caccgcgaca aaccaatacg cgagcaggcc gaaaatatca tccacctctt caccctcacc    4200
aacctcggcg ctccggcagc cttcaagtac ttcgacacca cgattgaccg gaagcggtac    4260
acgagcacga aggaggtgct cgatgcgacg ctgatccacc agagcatcac agggctctat    4320
gaaacacgca tcgacctgag ccagctgggc ggagacggtg gcggtggatc cctggatctt    4380
cagcttagac tgggcaagag accacgggac cgccacgatg gcgagctggg aggccgcaag    4440
cgggcaaggt ag                                                        4452
```

<210> SEQ ID NO 88
<211> LENGTH: 1420
<212> TYPE: PRT
<213> ORGANISM: artificial sequence
<220> FEATURE:
<223> OTHER INFORMATION: DCAS9-RP

<400> SEQUENCE: 88

```
Met Ala Pro Lys Lys Arg Lys Val Leu Asp Leu Gln Leu Arg Leu
1               5                   10                  15

Gly Gly Gly Gly Gly Ser Asp Lys Lys Tyr Ser Ile Gly Leu Ala Ile
                20                  25                  30

Gly Thr Asn Ser Val Gly Trp Ala Val Ile Thr Asp Glu Tyr Lys Val
            35                  40                  45

Pro Ser Lys Lys Phe Lys Val Leu Gly Asn Thr Asp Arg His Ser Ile
        50                  55                  60

Lys Lys Asn Leu Ile Gly Ala Leu Leu Phe Asp Ser Gly Glu Thr Ala
65                  70                  75                  80

Glu Ala Thr Arg Leu Lys Arg Thr Ala Arg Arg Arg Tyr Thr Arg Arg
                85                  90                  95

Lys Asn Arg Ile Cys Tyr Leu Gln Glu Ile Phe Ser Asn Glu Met Ala
            100                 105                 110

Lys Val Asp Asp Ser Phe Phe His Arg Leu Glu Glu Ser Phe Leu Val
        115                 120                 125

Glu Glu Asp Lys Lys His Glu Arg His Pro Ile Phe Gly Asn Ile Val
    130                 135                 140

Asp Glu Val Ala Tyr His Glu Lys Tyr Pro Thr Ile Tyr His Leu Arg
145                 150                 155                 160

Lys Lys Leu Val Asp Ser Thr Asp Lys Ala Asp Leu Arg Leu Ile Tyr
                165                 170                 175

Leu Ala Leu Ala His Met Ile Lys Phe Arg Gly His Phe Leu Ile Glu
            180                 185                 190

Gly Asp Leu Asn Pro Asp Asn Ser Asp Val Asp Lys Leu Phe Ile Gln
        195                 200                 205

Leu Val Gln Thr Tyr Asn Gln Leu Phe Glu Glu Asn Pro Ile Asn Ala
    210                 215                 220

Ser Gly Val Asp Ala Lys Ala Ile Leu Ser Ala Arg Leu Ser Lys Ser
225                 230                 235                 240
```

```
Arg Arg Leu Glu Asn Leu Ile Ala Gln Leu Pro Gly Glu Lys Lys Asn
                245                 250                 255

Gly Leu Phe Gly Asn Leu Ile Ala Leu Ser Leu Gly Leu Thr Pro Asn
            260                 265                 270

Phe Lys Ser Asn Phe Asp Leu Ala Glu Asp Ala Lys Leu Gln Leu Ser
        275                 280                 285

Lys Asp Thr Tyr Asp Asp Leu Asp Asn Leu Leu Ala Gln Ile Gly
    290                 295                 300

Asp Gln Tyr Ala Asp Leu Phe Leu Ala Ala Lys Asn Leu Ser Asp Ala
305                 310                 315                 320

Ile Leu Leu Ser Asp Ile Leu Arg Val Asn Thr Glu Ile Thr Lys Ala
                325                 330                 335

Pro Leu Ser Ala Ser Met Ile Lys Arg Tyr Asp Glu His His Gln Asp
            340                 345                 350

Leu Thr Leu Leu Lys Ala Leu Val Arg Gln Gln Leu Pro Glu Lys Tyr
        355                 360                 365

Lys Glu Ile Phe Phe Asp Gln Ser Lys Asn Gly Tyr Ala Gly Tyr Ile
    370                 375                 380

Asp Gly Gly Ala Ser Gln Glu Glu Phe Tyr Lys Phe Ile Lys Pro Ile
385                 390                 395                 400

Leu Glu Lys Met Asp Gly Thr Glu Glu Leu Leu Val Lys Leu Asn Arg
                405                 410                 415

Glu Asp Leu Leu Arg Lys Gln Arg Thr Phe Asp Asn Gly Ser Ile Pro
            420                 425                 430

His Gln Ile His Leu Gly Glu Leu His Ala Ile Leu Arg Arg Gln Glu
        435                 440                 445

Asp Phe Tyr Pro Phe Leu Lys Asp Asn Arg Glu Lys Ile Glu Lys Ile
    450                 455                 460

Leu Thr Phe Arg Ile Pro Tyr Tyr Val Gly Pro Leu Ala Arg Gly Asn
465                 470                 475                 480

Ser Arg Phe Ala Trp Met Thr Arg Lys Ser Glu Glu Thr Ile Thr Pro
                485                 490                 495

Trp Asn Phe Glu Glu Val Val Asp Lys Gly Ala Ser Ala Gln Ser Phe
            500                 505                 510

Ile Glu Arg Met Thr Asn Phe Asp Lys Asn Leu Pro Asn Glu Lys Val
        515                 520                 525

Leu Pro Lys His Ser Leu Leu Tyr Glu Tyr Phe Thr Val Tyr Asn Glu
    530                 535                 540

Leu Thr Lys Val Lys Tyr Val Thr Glu Gly Met Arg Lys Pro Ala Phe
545                 550                 555                 560

Leu Ser Gly Glu Gln Lys Lys Ala Ile Val Asp Leu Leu Phe Lys Thr
                565                 570                 575

Asn Arg Lys Val Thr Val Lys Gln Leu Lys Glu Asp Tyr Phe Lys Lys
            580                 585                 590

Ile Glu Cys Phe Asp Ser Val Glu Ile Ser Gly Val Glu Asp Arg Phe
        595                 600                 605

Asn Ala Ser Leu Gly Thr Tyr His Asp Leu Leu Lys Ile Ile Lys Asp
    610                 615                 620

Lys Asp Phe Leu Asp Asn Glu Glu Asn Glu Asp Ile Leu Glu Asp Ile
625                 630                 635                 640

Val Leu Thr Leu Thr Leu Phe Glu Asp Arg Glu Met Ile Glu Glu Arg
                645                 650                 655

Leu Lys Thr Tyr Ala His Leu Phe Asp Asp Lys Val Met Lys Gln Leu
```

-continued

```
            660                 665                 670
Lys Arg Arg Arg Tyr Thr Gly Trp Gly Arg Leu Ser Arg Lys Leu Ile
            675                 680                 685

Asn Gly Ile Arg Asp Lys Gln Ser Gly Lys Thr Ile Leu Asp Phe Leu
            690                 695                 700

Lys Ser Asp Gly Phe Ala Asn Arg Asn Phe Met Gln Leu Ile His Asp
705                 710                 715                 720

Asp Ser Leu Thr Phe Lys Glu Asp Ile Gln Lys Ala Gln Val Ser Gly
                    725                 730                 735

Gln Gly Asp Ser Leu His Glu His Ile Ala Asn Leu Ala Gly Ser Pro
                740                 745                 750

Ala Ile Lys Lys Gly Ile Leu Gln Thr Val Lys Val Val Asp Glu Leu
            755                 760                 765

Val Lys Val Met Gly Arg His Lys Pro Glu Asn Ile Val Ile Glu Met
            770                 775                 780

Ala Arg Glu Asn Gln Thr Thr Gln Lys Gly Gln Lys Asn Ser Arg Glu
785                 790                 795                 800

Arg Met Lys Arg Ile Glu Glu Gly Ile Lys Glu Leu Gly Ser Gln Ile
                    805                 810                 815

Leu Lys Glu His Pro Val Glu Asn Thr Gln Leu Gln Asn Glu Lys Leu
                820                 825                 830

Tyr Leu Tyr Tyr Leu Gln Asn Gly Arg Asp Met Tyr Val Asp Gln Glu
            835                 840                 845

Leu Asp Ile Asn Arg Leu Ser Asp Tyr Asp Val Asp Ala Ile Val Pro
            850                 855                 860

Gln Ser Phe Leu Lys Asp Asp Ser Ile Asp Asn Lys Val Leu Thr Arg
865                 870                 875                 880

Ser Asp Lys Asn Arg Gly Lys Ser Asp Asn Val Pro Ser Glu Glu Val
                    885                 890                 895

Val Lys Lys Met Lys Asn Tyr Trp Arg Gln Leu Leu Asn Ala Lys Leu
                900                 905                 910

Ile Thr Gln Arg Lys Phe Asp Asn Leu Thr Lys Ala Glu Arg Gly Gly
            915                 920                 925

Leu Ser Glu Leu Asp Lys Ala Gly Phe Ile Lys Arg Gln Leu Val Glu
            930                 935                 940

Thr Arg Gln Ile Thr Lys His Val Ala Gln Ile Leu Asp Ser Arg Met
945                 950                 955                 960

Asn Thr Lys Tyr Asp Glu Asn Asp Lys Leu Ile Arg Glu Val Lys Val
                    965                 970                 975

Ile Thr Leu Lys Ser Lys Leu Val Ser Asp Phe Arg Lys Asp Phe Gln
            980                 985                 990

Phe Tyr Lys Val Arg Glu Ile Asn Asn Tyr His His Ala His Asp Ala
            995                 1000                1005

Tyr Leu Asn Ala Val Val Gly Thr Ala Leu Ile Lys Lys Tyr Pro
            1010                1015                1020

Lys Leu Glu Ser Glu Phe Val Tyr Gly Asp Tyr Lys Val Tyr Asp
            1025                1030                1035

Val Arg Lys Met Ile Ala Lys Ser Glu Gln Glu Ile Gly Lys Ala
            1040                1045                1050

Thr Ala Lys Tyr Phe Phe Tyr Ser Asn Ile Met Asn Phe Phe Lys
            1055                1060                1065

Thr Glu Ile Thr Leu Ala Asn Gly Glu Ile Arg Lys Arg Pro Leu
            1070                1075                1080
```

Ile Glu Thr Asn Gly Glu Thr Gly Ile Val Trp Asp Lys Gly
    1085                1090                1095

Arg Asp Phe Ala Thr Val Arg Lys Val Leu Ser Met Pro Gln Val
    1100                1105                1110

Asn Ile Val Lys Lys Thr Glu Val Gln Thr Gly Gly Phe Ser Lys
    1115                1120                1125

Glu Ser Ile Leu Pro Lys Arg Asn Ser Asp Lys Leu Ile Ala Arg
    1130                1135                1140

Lys Lys Asp Trp Asp Pro Lys Lys Tyr Gly Gly Phe Asp Ser Pro
    1145                1150                1155

Thr Val Ala Tyr Ser Val Leu Val Val Ala Lys Val Glu Lys Gly
    1160                1165                1170

Lys Ser Lys Lys Leu Lys Ser Val Lys Glu Leu Leu Gly Ile Thr
    1175                1180                1185

Ile Met Glu Arg Ser Ser Phe Glu Lys Asn Pro Ile Asp Phe Leu
    1190                1195                1200

Glu Ala Lys Gly Tyr Lys Glu Val Lys Lys Asp Leu Ile Ile Lys
    1205                1210                1215

Leu Pro Lys Tyr Ser Leu Phe Glu Leu Glu Asn Gly Arg Lys Arg
    1220                1225                1230

Met Leu Ala Ser Ala Gly Glu Leu Gln Lys Gly Asn Glu Leu Ala
    1235                1240                1245

Leu Pro Ser Lys Tyr Val Asn Phe Leu Tyr Leu Ala Ser His Tyr
    1250                1255                1260

Glu Lys Leu Lys Gly Ser Pro Glu Asp Asn Glu Gln Lys Gln Leu
    1265                1270                1275

Phe Val Glu Gln His Lys His Tyr Leu Asp Glu Ile Ile Glu Gln
    1280                1285                1290

Ile Ser Glu Phe Ser Lys Arg Val Ile Leu Ala Asp Ala Asn Leu
    1295                1300                1305

Asp Lys Val Leu Ser Ala Tyr Asn Lys His Arg Asp Lys Pro Ile
    1310                1315                1320

Arg Glu Gln Ala Glu Asn Ile Ile His Leu Phe Thr Leu Thr Asn
    1325                1330                1335

Leu Gly Ala Pro Ala Ala Phe Lys Tyr Phe Asp Thr Thr Ile Asp
    1340                1345                1350

Arg Lys Arg Tyr Thr Ser Thr Lys Glu Val Leu Asp Ala Thr Leu
    1355                1360                1365

Ile His Gln Ser Ile Thr Gly Leu Tyr Glu Thr Arg Ile Asp Leu
    1370                1375                1380

Ser Gln Leu Gly Gly Asp Gly Gly Gly Ser Leu Asp Leu Gln
    1385                1390                1395

Leu Arg Leu Gly Lys Arg Pro Arg Asp Arg His Asp Gly Glu Leu
    1400                1405                1410

Gly Gly Arg Lys Arg Ala Arg
    1415                1420

<210> SEQ ID NO 89
<211> LENGTH: 3938
<212> TYPE: DNA
<213> ORGANISM: artificial sequence
<220> FEATURE:
<223> OTHER INFORMATION: RB-LOXP-OSACTIN PRO,INTRON-FRT1-MOPAT-35STERM-
      FRT87-LB

```
<400> SEQUENCE: 89
gtttacccgc caatatatcc tgtcaaacac tgatagttta aactgaaggc gggaaacgac    60
aatctgatca tgagcggaga attaagggag tcacgttatg accccgccg atgacgcggg   120
acaagccgtt ttacgtttgg aactgacaga accgcaacgt tgaaggagcc actcagcaag   180
ctggtacgat tgtaatacga ctcactatag ggcgaattga gcgctgttta aacgctcttc   240
aactggaaga gcggttacta ccggctggat ggcggggcct tgatcgtgca ccgccggcgt   300
ccggactaac taactagtcg agctagttac cctatgaggt gacatgaagc gctcacggtt   360
actatgacgg ttagcttcac gactgttggt ggcagtagcg tacgacttag ctatagttcc   420
ggacttaccc ttaagataac ttcgtatagc atacattata cgaagttata cctggtggcg   480
ccgctaggac cgaattatcg aattcctgca gcccatccct cagccgcctt tcactatctt   540
ttttgcccga gtcattgtca tgtgaacctt ggcatgtata atcggtgaat tgcgtcgatt   600
ttcctcttat aggtgggcca atgaatccgt gtgatcgcgt ctgattggct agagatatgt   660
ttcttccttg ttggatgtat tttcatacat aatcatatgc atacaaatat ttcattacac   720
tttatagaaa tggtcagtaa taaacccta cactatgtct ggtgttttcat tttatttgct   780
tttaaacgaa aattgacttc ctgattcaat atttaaggat cgtcaacggt gtgcagttac   840
taaattctgg tttgtaggaa ctatagtaaa ctattcaagt cttcacttat tgtgcactca   900
cctctcgcca catcaccaca gatgttattc acgtcttaaa tttgaactac acatcatatt   960
gacacaatat tttttttaaa taagcgatta aaacctagcc tctatgtcaa caatggtgta  1020
cataaccagc gaagtttagg gagtaaaaaa catcgcctta cacaaagttc gctttaaaaa  1080
ataaagagta aattttactt tggaccaccc ttcaaccaat gtttcacttt agaacgagta  1140
attttattat tgtcactttg gaccaccctc aaatcttttt tccatctaca tccaatttat  1200
catgtcaaag aaatggtcta catacagcta aggagattta tcgacgaata gtagctagca  1260
tactcgaggt cattcatatg cttgagaaga gagtcgggat agtccaaaat aaaacaaagg  1320
taagattacc tggtcaaaag tgaaaacatc agttaaaagg tggtataaag taaaatatcg  1380
gtaataaaag gtggcccaaa gtgaaattta ctcttttcta ctattataaa aattgaggat  1440
gttttttgtcg gtactttgat acgtcatttt tgtatgaatt ggttttttaag tttattcgct  1500
tttggaaatg catatctgta tttgagtcgg gttttaagtt cgtttgcttt tgtaaataca  1560
gagggatttg tataagaaat atctttaaaa aaacccatat gctaatttga cataattttt  1620
gagaaaaata tatattcagg cgaattctca caatgaacaa taataagatt aaaatagctt  1680
tccccgttg cagcgcatgg gtatttttc tagtaaaaat aaaagataaa cttagactca  1740
aaacatttac aaaacaaacc cctaaagttc ctaaagccca aagtgctatc cacgatccat  1800
agcaagccca gcccaaccca acccaaccca acccaccca gtccagccaa ctggacaata  1860
gtctccacac ccccccacta tcaccgtgag ttgtccgcac gcaccgcacg tctcgcagcc  1920
aaaaaaaaaa aagaaagaa aaaaagaaa agaaaaaac agcaggtggg tccgggtcgt  1980
gggggccgga aacgcgagga ggatcgcgag ccagcgacga ggccggccct cctccgctt  2040
ccaaagaaac gccccatc gccactatat acatacccc cctctcctc ccatccccc  2100
aaccctacca ccaccaccac caccacctcc acctcctccc cctcgctgc cggacgacga  2160
gctcctcccc cctcccctc cgccgccgcc gcgccggtaa ccacccgcc cctctcctct  2220
ttctttctcc gttttttttt tccgtctcgg tctcgatctt tggccttggt agtttgggtg  2280
ggcgagaggc ggcttcgtgc gcgcccagat cggtgcgcgg gaggggcggg atctcgcggc  2340
```

```
tggggctctc gccggcgtgg atcaggcccg gatctcgcgg ggaatggggc tctcggatgt    2400
agatctgcga tccgccgttg ttgggggaga tgatgggggg tttaaaattt ccgccatgct    2460
aaacaagatc aggaagaggg gaaaagggca ctatggttta tatttttata tatttctgct    2520
gcttcgtcag gcttagatgt gctagatctt tctttcttct ttttgtgggt agaatttgaa    2580
tccctcagca ttgttcatcg gtagtttttc ttttcatgat ttgtgacaaa tgcagcctcg    2640
tgcggagctt ttttgtaggt agaaggatct cgactctaga ggatcaattc gctagcgaag    2700
ttcctattcc gaagttccta ttctctagaa agtataggaa cttcagatcc accgggatcc    2760
acacgacacc atgtccccg agcgccgccc cgtcgagatc cgcccggcca ccgccgccga    2820
catggccgcc gtgtgcgaca tcgtgaacca ctacatcgag acctccaccg tgaacttccg    2880
caccgagccg cagaccccgc aggagtggat cgacgacctg gagcgcctcc aggaccgcta    2940
cccgtggctc gtggccgagg tggagggcgt ggtggccggc atcgcctacg ccggcccgtg    3000
gaaggcccgc aacgcctacg actggaccgt ggagtccacc gtgtacgtgt cccaccgcca    3060
ccagcgcctc ggcctcggct ccaccctcta cacccacctc ctcaagagca tggaggccca    3120
gggcttcaag tccgtggtgg ccgtgatcgg cctcccgaac gacccgtccg tgcgcctcca    3180
cgaggccctc ggctacaccg cccgcggcac cctccgcgcc gccggctaca agcacggcgg    3240
ctggcacgac gtcggcttct ggcagcgcga cttcgagctg ccggccccgc gcgcccggt    3300 gcgcccggtg acgcagatct gagtcgacct gcaggcatgc cgctgaaatc accagtctct    3360
ctctacaaat ctatctctct ctataataat gtgtgagtag ttcccagata agggaattag    3420
ggttcttata gggtttcgct catgtgttga gcatataaga aacccttagt atgtatttgt    3480
atttgtaaaa tacttctatc aataaaattt ctaattccta aaaccaaaat ccagtggcga    3540
gctcgagccc gggtggatcc tctagagtcg acctgcagaa gcttcggtcc tagcgtatac    3600
gaagttccta ttccgaagtt cctattctcc agaaagtata ggaacttctg tacacctgag    3660
ctgattccga tgacttcgta ggttcctagc tcaagccgct cgtgtccaag cgtcacttac    3720
gattagctaa tgattacggc atctaggacc gactagctaa ctaactagta cgtagaatta    3780
attcattccg attaatcgtg gcctcttgct cttcaggatg aagagctatg tttaaacgtg    3840
caagcgctac tagacaattc agtacattaa aaacgtccgc aatgtgttat taagttgtct    3900
aagcgtcaat ttgtttacac cacaatatat cctgccac                            3938
```

<210> SEQ ID NO 90
<211> LENGTH: 4682
<212> TYPE: DNA
<213> ORGANISM: artificial sequence
<220> FEATURE:
<223> OTHER INFORMATION: PG47 PRO-ZMAA1-IN2-1 TERM

<400> SEQUENCE: 90

```
aagcttgcat gcctgcaggt cgactctaga ggatctgcac cggacactgt ctggtggcat      60
accagacagt ccggtgtgcc agatcagggc acccttcggt tcctttgctc ctttgctttt     120
gaaccctaac tttgatcgtt tattggtttg tgttgaacct ttatgcacct gtggaatata     180
taatctagaa caaactagtt agtccaatca tttgtgttgg gcattcaacc accaaaatta     240
tttataggaa aaggttaaac cttatttccc tttcaatctc ccccttttg gtgattgatg      300 ccaacacaaa ccaagaaaaa tatataagtg cagaattgaa ctagtttgca taaggtaagt     360
gcataggtta cttagaatta aatcaattta tactttact tgatatgcat ggttgctttc      420
```

```
ttttatttta acattttgga ccacatttgc accacttgtt ttgttttttg caaatctttt        480
tggaaattct ttttcaaagt cttttgcaaa tagtcaaagg tatatgaata agattgtaag        540
aagcattttc aagatttgaa atttctcccc ctgtttcaaa tgcttttcct ttgactaaac        600
aaaactcccc ctgaataaaa ttctcctctt agctttcaag agggttttaa atagatatca        660
attggaaata tatttagatg ctaattttga aaatataccaa attgaaaatc aacataccaa       720
tttgaaatta aacataccaa tttaaaaaat ttcaaaaagt ggtggtgcgg tccttttgct        780
ttgggcttaa tatttctccc cctttggcat taatcgccaa aaacggagac tttgtgagcc        840
atttatactt tctccccatt ggtaaatgaa atatgagtga agattatac caaatttgga         900
cagtgatgcg gagtgacggc gaaggataaa cgataccgtt agagtggagt ggaagccttg        960
tcttcgccga agactccatt tcccttcaa tctacgactt agcatagaaa tacacttgaa        1020
aacacattag tcgtagccac gaaagagata tgatcaaagg tatacaaatg agctatgtgt       1080
gtaatgtttc aatcaaagtt tcgagaatca agaatattta gctcattcct aagtttgcta       1140
aaggttttat catctaatgg tttggtaaag atatcgacta attgttcttt ggtgctaaca       1200
taagcaatct cgatatcacc cctttgttgg tgatccctca aaaagtgata ccgaatgtct       1260
atgtgcttag tgcggctgtg ttcaacggga ttatccgcca tgcagatagc actctcattg      1320
tcacatagga gagggacttt gctcaatttg tagccatagt ccctaaggtt ttgcctcatc       1380
caaagtaatt gcacacaaca atgtcctgcg gcaatatact tggcttcggc ggtagaaaga       1440
gctattgagt tttgtttctt tgaagtccaa gacaccaggg atctccctag aaactgacaa       1500
gtccctgatg tgctcttcct atcaattta caccctgccc aatcggcatc tgaatatcct        1560
attaaatcaa aggtggatcc cttggggtac caaagaccaa atttaggagt gtaaactaaa       1620
tatctcatga ttcttttcac ggccctaagg tgaacttcct taggatcggc ttggaatctt       1680
gcacacatgc atatagaaag catactatct ggtcgagatg cacataaata gagtaaagat       1740
cctatcatcg accggtatac cttttggtct acggattac ctcccgtgtc gaggtcgaga        1800
tgcccattag ttcccatggg tgtcctgatg ggcttggcat ccttcattcc aaacttgttg       1860
agtatgtctt gaatgtactt tgtttggctg atgaaggtgc catctggag ttgcttgact        1920
tgaaatccta gaaaatattt caacttcccc atcatagaca tctcgaattt cggaatcatg       1980
atcctactaa actcttcaca gtagatttg ttagtagacc caaatataat atcatcaaca        2040
taaatttggc atacaaacaa aacttttgaa atggttttag taaagagagt aggatcggct       2100
ttactgactc tgaagccatt agtgataaga aaatctctta ggcattcata ccatgctgtt      2160
ggggcttgct tgagcccata aagcgccttt gagagtttat aaacatggtt agggtactca       2220
ctatcttcaa agccgagagg ttgctcaaca tagacctatt caccccattt gatcactttt       2280
ttggtccttc aggatctaat agttatgtat aatttagagt ctcttgttta atggccagat       2340
atttctaatt aatctaagaa tttatgatat tttttaattt tttatcatgt ctgatgagaa       2400
ttaacataaa ggctcaattg ggtcctgaat taataataga gtgaaaatta atccagaggc       2460
tctattagaa ccttcaatta gtaataccaa gatatatata agatagtaga gtatagttta      2520
aatgttggca ttgttcattc tttctttgt tatttaattt atgctttcca cggtggttag        2580
tggttacttc tgaagggtcc aaataatgca tgaagagttt gaggacaaga agtctgccct       2640
aaaaatagcg atgcaaaggc atggtgtcca agccatacat atagcgcact aattttatca       2700
gcagaacaat ggtatttata ggtcctagtg cccaggcaac aagagacacg aataaagcat       2760
cgatcacgac accatggcgg cgacaatggc agtgacgacg atggtgacga ggagcaagga       2820
```

```
gagctggtcg tcattgcagg tcccggcggt ggcattccct tggaagccac gaggtggcaa    2880
gaccggcggc ctcgagttcc ctcgccgggc gatgttcgcc agcgtcggcc tcaacgtgtg    2940 cccggcgtc  ccggcggggc gcgacccgcg ggagcccgat cccaaggtcg tccgggcggc    3000
ctgcggcctg gtccaggcac aagtcctctt ccaggggttt aactgggagt cgtgcaagca    3060
gcagggaggc tggtacaaca ggctcaaggc ccaggtcgac gacatcgcca aggccggcgt    3120
cacgcacgtc tggctgcctc caccctcgca ctccgtctcg ccacaaggct acatgccagg    3180
ccgcctatac gacctggacg cgtccaagta cggcacggcg gcggagctca agtccctgat    3240
agcggcgttc cacggcaggg gcgtgcagtg cgtggcggac atcgtcatca accaccggtg    3300
cgcggaaaag aaggacgcgc gcggcgtgta ctgcatcttc gagggcggga ctcccgacga    3360
ccgcctggac tggggccccg ggatgatctg cagcgacgac acgcagtact cggacgggac    3420
ggggcaccgc gacacgggcg aggggttcgc ggcggcgccc gacatcgacc acctcaaccc    3480
gcgcgtgcag cgggagctct ccgcctggct caactggctc aggtccgacg ccgtggggtt    3540
cgacggctgg cgcctcgact tcgccaaggg ctactcgccg gccgtcgcca gaatgtacgt    3600
ggagagcacg gggccgccga gcttcgtcgt cgcggagata tggaactcgc tgagctacag    3660
cggggacggc aagccggcgc ccaaccagga ccagtgccgg caggagctgc tggactggac    3720
gcgggccgtc ggcgggcccg ccatggcgtt cgacttcccc accaagggcc tgctgcaggc    3780
gggcgtgcag ggggagctgt ggcggctgcg cgacagctcc ggcaacgcgg ccggcctgat    3840
cgggtgggcg cccgagaagg ccgtcacctt cgtcgacaac catgacaccg ggtcgacgca    3900
gaagctctgg ccgttcccat ccgacaaggt catgcagggc tacgcctaca tcctcaccca    3960
tccaggagtc ccctgcattt tctacgacca catgttcgac tggaacctga agcaggagat    4020
atccacgctg tctgccatca gggcgcggaa cggcatccgc gccgggagca agctgcggat    4080
cctcgtggcg gacgcggacg cgtacgtggc cgtcgtcgac gagaaggtca tggtgaagat    4140
cgggacaagg tacggcgtga gcagcgtggt cccgtcggat ttccaccgg cggcgcacgg    4200 caaggactac tgcgtctggg agaaagcgag cctccgcgtc ccggcggggc gccacctcta    4260
gcagctcaga ttgctcagtc ttgtgctgca ttgcaaacac agcagcacga cactgcataa    4320 cgtctttttcc ttgagatctg acaaagcagc attagtccgt tgatcggtgg aagaccactc    4380
gtcagtgttg agttgaatgt tgatcaata aaatacggca atgctgtaag ggttgttttt    4440
tatgccattg ataatacact gtactgttca gttgttgaac tctatttctt agccatgcca    4500
agtgcttttc ttattttgaa taacattaca gcaaaaagtt gaaagacaaa aaaaaaaacc    4560
cccgaacaga gtgctttggg tcccaagcta ctttagactg tgttcggcgt tcccctaaa    4620 tttctccccc tatatctcac tcacttgtca catcagcgtt ctctttcccc tatatctcca    4680
cg                                                                  4682
```

<210> SEQ ID NO 91
<211> LENGTH: 3042
<212> TYPE: DNA
<213> ORGANISM: artificial sequence
<220> FEATURE:
<223> OTHER INFORMATION: LTP2 PRO-AMCYAN1-PINII TERM

<400> SEQUENCE: 91

```
gtgcagcgtg acccggtcgt gcccctctct agagataatg agcattgcat gtctaagtta    60
taaaaaatta ccacatattt ttttttgtcac acttgtttga agtgcagttt atctatcttt    120
```

```
atacatatat ttaaacttta ctctacgaat aatataatct atagtactac aataatatca      180
gtgttttaga gaatcatata aatgaacagt tagacatggt ctaaaggaca attgagtatt      240
ttgacaacag gactctacag ttttatcttt ttagtgtgca tgtgttctcc ttttttttg       300 caaatagctt cacctatata atacttcatc cattttatta gtacatccat ttagggttta      360
gggttaatgg ttttttataga ctaattttttt tagtacatct attttattct attttagcct    420
ctaaattaag aaaactaaaa ctctatttta gttttttttat ttaataattt agatataaaa     480
tagaataaaa taaagtgact aaaaattaaa caaatacccct ttaagaaatt aaaaaaacta     540
aggaaacatt tttcttgttt cgagtagata atgccagcct gttaaacgcc gtcgacgagt      600
ctaacggaca ccaaccagcg aaccagcagc gtcgcgtcgg gccaagcgaa gcagacggca      660
cggcatctct gtcgctgcct ctggaccccct ctcgagagtt ccgctccacc gttggacttg     720
ctccgctgtc ggcatccaga aattgcgtgg cggagcggca gacgtgagcc ggcacggcag      780
gcggcctcct cctcctctca cggcaccggc agctacgggg gattcctttc ccaccgctcc      840
ttcgctttcc cttcctcgcc cgccgtaata aatagacacc ccctccacac cctctttccc      900
caacctcgtg ttgttcggag cgcacacaca caacaccaga tctcccccaa atccacccgt      960
cggcacctcc gcttcaaggt acgccgctcg tcctccccccc ccccctctc taccttctct     1020 agatcggcgt tccggtccat gcatggttag ggccccggtag ttctacttct gttcatgttt   1080
gtgttagatc cgtgtttgtg ttagatccgt gctgctagcg ttcgtacacg gatgcgacct     1140
gtacgtcaga cacgttctga ttgctaactt gccagtgttt ctctttgggg aatcctggga     1200
tggctctagc cgttccgcag acgggatcga tttcatgatt ttttttgttt cgttgcatag     1260
ggtttggttt gcccttttcc tttatttcaa tatatgccgt gcacttgttt gtcgggtcat     1320
cttttcatgc ttttttttgt cttggttgtg atgatgtggt ctggttgggc ggtcgttcta     1380
gatcggagta gaattctgtt tcaaactacc tggtggattt attaattttg gatctgtatg     1440
tgtgtgccat acatattcat agttacgaat tgaagatgat ggatggaaat atcgatctag     1500
gataggtata catgttgatg cgggttttac tgatgcatat acagagatgc ttttttgttcg    1560 cttggttgtg atgatgtggt gtggttgggc ggtcgttcat tcgttctaga tcggagtaga   1620
atactgtttc aaactacctg gtgtatttat taattttgga actgtatgtg tgtgtcatac     1680
atcttcatag ttacgagttt aagatggatg gaaatatcga tctaggatag gtatacatgt     1740
tgatgtgggt tttactgatg catatacatg atggcatatg cagcatctat tcatatgctc     1800
taaccttgag tacctatcta ttataataaa caagtatgtt ttataattat tttgatcttg      1860
atatacttgg atgatggcat atgcagcagc tatatgtgga ttttttttagc cctgccttca    1920 tacgctattt atttgcttgg tactgttttct tttgtcgatg ctcaccctgt tgtttggtgt    1980
tacttctgca ggtcgactct agaggatcca ccggtcgcca ccatggccct gtccaacaag     2040
ttcatcggcg acgacatgaa gatgacctac cacatggacg gctgcgtgaa cggccactac     2100
ttcaccgtga agggcgaggg cagcggcaag ccctacgagg gcacccagac ctccaccttc    2160
aaggtgacca tggccaacgg cggccccctg gccttctcct tcgacatcct gtccaccgtg     2220
ttcatgtacg gcaaccgctg cttcaccgcc taccccacca gcatgcccga ctacttcaag     2280
caggccttcc ccgacggcat gtcctacgag agaaccttca cctacgagga cggcggcgtg    2340
gccaccgcca gctgggagat cagcctgaag ggcaactgct tcgagcacaa gtccaccttc    2400 cacgcgtga acttccccgc cgacggcccc gtgatggcca gaagaccac cggctgggac     2460 ccctccttcg agaagatgac cgtgtgcgac ggcatcttga agggcgacgt gaccgccttc    2520
```

```
ctgatgctgc agggcggcgg caactacaga tgccagttcc acacctccta caagaccaag   2580
aagcccgtga ccatgccccc caaccacgtg gtggagcacc gcatcgccag aaccgacctg   2640
gacaagggcg gcaacagcgt gcagctgacc gagcacgccg tggcccacat cacctccgtg   2700
gtgcccttct gaagcggccg caacctagac ttgtccatct tctggattgg ccaacttaat   2760
taatgtatga aataaaagga tgcacacata gtgacatgct aatcactata atgtgggcat   2820
caaagttgtg tgttatgtgt aattactagt tatctgaata aaagagaaag agatcatcca   2880
tatttcttat cctaaatgaa tgtcacgtgt ctttataatt ctttgatgaa ccagatgcat   2940
ttcattaacc aaatccatat acatataaat attaatcata taattaat atcaattggg   3000 ttagcaaaac aaatctagtc taggtgtgtt ttgcgaatgc gg                      3042
```

<210> SEQ ID NO 92
<211> LENGTH: 3118
<212> TYPE: DNA
<213> ORGANISM: artificial sequence
<220> FEATURE:
<223> OTHER INFORMATION: UBI1ZM PRO and INTRON-NPTII-PINII TERM

<400> SEQUENCE: 92

```
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc ttttttttg     300 caaatagctt cacctatata atacttcatc cattttatta gtacatccat ttagggttta    360
gggttaatgg ttttttataga ctaatttttt tagtacatct attttattct attttagcct    420
ctaaattaag aaaactaaaa ctctatttta gttttttttat ttaataattt agatataaaa    480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggaccccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgcttttc cttcctcgcc cgccgtaata aatagacacc cctccacac cctctttccc    900 caacctcgtg ttgttcggag cgcacacaca caaccagat ctcccccaa atccacccgt     960 cggcacctcc gcttcaaggt acgccgctcg tcctccccc ccccctctc taccttctct    1020 agatcggcgt tccggtccat gcatggttag ggcccggtag ttctacttct gttcatgttt    1080
gtgttagatc cgtgtttgtg ttagatccgt gctgctagcg ttcgtacacg gatgcgacct    1140
gtacgtcaga cacgttctga ttgctaactt gccagtgttt ctctttgggg aatcctggga    1200
tggctctagc cgttccgcag acgggatcga tttcatgatt ttttttgttt cgttgcatag    1260
ggtttggttt gcccttttcc tttatttcaa tatatgccgt gcacttgttt gtcgggtcat    1320
cttttcatgc ttttttttgt cttggttgtg atgatgtggt ctggttgggc ggtcgttcta    1380
gatcggagta gaattctgtt tcaaactacc tggtggattt attaattttg gatctgtatg    1440
tgtgtgccat acatattcat agttacgaat tgaagatgat ggatggaaat atcgatctag    1500
```

```
gataggtata catgttgatg cgggttttac tgatgcatat acagagatgc tttttgttcg    1560
cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920 tacgctattt atttgcttgg tactgtttct tttgtcgatg ctcaccctgt tgtttggtgt    1980
tacttctgca gttagatggt tgaacaagat ggattgcacg caggttctcc ggccgcttgg    2040
gtggagaggc tattcggcta tgactgggca acagacaa tcggctgctc tgatgccgcc     2100
gtgttccggc tgtcagcgca ggggcgcccg gttcttttg tcaagaccga cctgtccggt     2160
gccctgaatg aactgcagga cgaggcagcc cggctatcgt ggctggccac gacgggcgtt    2220
ccttgcgcag ctgtgctcga cgttgtcact gaagcgggaa gggactggct gctattgggc    2280
gaagtgccgg ggcaggatct cctgtcatct caccttgctc ctgccgagaa agtatccatc    2340
atggctgatg caatgcggcg gctgcatacg cttgatccgg ctacctgccc attcgaccac    2400
caagcgaaac atcgcatcga gcagcacgt actcggatgg aagccggtct tgtcgatcag    2460
gatgatctgg acgaagagca tcaggggctc gcgccagccg aactgttcgc caggctcaag    2520
gcgcgcatgc ccgacggcga tgatctcgtc gtgacccatg gcgatgcctg cttgccgaat    2580
atcatggtgg aaaatggccg cttttctgga ttcatcgact gtggccggct gggtgtggcg    2640
gaccgctatc aggacatagc gttggctacc cgtgatattg ctgaagagct tggcggcgaa    2700
tgggctgacc gcttcctcgt gctttacggt atcgccgctc ccgattcgca gcgcatcgcc    2760
ttctatcgcc ttcttgacga gttcttctga ggatccacca tggttaacct agacttgtcc    2820
atcttctgga ttggccaact taattaatgt atgaaataaa aggatgcaca catagtgaca    2880
tgctaatcac tataatgtgg gcatcaaagt tgtgtgttat gtgtaattac tagttatctg    2940
aataaaagag aaagagatca tccatatttc ttatcctaaa tgaatgtcac gtgtctttat    3000
aattctttga tgaaccagat gcatttcatt aaccaaatcc atatacatat aaatattaat    3060
catatataat taatatcaat tgggttagca aaacaaatct agtctaggtg tgttttgc     3118
```

<210> SEQ ID NO 93
<211> LENGTH: 690
<212> TYPE: DNA
<213> ORGANISM: artificial sequence
<220> FEATURE:
<223> OTHER INFORMATION: AMCYAN1 DNA

<400> SEQUENCE: 93

```
atggccctgt ccaacaagtt catcggcgac gacatgaaga tgacctacca catggacggc      60
tgcgtgaacg gccactactt caccgtgaag ggcgagggca gcggcaagcc ctacgagggc     120
acccagacct ccaccttcaa ggtgaccatg gccaacggcg gccccctggc cttctccttc     180
gacatcctgt ccaccgtgtt catgtacggc aaccgctgct tcaccgccta ccccaccagc     240
atgcccgact acttcaagca ggccttcccc gacggcatgt cctacgagag aaccttcacc     300
tacgaggacg gcggcgtggc caccgccagc tgggagatca gcctgaaggg caactgcttc     360
gagcacaagt ccaccttcca cggcgtgaac ttccccgccg acggccccgt gatggccaag     420
aagaccaccg gctgggaccc ctccttcgag aagatgaccg tgtgcgacgg catccttgaag     480
```

```
ggcgacgtga ccgccttcct gatgctgcag ggcggcggca actacagatg ccagttccac    540
acctcctaca agaccaagaa gcccgtgacc atgcccccca ccacgtggt ggagcaccgc     600 atcgccagaa ccgacctgga caagggcggc aacagcgtgc agctgaccga gcacgccgtg    660
gcccacatca cctccgtggt gcccttctga                                     690
```

<210> SEQ ID NO 94
<211> LENGTH: 229
<212> TYPE: PRT
<213> ORGANISM: artificial sequence
<220> FEATURE:
<223> OTHER INFORMATION: AMCYAN1 PRT

<400> SEQUENCE: 94

Met Ala Leu Ser Asn Lys Phe Ile Gly Asp Asp Met Lys Met Thr Tyr
1               5                   10                  15

His Met Asp Gly Cys Val Asn Gly His Tyr Phe Thr Val Lys Gly Glu
            20                  25                  30

Gly Ser Gly Lys Pro Tyr Glu Gly Thr Gln Thr Ser Thr Phe Lys Val
        35                  40                  45

Thr Met Ala Asn Gly Gly Pro Leu Ala Phe Ser Phe Asp Ile Leu Ser
    50                  55                  60

Thr Val Phe Met Tyr Gly Asn Arg Cys Phe Thr Ala Tyr Pro Thr Ser
65                  70                  75                  80

Met Pro Asp Tyr Phe Lys Gln Ala Phe Pro Asp Gly Met Ser Tyr Glu
                85                  90                  95

Arg Thr Phe Thr Tyr Glu Asp Gly Gly Val Ala Thr Ala Ser Trp Glu
            100                 105                 110

Ile Ser Leu Lys Gly Asn Cys Phe Glu His Lys Ser Thr Phe His Gly
        115                 120                 125

Val Asn Phe Pro Ala Asp Gly Pro Val Met Ala Lys Lys Thr Thr Gly
    130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Gly Asn Tyr Arg
                165                 170                 175

Cys Gln Phe His Thr Ser Tyr Lys Thr Lys Lys Pro Val Thr Met Pro
            180                 185                 190

Pro Asn His Val Val Glu His Arg Ile Ala Arg Thr Asp Leu Asp Lys
        195                 200                 205

Gly Gly Asn Ser Val Gln Leu Thr Glu His Ala Val Ala His Ile Thr
    210                 215                 220

Ser Val Val Pro Phe
225

<210> SEQ ID NO 95
<211> LENGTH: 2939
<212> TYPE: DNA
<213> ORGANISM: artificial sequence
<220> FEATURE:
<223> OTHER INFORMATION: OSACTIN PRO and INTRON-MOPAT-35S TERM

<400> SEQUENCE: 95

```
atccctcagc cgcctttcac tatcttttt gcccgagtca ttgtcatgtg aaccttggca     60
tgtataatcg gtgaattgcg tcgattttcc tcttataggt gggccaatga atccgtgtga   120
tcgcgtctga ttggctagag atatgtttct tccttgttgg atgtattttc atacataatc   180
```

-continued

| | |
|---|---|
| atatgcatac aaatatttca ttacacttta tagaaatggt cagtaataaa ccctatcact | 240 |
| atgtctggtg tttcatttta tttgctttta aacgaaaatt gacttcctga ttcaatattt | 300 |
| aaggatcgtc aacggtgtgc agttactaaa ttctggtttg taggaactat agtaaactat | 360 |
| tcaagtcttc acttattgtg cactcacctc tcgccacatc accacagatg ttattcacgt | 420 |
| cttaaatttg aactacacat catattgaca caatattttt tttaaataag cgattaaaac | 480 |
| ctagcctcta tgtcaacaat ggtgtacata accagcgaag tttagggagt aaaaaacatc | 540 |
| gccttacaca aagttcgctt taaaaaataa agagtaaatt ttactttgga ccaccsttca | 600 |
| accaatgttt cactttagaa cgagtaattt tattattgtc actttggacc accctcaaat | 660 |
| cttttttcca tctacatcca atttatcatg tcaaagaaat ggtctacata cagctaagga | 720 |
| gatttatcga cgaatagtag ctagcatact cgaggtcatt catatgcttg agaagagagt | 780 |
| cgggatagtc caaaataaaa caaaggtaag attacctggt caaaagtgaa aacatcagtt | 840 |
| aaaaggtggt ataagtaaa atatcggtaa taaaaggtgg cccaaagtga aatttactct | 900 |
| tttctactat tataaaaatt gaggatgttt ttgtcggtac tttgatacgt catttttgta | 960 |
| tgaattggtt tttaagttta ttcgcttttg gaaatgcata tctgtatttg agtcgggttt | 1020 |
| taagttcgtt tgcttttgta aatacagagg gatttgtata agaaatatct ttaaaaaaac | 1080 |
| ccatatgcta atttgacata attttttgaga aaaatatata ttcaggcgaa ttctcacaat | 1140 |
| gaacaataat aagattaaaa tagctttccc ccgttgcagc gcatgggtat tttttctagt | 1200 |
| aaaaataaaa gataaactta gactcaaaac atttacaaaa acaaccccta aagttcctaa | 1260 |
| agcccaaagt gctatccacg atccatagca agcccagccc aacccaaccc aacccaaccc | 1320 |
| accccagtcc agccaactgg acaatagtct ccacaccccc ccactatcac cgtgagttgt | 1380 |
| ccgcacgcac cgcacgtctc gcagccaaaa aaaaaaaaag aaagaaaaaa aagaaaaaga | 1440 |
| aaaaacagca ggtgggtccg ggtcgtgggg gccggaaacg cgaggaggat cgcgagccag | 1500 |
| cgacgaggcc ggccctccct ccgcttccaa agaaacgccc cccatcgcca ctatatacat | 1560 |
| accccccct ctcctcccat cccccaacc ctaccaccac caccaccacc acctccacct | 1620 |
| cctccccct cgctgccgga cgacgagctc ctccccctc cccctccgcc gccgccgcgc | 1680 |
| cggtaaccac cccgcccctc tcctctttct ttctccgttt ttttttttccg tctcggtctc | 1740 |
| gatctttggc cttggtagtt tgggtgggcg agaggcggct tcgtgcgcgc ccagatcggt | 1800 |
| gcgcgggagg ggcgggatct cgcggctggg gctctcgccg gcgtggatca ggcccggatc | 1860 |
| tcgcggggaa tggggctctc ggatgtagat ctgcgatccg ccgttgttgg gggagatgat | 1920 |
| gggggggttta aaatttccgc catgctaaac aagatcagga agaggggaaa agggcactat | 1980 |
| ggtttatatt tttatatatt tctgctgctt cgtcaggctt agatgtgcta gatctttctt | 2040 |
| tcttctttt gtgggtagaa tttgaatccc tcagcattgt tcatcggtag ttttttcttt | 2100 |
| catgatttgt gacaaatgca gcctcgtgcg gagcttttt gtaggtagaa ggatccacac | 2160 |
| gacaccatgt cccccgagcg ccgccccgtc gagatccgcc cggccaccgc cgccgacatg | 2220 |
| gccgccgtgt gcgacatcgt gaaccactac atcgagacct ccaccgtgaa cttccgcacc | 2280 |
| gagccgcaga ccccgcagga gtggatcgac gacctggagc cctccagga ccgctacccg | 2340 |
| tggctcgtgg ccgaggtgga gggcgtggtg gccggcatcg cctacgccgg cccgtggaag | 2400 |
| gcccgcaacg cctacgactg gaccgtggag tccaccgtgt acgtgtccca ccgccaccag | 2460 |
| cgcctcggcc tcggctccac cctctacacc cacctcctca gagcatggga ggcccagggc | 2520 |

| | | |
|---|---|---|
| ttcaagtccg tggtggccgt gatcggcctc ccgaacgacc cgtccgtgcg cctccacgag | 2580 | |
| gccctcggct acaccgcccg cggcaccctg cgcgccgccg gctacaagca cggcggctgg | 2640 | |
| cacgacgtcg gcttctggca gcgcgacttc gagctgccgg ccccgccgcg cccggtgcgc | 2700 | |
| ccggtgacgc agatctgagt cgacctgcag gcatgccgct gaaatcacca gtctctctct | 2760 | |
| acaaatctat ctctctctat aataatgtgt gagtagttcc cagataaggg aattagggtt | 2820 | |
| cttatagggt ttcgctcatg tgttgagcat ataagaaacc cttagtatgt atttgtattt | 2880 | |
| gtaaaatact tctatcaata aaatttctaa ttcctaaaac caaaatccag tggcgagct | 2939 |

<210> SEQ ID NO 96
<211> LENGTH: 4452
<212> TYPE: DNA
<213> ORGANISM: artificial sequence
<220> FEATURE:
<223> OTHER INFORMATION: NLS-EAR MOTIF-G4S LINKER-----LInker R-EAR
       MOTIF-VIRD2 NLS

<400> SEQUENCE: 96

| | | |
|---|---|---|
| atggcaccga agaagaagcg caaggtgctg atcttcagc ttagactggg cggtggcggt | 60 | |
| ggatccgaca gaagtacag catcggcctc gccatcggca ccaactcggt gggctgggcc | 120 | |
| gtcatcacgg acgaatataa ggtcccgtcg aagaagttca aggtcctcgg caatacagac | 180 | |
| cgccacagca tcaagaaaaa cttgatcggc gccctcctgt tcgatagcgg cgagaccgcg | 240 | |
| gaggcgacca ggctcaagag gaccgccagg agacggtaca ctaggcgcaa gaacaggatc | 300 | |
| tgctacctgc aggagatctt cagcaacgag atggcgaagg tggacgactc cttcttccac | 360 | |
| cgcctggagg aatcattcct ggtggaggag gacaagaagc atgagcggca cccaatcttc | 420 | |
| ggcaacatcg tcgacgaggt aagtttctgc ttctaccttt gatatatata taataattat | 480 | |
| cattaattag tagtaatata atatttcaaa tattttttc aaaataaaag aatgtagtat | 540 | |
| atagcaattg cttttctgta gtttataagt gtgtatattt taatttataa cttttctaat | 600 | |
| atatgaccaa acatggtga tgtgcaggtg gcctaccacg agaagtaccc gacaatctac | 660 | |
| cacctccgga gaaactggt ggacagcaca gacaaggcgg acctccggct catctacctt | 720 | |
| gccctcgcgc atatgatcaa gttccgcggc cacttcctca tcgagggcga cctgaacccg | 780 | |
| gacaactccg acgtggacaa gctgttcatc cagctcgtgc agacgtacaa tcaactgttc | 840 | |
| gaggagaacc cataaacgc tagcggcgtg gacgccaagg ccatcctctc ggccaggctc | 900 | |
| tcgaaatcaa gaaggctgga gaaccttatc gcgcagttgc caggcgaaaa gaagaacggc | 960 | |
| ctcttcggca accttattgc gctcagcctc ggcctgacgc cgaacttcaa atcaaacttc | 1020 | |
| gacctcgcgg aggacgccaa gctccagctc tcaaaggaca cctacgacga cgacctcgac | 1080 | |
| aacctcctgg cccagatagg agaccagtac gcggacctct cctcgccgc caagaacctc | 1140 | |
| tccgacgcta tcctgctcag cgacatcctt cgggtcaaca ccgaaattac caaggcaccg | 1200 | |
| ctgtccgcca gcatgattaa acgctacgac gagcaccatc aggacctcac gctgctcaag | 1260 | |
| gcactcgtcc gccagcagct ccccgagaag tacaaggaga tcttcttcga ccaatcaaaa | 1320 | |
| aacggctacg cgggatatat cgacggcggt gccagccagg aagagttcta caagttcatc | 1380 | |
| aaaccaatcc tggagaagat ggacggcacc gaggagttgc tggtcaagct caacagggag | 1440 | |
| gacctcctca ggaagcagag gaccttcgac aacggctcca tcccgcatca gatccacctg | 1500 | |
| ggcgaactgc atgccatcct gcggcgccag gaggacttct acccgttcct gaaggataac | 1560 | |
| cgggagaaga tcgagaagat cttgacgttc cgcatcccat actacgtggg cccgctggct | 1620 |

```
cgcggcaact cccggttcgc ctggatgacc cggaagtcgg aggagaccat cacaccctgg   1680
aactttgagg aggtggtcga taagggcgct agcgctcaga gcttcatcga gcgcatgacc   1740
aacttcgata aaaacctgcc caatgaaaaa gtcctcccca agcactcgct gctctacgag   1800
tacttcaccg tgtacaacga gctcaccaag gtcaaatacg tcaccgaggg catgcggaag   1860
ccggcgttcc tgagcggcga gcagaagaag gcgatagtgg acctcctctt caagaccaac   1920
aggaaggtga ccgtgaagca attaaaagag gactacttca agaaaataga gtgcttcgac   1980
tccgtggaga tctcgggcgt ggaggatcgg ttcaacgcct cactcggcac gtatcacgac   2040
ctcctcaaga tcattaaaga caaggacttc ctcgacaacg aggagaacga ggacatcctc   2100
gaggacatcg tcctcaccct gaccctgttc gaggaccgcg aaatgatcga ggagaggctg   2160
aagacctacg cgcacctgtt cgacgacaag gtcatgaaac agctcaagag cgccgctac   2220 actggttggg gaaggctgtc ccgcaagctc attaatggca tcaggacaa gcagagcggc   2280 aagaccatcc tggacttcct caagtccgac gggttcgcca accgaactt catgcagctc   2340 attcacgacg actcgctcac gttcaaggaa gacatccaga aggcacaggt gagcgggcag   2400
ggtgactccc tccacgaaca catcgccaac ctggccggct cgccggccat taaaaagggc   2460
atcctgcaga cggtcaaggt cgtcgacgag ctcgtgaagg tgatgggccg gcacaagccc   2520
gaaaatatcg tcatagagat ggccagggag aaccagacca cccaaaaagg gcagaagaac   2580
tcgcgcgagc ggatgaaacg gatcgaggag ggcattaaag agctcgggtc ccagatcctg   2640
aaggagcacc ccgtggaaaa tacccagctc cagaatgaaa agctctacct ctactacctg   2700
cagaacggcc gcgacatgta cgtggaccag gagctggaca ttaatcggct atcggactac   2760
gacgtcgacg ccatcgtgcc gcagtcgttc ctcaaggacg atagcatcga caacaaggtg   2820
ctcacccggt cggataaaaa tcggggcaag agcgacaacg tgcccagcga ggaggtcgtg   2880
aagaagatga aaaactactg gcgccagctc ctcaacgcga aactgatcac ccagcgcaag   2940
ttcgacaacc tgacgaaggc ggaacgcggt ggcttgagcg aactcgataa ggcgggcttc   3000
ataaaaaggc agctggtcga gacgcgccag atcacgaagc atgtcgccca gatcctggac   3060
agccgcatga atactaagta cgatgaaaac gacaagctga tccgggaggt gaaggtgatc   3120
acgctgaagt ccaagctcgt gtcggacttc cgcaaggact tccagttcta caaggtccgc   3180
gagatcaaca actaccacca cgcccacgac gcctacctga tgcggtggt cgggaccgcc   3240 ctgatcaaga agtacccgaa gctggagtcg gagttcgtgt acggcgacta caaggtctac   3300
gacgtgcgca aaatgatcgc caagtccgag caggagatcg gcaaggccac ggcaaaatac   3360
ttcttctact cgaacatcat gaacttcttc aagaccgaga tcaccctcgc gaacggcgag   3420
atccgcaagc gcccgctcat cgaaaccaac ggcgagacgg gcgagatcgt ctgggataag   3480
ggccgggatt tcgcgacggt ccgcaaggtg ctctccatgc cgcaagtcaa tatcgtgaaa   3540
aagacggagg tccagacggg cgggttcagc aaggagtcca tcctcccgaa gcgcaactcc   3600
gacaagctca tcgcgaggaa gaaggattgg gacccgaaaa atatggcgg cttcgacagc   3660 ccgaccgtcg catacagcgt cctcgtcgtg gcgaaggtgg agaagggcaa gtcaaagaag   3720
ctcaagtccg tgaaggagct gctcgggatc acgattatgg agcggtcctc cttcgagaag   3780
aacccgatcg acttcctaga ggccaaggga tataaggagg tcaagaagga cctgattatt   3840
aaactgccga gtactcgct cttcgagctg gaaaacggcc gcaagaggat gctcgcctcc   3900
gcaggcgagt tgcagaaggg caacgagctc gccctcccga gcaaatacgt caatttcctg   3960
tacctcgcta gccactatga aaagctcaag ggcagcccgg aggacaacga gcagaagcag   4020
```

```
ctcttcgtgg agcagcacaa gcattacctg gacgagatca tcgagcagat cagcgagttc    4080
tcgaagcggg tgatcctcgc cgacgcgaac ctgacaaggg tgctgtcggc atataacaag    4140
caccgcgaca aaccaatacg cgagcaggcc gaaaatatca tccacctctt caccctcacc    4200
aacctcggcg ctccggcagc cttcaagtac ttcgacacca cgattgaccg gaagcggtac    4260
acgagcacga aggaggtgct cgatgcgacg ctgatccacc agagcatcac agggctctat    4320
gaaacacgca tcgacctgag ccagctgggc ggagacggtg gcgtggatc cctggatctt    4380 cagcttagac tgggcaagag accacgggac cgccacgatg gcgagctggg aggccgcaag    4440
cgggcaaggt ag                                                        4452
```

<210> SEQ ID NO 97
<211> LENGTH: 606
<212> TYPE: DNA
<213> ORGANISM: artificial sequence
<220> FEATURE:
<223> OTHER INFORMATION: moLEXA DNA

<400> SEQUENCE: 97

```
atgaaagcgc tcaccgcccg ccaacaggag gtcttcgacc tgatcaggga tcacatctcc     60
cagacaggca tgccaccaac aagggcggaa atcgcacaga ggctcgggtt cgctcgccca    120
aacgctgccg aggagcacct taaggcgctc gcgcgcaaag gcgttatcga gattgtgagc    180
ggagccagcc gcggaatcag gctcttacag gaggaggaag agggacttcc acttgtgggc    240
agagtggccg ctgacgaacc actccttgcc cagcagcaca tcgaaggaca ctaccaggtc    300
gacccatccc tgttcaagcc aaacgccgat ttcctcctcc gcgtgtccgg gatggcgatg    360
aaagacatcg gcatcatgga cggcgacctg ctggccgtcc ataaaactca ggacgtgcgc    420
aacggccagg tggtggtggc ccgcatcgac gatgaggtca cggtgaaacg cctcaagaag    480
cagggcaata agtggagct cctcccccgaa aatagcgagt tcaaaccaat cgtggtcgac    540
cttcggcaac agtctttcac gattgagggc ctggcggtgg gcgttatcag gaacggcgat    600
tggctt                                                              606
```

<210> SEQ ID NO 98
<211> LENGTH: 202
<212> TYPE: PRT
<213> ORGANISM: artificial sequence
<220> FEATURE:
<223> OTHER INFORMATION: moLEXA PRT

<400> SEQUENCE: 98

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Asp Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110
```

```
Leu Arg Val Ser Gly Met Ala Met Lys Asp Ile Gly Ile Met Asp Gly
        115                 120                 125

Asp Leu Leu Ala Val His Lys Thr Gln Asp Val Arg Asn Gly Gln Val
        130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
                180                 185                 190

Val Gly Val Ile Arg Asn Gly Asp Trp Leu
                195                 200
```

<210> SEQ ID NO 99
<211> LENGTH: 17
<212> TYPE: DNA
<213> ORGANISM: Escherichia coli

<400> SEQUENCE: 99
cggaagactc tcctccg                                                  17

<210> SEQ ID NO 100
<211> LENGTH: 297
<212> TYPE: DNA
<213> ORGANISM: artificial sequence
<220> FEATURE:
<223> OTHER INFORMATION: moCBF1A

<400> SEQUENCE: 100
acctgcgcca aggacatcca gaaagcggct gcagaagctg ctctggcgtt ccaagacgaa     60
acctgcgaca ccacgacgac gaaccacggg ctcgatatgg aggagactat ggtggaggcg    120
atctacacgc cagaacagtc tgagggcgcc ttctacatgg acgaggagac catgttcggc    180
atgccaacac tgctggacaa catggccgag ggcatgcttc ttccgccacc atctgtgcag    240
tggaaccaca actacgatgg cgagggcgat ggcgacgtta gcctgtggag ctactag       297

<210> SEQ ID NO 101
<211> LENGTH: 98
<212> TYPE: PRT
<213> ORGANISM: artificial sequence
<220> FEATURE:
<223> OTHER INFORMATION: moCBF1A Maize-opt. gene for Arath CBF1
      activation domain

<400> SEQUENCE: 101

```
Thr Cys Ala Lys Asp Ile Gln Lys Ala Ala Ala Glu Ala Ala Leu Ala
1               5                   10                  15

Phe Gln Asp Glu Thr Cys Asp Thr Thr Thr Thr Asn His Gly Leu Asp
                20                  25                  30

Met Glu Glu Thr Met Val Glu Ala Ile Tyr Thr Pro Gln Ser Glu
        35                  40                  45

Gly Ala Phe Tyr Met Asp Glu Glu Thr Met Phe Gly Met Pro Thr Leu
        50                  55                  60

Leu Asp Asn Met Ala Glu Gly Met Leu Leu Pro Pro Ser Val Gln
65                  70                  75                  80

Trp Asn His Asn Tyr Asp Gly Glu Gly Asp Gly Asp Val Ser Leu Trp
                85                  90                  95

Ser Tyr
```

<210> SEQ ID NO 102
<211> LENGTH: 11596
<212> TYPE: DNA
<213> ORGANISM: artificial sequence
<220> FEATURE:
<223> OTHER INFORMATION: PG47-moLEXA-CBF1-IN2 PG47-MOCODA-PINII UBI-
NPTII-PINII

<400> SEQUENCE: 102

```
aagcttgcat gcctgcaggt cgactctaga ggatctgcac cggacactgt ctggtggcat      60
accagacagt ccggtgtgcc agatcagggc acccttcggt tcctttgctc ctttgctttt     120
gaaccctaac tttgatcgtt tattggtttg tgttgaacct ttatgcacct gtggaatata     180
taatctagaa caaactagtt agtccaatca tttgtgttgg gcattcaacc accaaaatta     240
tttataggaa aaggttaaac cttatttccc tttcaatctc cccctttttg gtgattgatg     300
ccaacacaaa ccaaagaaaa tatataagtg cagaattgaa ctagtttgca taaggtaagt     360
gcataggtta cttagaatta aatcaattta tactttact tgatatgcat ggttgctttc     420
ttttatttta acattttgga ccacatttgc accacttgtt ttgttttttg caaatctttt     480
tggaaattct ttttcaaagt cttttgcaaa tagtcaaagg tatatgaata agattgtaag     540
aagcattttc aagatttgaa atttctcccc ctgtttcaaa tgcttttcct ttgactaaac     600
aaaactcccc ctgaataaaa ttctcctctt agctttcaag agggttttaa atagatatca     660
attggaaata tatttagatg ctaattttga aaatataccca attgaaaatc aacataccaa     720
tttgaaatta aacataccaa tttaaaaaat ttcaaaaagt ggtggtgcgg tccttttgct     780
ttgggcttaa tatttctccc ccttttggcat taatcgccaa aaacggagac tttgtgagcc     840
atttatactt tctccccatt ggtaaatgaa atatgagtga aagattatac caaatttgga     900
cagtgatgcg gagtgacggc gaaggataaa cgataccgtt agagtggagt ggaagccttg     960
tcttcgccga agactccatt tcccttcaa tctacgactt agcatagaaa tacacttgaa    1020
aacacattag tcgtagccac gaaagagata tgatcaaagg tatacaaatg agctatgtgt    1080
gtaatgtttc aatcaaagtt tcgagaatca agaatattta gctcattcct aagtttgcta    1140
aaggttttat catctaatgg tttggtaaag atatcgacta attgttcttt ggtgctaaca    1200
taagcaatct cgatatcacc cctttgttgg tgatccctca aaaagtgata ccgaatgtct    1260
atgtgcttag tgcggctgtg ttcaacggga ttatccgcca tgcagatagc actctcattg    1320
tcacatagga gagggacttt gctcaatttg tagccatagt ccctaaggtt ttgcctcatc    1380
caaagtaatt gcacacaaca atgtcctgcg gcaatatact tggcttcggc ggtagaaaga    1440
gctattgagt tttgtttctt tgaagtccaa gacaccaggg atctccctag aaactgacaa    1500
gtccctgatg tgctcttcct atcaattta caccctgccc aatcggcatc tgaatatcct    1560
attaaatcaa aggtggatcc cttggggtac caaagaccaa atttaggagt gtaaactaaa    1620
tatctcatga ttcttttcac ggccctaagg tgaacttcct taggatcggc ttggaatctt    1680
gcacacatgc atatagaaag catactatct ggtcgagatg cacataaata gagtaaagat    1740
cctatcatcg accggtatac cttttggtct acggatttac ctcccgtgtc gaggtcgaga    1800
tgcccattag ttcccatggg tgtcctgatg ggcttggcat ccttcattcc aaacttgttg    1860
agtatgtctt gaatgtactt tgtttggctg atgaaggtgc catcttggag ttgcttgact    1920
tgaaatccta gaaatatttt caacttcccc atcatagaca tctcgaattt cggaatcatg    1980
atcctactaa actcttcaca agtagatttg ttagtagacc caaatataat atcatcaaca    2040
```

```
taaatttggc atacaaacaa aacttttgaa atggttttag taaagagagt aggatcggct    2100
ttactgactc tgaagccatt agtgataaga aaatctctta ggcattcata ccatgctgtt    2160
ggggcttgct tgagcccata aagcgccttt gagagtttat aaacatggtt agggtactca    2220
ctatcttcaa agccgagagg ttgctcaaca tagacctatt cacccccattt gatcacttttt  2280 ttggtccttc aggatctaat agttatgtat aatttagagt ctcttgttta atggccagat    2340
atttctaatt aatctaagaa tttatgatat ttttttaattt tttatcatgt ctgatgagaa   2400
ttaacataaa ggctcaattg ggtcctgaat taataataga gtgaaaatta atccagaggc    2460
tctattagaa ccttcaatta gtaataccaa gatatatata agatagtaga gtatagttta   2520
aatgttggca ttgttcattc tttcttttgt tatttaattt atgctttcca cggtggttag    2580
tggttacttc tgaagggtcc aaataatgca tgaagagttt gaggacaaga agtctgccct    2640
aaaaatagcg atgcaaaggc atggtgtcca agccatacat atagcgcact aattttatca    2700
gcagaacaat ggtatttata ggtcctagtg cccaggcaac aagagacacg aataaagcat    2760
cgatcacgac accatgaaag cgctcaccgc ccgccaacag gaggtcttcg acctgatcag    2820
ggatcacatc tcccagacag gcatgccacc aacaagggcg gaaatcgcac agaggctcgg    2880
gtttcgctcg ccaaacgctg ccgaggagca ccttaaggcg ctcgcgcgca aaggcgttat    2940
cgagattgtg agcggagcca gccgcggaat caggctctta caggaggagg aagagggact    3000
tccacttgtg ggcagagtgg ccgctgacga accactcctt gcccagcagc acatcgaagg    3060
acactaccag gtcgacccat ccctgttcaa gccaaacgcc gatttcctcc tccgcgtgtc    3120
cgggatggcg atgaaagaca tcggcatcat ggacggcgac ctgctggccg tccataaaac    3180
tcaggacgtg cgcaacggcc aggtggtggt ggcccgcatc gacgatgagg tcacggtgaa    3240
acgcctcaag aagcagggca ataaagtgga gctcctcccc gaaaatagcg agttcaaacc    3300
aatcgtggtc gaccttcggc aacagtcttt cacgattgag ggcctggcgg tgggcgttat    3360
caggaacggc gattggctta cctgcgccaa ggacatccag aaagcggctg cagaagctgc    3420
tctggcgttc caagacgaaa cctgcgacac cacgacgacg aaccacgggc tcgatatgga    3480
ggagactatg gtggaggcga tctacacgcc agaacagtct gagggcgcct tctacatgga    3540
cgaggagacc atgttcggca tgccaacact gctggacaac atggccgagg catgcttct    3600 tccgccacca tctgtgcagt ggaaccacaa ctacgatggc gagggcgatg gcgacgttag    3660
cctgtggagc tactagcgac gcggccgatc tgacaaagca gcattagtcc gttgatcggt    3720
ggaagaccac tcgtcagtgt tgagttgaat gtttgatcaa taaaatacgg caatgctgta    3780
agggttgttt tttatgccat tgataataca ctgtactgtt cagttgttga actctatttc    3840
ttagccatgc caagtgcttt tcttattttg aataacatta cagcaaaaag ttgaaagaca    3900
aaaaaaaaaa cccccgaaca gagtgctttg ggtcccaagc tactttagac tgtgttcggc    3960 gttccccta aatttctccc cctatatctc actcacttgt cacatcagcg ttctcttttcc    4020 cctatatctc cacgtcgacg cggaagctaa gcttgcatgc ctgcaggtcg actctagagg    4080
atctgcaccg gacactgtct ggtggcatac cagacagtcc ggtgtgccag atcagggcac    4140
ccttcggttc ctttgctcct ttgcttttga accctaactt tgatcgttta ttggtttgtg    4200
ttgaaccttt atgcacctgt ggaatatata atctagaaca aactagttag tccaatcatt    4260
tgtgttgggc attcaaccac caaaattatt tataggaaaa ggttaaacct tatttcccctt   4320 tcaatctccc cctttttggt gattgatgcc aacacaaacc aaagaaaata tataagtgca    4380
```

```
gaattgaact agtttgcata aggtaagtgc ataggttact tagaattaaa tcaatttata    4440
cttttacttg atatgcatgg ttgctttctt ttattttaac attttggacc acatttgcac    4500
cacttgtttt gttttttgca aatctttttg gaaattcttt ttcaaagtct tttgcaaata    4560
gtcaaaggta tatgaataag attgtaagaa gcattttcaa gatttgaaat ttctccccct    4620
gtttcaaatg cttttccttt gactaaacaa aactccccct gaataaaatt ctcctcttag    4680
ctttcaagag ggttttaaat agatatcaat tggaaatata tttagatgct aattttgaaa    4740
ataccaat tgaaaatcaa catccaatt tgaaattaaa cataccaatt taaaaaattt    4800
caaaaagtgg tggtgcggtc cttttgcttt gggcttaata tttctccccc tttggcatta    4860
atcgccaaaa acggagactt tgtgagccat ttatactttc tccccattgg taaatgaaat    4920
atgagtgaaa gattatacca aatttggaca gtgatgcgga gtgacggcga aggataaacg    4980
ataccgttag agtggagtgg aagccttgtc ttcgccgaag actccatttc cctttcaatc    5040
tacgacttag catagaaata cacttgaaaa cacattagtc gtagccacga aagagatatg    5100
atcaaaggta tacaaatgag ctatgtgtgt aatgtttcaa tcaaagtttc gagaatcaag    5160
aatatttagc tcattcctaa gtttgctaaa ggttttatca tctaatggtt tggtaaagat    5220
atcgactaat tgttctttgg tgctaacata agcaatctcg atatcacccc tttgttggtg    5280
atccctcaaa aagtgatacc gaatgtctat gtgcttagtg cggctgtgtt caacgggatt    5340
atccgccatg cagatagcac tctcattgtc acataggaga gggactttgc tcaatttgta    5400
gccatagtcc ctaaggtttt gcctcatcca agtaattgc acacaacaat gtcctgcggc    5460
aatatacttg gcttcggcgg tagaaagagc tattgagttt tgtttctttg aagtccaaga    5520
caccagggat ctccctagaa actgacaagt ccctgatgtg ctcttcctat caattttaca    5580
ccctgcccaa tcggcatctg aatatcctat taaatcaaag gtggatccct tggggtacca    5640
aagaccaaat ttaggagtgt aaactaaata tctcatgatt cttttcacgg ccctaaggtg    5700
aacttcctta ggatcggctt ggaatcttgc acacatgcat atagaaagca tactatctgg    5760
tcgagatgca cataaataga gtaaagatcc tatcatcgac cggtatacct tttggtctac    5820
ggatttacct cccgtgtcga ggtcgagatg cccattagtt cccatgggtg tcctgatggg    5880
cttggcatcc ttcattccaa acttgttgag tatgtcttga atgtactttg tttggctgat    5940
gaaggtgcca tctggagtt gcttgacttg aaatcctaga aaatatttca acttccccat    6000
catagacatc tcgaatttcg gaatcatgat cctactaaac tcttcacaag tagatttgtt    6060
agtagaccca aatataatat catcaacata aatttggcat acaaacaaaa cttttgaaat    6120
ggttttagta aagagagtag gatcggcttt actgactctg aagccattag tgataagaaa    6180
atctcttagg cattcatacc atgctgttgg ggcttgcttg agcccataaa gcgcctttga    6240
gagtttataa acatggttag ggtactcact atcttcaaag ccgagaggtt gctcaacata    6300
gacctattca ccccatttga tcactttttt ggtccttcag gatctaatag ttatgtataa    6360
tttagagtct cttgtttaat ggccagatat ttctaattaa tctaagaatt tatgatattt    6420
tttaattttt tatcatgtct gatgagaatt aacataaagg ctcaattggg tcctgaatta    6480
ataatagagt gaaaattaat ccagaggctc tattagaacc ttcaattagt aataccaaga    6540
tatatataag atagtagagt atagtttaaa tgttggcatt gttcattctt tcttttgtta    6600
tttaattttat gctttccacg gtggttagtg gttacttctg aagggtccaa ataatgcatg    6660
aagagtttga ggacaagaag tctgccctaa aaatagcgat gcaaaggcat ggtgtccaag    6720
ccatacatat agcgcactaa ttttatcagc agaacaatgg tatttatagg tcctagtgcc    6780
```

```
caggcaacaa gagacacgaa taaagcatcg atcacgacac catgagcaac aacgccctcc    6840
agaccataat aaacgcgagg ctgccgggga aagagggcct ctggcagatc cacctccaag    6900
acggcaagat cagcgctata gacgcccaat cgggcgtgat gccaatcacc gagaactccc    6960
tcgacgccga acaaggtctc gtgatccctc cattcgtcga accccacatc cacctcgaca    7020
cgacccaaac agcaggtcaa cccaactgga accaatccgg cacactcttc gaaggcatcg    7080
agcgctgggc agaaaggaag gcgttgctca cacacgacga tgtgaagcag cgcgcatggc    7140
aaacgctcaa gtggcagata gccaacggca tccagcacgt cagaacgcac gtcgacgtgt    7200
ccgacgccac gcttacagct ctgaaggcta tgctcgaggt caagcaggag gtcgcaccct    7260
ggatagacct gcagatcgtc gcattcccac aggagggaat cctctcatac cccaatgggg    7320
aagccctcct cgaggaagct ctgaggttgg gtgctgacgt tgtcggcgct atcccacact    7380
tcgagttcac caggagtac ggagtcgagt cgttgcataa aaccttcgca ctggctcaaa    7440
aatacgacag actcatcgac gtccactgcg acgaaatcga cgacgagcag agcagattcg    7500
tcgagaccgt ggctgcactg gcccataggg aaggaatggg tgctagggtt acggcgtcac    7560
ataccaccgc aatgcacagc tacaacgggg catacacctc ccggctcttt aggctcctca    7620
aaatgtccgg aatcaacttc gtcgccaacc ccctggtcaa tatacacctc cagggacggt    7680
tcgacacata cccgaaacgc cgcgggataa ccagggtgaa ggagatgctg gagagcggca    7740
tcaacgtctg ctttggccac gacgacgtct tcgatccatg gtacccactc ggcaccgcta    7800
acatgctcca gtgctgcac atgggtctgc acgtctgcca gctcatgggc tatggacaga    7860
tcaacgacgg cctcaacctc atcacccacc actctgctcg gacactcaac ctccaggact    7920
acggcatagc cgccgggaac tcggctaatc tcatcatcct cccggcggag aatggattcg    7980
atgcacttag gcgccaggtg ccagtcaggt attcagtgcg cggaggaaag gtgatagcct    8040
ccacccaacc agcacagacc accgtctacc tcgaacagcc ggaagcgatc gactacaagc    8100
gctagcacta gacttgtcca tcttctggat tggccaactt aattaatgta tgaaataaaa    8160
ggatgcacac atagtgacat gctaatcact ataatgtggg catcaaagtt gtgtgttatg    8220
tgtaattact agttatctga ataaaagaga aagagatcat ccatatttct tatcctaaat    8280
gaatgtcacg tgtctttata attctttgat gaaccagatg catttcatta accaaatcca    8340
tatacatata aatattaatc atatataatt aatatcaatt gggttagcaa aacaaatcta    8400
gtctaggtgt gttttgcgga tcagctgcag tgcagcgtga cccggtcgtg cccctctcta    8460
gagataatga gcattgcatg tctaagttat aaaaaattac cacatatttt ttttgtcaca    8520
cttgtttgaa gtgcagttta tctatcttta tacatatatt taaactttac tctacgaata    8580
atataatcta tagtactaca ataatatcag tgttttagag aatcatataa atgaacagtt    8640
agacatggtc taaaggacaa ttgagtattt tgacaacagg actctacagt tttatctttt    8700
tagtgtgcat gtgttctcct ttttttttgc aaatagcttc acctatataa tacttcatcc    8760
attttattag tacatccatt tagggtttag ggttaatggt tttatagac taattttttt    8820 agtacatcta tttttattcta ttttagcctc taaattaaga aaactaaaac tctatttttag    8880 ttttttttatt taataattta gatataaaat agaataaaat aaagtgacta aaaattaaac    8940 aaatacccctt taagaaatta aaaaaactaa ggaaacattt tccttgtttc gagtagataa    9000
tgccagcctt ttaaacgccg tcgacgagtc taacggacac caaccagcga accagcagcg    9060
tcgcgtcggg ccaagcgaag cagacggcac ggcatctctg tcgctgcctc tggaccccctc    9120
```

| | |
|---|---|
| tcgagagttc cgctccaccg ttggacttgc tccgctgtcg gcatccagaa attgcgtggc | 9180 |
| ggagcggcag acgtgagccg gcacggcagg cggcctcctc ctcctctcac ggcacggcag | 9240 |
| ctacggggga ttcctttccc accgctcctt cgctttccct tcctcgcccg ccgtaataaa | 9300 |
| tagacacccc ctccacaccc tctttcccca acctcgtgtt gttcggagcg cacacacaca | 9360 |
| caaccagatc tcccccaaat ccacccgtcg gcacctccgc ttcaaggtac gccgctcgtc | 9420 |
| ctccccccc cccctctct accttctcta gatcggcgtt ccggtccatg gttagggccc | 9480 |
| ggtagttcta cttctgttca tgtttgtgtt agatccgtgt ttgtgttaga tccgtgctgc | 9540 |
| tagcgttcgt acacggatgc gacctgtacg tcagacacgt tctgattgct aacttgccag | 9600 |
| tgtttctctt tggggaatcc tgggatggct ctagccgttc cgcagacggg atcgatttca | 9660 |
| tgatttttt tgtttcgttg catagggttt ggtttgccct tttcctttat ttaatatat | 9720 |
| gccgtgcact tgtttgtcgg gtcatctttt catgctttt tttgtcttgg ttgtgatgat | 9780 |
| gtggtctggt tgggcggtcg ttctagatcg gagtagaatt ctgtttcaaa ctacctggtg | 9840 |
| gatttattaa ttttgatct gtatgtgtgt gccatacata ttcatagtta cgaattgaag | 9900 |
| atgatggatg gaaatatcga tctaggatag gtatacatgt tgatgcgggt tttactgatg | 9960 |
| catatacaga gatgctttt gttcgcttgg ttgtgatgat gtggtgtggt tgggcggtcg | 10020 |
| ttcattcgtt ctagatcgga gtagaatact gtttcaaact acctggtgta tttattaatt | 10080 |
| ttggaactgt atgtgtgtgt catacatctt catagttacg agtttaagat ggatggaaat | 10140 |
| atcgatctag gataggtata catgttgatg tgggttttac tgatgcatat acatgatggc | 10200 |
| atatgcagca tctattcata tgctctaacc ttgagtacct atctattata ataaacaagt | 10260 |
| atgttttata attattttga tcttgatata cttggatgat ggcatatgca gcagctatat | 10320 |
| gtggattttt ttagccctgc cttcatacgc tatttatttg cttggtactg tttcttttgt | 10380 |
| cgatgctcac cctgttgttt ggtgttactt ctgcagatgg ttgaacaaga tggattgcac | 10440 |
| gcaggttctc cggccgcttg ggtggagagg ctattcggct atgactgggc acaacagaca | 10500 |
| atcggctgct ctgatgccgc cgtgttccgg ctgtcagcgc agggggcgccc ggttcttttt | 10560 |
| gtcaagaccg acctgtccgg tgccctgaat gaactgcagg acgaggcagc gcggctatcg | 10620 |
| tggctggcca cgacgggcgt tccttgcgca gctgtgctcg acgttgtcac tgaagcggga | 10680 |
| agggactggc tgctattggg cgaagtgccg gggcaggatc tcctgtcatc tcaccttgct | 10740 |
| cctgccgaga aagtatccat catggctgat gcaatgcggc ggctgcatac gcttgatccg | 10800 |
| gctacctgcc cattcgacca ccaagcgaaa catcgcatcg agcgagcacg tactcggatg | 10860 |
| gaagccggtc ttgtcgatca ggatgatctg gacgaagagc atcaggggct cgcgccagcc | 10920 |
| gaactgttcg ccaggctcaa ggcgcgcatg cccgacggcg atgatctcgt cgtgacccat | 10980 |
| ggcgatgcct gcttgccgaa tatcatggtg gaaaatggcc gcttttctgg attcatcgac | 11040 |
| tgtggccggc tgggtgtggc ggaccgctat caggacatag cgttggctac ccgtgatatt | 11100 |
| gctgaagagc ttggcggcga atgggctgac cgcttcctcg tgctttacgg tatcgccgct | 11160 |
| cccgattcgc agcgcatcgc cttctatcgc cttcttgacg agttcttctg agagcttact | 11220 |
| gaaaaaatta acatctcttg ctaagatcca tggatattcg aacgcgtagg taccacatgg | 11280 |
| ttaacctaga cttgtccatc ttctggattg gccaacttaa ttaatgtatg aaataaaagg | 11340 |
| atgcacacat agtgacatgc taatcactat aatgtgggca tcaaagttgt gtgttatgtg | 11400 |
| taattactag ttatctgaat aaaagagaaa gagatcatcc atatttctta tcctaaatga | 11460 |
| atgtcacgtg tcttttataat tctttgatga accagatgca tttcattaac caaatccata | 11520 |

-continued

```
tacatataaa tattaatcat atataattaa tatcaattgg gttagcaaaa caaatctagt    11580
ctaggtgtgt tttgcg                                                   11596

<210> SEQ ID NO 103
<211> LENGTH: 10091
<212> TYPE: DNA
<213> ORGANISM: artificial sequence
<220> FEATURE:
<223> OTHER INFORMATION: 5xUAS-45 35s PRO-ZMAA1-IN2-1 TERM-----INTRON-
      PMI-PINII

<400> SEQUENCE: 103
ctgtatatac tcacagtcga ctctatcagt gatagagtct gtatatactc acagactcta      60
tcagtgatag agtctgtata tactcacaga ctctatcagt gatagagtac tgtatatact     120
cacagactct atcagtgata gagtgcactg tatatactca cagactctat cagtgataga     180
gtcgcgacga gacccttcct ctatataagg aagttcattt catttggaga ggaccggatg     240
gcggcgacaa tggcagtgac gacgatggtg acgaggagca aggagagctg gtcgtcattg     300
caggtcccgg cggtggcatt cccttggaag ccacgaggtg gcaagaccgg cggcctcgag     360
ttccctcgcc gggcgatgtt cgccagcgtc ggcctcaacg tgtgcccggg cgtcccggcg     420
gggcgcgacc cgcgggagcc cgatcccaag gtcgtccggg cggcctgcgg cctggtccag     480
gcacaagtcc tcttccaggg gtttaactgg gagtcgtgca agcagcaggg aggctggtac     540
aacaggctca aggcccaggt cgacgacatc gccaaggccg gcgtcacgca cgtctggctg     600
cctccaccct cgcactccgt ctcgccacaa ggctacatgc caggccgcct atacgacctg     660
gacgcgtcca gtacggcac ggcggcggag ctcaagtccc tgatagcggc gttccacggc      720
aggggcgtgc agtgcgtggc ggacatcgtc atcaaccacc ggtgcgcgga aaagaaggac     780
gcgcgcggcg tgtactgcat cttcgagggc gggactcccg acgaccgcct ggactggggc     840
cccgggatga tctgcagcga cgacacgcag tactcggacg ggacggggca ccgcgacacg     900
ggcgaggggt tcgcggcggc gcccgacatc gaccacctca acccgcgcgt gcagcgggag     960
ctctccgcct ggctcaactg gctcaggtcc gacgccgtgg ggttcgacgg ctggcgcctc    1020
gacttcgcca agggctactc gccggccgtc gccagaatgt acgtggagag cacggggccg    1080
ccgagcttcg tcgtcgcgga gatatggaac tcgctgagct acagcgggga cggcaagccg    1140
gcgcccaacc aggaccagtg ccggcaggag ctgctggact ggacgcgggc cgtcggcggg    1200
cccgccatgg cgttcgactt ccccaccaag ggcctgctgc aggcgggcgt gcaggggag    1260 ctgtggcggc tgcgcgacag ctccggcaac gcggccggcc tgatcgggtg ggcgcccgag    1320
aaggccgtca ccttcgtcga caaccatgac accgggtcga cgcagaagct ctggccgttc    1380
ccatccgaca aggtcatgca gggctacgcc tacatcctca cccatccagg agtcccctgc    1440
attttctacg accacatgtt cgactggaac ctgaagcagg agatatccac gctgtctgcc    1500
atcagggcgc ggaacggcat ccgcgccggg agcaagctgc ggatcctcgt ggcggacgcg    1560
gacgcgtacg tggccgtcgt cgacgagaag gtcatggtga agatcgggac aaggtacggc    1620
gtgagcagcg tggtcccgtc ggatttccac ccggcggcgc acggcaagga ctactgcgtc    1680
tgggagaaag cgagcctccg cgtcccggcg gggcgccacc tctagcagct cagattgctc    1740
agtcttgtgc tgcattgcaa acacagcagc acgacactgc ataacgtctt ttccttgacc    1800
gatctgacaa agcagcatta gtccgttgat cggtggaaga ccactcgtca gtgttgagtt    1860
gaatgtttga tcaataaaat acggcaatgc tgtaagggtt gttttttatg ccattgataa    1920
```

```
tacactgtac tgttcagttg ttgaactcta tttcttagcc atgccaagtg cttttcttat      1980
tttgaataac attacagcaa aaagttgaaa gacaaaaaaa aaaaccccg aacagagtgc        2040 tttgggtccc aagctacttt agactgtgtt cggcgttccc cctaaatttc tccccctata      2100
tctcactcac ttgtcacatc agcgttctct ttcccctata tctccacgtc gacgcggaag      2160
ctaagcttgc atgcctgcag gtcgactcta gaggatctgc accggacact gtctggtggc      2220
ataccagaca gtccggtgtg ccagatcagg gcacccttcg gttcctttgc tcctttgctt      2280
ttgaacccta actttgatcg tttattggtt tgtgttgaac ctttatgcac ctgtggaata      2340
tataatctag aacaaactag ttagtccaat catttgtgtt gggcattcaa ccaccaaaat      2400
tatttatagg aaaaggttaa accttatttc cctttcaatc tcccccttttt tggtgattga     2460 tgccaacaca aaccaaagaa aatatataag tgcagaattg aactagtttg cataaggtaa      2520
gtgcataggt tacttagaat taaatcaatt tatactttta cttgatatgc atggttgctt      2580 tcttttatttt taacattttg gaccacattt gcaccacttg ttttgttttt tgcaaatctt     2640
tttggaaatt ctttttcaaa gtcttttgca aatagtcaaa ggtatatgaa taagattgta     2700
agaagcattt tcaagatttg aaatttctcc ccctgtttca aatgctttc ctttgactaa      2760 acaaaactcc ccctgaataa aattctcctc ttagctttca agagggtttt aaatagatat     2820
caattggaaa tatatttaga tgctaatttt gaaaatatac caattgaaaa tcaacatacc     2880
aatttgaaat taaacatacc aatttaaaaa atttcaaaaa gtggtggtgc ggtccttttg     2940
ctttgggctt aatatttctc cccctttggc attaatcgcc aaaaacggag actttgtgag     3000
ccatttatac tttctcccca ttggtaaatg aaatatgagt gaaagattat accaaatttg     3060
gacagtgatg cggagtgacg gcgaaggata acgataccg ttagagtgga gtggaagcct      3120
tgtcttcgcc gaagactcca tttcccttc aatctacgac ttagcataga aatacacttg      3180
aaaacacatt agtcgtagcc acgaaagaga tatgatcaaa ggtatacaaa tgagctatgt     3240
gtgtaatgtt tcaatcaaag tttcgagaat caagaatatt tagctcattc ctaagtttgc     3300
taaaggtttt atcatctaat ggtttggtaa agatatcgac taattgttct ttggtgctaa     3360
cataagcaat ctcgatatca ccccttttgt ggtgatccct caaaaagtga taccgaatgt     3420
ctatgtgctt agtgcggctg tgttcaacgg gattatccgc catgcagata gcactctcat     3480
tgtcacatag gagagggact ttgctcaatt tgtagccata gtccctaagg ttttgcctca     3540
tccaaagtaa ttgcacacaa caatgtcctg cggcaatata cttggcttcg gcggtagaaa     3600
gagctattga gtttttgttt tttgaagtcc aagacaccag ggatctccct agaaactgac      3660
aagtccctga tgtgctcttc ctatcaattt tacaccctgc ccaatcggca tctgaatatc     3720
ctattaaatc aaaggtggat cccttgggt accaagacc aaatttagga gtgtaaacta       3780
aatatctcat gattctttc acggccctaa ggtgaacttc cttaggatcg cttggaatc       3840 ttgcacacat gcatatagaa agcatactat ctggtcgaga tgcacataaa tagagtaaag     3900
atcctatcat cgaccggtat accttttggt ctacggattt acctcccgtg tcgaggtcga     3960
gatgcccatt agttcccatg ggtgtcctga tgggcttggc atccttcatt ccaaacttgt     4020
tgagtatgtc ttgaatgtac tttgtttggc tgatgaaggt gccatcttgg agttgcttga     4080
cttgaaatcc tagaaaatat ttcaacttcc ccatcataga catctcgaat ttcggaatca     4140
tgatcctact aaactcttca caagtagatt tgttagtaga cccaaatata atatcatcaa     4200
cataaatttg gcatacaaac aaaacttttg aaatggtttt agtaaagaga gtaggatcgg     4260
```

```
ctttactgac tctgaagcca ttagtgataa gaaaatctct taggcattca taccatgctg    4320
ttggggcttg cttgagccca taaagcgcct ttgagagttt ataaacatgg ttagggtact    4380
cactatcttc aaagccgaga ggttgctcaa catagaccta ttcaccccat ttgatcactt    4440
ttttggtcct tcaggatcta atagttatgt ataatttaga gtctcttgtt taatggccag    4500
atatttctaa ttaatctaag aatttatgat attttttaat tttttatcat gtctgatgag    4560
aattaacata aaggctcaat tgggtcctga attaataata gagtgaaaat taatccagag    4620
gctctattag aaccttcaat tagtaatacc aagatatata taagatagta gagtatagtt    4680
taaatgttgg cattgttcat tctttctttt gttatttaat ttatgctttc cacggtggtt    4740
agtggttact tctgaagggt ccaaataatg catgaagagt ttgaggacaa gaagtctgcc    4800
ctaaaaatag cgatgcaaag gcatggtgtc caagccatac atatagcgca ctaattttat    4860
cagcagaaca atggtattta taggtcctag tgcccaggca acaagagaca cgaataaagc    4920
atcgatcacg acaccatgag caacaacgcc ctccagacca taataaacgc gaggctgccg    4980
gggaaagagg gcctctggca gatccactc caagacggca agatcagcgc tatagacgcc    5040
caatcgggcg tgatgccaat caccgagaac tccctcgacg ccgaacaagg tctcgtgatc    5100
cctccattcg tcgaacccca catccacctc gacacgaccc aaacagcagg tcaacccaac    5160
tggaaccaat ccggcacact cttcgaaggc atcgagcgct gggcagaaag gaaggcgttg    5220
ctcacacacg acgatgtgaa gcagcgcgca tggcaaacgc tcaagtggca gatagccaac    5280
ggcatccagc acgtcagaac gcacgtcgac gtgtccgacg ccacgcttac agctctgaag    5340
gctatgctcg aggtcaagca ggaggtcgca ccctggatag acctgcagat cgtcgcattc    5400
ccacaggagg gaatcctctc ataccccaat ggggaagccc tcctcgagga agctctgagg    5460
ttgggtgctg acgttgtcgg cgctatccca cacttcgagt tcaccaggga gtacggagtc    5520
gagtcgttgc ataaaacctt cgcactggct caaaaatacg acagactcat cgacgtccac    5580
tgcgacgaaa tcgacgacga gcagagcaga ttcgtcgaga ccgtggctgc actgccccat    5640
agggaaggaa tgggtgctag ggttacggcg tcatatacca ccgcaatgca cagctacaac    5700
ggggcataca cctcccggct ctttaggctc ctcaaaatgt ccggaatcaa cttcgtcgcc    5760
aaccccctgg tcaatataca cctccaggga cggttcgaca catacccgaa acgccgcggg    5820
ataaccaggt gaaggagat gctggagagc ggcatcaacg tctgctttgg ccacgacgac    5880
gtcttcgatc catggtaccc actcggcacc gctaacatgc tccaagtgct gcacatgggt    5940
ctgcacgtct gccagctcat gggctatgga cagatcaacg acggcctcaa cctcatcacc    6000
caccactctg ctcggacact caacctccag gactacggca tagccgccgg gaactcggct    6060
aatctcatca tcctcccggc ggagaatgga ttcgatgcac ttaggcgcca ggtgccagtc    6120
aggtattcag tgcgcggagg aaaggtgata gcctccaccc aaccagcaca gaccaccgtc    6180
tacctcgaac agccggaagc gatcgactac aagcgctagc actagacttg tccatcttct    6240
ggattggcca acttaattaa tgtatgaaat aaaaggatgc acacatagtg acatgctaat    6300
cactataatg tgggcatcaa agttgtgtgt tatgtgtaat tactagttat ctgaataaaa    6360
gagaaagaga tcatccatat ttcttatcct aaatgaatgt cacgtgtctt tataattctt    6420
tgatgaacca gatgcatttc attaaccaaa tccatataca tataaatatt aatcatatat    6480
aattaatatc aattgggtta gcaaaacaaa tctagtctag gtgtgttttg cggatcagct    6540
gcagtgcagc gtgacccggt cgtgcccctc tctagagata atgagcattg catgtctaag    6600
ttataaaaaa ttaccacata ttttttttgt cacacttgtt tgaagtgcag tttatctatc    6660
```

```
tttatacata tatttaaact ttactctacg aataatataa tctatagtac tacaataata   6720
tcagtgtttt agagaatcat ataaatgaac agttagacat ggtctaaagg acaattgagt   6780
attttgacaa caggactcta cagttttatc ttttttagtgt gcatgtgttc tccttttttt   6840
ttgcaaatag cttcacctat ataatacttc atccatttta ttagtacatc catttagggt   6900
ttagggttaa tggtttttat agactaattt ttttagtaca tctattttat tctattttag   6960
cctctaaatt aagaaaacta aaactctatt ttagttttttt tatttaataa tttagatata   7020
aaatagaata aaataaagtg actaaaaatt aaacaaatac cctttaagaa attaaaaaaa   7080
ctaaggaaac atttttcttg tttcgagtag ataatgccag cctgttaaac gccgtcgacg   7140
agtctaacgg acaccaacca gcgaaccagc agcgtcgcgt cgggccaagc gaagcagacg   7200
gcacggcatc tctgtcgctg cctctggacc cctctcgaga gttccgctcc accgttggac   7260
ttgctccgct gtcggcatcc agaaattgcg tggcggagcg gcagacgtga gccggcacgg   7320
caggcggcct cctcctcctc tcacggcacg gcagctacgg gggattcctt tcccaccgct   7380
ccttcgcttt cccttcctcg cccgccgtaa taaatagaca ccccctccac accctctttc   7440
cccaacctcg tgttgttcgg agcgcacaca cacacaacca gatctccccc aaatccaccc   7500
gtcggcacct ccgcttcaag gtacgccgct cgtcctcccc cccccccct ctctaccttc    7560
tctagatcgg cgttccggtc catggttagg gcccggtagt tctacttctg ttcatgtttg   7620
tgttagatcc gtgtttgtgt tagatccgtg ctgctagcgt tcgtacacgg atgcgacctg   7680
tacgtcagac acgttctgat tgctaacttg ccagtgtttc tctttgggga atcctgggat   7740
ggctctagcc gttccgcaga cgggatcgat ttcatgattt ttttttgttttc gttgcatagg   7800
gtttggtttg ccctttttcct ttatttcaat atatgccgtg cacttgtttg tcgggtcatc   7860
ttttcatgct tttttttgtc ttggttgtga tgatgtggtc tggttgggcg gtcgttctag   7920
atcggagtag aattctgttt caaactacct ggtggattta ttaattttgg atctgtatgt   7980
gtgtgccata catattcata gttacgaatt gaagatgatg gatggaaata tcgatctagg   8040
ataggtatac atgttgatgc gggttttact gatgcatata cagagatgct ttttgttcgc   8100
ttggttgtga tgatgtggtg tggttgggcg gtcgttcatt cgttctagat cggagtagaa   8160
tactgtttca aactacctgg tgtatttatt aattttggaa ctgtatgtgt gtgtcataca   8220
tcttcatagt tacgagttta agatggatgg aaatatcgat ctaggatagg tatacatgtt   8280
gatgtgggtt ttactgatgc atatacatga tggcatatgc agcatctatt catatgctct   8340
aaccttgagt acctatctat tataataaac aagtatgttt tataattatt ttgatcttga   8400
tatacttgga tgatggcata tgcagcagct atatgtggat tttttttagcc ctgccttcat   8460
acgctattta tttgcttggt actgtttctt ttgtcgatgc tcaccctgtt gtttggtgtt   8520
acttctgcag atgcaaaaac tcattaactc agtgcaaaac tatgcctggg gcagcaaaac   8580
ggcgttgact gaactttatg gtatggaaaa tccgtccagc cagccgatgg ccgagctgtg   8640
gatgggcgca catccgaaaa gcagttcacg agtgcagaat gccgccggag atatcgtttc   8700
actgcgtgat gtgattgaga gtgataaatc gactctgctc ggagaggccg ttgccaaacg   8760
cttttggcgaa ctgcctttcc tgttcaaagt attatgcgca gcacagccac tctccattca   8820
ggttcatcca aacaaacaca attctgaaat cggttttgcc aaagaaaatg ccgcaggtat   8880
cccgatggat gccgccgagc gtaactataa agatcctaac cacaagccgg agctggtttt   8940
tgcgctgacg ccttttcctt gcgatgaacgc gtttcgtgaa ttttccgaga ttgtctccct   9000
```

-continued

```
actccagccg gtcgcaggtg cacatccggc gattgctcac ttttttacaac agcctgatgc    9060 cgaacgttta agcgaactgt tcgccagcct gttgaatatg cagggtgaag aaaaatcccg    9120
cgcgctggcg atttttaaaat cggccctcga tagccagcag ggtgaaccgt ggcaaacgat    9180
tcgtttaatt tctgaatttt acccggaaga cagcggtctg ttctccccgc tattgctgaa    9240
tgtggtgaaa ttgaaccctg gcgaagcgat gttcctgttc gctgaaacac cgcacgctta    9300
cctgcaaggc gtggcgctgg aagtgatggc aaactccgat aacgtgctgc gtgcgggtct    9360
gacgcctaaa tacattgata ttccggaact ggttgccaat gtgaaattcg aagccaaacc    9420
ggctaaccag ttgttgaccc agccggtgaa acaaggtgca gaactggact cccgattcc     9480 agtggatgat tttgccttct cgctgcatga ccttagtgat aaagaaacca ccattagcca    9540
gcagagtgcc gccatttttgt tctgcgtcga aggcgatgca acgttgtgga aaggttctca    9600
gcagttacag cttaaaccgg gtgaatcagc gtttattgcc gccaacgaat caccggtgac    9660
tgtcaaaggc cacggccgtt tagcgcgtgt ttacaacaag ctgtaagagc ttactgaaaa    9720
aattaacatc tcttgctaag atccatggat attcgaacgc gtaggtacca catggttaac    9780
ctagacttgt ccatcttctg gattggccaa cttaattaat gtatgaaata aaaggatgca    9840
cacatagtga catgctaatc actataatgt gggcatcaaa gttgtgtgtt atgtgtaatt    9900
actagttatc tgaataaaag agaaagagat catccatatt tcttatccta aatgaatgtc    9960
acgtgtcttt ataattcttt gatgaaccag atgcatttca ttaaccaaat ccatatacat   10020
ataaatatta atcatatata attaatatca attgggttag caaaacaaat ctagtctagg   10080
tgtgttttgc g                                                        10091
```

<210> SEQ ID NO 104
<211> LENGTH: 189
<212> TYPE: DNA
<213> ORGANISM: Solanum tuberosum

<400> SEQUENCE: 104

```
gtaagtttct gcttctacct ttgatatata tataataatt atcattaatt agtagtaata      60
taatatttca aatattttttt tcaaaataaa agaatgtagt atatagcaat tgcttttctg    120
tagtttataa gtgtgtatat tttaatttat aacttttcta atatatgacc aaaacatggt    180
gatgtgcag                                                             189
```

<210> SEQ ID NO 105
<211> LENGTH: 20
<212> TYPE: DNA
<213> ORGANISM: artificial sequence
<220> FEATURE:
<223> OTHER INFORMATION: CYS4 RECOGNITION SITE

<400> SEQUENCE: 105

```
gttcactgcc gtataggcag                                                  20
```

<210> SEQ ID NO 106
<211> LENGTH: 564
<212> TYPE: DNA
<213> ORGANISM: artificial sequence
<220> FEATURE:
<223> OTHER INFORMATION: CYS4 (MO) DNA

<400> SEQUENCE: 106

```
atggatcact atctcgacat taggctgagg ccagatcctg agtttccacc tgctcagctt      60
atgagcgttt tgttcggtaa gctccaccag gccctggtgg cacagggcgg agacagaatt     120
```

-continued

```
ggtgttagct tcccagatct tgacgaaagc cgtagcaggt tgggcgagag actccgtatt    180
cacgctagcg ccgatgacct gagggcactt ttggctagac cttggctcga aggactgcgt    240
gatcaccttc agtttggtga gccagccgtg gttcctcacc caaccccttta caggcaggtg   300 agcagagttc aggcaaagag caatccagaa cgtttgagga gaaggctcat gcgtaggcac    360
gacctgagcg aggaagaggc tagaaagcgt attcctgata ccgtggccag ggcacttgac    420
ttgccattcg ttaccctcag aagccagagc accggccagc acttccgtct gtttattagg    480
cacggacctc ttcaggtgac cgctgaagag ggtggcttca cctgctatgg attgagcaag    540
ggtggcttcg ttccatggtt ttga                                           564
```

<210> SEQ ID NO 107
<211> LENGTH: 187
<212> TYPE: PRT
<213> ORGANISM: artificial sequence
<220> FEATURE:
<223> OTHER INFORMATION: CYS4 (MO) PRT

<400> SEQUENCE: 107

```
Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu His Gln Ala Leu
            20                  25                  30

Val Ala Gln Gly Gly Asp Arg Ile Gly Val Ser Phe Pro Asp Leu Asp
        35                  40                  45

Glu Ser Arg Ser Arg Leu Gly Glu Arg Leu Arg Ile His Ala Ser Ala
    50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Ala Lys Ser Asn Pro Glu Arg Leu
            100                 105                 110

Arg Arg Arg Leu Met Arg Arg His Asp Leu Ser Glu Glu Glu Ala Arg
        115                 120                 125

Lys Arg Ile Pro Asp Thr Val Ala Arg Ala Leu Asp Leu Pro Phe Val
    130                 135                 140

Thr Leu Arg Ser Gln Ser Thr Gly Gln His Phe Arg Leu Phe Ile Arg
145                 150                 155                 160

His Gly Pro Leu Gln Val Thr Ala Glu Glu Gly Gly Phe Thr Cys Tyr
                165                 170                 175

Gly Leu Ser Lys Gly Gly Phe Val Pro Trp Phe
            180                 185
```

<210> SEQ ID NO 108
<211> LENGTH: 77
<212> TYPE: DNA
<213> ORGANISM: artificial sequence
<220> FEATURE:
<223> OTHER INFORMATION: DNA version of GUIDE RNA

<400> SEQUENCE: 108

```
gttttagagc tagaaatagc aagttaaaat aaggctagtc cgttatcaac ttgaaaaagt    60
ggcaccgagt cggtgct                                                    77
```

<210> SEQ ID NO 109

<211> LENGTH: 3697
<212> TYPE: DNA
<213> ORGANISM: artificial sequence
<220> FEATURE:
<223> OTHER INFORMATION: PG46 PRO-CYS4(MO)-IN2-1 TERM

<400> SEQUENCE: 109

| | | | | | |
|---|---|---|---|---|---:|
| aagcttgcat | gcctgcaggt | cgactctaga | ggatctgcac | cggacactgt | ctggtggcat | 60 |
| accagacagt | ccggtgtgcc | agatcagggc | acccttcggt | tcctttgctc | ctttgctttt | 120 |
| gaaccctaac | tttgatcgtt | tattggtttg | tgttgaacct | ttatgcacct | gtggaatata | 180 |
| taatctagaa | caaactagtt | agtccaatca | tttgtgttgg | gcattcaacc | accaaaatta | 240 |
| tttataggaa | aaggttaaac | cttatttccc | tttcaatctc | ccccttttg | gtgattgatg | 300 |
| ccaacacaaa | ccaaagaaaa | tatataagtg | cagaattgaa | ctagtttgca | taaggtaagt | 360 |
| gcataggtta | cttagaatta | aatcaattta | tactttact | tgatatgcat | ggttgctttc | 420 |
| ttttatttta | acattttgga | ccacatttgc | accacttgtt | ttgttttttg | caaatctttt | 480 |
| tggaaattct | ttttcaaagt | cttttgcaaa | tagtcaaagg | tatatgaata | agattgtaag | 540 |
| aagcattttc | aagatttgaa | atttctcccc | ctgtttcaaa | tgcttttcct | ttgactaaac | 600 |
| aaaactcccc | ctgaataaaa | ttctcctctt | agctttcaag | agggttttaa | atagatatca | 660 |
| attggaaata | tatttagatg | ctaattttga | aaatatacca | attgaaaatc | aacataccaa | 720 |
| tttgaaatta | aacataccaa | tttaaaaaat | ttcaaaaagt | ggtggtgcgg | tccttttgct | 780 |
| ttgggcttaa | tatttctccc | cctttggcat | taatcgccaa | aaacggagac | tttgtgagcc | 840 |
| atttatactt | tctccccatt | ggtaaatgaa | atatgagtga | aagattatac | caaatttgga | 900 |
| cagtgatgcg | gagtgacggc | gaaggataaa | cgataccgtt | agagtggagt | ggaagccttg | 960 |
| tcttcgccga | agactccatt | tcccttcaa | tctacgactt | agcatagaaa | tacacttgaa | 1020 |
| aacacattag | tcgtagccac | gaaagagata | tgatcaaagg | tatacaaatg | agctatgtgt | 1080 |
| gtaatgtttc | aatcaaagtt | tcgagaatca | agaatattta | gctcattcct | aagtttgcta | 1140 |
| aaggttttat | catctaatgg | tttggtaaag | atatcgacta | attgttcttt | ggtgctaaca | 1200 |
| taagcaatct | cgatatcacc | cctttgttgg | tgatccctca | aaaagtgata | ccgaatgtct | 1260 |
| atgtgcttag | tgcggctgtg | ttcaacggga | ttatccgcca | tgcagatagc | actctcattg | 1320 |
| tcacatagga | gagggacttt | gctcaatttg | tagccatagt | ccctaaggtt | ttgcctcatc | 1380 |
| caaagtaatt | gcacacaaca | atgtcctgcg | gcaatatact | tggcttcggc | ggtagaaaga | 1440 |
| gctattgagt | tttgtttctt | tgaagtccaa | gacaccaggg | atctccctag | aaactgacaa | 1500 |
| gtccctgatg | tgctcttcct | atcaatttta | caccctgccc | aatcggcatc | tgaatatcct | 1560 |
| attaaatcaa | aggtggatcc | cttggggtac | caaagaccaa | atttaggagt | gtaaactaaa | 1620 |
| tatctcatga | ttcttttcac | ggccctaagg | tgaacttcct | taggatcggc | ttggaatctt | 1680 |
| gcacacatgc | atatagaaag | catactatct | ggtcgagatg | cacataaata | gagtaaagat | 1740 |
| cctatcatcg | accggtatac | cttttggtct | acgatttac | ctcccgtgtc | gaggtcgaga | 1800 |
| tgcccattag | ttcccatggg | tgtcctgatg | ggcttggcat | ccttcattcc | aaacttgttg | 1860 |
| agtatgtctt | gaatgtactt | tgtttggctg | atgaaggtgc | catctggag | ttgcttgact | 1920 |
| tgaaatccta | gaaatatttt | caacttcccc | atcatagaca | tctcgaattt | cggaatcatg | 1980 |
| atcctactaa | actcttcaca | gtagatttg | ttagtagacc | caaatataat | atcatcaaca | 2040 |
| taaatttggc | atacaaacaa | aacttttgaa | atggttttag | taaagagagt | aggatcggct | 2100 |
| ttactgactc | tgaagccatt | agtgataaga | aaatctctta | ggcattcata | ccatgctgtt | 2160 |

```
ggggcttgct tgagcccata aagcgccttt gagagtttat aaacatggtt agggtactca    2220
ctatcttcaa agccgagagg ttgctcaaca tagacctatt caccccarrt gatcactttt    2280
ttggtccttc aggatctaat agttatgtat aatttagagt ctcttgttta atggccagat    2340
atttctaatt aatctaagaa tttatgatat tttttaattt tttatcatgt ctgatgagaa    2400
ttaacataaa ggctcaattg ggtcctgaat taataataga gtgaaaatta atccagaggc    2460
tctattagaa ccttcaatta gtaataccaa gatatatata agatagtaga gtatagttta    2520
aatgttggca ttgttcattc tttcttttgt tatttaattt atgctttcca cggtggttag    2580
tggttacttc tgaagggtcc aaataatgca tgaagagttt gaggacaaga agtctgccct    2640
aaaaatagcg atgcaaaggc atggtgtcca agccatacat atagcgcact aattttatca    2700
gcagaacaat ggtatttata ggtcctagtg cccaggcaac aagagacacg aataaagcat    2760
cgatcacgac accggatcca tggatcacta tctcgacatt aggctgaggc cagatcctga    2820
gtttccacct gctcagctta tgagcgtttt gttcggtaag ctccaccagg ccctggtggc    2880
acagggcgga gacagaattg gtgttagctt cccagatctt gacgaaagcc gtagcaggtt    2940
gggcgagaga ctccgtattc acgctagcgc cgatgacctg agggcacttt tggctagacc    3000
ttggctcgaa ggactgcgtg atcaccttca gtttggtgag ccagccgtgg ttcctcaccc    3060
aaccccttac aggcaggtga gcagagttca ggcaaagagc aatccagaac gtttgaggag    3120
aaggctcatg cgtaggcacg acctgagcga ggaagaggct agaaagcgta ttcctgatac    3180
cgtggccagg gcacttgact tgccattcgt taccctcaga agccagagca ccggccagca    3240
cttccgtctg tttattaggc acggacctct tcaggtgacc gctgaagagg gtggcttcac    3300
ctgctatgga ttgagcaagg gtggcttcgt tccatggttt tgaggtaccg atctgacaaa    3360
gcagcattag tccgttgatc ggtggaagac cactcgtcag tgttgagttg aatgtttgat    3420
caataaaata cggcaatgct gtaagggttg ttttttatgc cattgataat acactgtact    3480
gttcagttgt tgaactctat ttcttagcca tgccaagtgc ttttcttatt ttgaataaca    3540
ttacagcaaa aagttgaaag acaaaaaaaa aaacccccga acagagtgct ttgggtccca    3600
agctacttta gactgtgttc ggcgttcccc ctaaatttct ccccctatat ctcactcact    3660
tgtcacatca gcgttctctt tccccctatat ctccacg                            3697
```

<210> SEQ ID NO 110
<211> LENGTH: 18
<212> TYPE: DNA
<213> ORGANISM: artificial sequence
<220> FEATURE:
<223> OTHER INFORMATION: GT1 PRO TARGET1

<400> SEQUENCE: 110
gtgcatcatg gactcatg                                                  18

<210> SEQ ID NO 111
<211> LENGTH: 20
<212> TYPE: DNA
<213> ORGANISM: artificial sequence
<220> FEATURE:
<223> OTHER INFORMATION: GT1 PRO TARGET2

<400> SEQUENCE: 111
cgctgtacgg cgtggtagac                                                20

<210> SEQ ID NO 112

```
<211> LENGTH: 19
<212> TYPE: DNA
<213> ORGANISM: artificial sequence
<220> FEATURE:
<223> OTHER INFORMATION: GT1 PRO TARGET3

<400> SEQUENCE: 112
ccagcaacgt ccagcgcgc                                                   19

<210> SEQ ID NO 113
<211> LENGTH: 19
<212> TYPE: DNA
<213> ORGANISM: artificial sequence
<220> FEATURE:
<223> OTHER INFORMATION: GT1 PRO TARGET4

<400> SEQUENCE: 113
gggtgcccgt gcgttgcaa                                                   19

<210> SEQ ID NO 114
<211> LENGTH: 20
<212> TYPE: DNA
<213> ORGANISM: artificial sequence
<220> FEATURE:
<223> OTHER INFORMATION: GT1 PRO TARGET5

<400> SEQUENCE: 114
gcatttcgcg agtcaaattt                                                  20

<210> SEQ ID NO 115
<211> LENGTH: 1000
<212> TYPE: DNA
<213> ORGANISM: artificial sequence
<220> FEATURE:
<223> OTHER INFORMATION: ZM-U6 POLIII CHR8 PRO

<400> SEQUENCE: 115
tgagagtaca atgatgaacc tagattaatc aatgccaaag tctgaaaaat gcaccctcag       60
tctatgatcc agaaaatcaa gattgcttga ggccctgttc ggttgttccg gattagagcc      120
ccggattaat tcctagccgg attacttctc taatttatat agattttgat gagctggaat      180
gaatcctggc ttattccggt acaaccgaac aggccctgaa ggataccagt aatcgctgag      240
ctaaattggc atgctgtcag agtgtcagta ttgcagcaag gtagtgagat aaccggcatc      300
atggtgccag tttgatggca ccattagggt tagagatggt ggccatgggc gcatgtcctg      360
gccaactttg tatgatatat ggcagggtga ataggaaagt aaaattgtat tgtaaaaagg      420
gatttcttct gtttgttagc gcatgtacaa ggaatgcaag ttttgagcga gggggcatca      480
aagatctggc tgtgttttcca gctgtttttg ttagccccat cgaatccttg acataatgat      540
cccgcttaaa taagcaacct cgcttgtata gttccttgtg ctctaacaca cgatgatgat      600
aagtcgtaaa atagtggtgt ccaaagaatt tccaggccca gttgtaaaag ctaaatgct       660 attcgaattt ctactagcag taagtcgtgt ttagaaatta ttttttttata tacctttttt      720 ccttctatgt acagtaggac acagtgtcag cgccgcgttg acggagaata tttgcaaaaa      780
agtaaaagag aaagtcatag cggcgtatgt gccaaaaact tcgtcacaga gagggccata      840
agaaacatgg cccacggccc aatacgaagc accgcgacga agcccaaaca gcagtccgta      900
ggtggagcaa agcgctgggt aatacgcaaa cgttttgtcc caccttgact aatcacaaga      960
gtggagcgta ccttataaac cgagccgcaa gcaccgaatt                           1000
```

```
<210> SEQ ID NO 116
<211> LENGTH: 12792
<212> TYPE: DNA
<213> ORGANISM: artificial sequence
<220> FEATURE:
<223> OTHER INFORMATION: UBI-PMI-PINII TERM ----PRO-ZMAA1-IN2-1 TERM

<400> SEQUENCE: 116
```

| | | | | | |
|---|---|---|---|---|---|
| gtgcagcgtg | acccggtcgt | gcccctctct | agagataatg | agcattgcat gtctaagtta | 60 |
| taaaaaatta | ccacatattt | tttttgtcac | acttgtttga | agtgcagttt atctatcttt | 120 |
| atacatatat | ttaaacttta | ctctacgaat | aatataatct | atagtactac aataatatca | 180 |
| gtgttttaga | gaatcatata | aatgaacagt | tagacatggt | ctaaaggaca attgagtatt | 240 |
| ttgacaacag | gactctacag | ttttatcttt | ttagtgtgca | tgtgttctcc ttttttttg | 300 |
| caaatagctt | cacctatata | atacttcatc | cattttatta | gtacatccat ttagggttta | 360 |
| gggttaatgg | tttttataga | ctaattttt | tagtacatct | attttattct attttagcct | 420 |
| ctaaattaag | aaaactaaaa | ctctatttta | gttttttat | ttaataattt agatataaaa | 480 |
| tagaataaaa | taaagtgact | aaaaattaaa | caaatacct | ttaagaaatt aaaaaaacta | 540 |
| aggaaacatt | tttcttgttt | cgagtagata | atgccagcct | gttaaacgcc gtcgacgagt | 600 |
| ctaacggaca | ccaaccagcg | aaccagcagc | gtcgcgtcgg | gccaagcgaa gcagacggca | 660 |
| cggcatctct | gtcgctgcct | ctggaccct | ctcgagagtt | ccgctccacc gttggacttg | 720 |
| ctccgctgtc | ggcatccaga | aattgcgtgg | cggagcggca | gacgtgagcc ggcacggcag | 780 |
| gcggcctcct | cctcctctca | cggcaccggc | agctacgggg | gattcctttc ccaccgctcc | 840 |
| ttcgctttcc | cttcctcgcc | cgccgtaata | aatagacacc | cctccacac cctctttccc | 900 |
| caacctcgtg | ttgttcggag | cgcacacaca | cacaaccaga | tctcccccaa atccacccgt | 960 |
| cggcacctcc | gcttcaaggt | acgccgctcg | tcctccccc | cccccctctc taccttctct | 1020 |
| agatcggcgt | tccggtccat | gcatggttag | ggcccggtag | ttctacttct gttcatgttt | 1080 |
| gtgttagatc | cgtgtttgtg | ttagatccgt | gctgctagcg | ttcgtacacg gatgcgacct | 1140 |
| gtacgtcaga | cacgttctga | ttgctaactt | gccagtgttt | ctctttgggg aatcctggga | 1200 |
| tggctctagc | cgttccgcag | acgggatcga | tttcatgatt | ttttttgttt cgttgcatag | 1260 |
| ggtttggttt | gcccttttcc | tttatttcaa | tatatgccgt | gcacttgttt gtcgggtcat | 1320 |
| cttttcatgc | ttttttttgt | cttggttgtg | atgatgtggt | ctggttgggc ggtcgttcta | 1380 |
| gatcggagta | gaattctgtt | tcaaactacc | tggtggattt | attaattttg gatctgtatg | 1440 |
| tgtgtgccat | acatattcat | agttacgaat | tgaagatgat | ggatggaaat atcgatctag | 1500 |
| gataggtata | catgttgatg | cgggtttac | tgatgcatat | acagagatgc tttttgttcg | 1560 |
| cttggttgtg | atgatgtggt | gtggttgggc | ggtcgttcat | tcgttctaga tcggagtaga | 1620 |
| atactgtttc | aaactacctg | gtgtatttat | taattttgga | actgtatgtg tgtgtcatac | 1680 |
| atcttcatag | ttacgagttt | aagatggatg | gaaatatcga | tctaggatag gtatacatgt | 1740 |
| tgatgtgggt | tttactgatg | catatacatg | atggcatatg | cagcatctat tcatatgctc | 1800 |
| taaccttgag | tacctatcta | ttataataaa | caagtatgtt | ttataattat tttgatcttg | 1860 |
| atatacttgg | atgatggcat | atgcagcagc | tatatgtgga | tttttttagc cctgccttca | 1920 |
| tacgctattt | atttgcttgg | tactgtttct | tttgtcgatg | ctcaccctgt tgtttggtgt | 1980 |
| tacttctgca | ggtcgacttt | aacttagcct | agcgaagttc | ctattccgaa gttcctattc | 2040 |
| tctagaaagt | ataggaactt | cagatccacc | gggatcccg | atcatgcaaa aactcattaa | 2100 |

```
ctcagtgcaa aactatgcct ggggcagcaa aacggcgttg actgaacttt atggtatgga    2160
aaatccgtcc agccagccga tggccgagct gtggatgggc gcacatccga aaagcagttc    2220
acgagtgcag aatgccgccg gagatatcgt ttcactgcgt gatgtgattg agagtgataa    2280
atcgactctg ctcggagagg ccgttgccaa acgctttggc gaactgcctt tcctgttcaa    2340
agtattatgc gcagcacagc cactctccat tcaggttcat ccaaacaaac acaattctga    2400
aatcggtttt gccaaagaaa atgccgcagg tatcccgatg gatgccgccg agcgtaacta    2460
taaagatcct aaccacaagc cggagctggt ttttgcgctg acgcctttcc ttgcgatgaa    2520
cgcgtttcgt gaattttccg agattgtctc cctactccag ccggtcgcag gtgcacatcc    2580
ggcgattgct cacttttac aacagcctga tgccgaacgt ttaagcgaac tgttcgccag    2640
cctgttgaat atgcagggtg aagaaaaatc ccgcgcgctg gcgattttaa aatcggccct    2700
cgatagccag cagggtgaac cgtggcaaac gattcgttta atttctgaat tttacccgga    2760
agacagcggt ctgttctccc cgctattgct gaatgtggtg aaattgaacc ctggcgaagc    2820
gatgttcctg ttcgctgaaa caccgcacgc ttacctgcaa ggcgtggcgc tggaagtgat    2880
ggcaaactcc gataacgtgc tgcgtgcggg tctgacgcct aaatacattg atattccgga    2940
actggttgcc aatgtgaaat cgaagccaa accggctaac cagttgttga cccagccggt    3000
gaaacaaggt gcagaactgg acttcccgat tccagtggat gattttgcct tctcgctgca    3060
tgaccttagt gataaagaaa ccaccattag ccagcagagt gccgccattt tgttctgcgt    3120
cgaaggcgat gcaacgttgt ggaaaggttc tcagcagtta cagcttaaac cgggtgaatc    3180
agcgtttatt gccgccaacg aatcaccggt gactgtcaaa ggccacggcc gtttagcgcg    3240
tgtttacaac aagctgtaag agcttactga aaaaattaac atctcttgct aagctggggg    3300
tggaacctag acttgtccat cttctggatt ggccaactta attaatgtat gaataaaag    3360 gatgcacaca tagtgacatg ctaatcacta taatgtgggc atcaaagttg tgtgttatgt    3420
gtaattacta gttatctgaa taaaagagaa agagatcatc catatttctt atcctaaatg    3480
aatgtcacgt gtctttataa ttctttgatg aaccagatgc atttcattaa ccaaatccat    3540
atacatataa atattaatca tatataatta atatcaattg ggttagcaaa acaaatctag    3600
tctaggtgtg ttttgcgaat gcgaccttct tatgtgcttc tagtctccaa atgtggttga    3660
tagttatttt gctctaagat caacagtaat gaagtataaa tcatcgttgt ggtgtgctac    3720
tcggttaatt gagcattaac acacacaaac atgacgagga tggtataatc tccaaaaatg    3780
tgtactttgt taggtgggac cctatagcct tgattaatgt gctatgttag gcatgcctgg    3840
aaacgtgtga cgcatatgtt ttgtgaacct gttgatatta tatgtgcttt tatattacca    3900
tattttatta aaatactaat atttattact agtaagatat aacattctat ctagcttaaa    3960
aactaaccat aaatattcca taataactag atttaccaaa ctaatatact aaatatacat    4020
aataaataca aaattaacaa gacaataatc aatatttatg agcttaatat atttagacat    4080
tatggttggt cgacgataat catgctaact tttcgtaatt gcttgattga aatatgctta    4140
gaataatgcc tctttgttct acatggcaaa tagggaccat tatggtgtaa caccctggga    4200
accacaaaca ccccgaaatg ctactaaact acacaactaa ccttcatata taaaatttcg    4260
acagcatctc ctttgaaaat ttgcatagac gtggaagcaa cagagtataa acagatatca    4320
tgataagaaa acatactaga cattaataat ctgctagaaa tgggaagaat cgctgcacct    4380
gtgcagcgtg acccggtcgt gcccctctct agagataatg agcattgcat gtctaagtta    4440
taaaaaatta ccacatattt tttttgtcac acttgtttga agtgcagttt atctatcttt    4500
```

```
atacatatat ttaaacttta ctctacgaat aatataatct atagtactac aataatatca    4560
gtgttttaga gaatcatata aatgaacagt tagacatggt ctaaaggaca attgagtatt    4620
ttgacaacag gactctacag ttttatcttt ttagtgtgca tgtgttctcc tttttttttg    4680
caaatagctt cacctatata atacttcatc cattttatta gtacatccat ttagggttta    4740
gggttaatgg tttttataga ctaattttt tagtacatct attttattct attttagcct    4800
ctaaattaag aaaactaaaa ctctatttta gttttttat ttaataattt agatataaaa    4860
tagaataaaa taaagtgact aaaaattaaa caaatacccct ttaagaaatt aaaaaaacta    4920
aggaaacatt tttcttgttt cgagtagata atgccagcct gttaaacgcc gtcgacgagt    4980
ctaacggaca ccaaccagcg aaccagcagc gtcgcgtcgg gccaagcgaa gcagacggca    5040
cggcatctct gtcgctgcct ctggacccct ctcgagagtt ccgctccacc gttggacttg    5100
ctccgctgtc ggcatccaga aattgcgtgg cggagcggca gacgtgagcc ggcacggcag    5160
gcggcctcct cctcctctca cggcaccggc agctacgggg gattcctttc ccaccgctcc    5220
ttcgctttcc cttcctcgcc cgccgtaata aatagacacc ccctccacac cctctttccc    5280
caacctcgtg ttgttcggag cgcacacaca cacaaccaga tctcccccaa atccaccccgt    5340 cggcacctcc gcttcaaggt acgccgctcg tcctcccccc cccccctctc taccttctct    5400
agatcggcgt tccggtccat gcatggttag ggcccggtag ttctacttct gttcatgttt    5460
gtgttagatc cgtgtttgtg ttagatccgt gctgctagcg ttcgtacacg gatgcgacct    5520
gtacgtcaga cacgttctga ttgctaactt gccagtgttt ctctttgggg aatcctggga    5580
tggctctagc cgttccgcag acgggatcga tttcatgatt tttttttgttt cgttgcatag    5640 ggtttggttt gcccttttcc tttatttcaa tatatgccgt gcacttgttt gtcgggtcat    5700
cttttcatgc ttttttttgt cttggttgtg atgatgtggt ctggttgggc ggtcgttcta    5760
gatcggagta gaattctgtt tcaaactacc tggtggattt attaattttg gatctgtatg    5820
tgtgtgccat acatattcat agttacgaat tgaagatgat ggatggaaat atcgatctag    5880
gataggtata catgttgatg cgggttttac tgatgcatat acagagatgc ttttgttcg    5940 cttggttgtg atgatgtggt gtggttgggc ggtcgttcat tcgttctaga tcggagtaga    6000
atactgtttc aaactacctg gtgtatttat taattttgga actgtatgtg tgtgtcatac    6060
atcttcatag ttacgagttt aagatggatg gaaatatcga tctaggatag gtatacatgt    6120
tgatgtgggt tttactgatg catatacatg atggcatatg cagcatctat tcatatgctc    6180
taaccttgag tacctatcta ttataataaa caagtatgtt ttataattat tttgatcttg    6240
atatacttgg atgatggcat atgcagcagc tatatgtgga ttttttttagc cctgccttca    6300 tacgctattt atttgcttgg tactgttct tttgtcgatg ctcaccctgt tgtttggtgt    6360
tacttctgca gatggcccac agcaagcacg gcctgaagga ggagatgacc atgaagtacc    6420
acatggaggg ctgcgtgaac ggccacaagt tcgtgatcac cggcgagggc atcggctacc    6480
ccttcaaggg caagcagacc atcaacctgt gcgtgatcga gggcggcccc ctgcccttca    6540
gcgaggacat cctgagcgcc ggcttcaagt acggcgaccg gatcttcacc gagtaccccc    6600
aggacatcgt ggactacttc aagaacagct gccccgccgg ctacacctgg ggccggagct    6660
tcctgttcga ggacggcgcc gtgtgcatct gtaacgtgga catcaccgtg agcgtgaagg    6720
agaactgcat ctaccacaag agcatcttca acggcgtgaa cttccccgcc gacggcccccg    6780 tgatgaagaa gatgaccacc aactgggagg ccagctgcga agatcatg cccgtgccta    6840
```

-continued

```
agcagggcat cctgaagggc gacgtgagca tgtacctgct gctgaaggac ggcggccggt   6900
accggtgcca gttcgacacc gtgtacaagg ccaagagcgt gcccagcaag atgcccgagt   6960
ggcacttcat ccagcacaag ctgctgcggg aggaccggag cgacgccaag aaccagaagt   7020
ggcagctgac cgagcacgcc atcgccttcc ccagcgccct ggcctgagga tctcgatagg   7080
gatctgttaa cgatccccgg cggtgtcccc cactgaagaa actatgtgct gtagtatagc   7140
cgctgcccgc tggctagcta gctagttgag tcatttagcg gcgatgattg agtaataatg   7200
tgtcacgcat caccatgcat gggtggcagt gtcagtgtga gcaatgacct gaatgaacaa   7260
ttgaaatgaa aagaaaaaag tattgttcca aattaaacgt tttaaccttt taataggttt   7320
atacaataat tgatatatgt tttctgtata tgtctaattt gttatcatcc atttagatat   7380
agacaaaaaa aatctaagaa ctaaaacaaa tgctaatttg aaatgaaggg agtatatatt   7440
gggataatgt cgatgagatc cctcgtaata tcaccgacat cacacgtgtc cagttaatgt   7500
atcagtgata cgtgtattca catttgttgc gcgtaggcgt acccaacaat tttgatcgac   7560
tatcagaaag tcaacggaag cgagtcgacc tcgagggggg gcccctgggc tcgaaggcat   7620
ggagtcaaag attcaaatag aggacctaac agaactcgcc gtaaagactg gcgaacagtt   7680
catacagagt ctcttacgac tcaatgacaa gaagaaaatc ttcgtcaaca tggtggagca   7740
cgacacgctt gtctactcca aaaatatcaa agatacagtc tcagaagacc aaagggcaat   7800
tgagactttt caacaaaggg taatatccgg aaacctcctc ggattccatt gcccagctat   7860
ctgtcacttt attgtgaaga gtgtggaaaa ggaaggtggc tcctacaaat gccatcattg   7920
cgataaagga aaggccatcg ttgaagatgc ctctgccgac agtggtccca agatggacc    7980
cccacccacg aggagcatcg tggaaaaaga agacgttcca accacgtctt caaagcaagt   8040
ggattgatgt gatatctcca ctgacgtaag ggatgacgca caatcccact aagctgaccg   8100
gcccggccg aagcttgcat gcctgcaggt cgactctaga ggatctgcac cggacactgt    8160
ctggtggcat accagacagt ccggtgtgcc agatcagggc acccttcggt tccttttgctc  8220
cttttgcttt tgaaccctaac tttgatcgtt tattggttg tgttgaacct ttatgcacct    8280
gtggaatata taatctagaa caaactagtt agtccaatca tttgtgttgg gcattcaacc   8340
accaaaatta tttataggaa aaggttaaac cttatttccc tttcaatctc cccctttttg    8400
gtgattgatg ccaacacaaa ccaaagaaaa tatataagtg cagaattgaa ctagtttgca   8460
taaggtaagt gcataggtta cttagaatta aatcaattta acttttact tgatatgcat     8520
ggttgctttc ttttatttta acattttgga ccacatttgc caccttgtt ttgttttttg     8580
caaatcttt tggaaattct ttttcaaagt cttttgcaaa tagtcaaagg tatatgaata    8640
agattgtaag aagcatttc aagatttgaa atttctcccc ctgtttcaaa tgcttttct      8700
ttgactaaac aaaactcccc ctgaataaaa ttctcctctt agctttcaag agggttttaa   8760
atagatatca attggaaata tatttagatg ctaattttga aaatataccc attgaaaatc    8820
aacataccaa tttgaaatta acataccaa tttaaaaaat ttcaaaagt ggtggtgcgg     8880
tccttttgct ttgggcttaa tatttctccc cctttggcat taatcgccaa aaacggagac   8940
tttgtgagcc atttatactt tctccccatt ggtaaatgaa atatgagtga agattatac   9000
caaatttgga cagtgatgcg gagtgacggc gaaggataaa cgataccgtt agagtggagt   9060
ggaagccttg tcttcgccga agactccatt tcccttcaa tctacgactt agcatagaaa   9120
tacacttgaa aacacattag tcgtagccac gaaagagata tgatcaaagg tatacaaatg   9180
agctatgtgt gtaatgtttc aatcaaagtt tcgagaatca agaatattta gctcattcct   9240
```

```
aagtttgcta aaggtttat  catctaatgg tttggtaaag atatcgacta attgttcttt   9300
ggtgctaaca taagcaatct cgatatcacc cctttgttgg tgatccctca aaaagtgata   9360
ccgaatgtct atgtgcttag tgcggctgtg ttcaacggga ttatccgcca tgcagatagc   9420
actctcattg tcacatagga gagggacttt gctcaatttg tagccatagt ccctaaggtt   9480
ttgcctcatc caaagtaatt gcacacaaca atgtcctgcg gcaatatact tggcttcggc   9540
ggtagaaaga gctattgagt tttgtttctt tgaagtccaa gacaccaggg atctccctag   9600
aaactgacaa gtccctgatg tgctcttcct atcaatttta caccctgccc aatcggcatc   9660
tgaatatcct attaaatcaa aggtggatcc cttggggtac caaagaccaa atttaggagt   9720
gtaaactaaa tatctcatga ttcttttcac ggccctaagg tgaacttcct taggatcggc   9780
ttggaatctt gcacacatgc atatagaaag catactatct ggtcgagatg cacataaata   9840
gagtaaagat cctatcatcg accggtatac cttttggtct acggatttac ctcccgtgtc   9900
gaggtcgaga tgcccattag ttcccatggg tgtcctgatg ggcttggcat ccttcattcc   9960
aaacttgttg agtatgtctt gaatgtactt tgtttggctg atgaaggtgc catcttggag   10020
ttgcttgact tgaaatccta gaaaatattt caacttcccc atcatagaca tctcgaattt   10080
cggaatcatg atcctactaa actcttcaca gtagatttg  ttagtagacc caaatataat   10140
atcatcaaca taaatttggc atacaaacaa aactttgaa  atggttttag taagagagt    10200 aggatcggct ttactgactc tgaagccatt agtgataaga aaatctctta ggcattcata   10260
ccatgctgtt ggggcttgct tgagcccata aagcgccttt gagagtttat aaacatggtt   10320
agggtactca ctatcttcaa agccgagagg ttgctcaaca tagacctatt caccccattt   10380
gatcactttt ttggtccttc aggatctaat agttatgtat aatttagagt ctcttgttta   10440
atggccagat atttctaatt aatctaagaa tttatgatat tttttaattt tttatcatgt   10500
ctgatgagaa ttaacataaa ggctcaattg ggtcctgaat taataataga gtgaaaatta   10560
atccagaggc tctattagaa ccttcaatta gtaataccaa gatatatata agatagtaga   10620
gtatagttta aatgttggca ttgttcattc tttcttttgt tatttaattt atgctttcca   10680
cggtggttag tggttacttc tgaagggtcc aaataatgca tgaagagttt gaggacaaga   10740
agtctgccct aaaaatagcg atgcaaaggc atggtgtcca agccatacat atagcgcact   10800
aattttatca gcagaacaat ggtatttata ggtcctagtg cccaggcaac aagagacacg   10860
aataaagcat cgatcacgac accatggcgg cgacaatggc agtgacgacg atggtgacga   10920
ggagcaagga gagctggtcg tcattgcagg tcccggcggt ggcattccct tggaagccac   10980
gaggtggcaa gaccggcggc ctcgagttcc ctcgccgggc gatgttcgcc agcgtcggcc   11040
tcaacgtgtg cccgggcgtc ccggcgggc  gcgaccgcg  ggagcccgat ccaaggtcg    11100 tccgggcggc ctgcggcctg gtccaggcac aagtcctctt ccaggggttt aactgggagt   11160
cgtgcaagca gcagggaggc tggtacaaca ggctcaaggc ccaggtcgac gacatcgcca   11220
aggccggcgt cacgcacgtc tggctgcctc caccctcgca ctccgtctcg ccacaaggct   11280
acatgccagg ccgcctatac gacctggacg cgtccaagta cggcacggcg gcggagctca   11340
agtccctgat agcggcgttc cacggcaggg gcgtgcagtg cgtggcggac atcgtcatca   11400
accaccggtg cgcggaaaag aaggacgcgc gcggcgtgta ctgcatcttc gagggcggga   11460
ctcccgacga ccgcctggac tggggccccg ggatgatctg cagcgacgac acgcagtact   11520
cggacgggac ggggcaccgc gacacgggcg agggggttcgc ggcggcgccc gacatcgacc   11580
```

| | | | |
|---|---|---|---|
| acctcaacccc | gcgcgtgcag | cgggagctct | ccgcctggct caactggctc aggtccgacg | 11640 |
| ccgtggggtt | cgacggctgg | cgcctcgact | tcgccaaggg ctactcgccg gccgtcgcca | 11700 |
| gaatgtacgt | ggagagcacg | gggccgccga | gcttcgtcgt cgcggagata tggaactcgc | 11760 |
| tgagctacag | cggggacggc | aagcggcgc | ccaaccagga ccagtgccgg caggagctgc | 11820 |
| tggactggac | gcgggccgtc | ggcgggcccg | ccatggcgtt cgacttcccc accaagggcc | 11880 |
| tgctgcaggc | gggcgtgcag | ggggagctgt | ggcggctgcg cgacagctcc ggcaacgcgg | 11940 |
| ccggcctgat | cgggtgggcg | cccgagaagg | ccgtcacctt cgtcgacaac catgacaccg | 12000 |
| ggtcgacgca | gaagctctgg | ccgttcccat | ccgacaaggt catgcagggc tacgcctaca | 12060 |
| tcctcacccca | tccaggagtc | ccctgcattt | tctacgacca catgttcgac tggaacctga | 12120 |
| agcaggagat | atccacgctg | tctgccatca | gggcgcggaa cggcatccgc gccgggagca | 12180 |
| agctgcggat | cctcgtggcg | gacgcggacg | cgtacgtggc cgtcgtcgac gagaaggtca | 12240 |
| tggtgaagat | cgggacaagg | tacggcgtga | gcagcgtggt cccgtcggat ttccacccgg | 12300 |
| cggcgcacgg | caaggactac | tgcgtctggg | agaaagcgag cctccgcgtc ccggcggggc | 12360 |
| gccacctcta | gcagctcaga | ttgctcagtc | ttgtgctgca ttgcaaacac agcagcacga | 12420 |
| cactgcataa | cgtcttttcc | ttgagatctg | acaaagcagc attagtccgt tgatcggtgg | 12480 |
| aagaccactc | gtcagtgttg | agttgaatgt | ttgatcaata aaatacggca atgctgtaag | 12540 |
| ggttgttttt | tatgccattg | ataatacact | gtactgttca gttgttgaac tctatttctt | 12600 |
| agccatgcca | agtgcttttc | ttattttgaa | taacattaca gcaaaaagtt gaaagacaaa | 12660 |
| aaaaaaaacc | cccgaacaga | gtgctttggg | tcccaagcta cttagactg tgttcggcgt | 12720 |
| tccccctaaa | tttctccccc | tatatctcac | tcacttgtca catcagcgtt ctctttcccc | 12780 |
| tatatctcca | cg | | | 12792 |

<210> SEQ ID NO 117
<211> LENGTH: 11637
<212> TYPE: DNA
<213> ORGANISM: artificial sequence
<220> FEATURE:
<223> OTHER INFORMATION: UBI-FLP-PINII TERM OSACTIN-PINII UBI-ODP2-PINII

<400> SEQUENCE: 117

| | | | |
|---|---|---|---|
| ctgcagtgca | gcgtgacccg | gtcgtgcccc | tctctagaga taatgagcat tgcatgtcta | 60 |
| agttataaaa | aattaccaca | tatttttttt | gtcacacttg tttgaagtgc agtttatcta | 120 |
| tctttataca | tatatttaaa | ctttactcta | cgaataatat aatctatagt actacaataa | 180 |
| tatcagtgtt | ttagagaatc | atataaatga | acagttagac atggtctaaa ggacaattga | 240 |
| gtatttgac | aacaggactc | tacagttta | tcttttagt gtgcatgtgt tctccttttt | 300 |
| tttgcaaat | agcttcacct | atataatact | tcatccattt tattagtaca tccatttagg | 360 |
| gtttagggtt | aatggttttt | atagactaat | ttttttagta catctatttt attctatttt | 420 |
| agcctctaaa | ttaagaaaac | taaaactcta | ttttagtttt tttatttaat aatttagata | 480 |
| taaaatagaa | taaaataaag | tgactaaaaa | ttaaacaaat ccctttaag aaattaaaaa | 540 |
| aactaaggaa | acatttttct | tgtttcgagt | agataatgcc agcctgttaa acgccgtcga | 600 |
| cgagtctaac | ggacaccaac | cagcgaacca | gcagcgtcgc gtcgggccaa gcgaagcaga | 660 |
| cggcacggca | tctctgtcgc | tgcctctgga | cccctctcga gagttccgct ccaccgttgg | 720 |
| acttgctccg | ctgtcggcat | ccagaaattg | cgtggcggag cggcagacgt gagccggcac | 780 |
| ggcaggcggc | ctcctcctcc | tctcacggca | cggcagctac gggggattcc tttcccaccg | 840 |

-continued

```
ctccttcgct ttcccttcct cgcccgccgt aataaataga cacccctcc acaccctctt    900
tccccaacct cgtgttgttc ggagcgcaca cacacacaac cagatctccc ccaaatccac    960
ccgtcggcac ctccgcttca aggtacgccg ctcgtcctcc cccccccccc ctctctacct   1020
tctctagatc ggcgttccgg tccatggtta gggcccggta gttctacttc tgttcatgtt   1080
tgtgttagat ccgtgtttgt gttagatccg tgctgctagc gttcgtacac ggatgcgacc   1140
tgtacgtcag acacgttctg attgctaact tgccagtgtt tctctttggg gaatcctggg   1200
atggctctag ccgttccgca gacgggatcg atttcatgat ttttttttgtt tcgttgcata   1260
gggtttggtt tgccctttc ctttatttca atatatgccg tgcacttgtt tgtcgggtca   1320
tcttttcatg cttttttttg tcttggttgt gatgatgtgg tctggttggg cggtcgttct   1380
agatcggagt agaattctgt ttcaaactac ctggtggatt tattaatttt ggatctgtat   1440
gtgtgtgcca tacatattca tagttacgaa ttgaagatga tggatggaaa tatcgatcta   1500
ggataggtat acatgttgat gcgggtttta ctgatgcata tacagagatg cttttttgttc   1560
gcttggttgt gatgatgtgg tgtggttggg cggtcgttca ttcgttctag atcggagtag   1620
aatactgttt caaactacct ggtgtattta ttaattttgg aactgtatgt gtgtgtcata   1680
catcttcata gttacgagtt taagatggat ggaaatatcg atctaggata ggtatacatg   1740
ttgatgtggg ttttactgat gcatatacat gatggcatat gcagcatcta ttcatatgct   1800
ctaaccttga gtacctatct attataataa acaagtatgt tttataatta ttttgatctt   1860
gatatacttg gatgatggca tatgcagcag ctatatgtgg attttttttag ccctgccttc   1920
atacgctatt tatttgcttg gtactgtttc ttttgtcgat gctcaccctg ttgtttggtg   1980
ttacttctgc aggtcgactc tagaggatcc aacaatgccc cagttcgaca tcctctgcaa   2040
gaccccccccc aaggtgctcg tgaggcagtt cgtggagagg ttcgagaggc cctccggcga   2100
gaagatcgcc ctctgcgccg ccgagctcac ctacctctgc tggatgatca cccacaacgg   2160
caccgccatt aagagggcca ccttcatgtc atacaacacc atcatctcca actccctctc   2220
cttcgacatc gtgaacaagt ccctccagtt caaatacaag acccagaagg ccaccatcct   2280
cgaggcctcc ctcaagaagc tcatccccgc ctgggagttc accatcatcc cctactacgg   2340
ccagaagcac cagtccgaca tcaccgacat cgtgtcatcc ctccagcttc agttcgagtc   2400
ctccgaggag gctgacaagg gcaactccca ctccaagaag atgctgaagg ccctcctctc   2460
cgagggcgag tccatctggg agatcaccga gaagatcctc aactccttcg agtacacctc   2520
caggttcact aagaccaaga ccctctacca gttcctcttc ctcgccacct tcatcaactg   2580
cggcaggttc tcagacatca agaacgtgga ccccaagtcc ttcaagctcg tgcagaacaa   2640
gtacctcggc gtgatcatcc agtgcctcgt gaccgagacc aagacctccg tgtccaggca   2700
catctacttc ttctccgctc gcggcaggat cgaccccctc gtgtacctcg acgagttcct   2760
caggaactca gagcccgtgc tcaagagggt gaacaggacc ggcaactcct cctccaacaa   2820
gcaggagtac cagctcctca aggacaacct cgtgaggtcc tacaacaagg ccctcaagaa   2880
gaacgccccc tactccatct cgccatcaa gaacggcccc aagtcccaca tcggtaggca   2940
cctcatgacc tccttcctct caatgaaggg cctcaccgag ctcaccaacg tggtgggcaa   3000
ctggtccgac aagagggcct ccgccgtggc caggaccacc tacacccacc agatcaccgc   3060
catccccgac cactacttcg ccctcgtgtc aaggtactac gcctacgacc ccatctccaa   3120
ggagatgatc gccctcaagg acgagactaa ccccatcgag gagtggcagc acatcgagca   3180
```

```
gctcaagggc tccgccgagg gctccatcag gtaccccgcc tggaacggca tcatctccca    3240
ggaggtgctc gactacctct cctcctacat caacaggagg atctgagtta acctagactt    3300
gtccatcttc tggattggcc aacttaatta atgtatgaaa taaaaggatg cacacatagt    3360
gacatgctaa tcactataat gtgggcatca aagttgtgtg ttatgtgtaa ttactagtta    3420
tctgaataaa agagaaagag atcatccata tttcttatcc taaatgaatg tcacgtgtct    3480
ttataattct ttgatgaacc agatgcattt cattaaccaa atccatatac atataaatat    3540
taatcatata taattaatat caattgggtt agcaaaacaa atctagtcta ggtgtgtttt    3600
gcccgggatc cctcagccgc cttttcactat cttttttgcc cgagtcattg tcatgtgaac    3660
cttggcatgt ataatcggtg aattgcgtcg attttcctct tataggtggg ccaatgaatc    3720
cgtgtgatcg cgtctgattg gctagagata tgtttcttcc ttgttggatg tattttcata    3780
cataatcata tgcatacaaa tatttcatta cactttatag aaatggtcag taataaaccc    3840
tatcactatg tctggtgttt cattttattt gcttttaaac gaaaattgac ttcctgattc    3900
aatatttaag gatcgtcaac ggtgtgcagt tactaaattc tggtttgtag gaactatagt    3960
aaactattca agtcttcact tattgtgcac tcacctctcg ccacatcacc acagatgtta    4020
ttcacgtctt aaatttgaac tacacatcat attgacacaa tatttttttt aaataagcga    4080
ttaaaaccta gcctctatgt caacaatggt gtacataacc agcgaagttt agggagtaaa    4140
aaacatcgcc ttacacaaag ttcgctttaa aaataaaga gtaaattta ctttggacca    4200 cccttcaacc aatgtttcac tttagaacga gtaattttat tattgtcact ttggaccacc    4260
ctcaaatctt ttttccatct acatccaatt tatcatgtca agaaatggt ctacatacag    4320 ctaaggagat ttatcgacga atagtagcta gcatactcga ggtcattcat atgcttgaga    4380
agagagtcgg gatagtccaa aataaaacaa aggtaagatt acctggtcaa aagtgaaaac    4440
atcagttaaa aggtggtata aagtaaaata tcggtaataa aaggtggccc aaagtgaaat    4500 ttactcttt ctactattat aaaaattgag gatgttttg tcggtacttt gatcgtcat    4560 ttttgtatga attggttttt aagtttattc gcttttggaa atgcatatct gtatttgagt    4620
cgggttttaa gttcgtttgc ttttgtaaat acagagggat ttgtataaga aatatcttta    4680
aaaaaaccca tatgctaatt tgacataatt tttgagaaaa atatatattc aggcgaattc    4740
tcacaatgaa caataataag attaaaatag ctttccccg ttgcagcgca tgggtatttt    4800
ttctagtaaa aataaaagat aaacttagac tcaaaacatt tacaaaaaca acccctaaag    4860
ttcctaaagc ccaaagtgct atccacgatc catagcaagc ccagcccaac ccaacccaac    4920
ccaacccacc ccagtccagc caactggaca atagtctcca caccccccca ctatcaccgt    4980
gagttgtccg cacgcaccgc acgtctcgca gccaaaaaaa aaaaagaaa gaaaaaaaag    5040 aaaagaaaa aacagcaggt gggtccgggt cgtggggcc ggaaacgcga ggaggatcgc    5100
gagccagcga cgaggccggc cctccctccg cttccaaaga aacgcccccc atcgccacta    5160
tatacatacc ccccctctc ctcccatccc cccaaccca ccaccaccac caccaccacc    5220
tccacctcct cccccctcgc tgccggacga cgagctcctc cccctcccc ctccgccgcc    5280 gccgcgccgg taaccacccc gccccctctcc tctttcttc tccgtttttt ttttccgtct    5340
cggtctcgat ctttggcctt ggtagtttgg gtgggcgaga ggcggcttcg tgcgcgccca    5400
gatcggtgcg cggagggggc gggatctcgc ggctgggct ctcgccggcg tggatcaggc    5460
ccggatctcg cggggaatgg ggctctcgga tgtagatctg cgatccgccg ttgttggggg    5520
agatgatggg gggtttaaaa tttccgccat gctaaacaag atcaggaaga ggggaaaagg    5580
```

-continued

```
gcactatggt ttatatttct atatatttct gctgcttcgt caggcttaga tgtgctagat    5640
ctttctttct tcttttttgtg ggtagaattt gaatccctca gcattgttca tcggtagttt    5700
ttcttttcat gatttgtgac aaatgcagcc tcgtgcggag cttttttgta ggtagaagct    5760
gcatggcggc caatgcgggc ggcggtggag cgggaggagg cagcggcagc ggcagcgtgg    5820
ctgcgccggc ggtgtgccgc cccagcggct cgcggtggac gccgacgccg gagcagatca    5880
ggatgctgaa ggagctctac tacgctgcg gcatccggtc gcccagctcg gagcagatcc     5940
agcgcatcac cgccatgctg cggcagcacg gcaagatcga gggcaagaac gtcttctact    6000
ggttccagaa ccacaaggcc cgcgagcgcc agaagcgccg cctcaccagc ctcgacgtca    6060
acgtgcccgc cgccggcgcg gccgacgcca ccaccagcca actcggcgtc ctctcgctgt    6120
cgtcgccgcc gccttcaggc gcggcgcctc cctcgcccac cctcggcttc tacgccgccg    6180
gcaatggcgg cggatcggct gtgctgctgg acacgagttc cgactggggc agcagcggcg    6240
ctgctatggc caccgagaca tgcttcctgc aggactacat gggcgtgacg gacacgggca    6300
gctcgtcgca gtgccacgc ttctcgtcgt cggacacgat aatggcggcg ccgcggcgc     6360 gggcggcgac gacgcgggcg cccgagacgc tccctctctt cccgacctgc ggcgacgacg    6420
gcggcagcgg tagcagcagc tacttgccgt tctggggtgc cgcgtccaca actgccggcg    6480
ccacttcttc cgttgcgatc caacagcaac accagctgca ggagcagtac agcttttaca    6540
gcaacagcaa cagcacccag ctggccggca ccggcaacca agacgtatcg caacagcag    6600 cagcagccgc cgccctggag ctgagcctca gctcatggtg ctccccttac cctgctgcag    6660
ggagtatgtg agagcaacgc gagctgccac tgctcttcac tgatgtctct ggaatggaag    6720
gaggaggaag tgagcatagc gttggtgcgt tgctgtcaag ggcgaattgt accacatggt    6780
taacctagac ttgtccatct tctggattgg ccaacttaat taatgtatga aataaaagga    6840
tgcacacata gtgacatgct aatcactata atgtgggcat caaagttgtg tgttatgtgt    6900
aattactagt tatctgaata aaagagaaag agatcatcca tatttcttat cctaaatgaa    6960
tgtcacgtgt ctttataatt ctttgatgaa ccagatgcat ttcattaacc aaatccatat    7020
acatataaat attaatcata tataattaat atcaattggg ttagcaaaac aaatctagtc    7080
taggtgtgtt ttgcgaggaa ttcctcgtgc agcgtgaccc ggtcgtgccc ctctctagag    7140
ataatgagca ttgcatgtct aagttataaa aaattaccac atattttttt tgtcacactt    7200
gtttgaagtg cagtttatct atctttatac atatatttaa actttactct acgaataata    7260
taatctatag tactacaata atatcagtgt tttagagaat catataaatg aacagttaga    7320
catggtctaa aggacaattg agtattttga caacaggact ctacagtttt atcttttttag   7380 tgtgcatgtg ttctccttt tttttgcaaa tagcttcacc tatataatac ttcatccatt    7440
ttattagtac atccatttag ggtttagggt taatggtttt tatagactaa ttttttttagt   7500 acatctattt tattctattt tagcctctaa attaagaaaa ctaaaactct attttagttt    7560
ttttatttaa taatttagat ataaaataga ataaaataaa gtgactaaaa attaaacaaa    7620 tacccttaa gaaattaaaa aaactaagga aacatttttc ttgtttcgag tagataatgc     7680
cagcctgtta aacgccgtcg acgagtctaa cggacaccaa ccagcgaacc agcagcgtcg    7740
cgtcgggcca agcgaagcag acggcacggc atctctgtcg ctgcctctgg accctctcg     7800 agagttccgc tccaccgttg gacttgctcc gctgtcggca tccagaaatt gcgtggcgga    7860
gcggcagacg tgagccggca cggcaggcgg cctcctcctc ctctcacggc accggcagct    7920
```

| | |
|---|---|
| acggggatt cctttcccac cgctccttcg ctttcccttc ctcgcccgcc gtaataaata | 7980 |
| gacaccccct ccacaccctc tttcccaac ctcgtgttgt tcggagcgca cacacacaca | 8040 |
| accagatctc ccccaaatcc acccgtcggc acctccgctt caaggtacgc cgctcgtcct | 8100 |
| cccccccccc cctctctacc ttctctagat cggcgttccg gtccatgcat ggttagggcc | 8160 |
| cggtagttct acttctgttc atgtttgtgt tagatccgtg tttgtgttag atccgtgctg | 8220 |
| ctagcgttcg tacacggatg cgacctgtac gtcagacacg ttctgattgc taacttgcca | 8280 |
| gtgtttctct ttggggaatc ctgggatggc tctagccgtt ccgcagacgg gatcgatttc | 8340 |
| atgatttttt ttgtttcgtt gcatagggtt tggtttgccc ttttccttta tttcaatata | 8400 |
| tgccgtgcac ttgtttgtcg ggtcatcttt tcatgctttt ttttgtcttg gttgtgatga | 8460 |
| tgtggtctgg ttgggcggtc gttctagatc ggagtagaat tctgtttcaa actacctggt | 8520 |
| ggatttatta attttggatc tgtatgtgtg tgccatacat attcatagtt acgaattgaa | 8580 |
| gatgatggat ggaaatatcg atctaggata ggtatacatg ttgatgcggg ttttactgat | 8640 |
| gcatatacag agatgctttt tgttcgcttg gttgtgatga tgtggtgtgg ttgggcggtc | 8700 |
| gttcattcgt tctagatcgg agtagaatac tgtttcaaac tacctggtgt atttattaat | 8760 |
| tttgaactga tatgtgtgtg tcatacatct tcatagttac gagtttaaga tggatggaaa | 8820 |
| tatcgatcta ggataggtat acatgttgat gtgggttta ctgatgcata tacatgatgg | 8880 |
| catatgcagc atctattcat atgctctaac cttgagtacc tatctattat aataaacaag | 8940 |
| tatgttttat aattattttg atcttgatat acttggatga tggcatatgc agcagctata | 9000 |
| tgtggatttt tttagccctg ccttcatacg ctatttattt gcttggtact gtttcttttg | 9060 |
| tcgatgctca ccctgttgtt tggtgttact tctgcaggtc gactctagag gatccatggc | 9120 |
| cactgtgaac aactggctcg ctttctccct ctccccgcag gagctgccgc cctcccagac | 9180 |
| gacggactcc acactcatct cggccgccac cgccgaccat gtctccggcg atgtctgctt | 9240 |
| caacatcccc caagattgga gcatgagggg atcagagctt tcggcgctcg tcgcggagcc | 9300 |
| gaagctggag gacttcctcg gcggcatctc cttctccgag cagcatcaca aggccaactg | 9360 |
| caacatgata cccagcacta gcagcacagt ttgctacgcg agctcaggtg ctagcaccgg | 9420 |
| ctaccatcac cagctgtacc accagcccac cagctcagcg ctccacttcg cggactccgt | 9480 |
| aatggtggcc tcctcggccg gtgtccacga cggcggtgcc atgctcagcg cggccgccgc | 9540 |
| taacggtgtc gctggcgctg ccagtgccaa cggcggcggc atcggctgt ccatgattaa | 9600 |
| gaactggctg cggagccaac cggcgcccat gcagccgagg gtggcggcgg ctgagggcgc | 9660 |
| gcaggggctc tctttgtcca tgaacatggc ggggacgacc caaggcgctg ctggcatgcc | 9720 |
| acttctcgct ggagagcgcg cacggccgcc cgagagtgta tcgacgtcag cacagggtgg | 9780 |
| agccgtcgtc gtcacggcgc cgaaggagga tagcggtggc agcggtgttg ccggcgctct | 9840 |
| agtagccgtg agcacggaca cgggtggcag cggcggcgcg tcggctgaca acacggcaag | 9900 |
| gaagacggtg gacacgttcg ggcagcgcac gtcgatttac cgtggcgtga caaggcatag | 9960 |
| atggactggg agatatgagg cacatctttg ggataacagt tgcagaaggg aagggcaaac | 10020 |
| tcgtaagggt cgtcaagtct atttaggtgg ctatgataaa gaggagaaag ctgctagggc | 10080 |
| ttatgatctt gctgctctga agtactgggg tgccacaaca acaacaaatt ttccagtgag | 10140 |
| taactacgaa aaggagctcg aggacatgaa gcacatgaca aggcaggagt ttgtagcgtc | 10200 |
| tctgagaagg aagagcagtg gtttctccag aggtgcatcc atttacaggg gagtgactag | 10260 |
| gcatcaccaa catggaagat ggcaagcacg gattggacga gttgcaggga acaaggatct | 10320 |

```
ttacttgggc accttcagca cccaggagga ggcagcggag gcgtacgaca tcgcggcgat    10380
caagttccgc ggcctcaacg ccgtcaccaa cttcgacatg agccgctacg acgtgaagag    10440
catcctggac agcagcgccc tccccatcgg cagcgccgcc aagcgcctca aggaggccga    10500
ggccgcagcg tccgcgcagc accaccacgc cggcgtggtg agctacgacg tcggccgcat    10560
cgcctcgcag ctcggcgacg gcggagccct ggcggcggcg tacggcgcgc actaccacgg    10620
cgccgcctgg ccgaccatcg cgttccagcc gggcgccgcc agcacaggcc tgtaccaccc    10680
gtacgcgcag cagccaatgc gcggcggcgg gtggtgcaag caggagcagg accacgcggt    10740
gatcgcggcc gcgcacagcc tgcaggacct ccaccacctg aacctgggcg cggccggcgc    10800
gcacgacttt ttctcggcag ggcagcaggc cgccgccgct gcgatgcacg gcctgggtag    10860
catcgacagt gcgtcgctcg agcacagcac cggctccaac tccgtcgtct acaacggcgg    10920
ggtcggcgac agcaacggcg ccagcgccgt cggcggcagt ggcggtggct acatgatgcc    10980
gatgagcgct gccggagcaa ccactacatc ggcaatggtg agccacgagc aggtgcatgc    11040
acgggcctac gacgaagcca agcaggctgc tcagatgggg tacgagagct acctggtgaa    11100
cgcggagaac aatggtggcg gaaggatgtc tgcatggggg actgtcgtgt ctgcagccgc    11160
ggcggcagca gcaagcagca acgacaacat ggccgccgac gtcggccatg cggcgcgca    11220 gctcttcagt gtctggaacg acacttaagc gtacgtgccg gcctggctct ccgaaagggc    11280
gaattccagc acactggcgg ccgttactag acccaaccta gacttgtcca tcttctggat    11340
tggccaactt aattaatgta tgaaataaaa ggatgcacac atagtgacat gctaatcact    11400
ataatgtggg catcaaagtt gtgtgttatg tgtaattact agttatctga ataaaagaga    11460
aagagatcat ccatatttct tatcctaaat gaatgtcacg tgtctttata attctttgat    11520
gaaccagatg catttcatta accaaatcca tatacatata aatattaatc atatataatt    11580
aatatcaatt gggttagcaa acaaatctag tctaggtgt gttttgcgaa tgcggcc      11637
```

<210> SEQ ID NO 118
<211> LENGTH: 1272
<212> TYPE: DNA
<213> ORGANISM: Artificial Sequence
<220> FEATURE:
<223> OTHER INFORMATION: FLPm DNA

<400> SEQUENCE: 118

```
atgccccagt tcgacatcct ctgcaagacc ccccccaagg tgctcgtgag gcagttcgtg      60
gagaggttcg agaggccctc cggcgagaag atcgccctct gcgccgccga gctcacctac     120
ctctgctgga tgatcacccca caacggcacc gccattaaga gggccacctt catgtcatac     180
aacaccatca tctccaactc cctctccttc gacatcgtga caagtccct ccagttcaaa      240 tacaagaccc agaaggccac catcctcgag gcctccctca agaagctcat cccgcctgg      300 gagttcacca tcatccccta ctacggccag aagcaccagt ccgacatcac cgacatcgtg      360
tcatccctcc agcttcagtt cgagtcctcc gaggaggctg acaagggcaa ctcccactcc      420
aagaagatgc tgaaggccct cctctccgag ggcgagtcca tctgggagat caccgagaag     480
atcctcaact ccttcgagta cacctccagg ttcactaaga ccaagaccct ctaccagttc     540
ctcttcctcg ccaccttcat caactgcggc aggttctcag acatcaagaa cgtggacccc     600
aagtccttca gctcgtgca gaacaagtac ctcggcgtga tcatccagtg cctcgtgacc     660
gagaccaaga cctccgtgtc caggcacatc tacttcttct ccgctcgcgg caggatcgac     720
```

-continued

```
cccctcgtgt acctcgacga gttcctcagg aactcagagc ccgtgctcaa gagggtgaac    780
aggaccggca actcctcctc caacaagcag gagtaccagc tcctcaagga caacctcgtg    840
aggtcctaca caaggcccct caagaagaac gcccccctact ccatcttcgc catcaagaac   900
ggccccaagt cccacatcgg taggcacctc atgacctcct tcctctcaat gaagggcctc    960
accgagctca ccaacgtggt gggcaactgg tccgacaaga gggcctccgc cgtggccagg   1020
accacctaca cccaccagat caccgccatc cccgaccact acttcgccct cgtgtcaagg   1080
tactacgcct acgaccccat ctccaaggag atgatcgccc tcaaggacga gactaacccc   1140
atcgaggagt ggcagcacat cgagcagctc aagggctccg ccgagggctc catcaggtac   1200
cccgcctgga acggcatcat ctcccaggag gtgctcgact acctctcctc ctacatcaac   1260
aggaggatct ga                                                       1272
```

<210> SEQ ID NO 119
<211> LENGTH: 423
<212> TYPE: PRT
<213> ORGANISM: artificial sequence
<220> FEATURE:
<223> OTHER INFORMATION: FLPm PRT

<400> SEQUENCE: 119

```
Met Pro Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
            20                  25                  30

Leu Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Tyr Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
```

```
                260                 265                 270
Gln Leu Leu Lys Asp Asn Leu Val Arg Ser Tyr Asn Lys Ala Leu Lys
        275                 280                 285

Lys Asn Ala Pro Tyr Ser Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
            325                 330                 335

Ala Val Ala Arg Thr Thr Tyr Thr His Gln Ile Thr Ala Ile Pro Asp
        340                 345                 350

His Tyr Phe Ala Leu Val Ser Arg Tyr Tyr Ala Tyr Asp Pro Ile Ser
    355                 360                 365

Lys Glu Met Ile Ala Leu Lys Asp Glu Thr Asn Pro Ile Glu Glu Trp
370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
            405                 410                 415

Ser Tyr Ile Asn Arg Arg Ile
            420
```

<210> SEQ ID NO 120
<211> LENGTH: 30
<212> TYPE: DNA
<213> ORGANISM: Artificial sequence
<220> FEATURE:
<223> OTHER INFORMATION: minimal FRT5 mutant recombination site

<400> SEQUENCE: 120
agttcctatt cttcaaaagg tataggaact                                           30

<210> SEQ ID NO 121
<211> LENGTH: 30
<212> TYPE: DNA
<213> ORGANISM: Artificial sequence
<220> FEATURE:
<223> OTHER INFORMATION: minimal FRT6  mutant recombination site

<400> SEQUENCE: 121
agttcctatt cttcaaaaag tataggaact                                           30

<210> SEQ ID NO 122
<211> LENGTH: 30
<212> TYPE: DNA
<213> ORGANISM: Artificial sequence
<220> FEATURE:
<223> OTHER INFORMATION: minimal FRT12 mutant recombination site

<400> SEQUENCE: 122
agttcctatt ctacatagag tataggaact                                           30

METHODS AND COMPOSITIONS FOR ACCELERATED TRAIT INTROGRESSION

CROSS-REFERENCE TO RELATED APPLICATIONS

This application is a 371 National Stage Entry of PCT Application No. PCT/US2016/022621 filed 16 Mar. 2016, which claims the benefit of U.S. Provisional Application No. 62/135,261, filed Mar. 19, 2015, each of which is incorporated herein in its entirety by reference.

FIELD

The disclosure relates to the field of plant molecular biology. In particular, methods and compositions are provided for introducing and using pollen-inhibitor loci and color marker loci in accelerated trait introgression

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 20160223_BB2237WOPCT_SeqLst.txt, created Feb. 23, 2016, and having a size of 387 KB and is filed concurrently with the specification. The sequence listing contained in this ASCII formatted document is part of the specification and is herein incorporated by reference in its entirety.

BACKGROUND

Recombinant DNA technology has made it possible to insert foreign DNA sequences into the genome of an organism, as well as altering endogenous genes of an organism, thus, altering the organism's phenotype. The most commonly used plant transformation methods are *Agrobacterium* infection and biolistic particle bombardment in which transgenes integrate into a plant genome in a random fashion and in an unpredictable copy number.

Site-specific integration techniques, which employ site-specific recombination systems, as well as, other types of recombination technologies, have been used to generate targeted insertions of genes of interest in a variety of organism. Other methods for inserting or modifying a DNA sequence involve homologous DNA recombination by introducing a transgenic DNA sequence flanked by sequences homologous to the genomic target. U.S. Pat. No. 5,527,695 describes transforming eukaryotic cells with DNA sequences that are targeted to a predetermined sequence of the eukaryote's DNA. Transformed cells are identified through use of a selectable marker included as a part of the introduced DNA sequences. While such systems have provided useful techniques for targeted insertion of sequences of interest, there remains a need for methods and compositions which improve these systems and allow for improved breeding methods and compositions and methods useful for accelerated trait introgression.

BRIEF SUMMARY

Compositions and methods are provided for the use of pollen-inhibitor genes and/or color maker genes in accelerated trait introgression. Compositions and methods are also provided for introducing a pollen-inhibitor gene and/or a color marker gene in close proximity to a trait locus of interest. Breeding methods and methods for selecting plants comprising a trait locus of interest in close proximity to at least one pollen-inhibitor gene and/or a color marker gene are also disclosed.

In one embodiment of the disclosure, the method comprises a method for introducing a pollen-inhibitor gene in close proximity to a trait locus of interest in the genome of a progeny plant, said method comprising: a) providing a first plant having within a genomic window at least one trait gene of interest integrated into a first target site located proximal to a telomere, wherein said genomic window is about 10 cM in length, wherein said first plant does not comprise a pollen-inhibitor gene; b) breeding to said first plant a second plant, wherein said second plant comprises in said genomic window a pollen-inhibitor gene integrated into a second target site located proximal to both the telomere and the trait gene of interest of (a); and, c) selecting a progeny plant from step (b) comprising said trait gene of interest and said pollen-inhibitor gene, wherein said trait gene of interest and said pollen-inhibitor gene are genetically linked In another embodiment, the method comprises a method for introducing two pollen-inhibitor genes in close proximity to a trait locus of interest in the genome of a progeny plant, said method comprising: (a) providing a first plant having within a genomic window a first pollen-inhibitor gene integrated into a first target site, wherein said genomic window is about 10 cM in length; (b) breeding to said first plant a second plant having a trait gene of interest integrated into a second target site within said genomic window; (c) selecting a progeny plant from step (b) comprising said first pollen-inhibitor gene and said trait gene of interest in said genomic widow; (d) providing a third plant having a second pollen-inhibitor gene integrated into a third target site within said genomic window; (e) breeding to said third plant a fourth plant, wherein said fourth plant comprises a pollen-inhibitor maintainer (PIM) gene; (f) selecting a progeny plant from step (e) comprising said second pollen-inhibitor gene and said pollen-inhibitor maintainer (PIM) gene; and, (g) cross pollinating the progeny plant of (c) with the progeny plant of (f) and selecting for a progeny plant that comprises said first pollen-inhibitor gene, said trait gene of interest, and said second pollen-inhibitor gene, wherein said first pollen-inhibitor gene, said trait gene of interest, and said second pollen-inhibitor gene are genetically linked. Optionally, the PIM gene is not genetically linked or has been segregated away from said first pollen-inhibitor gene said trait gene of interest and said second pollen-inhibitor gene. The target sites as described herein can be selected from the group consisting of a recombinase target site, a transgenic SSI target site, a single-strand-break-inducing-agent target site, and a double-strand-break-inducing-agent target site, or any one combination thereof. The double-strand-break-inducing-agent target site includes a target site any double strand break inducing agent. For example, but not limiting to an agent selected from the group of a Cas9 endonuclease, a zinc-finger nuclease, a Tal Effector nuclease (TALEN), a meganuclease, and an engineered endonuclease.

In one embodiment, the method comprises a method for introducing a pollen-inhibitor gene and a color marker gene in close proximity to a trait locus of interest in the genome of a plant, said method comprising: (a) providing a first plant having a trait of interest located within a genomic window, wherein said genomic window is about 10 cM in length; (b) introducing into said genomic window of the plant of (a) a color marker gene; (c) breeding to the plant of (b) a second plant, wherein said second plant is a haploid inducer line capable of producing haploid embryos; (d) selecting haploid embryos from the plant of (c) and introducing into said haploid embryos, a pollen-inhibitor gene; and, (e) producing a double haploid plant from the haploid embryo of (d).

In one embodiment, the method comprises a method for introducing two color marker genes in close proximity to a trait locus of interest in the genome of a plant, said method comprising: (a) providing a first plant having a trait of interest located within a genomic window, wherein said genomic window is about 10 cM in length; (b) introducing into said genomic window of the plant of (a) a color marker gene; (c) breeding to the plant of (b) a second plant, wherein said second plant is a haploid inducer line capable of producing haploid embryos; (d) selecting haploid embryos from the plant of (c) and introducing into said haploid embryos, a second color marker gene; and, (e) producing a double haploid plant from the haploid embryo of for introducing. As described herein, the color marker or the pollen-inhibitor gene can be introduced into any target site of a double-strand-break-inducing-agent.

In another embodiment, the method comprises a method for introducing a pollen-inhibitor gene in close proximity to a trait locus of interest in the genome of a progeny plant, said method comprising: a) providing a first plant having within a genomic window at least a first transgenic SSI target site located proximal to a telomere, wherein said first transgenic SSI target site comprises at least one trait gene of interest, wherein said genomic window is about 5 cM in length and located within 0.1 cM to 10 cM of the telomere, and wherein said first plant does not comprise a pollen-inhibitor gene; (b) breeding to said first plant a second plant, wherein said second plant comprises in said genomic window a second transgenic SSI target site located proximal to both the telomere and the trait gene of interest, wherein said second transgenic SSI target site comprises a pollen-inhibitor gene, wherein said second plant does not comprise said first transgenic target site; and, (c) selecting a progeny plant from step (b) comprising said trait gene of interest and said pollen-inhibitor gene, wherein said trait gene of interest and said pollen-inhibitor gene are genetically linked in said genomic window.

In another embodiment, the method comprises a method for accelerated trait introgression in the genome of a plant, the method comprising: (a) providing a first progeny plant having within a genomic window at least a first transgenic SSI target site located proximal to a telomere and a second transgenic SSI target site located proximal to both the telomere and the trait gene of interest, wherein said first transgenic SSI target site comprises at least one trait gene of interest, wherein said second transgenic SSI target site comprises a pollen-inhibitor gene, wherein said first transgenic target site and said pollen-inhibitor gene are genetically linked in said genomic window, wherein said genomic window is about 5 cM in length and located within 10 cM of the telomere; (b) cross pollinating the first plant of (a) with pollen from a second plant; and (c) selecting a progeny plant from step (b) comprising said first transgenic target site and said pollen-inhibitor gene. The second plant can be an elite inbred line.

In another embodiment, the method comprises a method for introducing two pollen-inhibitor genes in close proximity to a trait locus of interest in the genome of a progeny plant, said method comprising: (a) providing a first plant having within a genomic window at least a first transgenic SSI target site, wherein said first transgenic SSI target site comprises a first pollen-inhibitor gene, wherein said genomic window is about 5 cM in length; (b) breeding to said first plant a second plant, wherein said second plant comprises in said genomic window a second transgenic SSI target site, wherein said second transgenic SSI target site comprises at least one trait gene of interest wherein said second plant does not comprise said first transgenic target site; (c) selecting a progeny plant from step (b) comprising said first transgenic target site and said second transgenic target site genetically linked in said genomic widow, (d) providing a third plant having within said genomic window at least a third transgenic SSI target site and a pollen-inhibitor maintainer (PIM), wherein said third transgenic SSI target site comprises a second pollen-inhibitor gene, (e) using the third plant of step (d) to pollinate the plant of step (c) and selecting a progeny plant wherein said first transgenic SSI target site, said second transgenic SSI target site, and said third transgenic SSI target site are genetically linked to each other, and optionally, wherein the PIM gene has been segregated away In one embodiment, the method comprises a method for introducing two pollen-inhibitor genes in close proximity to a trait locus of interest in the genome of a progeny plant, said method comprising: (a) providing a first plant having within a genomic window at least a first transgenic SSI target site, wherein said first transgenic SSI target site comprises a first pollen-inhibitor gene, wherein said genomic window is about 5 cM in length; (b) breeding to said first plant a second plant, wherein said second plant comprises in said genomic window a second transgenic SSI target site, wherein said second transgenic SSI target site comprises at least one trait gene of interest wherein said second plant does not comprise said first transgenic target site; (c) selecting a progeny plant from step (b) comprising said first transgenic target site and said second transgenic target site genetically linked in said genomic widow; (d) providing a third plant having within said genomic window at least a third transgenic SSI target site, wherein said third transgenic SSI target site comprises a second pollen-inhibitor gene; (e) Breeding to said third plant a fourth plant, wherein said fourth plant comprises a pollen-inhibitor maintainer (PIM) gene; (f) selecting a progeny plant from step (e) comprising said third transgenic target site and pollen-inhibitor maintainer (PIM) gene; and, (g) cross pollinating the progeny plant of (c) with the progeny plant of (f) and selecting for a progeny plant that comprises said first transgenic SSI target site, said second transgenic SSI target site and said third transgenic SSI target site, wherein said first transgenic SSI target site, said second transgenic SSI target site and said third transgenic SSI target site, are genetically linked.

Compositions and methods are provided for the use of pollen-inhibitor genes and/or color maker genes in accelerated trait introgression.

In one embodiment, the method comprises a method of accelerated trait introgression in the genome of a plant, the method comprising: (a) providing a first plant having within a genomic window at least one trait of interest located proximal to a telomere, and at least one pollen-inhibitor gene located proximal to both the telomere and the trait of interest, wherein said trait of interest and said pollen-inhibitor gene are genetically linked in said genomic window, wherein said genomic window is about 5 cM in length and located within 10 cM of the telomere; (b) cross pollinating the first plant of (a) with pollen from a second plant; and, (c) selecting a progeny plant from step (b) comprising said trait of interest and said pollen-inhibitor gene; and, (d) optionally, backcrossing the progeny plant of (c) as the pollen donor onto a recurrent parent plant and selecting progeny plants comprising the trait of interest.

In one embodiment, the method comprises a method of accelerated trait introgression in the genome of a plant, the method comprising: (a) providing a first plant having within a genomic window at least one trait of interest located proximal to a telomere, and at least one color marker gene located proximal to both the telomere and the trait of interest, wherein said trait of interest and said color marker gene are genetically linked in said genomic window, wherein said genomic window is about 5 cM in length and located within 10 cM of the telomere; (b) cross pollinating the first plant of (a) with pollen from a second plant; and, (c) selecting a progeny plant from step (b) comprising said trait of interest site and said color marker gene; and, (d) optionally, backcrossing the progeny plant of (c) as the pollen donor onto a recurrent parent plant and selecting progeny plants comprising the trait of interest.

In one embodiment, the method comprises a method of accelerated trait introgression in the genome of a plant comprising: (a) providing a first plant having within a genomic window at least one trait of interest, a first pollen-inhibitor gene, and a second pollen-inhibitor gene wherein said genomic window is about 5 cM in length, and wherein said trait of interest is flanked by said first and second pollen-inhibitor gene; (b) cross-pollinating the first plant of (a) with pollen from a second plant; and, (c) selecting a progeny plant from step (b) comprising said first pollen-inhibitor gene, said trait of interest, and said second pollen-inhibitor gene; and, (d) optionally, cross pollinating the progeny plant from step (c) to a recurrent parent plant and selecting progeny plants comprising the trait of interest.

In one embodiment, the method comprises a method of accelerated trait introgression in the genome of a plant comprising: (a) providing a first plant having within a genomic window at least one trait of interest, a pollen-inhibitor gene and a color marker gene, wherein said genomic window is about 5 cM in length, and wherein trait of interest is flanked by said first and second pollen-inhibitor gene; (b) cross-pollinating the first plant of (a) with pollen from a second plant; and, (c) selecting a progeny plant from step (b) comprising said first pollen-inhibitor gene, said trait of interest, and said second pollen-inhibitor gene; and, (d) optionally, cross pollinating the progeny plant from step (c) to a recurrent parent plant and selecting progeny plants comprising the trait of interest.

In one embodiment, the method comprises a method accelerated trait introgression in the genome of a plant comprising: (a) providing a first plant having within a genomic window at least one trait of interest and at least a first color marker gene integrated into a first target site, a second color marker gene integrated into a second target site for, wherein said genomic window is about 5 cM in length, and wherein trait of interest is flanked by said first and second pollen-inhibitor gene; (b) cross-pollinating the first plant of (a) with pollen from a second plant; and, (c) selecting a progeny plant from step (b) comprising said first pollen-inhibitor gene, said trait of interest, and said second pollen-inhibitor gene; and, (d) optionally, cross pollinating the progeny plant from step (c) to a recurrent parent plant and selecting progeny plants comprising the trait of interest.

Also provided are nucleic acid constructs, plants, plant cells, explants, seeds and grain having at least one pollen-inhibitor gene and/or color marker linked to a trait locus of interest. Additional embodiments of the methods and compositions of the present disclosure are shown herein.

BRIEF DESCRIPTION OF THE DRAWINGS AND SEQUENCE LISTINGS

The invention can be more fully understood from the following detailed description and the accompanying drawings and Sequence Listing that form a part of this application.

FIG. 9M shows a schematic of the components located between the right border (RB) and left border (LB) of PHP06.

FIG. 9N shows a schematic of the components located between the right border (RB) and left border (LB) of PHP07.

FIG. 9Q shows a schematic of the components located between the right border (RB) and left border (LB) of PHP10 FIG. 9R shows a schematic of the components located between the right border (RB) and left border (LB) of PHP11.

Figure 11:
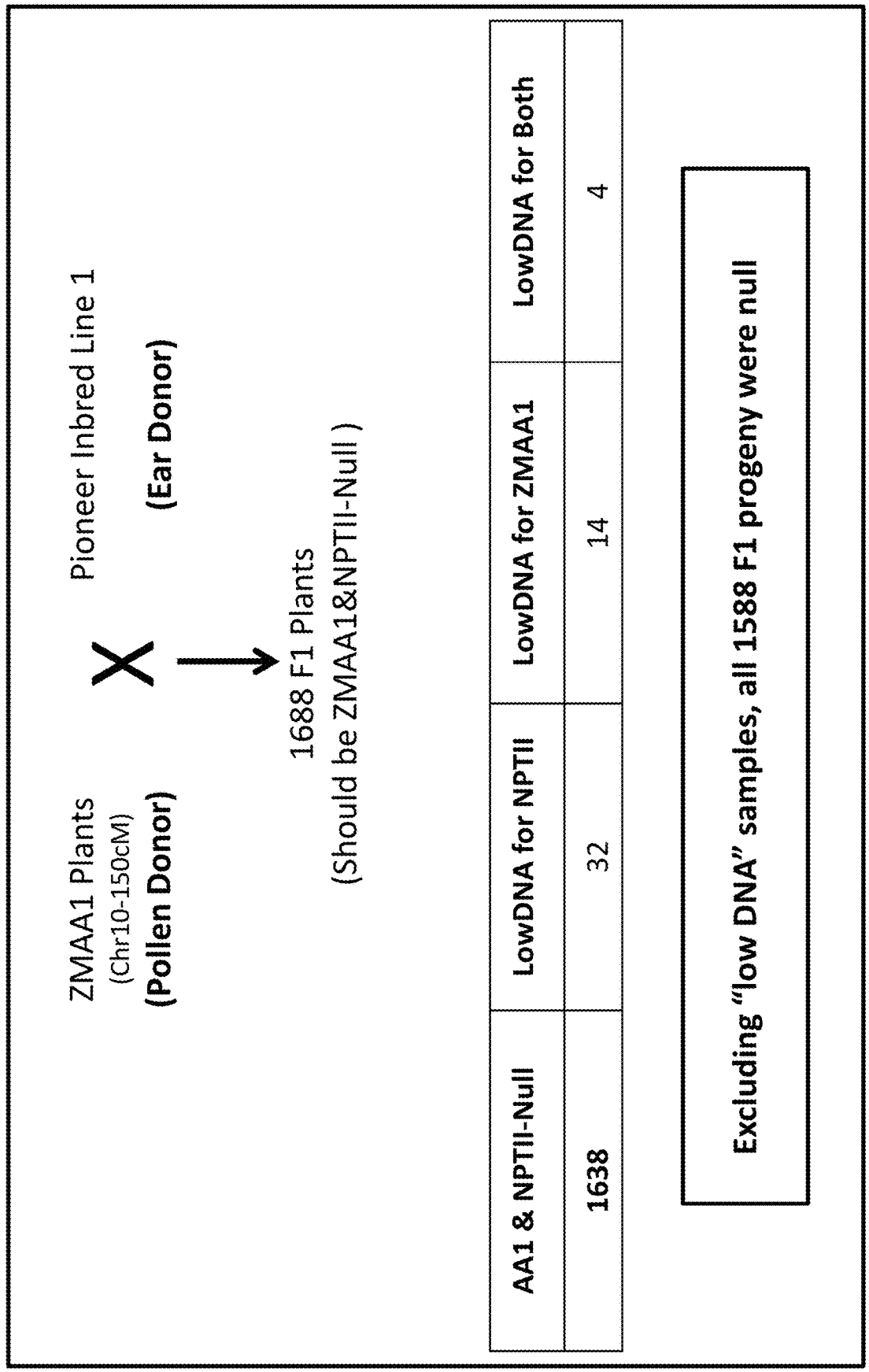

FIG. 11 shows the crossing scheme and subsequent PCR analysis that was performed to demonstrate efficacy of the pollen-inhibitor in the Pioneer Inbred Line 1 (PHN46). Transgenic plants (ZMAA1 plants) were used as the pollen donor onto wild-type PHN46 ears. In a population of 1638 F1 plants, the DNA concentration after extraction of genomic DNA from leaf tissue was too low for reliable PCR, but in the remaining 1588 progeny, no transmission of AA1 and NPTII was observed, demonstrating good efficacy of the pollen-inhibitor in terms of preventing fertilization.

Figure 12:
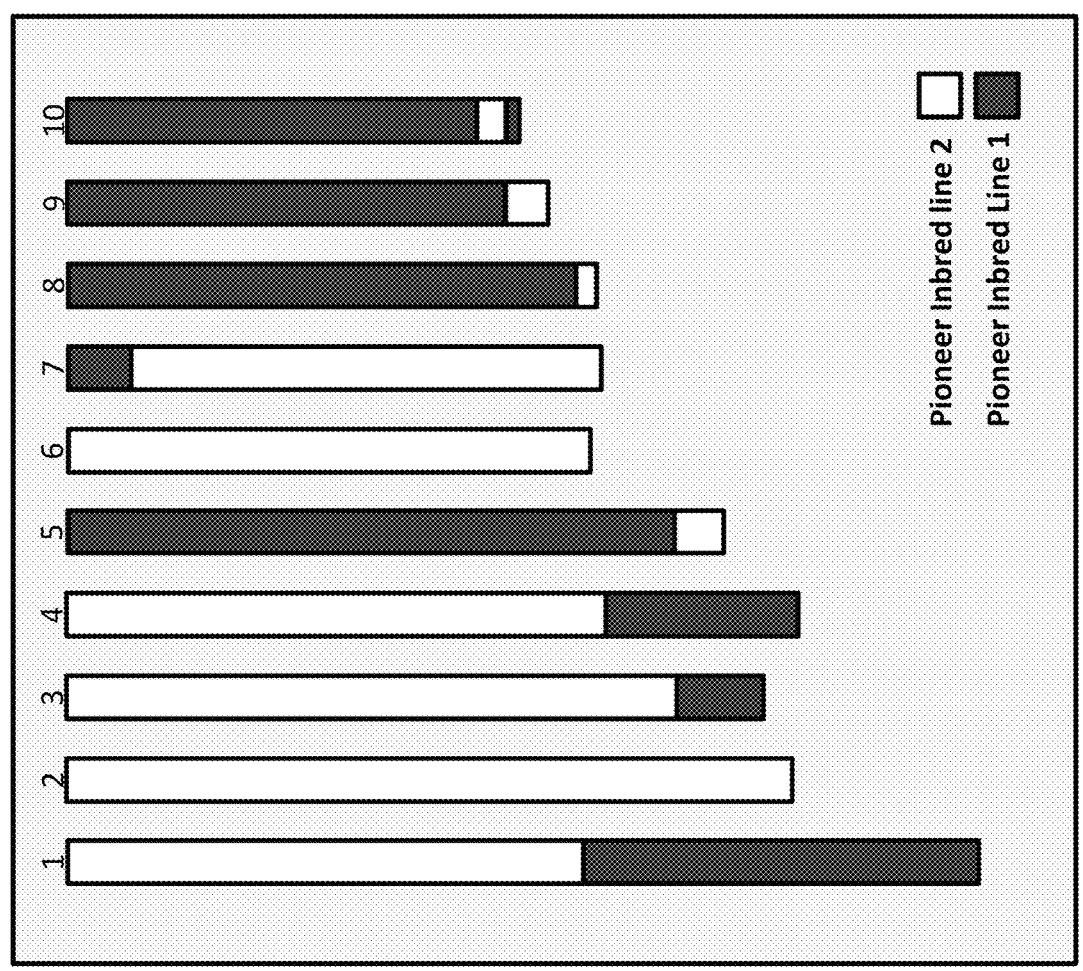

FIG. 12 shows a cartoon depicting the results of high-resolution mapping (using 2 restriction enzyme Genotype-by-Sequencing single nucleotide polymorphism (SNP) analysis) of chromosomal segments in an undesirable BC1 F1 progeny plant after using the F1 hybrid to pollinate the recurrent parent Pioneer Inbred Line 2. As evidenced by the white chromosomal segments, over 65% of the genome was converted to Inbred Line 2. However, the majority of chromosome 10 remained Pioneer Inbred Line 1, and thus this was an example of a progeny plant that even though the pollen-inhibitor locus had been lost (while the trait locus remained), only a small segment of chromosome 10 had converted to Inbred 2 and plants of this type were discarded.

Figure 13:
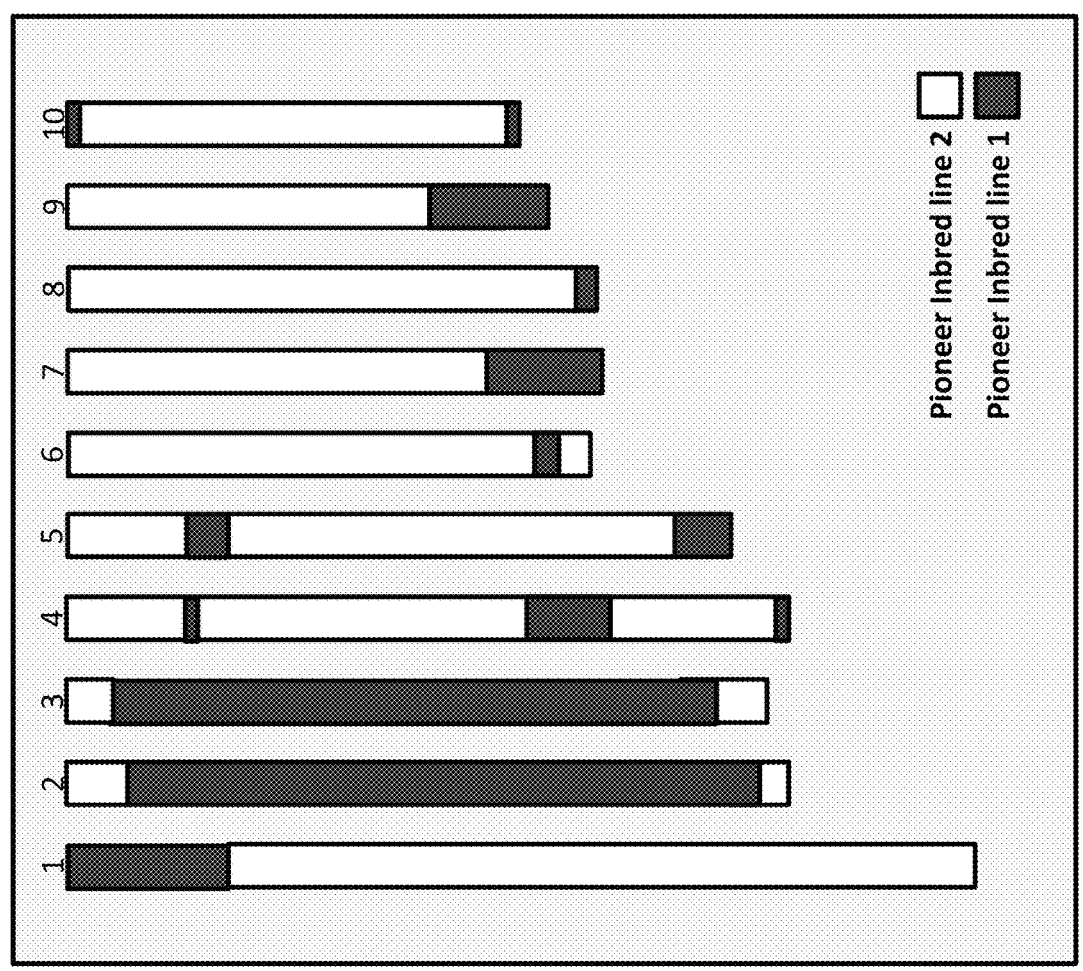

FIG. 13 shows a cartoon depicting the results of high-resolution mapping (using 2 restriction enzyme Genotype-by-Sequencing SNP analysis) of chromosomal segments in a desirable BC1 F1 progeny plant after using the F1 hybrid to pollinate the recurrent parent Pioneer Inbred Line 2. As evidenced by the white chromosomal segments, over 67% of the genome was converted to Inbred Line 2. In this example, the linkage was broken between the pollen-inhibitor locus and the trait locus (leaving the trait locus behind) while the majority of chromosome 10 converted to inbred line 2, with only small residual segments of Inbred 1 at the telomeres. This type of result was found in the majority of the 28 plants that had lost the pollen-inhibitor locus, while maintaining the trait, representing a rapid (one generation), precise and almost complete introgression of the trait into the new inbred.

Figure 14:
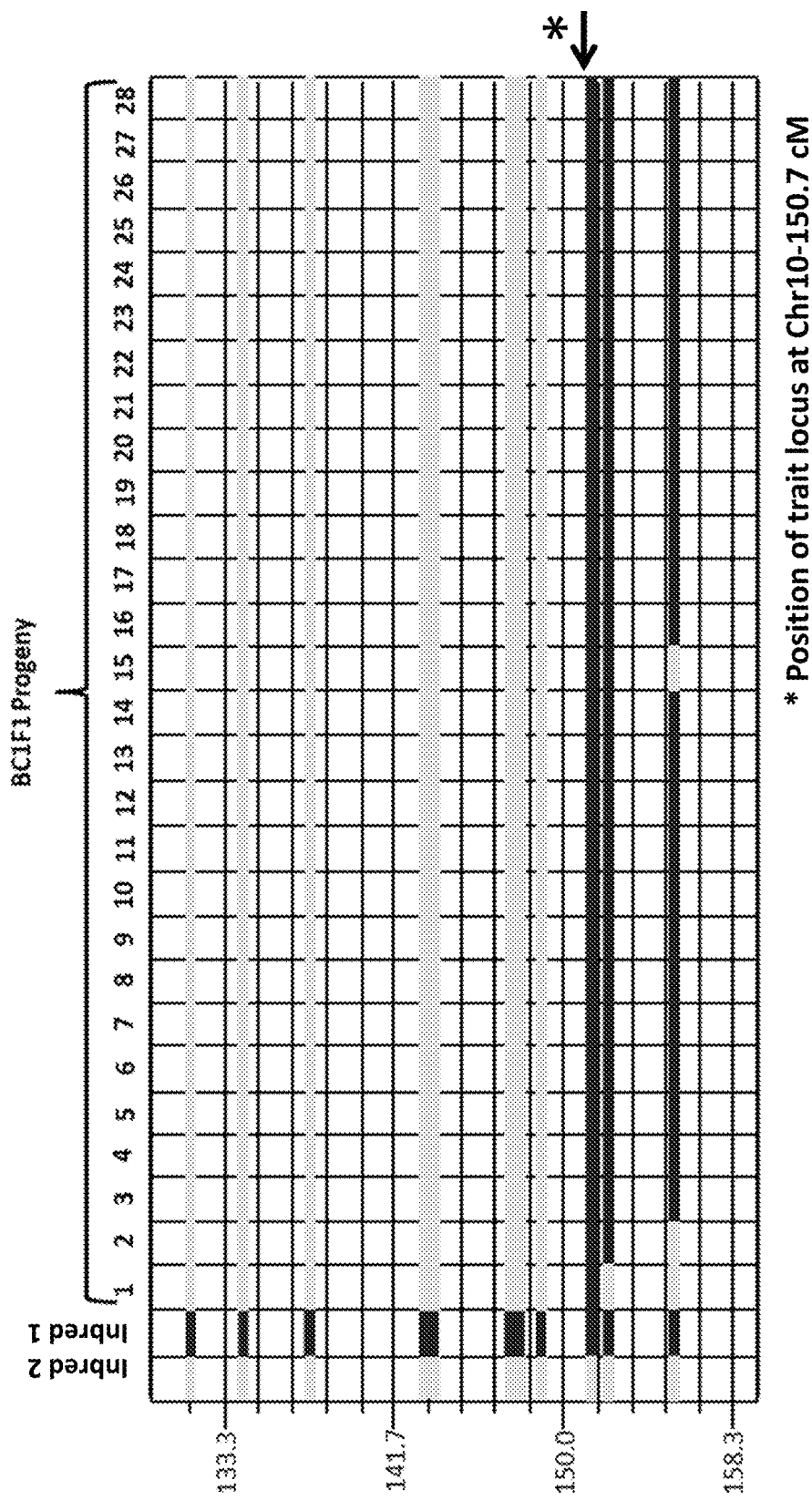

FIG. 14 shows the results of haplotype analysis focused on the telomeric segment of chromosome 10 that contained the trait locus (at position 150.7 cM, see asterisk). Haplotype results for wild-type Inbred 1 (black bars) are shown in lane 2, and for wild-type Inbred 2 in lane 1. For the 28 progeny analyzed in this manner, all the haplotype markers proximal to the marker that sat on the trait locus (or above the position of the asterisk) were observed to be SNPs found on Chr10 of Inbred 2. The marker at the trait locus and the two SNP calls closest to the telomere (below) were observed to be those of Inbred 1, with three exceptions. Progeny plant 1 contained only the SNP at the trait locus, indicating that a crossover had occurred within 0.7 cM on the proximal side of the trait and within 1.5 cM on the distal side (the position of the next marker). For progeny plants 2 and 15, two closely-spaced crossovers had also occurred at <0.7 cM and between 1.5-4 cM on the proximal and distal side of the trait locus.

Figure 15:
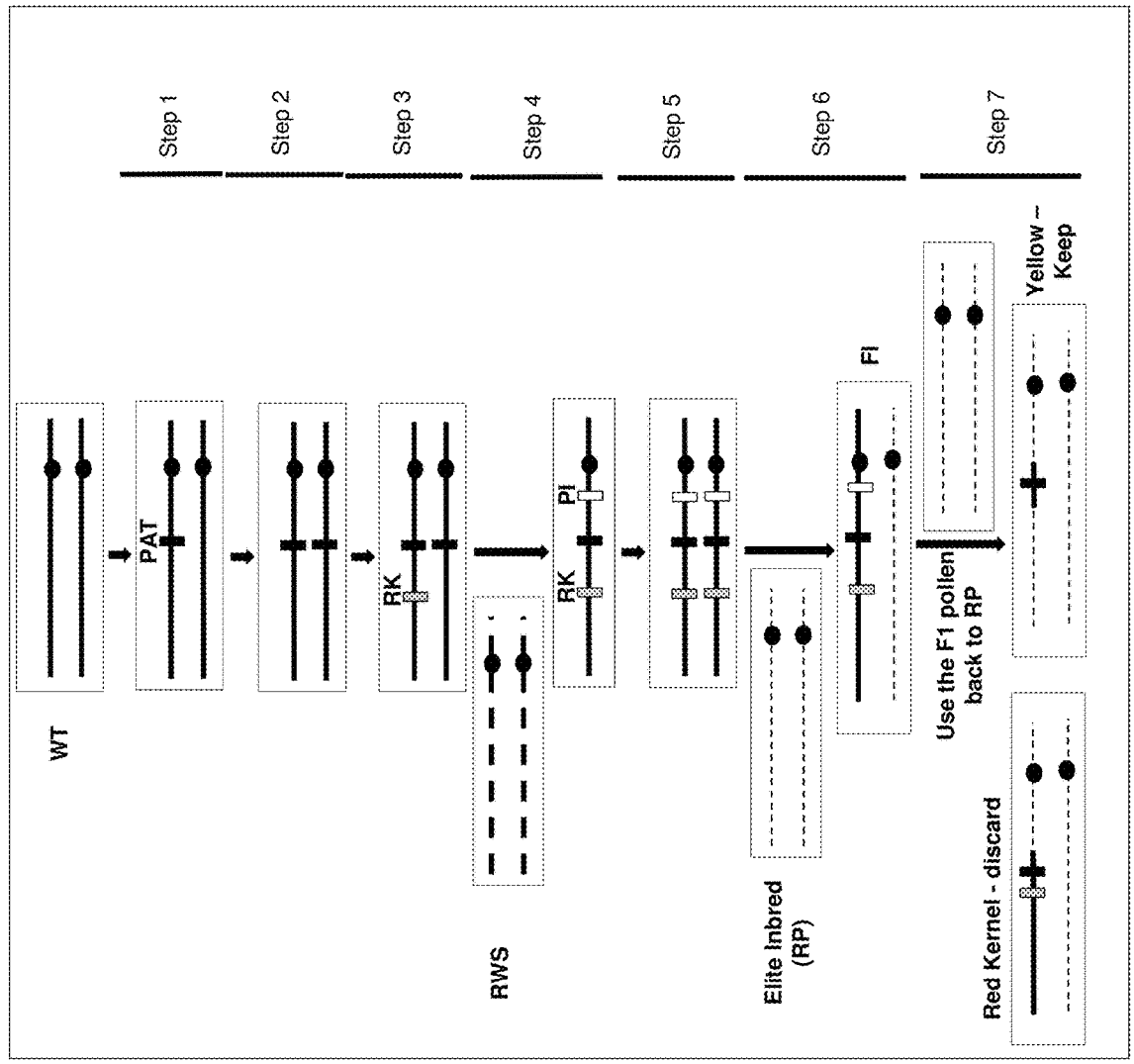

FIG. 15 shows a schematic of introducing an aleurone-specific anthocyanin locus (a color marker) on one side of an internal chromosome location containing a trait with an aleurone-specific anthocyanin locus (color marker) being introduced on the opposite side, and using the triple-linked site to rapidly introgress the trait into other inbreds. PAT=Trait Locus, RK=Red Kernel Locus (color marker locus) and PI=Pollen-inhibitor locus.

Figure 16:
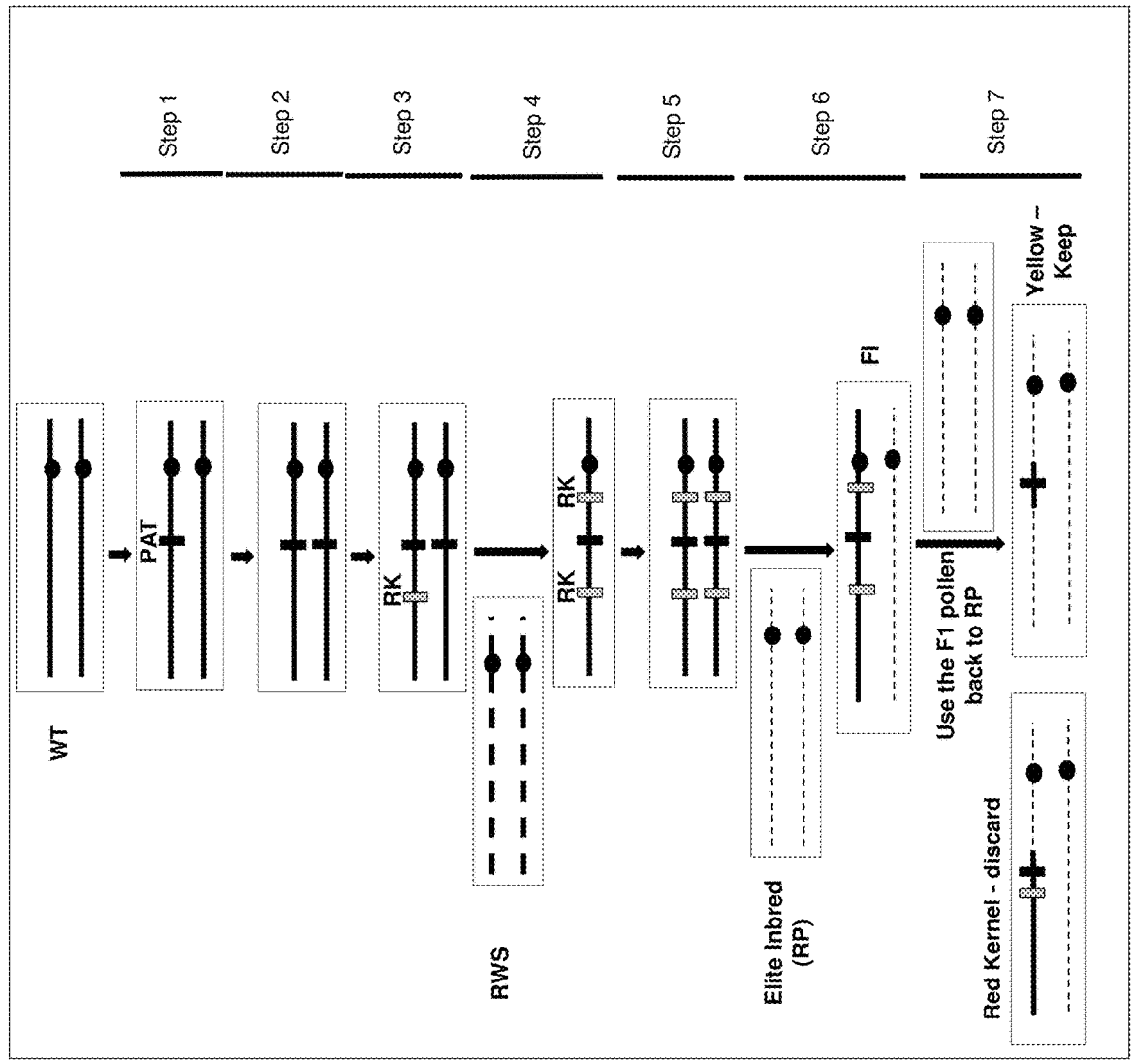

FIG. 16 shows a schematic of introducing a flanking aleurone-specific anthocyanin loci (color marker locus) on both sides of an internal chromosome location containing a trait, and using the triple-linked site to rapidly introgress the trait into other inbreds. PAT=Trait Locus, RK=Red Kernel Locus (color marker locus) and PI=Pollen-inhibitor locus.

Figure 17:
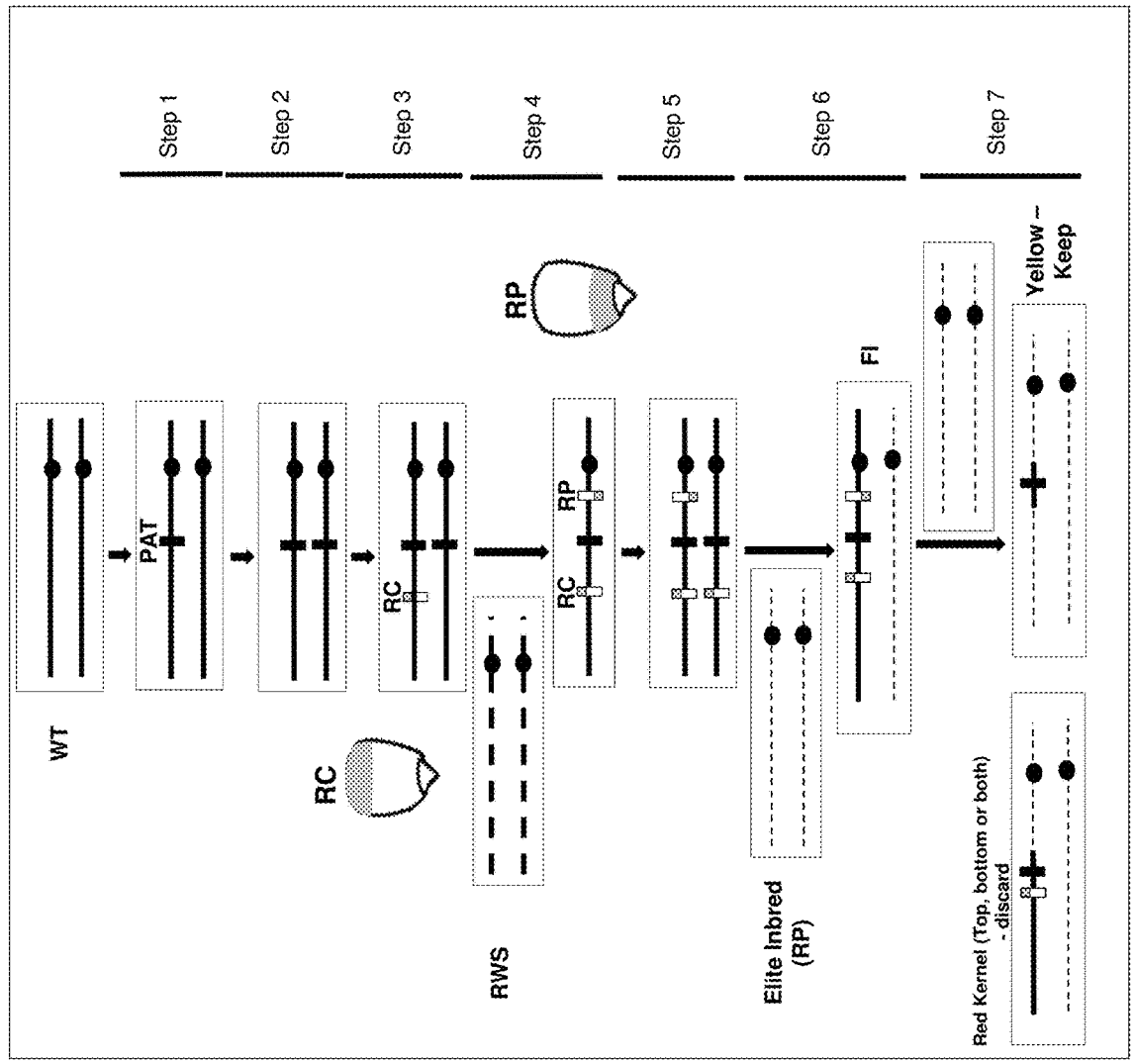

FIG. 17 shows a schematic of introducing an crown-specific anthocyanin locus on one side of an internal chromosome location containing a trait with an base-specific anthocyanin locus being introduced on the opposite side, and using the triple-linked site to rapidly introgress the trait into other inbreds. PAT=Trait Locus, RC=Red crown (Top of kernel), RP=Red pedicel (bottom of kernel).

The sequence descriptions summarize the Sequence Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219 (2):345-373 (1984). The symbols and format used for nucleotide and amino acid sequence data comply with the rules set forth in 37 C.F.R. § 1.822.

TABLE 1

Description of Sequences.

| SEQ ID NO: | Description |
|---|---|
| 1 | FRT1 |
| 2 | FRT87 |
| 3 | Zm-AA1 PRT |
| 4 | Zm-AA1 DNA |
| 5 | NPTII PRT |
| 6 | NPTII DNA |
| 7 | 35S TERM |
| 8 | PINII TERM |
| 9 | LTP2 PRO |
| 10 | TAGBFP PRT |
| 11 | TAGBFP DNA |

TABLE 1-continued

Description of Sequences.

| SEQ ID NO: | Description |
|---|---|
| 12 | GZ-W64 TERM |
| 13 | PG47 PRO |
| 14 | BT1 Transit peptide PRT |
| 15 | BT1 Transit peptide DNA |
| 16 | IN2 TERM |
| 17 | BA-BARSTAR PRT |
| 18 | BA-BARSTAR DNA |
| 19 | UBI1ZM PRO |
| 20 | UBI1ZM INTRON |
| 21 | DS-RED2 PRT |
| 22 | DS-RED2 DNA |
| 23 | PMI PRT |
| 24 | PMI DNA |
| 25 | BA-BARNASE-INT PRT |
| 26 | BA-BARNASE-INT DNA |
| 27 | 35S ENH DNA |
| 28 | GAT891G3 PRT |
| 29 | GAT891G3 DNA |
| 30 | UBIQ3 TERM |
| 31 | CZ19B1 TERM |
| 32 | OS-ACTIN PRO |
| 33 | OS-ACTIN INTRON |
| 34 | MO-PAT PRT |
| 35 | MO-PAT DNA |
| 36 | ZS-YELLOW1 N1 PRT |
| 37 | ZS-YELLOW1 N1 DNA |
| 38 | TETR PRT |
| 39 | TETR DNA |
| 40 | TOP DNA (TET OPERATOR) |
| 41 | LOX-FAS DNA |
| 42 | LOX-2272 DNA |
| 43 | PHP70154 |
| 44 | FRT1-87 from PHP69519: FRT1-NPTII 3XENH-UBI: GAT LTP2: DSRED-FRT87 |
| 45 | UBI PRO-FLPm-PINII DNA |
| 46 | FRT1-87 from PHP68884: FRT1-NPTIIENH: LTP2: TAGBFP ENH: PG47: AA1 |
| 47 | T-DNA FROM PHP66566 UBI: BARSTAR LTP2: DSRED UBI: PMI |
| 48 | PHP71464: FRT1-NPTII LTP2: YELLOW PG47: BARNASE-FRT87 |
| 49 | DPZM03g014880 - ZM-GT1 PRO DNA |
| 50 | PHP5096 |
| 51 | PHP01 |
| 52 | PHP02 |
| 53 | PHP03 |
| 54 | PHP04 |
| 55 | PHP05 |
| 56 | RB |
| 57 | LB |
| 58 | LOXP |
| 59 | MO-PMI DNA |
| 60 | MO-PMI PRT |
| 61 | ALL STOPS |
| 62 | SB-SAG12 TERM |
| 63 | NP-INTE-C DNA |
| 64 | NP-INTE-C PRT |
| 65 | NP-INTE-N DNA |
| 66 | NP-INTE-N PRT |
| 67 | KID-N DNA |
| 68 | KID-N PRT |
| 69 | KID-C DNA |
| 70 | KID-C PRT |
| 71 | MO-CYAN DNA |
| 72 | MO-CYAN PRT |
| 73 | LTP2 PRO-AMCYAN-GZW64A TERM |
| 74 | UBI1ZM PRO-UBI1ZM INTRON-AMCYAN-PINII TERM |
| 75 | RAB17 PRO-MOCRE-PINII TERM |
| 76 | PHP06 |
| 77 | PG47 PRO-ZM-BT1 TP~ZM-AA1-IN2-1 TERM |
| 78 | PG47 PRO-BA-BARNASE-IN2-1 TERM |
| 79 | CYP105A1 DNA |
| 80 | CYP105A1 PRT |
| 81 | CODA DNA |
| 82 | CODA PRT |
| 83 | ZM-U6 POLIII CHR8 PRO-GT1 GUIDE RNA-ZM-U6 POLIII CHR8 TERM |
| 84 | MOCAS9 EXON1-STLS1 INTRON-MOCAS9 EXON2 DNA |
| 85 | MOCAS9 PRT |
| 86 | ZM-U6 PRO |
| 87 | DCAS9~RP DNA |
| 88 | DCAS9~RP PRT |
| 89 | RB-LOXP-OSACTIN PRO & INTRON-FRT1-MOPAT-35S TERM-FRT87-LB |
| 90 | PG47 PRO-BT1 TP-ZMAA1-IN2-1 TERM |
| 91 | LTP2 PRO-AMCYAN1-PINII TERM |
| 92 | UBI1ZM PRO & INTRON-NPTII-PINII TERM |
| 93 | AMCYAN1 DNA |
| 94 | AMCYAN1 PRT |
| 95 | OSACTIN PRO & INTRON-MOPAT-35S TERM |
| 96 | DCAS9~RP-NLS Fusion |
| 97 | moLEXA DNA |
| 98 | moLEXA PRT |
| 99 | LEXA UAS DNA |
| 100 | moCBF1A DNA |
| 101 | moCBF1A PRT |
| 102 | PG47-moLEXA~moCBF1A-IN2-1-PG47 PRO-MOCODA-PINII-UBI1ZM PRO-NPTII-PINII |
| 103 | 5xUAS-45 35s PRO::ZMAA1-IN2-1 TERM-PG47-MOCODA-PINII-UBI PRO&INTRON-PMI-PINII |
| 104 | ST-LS1 INTRON1 |
| 105 | CYS4 RECOGNITION SITE |
| 106 | CYS4 (MO) DNA |
| 107 | CYS4 (MO) PRT |
| 108 | GUIDE RNA |
| 109 | PG46 PRO-CYS4(MO)-IN2-1 TERM |
| 110 | GT1 PRO TARGET1 |
| 111 | GT1 PRO TARGET2 |
| 112 | GT1 PRO TARGET3 |
| 113 | GT1 PRO TARGET4 |
| 114 | GT1 PRO TARGET5 |
| 115 | ZM-U6 POLIII CHR8 PRO |
| 116 | UBI-PMI-PINII UBI-ZS-YELLOW1N1-GZW64A 35S ENH-PG47 PRO-ZMAA1-IN2-1 |
| 117 | UBI-FLPm-PINII TERM OSACTIN-PINII UBI-ODP2-PINII |
| 118 | FLPm DNA |
| 119 | FLPm PRT |
| 120 | minimal FRT5 mutant recombination site |
| 121 | minimal FRT6 mutant recombination site |
| 122 | minimal FRT12 mutant recombination site |

DETAILED DESCRIPTION

Many modifications and other embodiments of the disclosures set forth herein will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Compositions and methods are provided herein for use of a pollen-inhibitor gene, a color marker gene or a pollen-inhibitor and/or color marker expression cassette in the genome of a plant.

As used herein, a "Pollen-Inhibitor gene" refers to a gene that when expressed in pollen or during pollen development, encodes a protein that renders the pollen grain incapable of germinating to produce a pollen tube, or produces a compromised pollen tube incapable of reaching the ovule and fertilizing the egg. Pollen-inhibitor genes also include genes that, when suppressed or silenced, render the pollen grain incapable of germinating to produce a pollen tube, or produces a compromised pollen tube incapable of reaching the ovule and fertilizing the egg.

A pollen-inhibitor gene (pollen inhibitor gene) can be expressed by a pollen-inhibitor expression cassette. A pollen-inhibitor expression cassette refers to a recombinant DNA construct comprising a promoter that stimulates transcription in pollen or during pollen development operably linked to a pollen-inhibitor gene and a 3' regulatory sequence such as a terminator.

A pollen-inhibitor locus (pollen inhibitor locus) refers to a genomic location defined by a genetic and physical position, where a pollen-inhibitor gene is located, or into which a pollen-inhibitor expression cassette has integrated. The genomic location defined by a genetic and physical position, into which a pollen-inhibitor expression cassette has integrated is referred to as a "pollen-inhibitor locus".

A non-conditional pollen-inhibitor gene includes a gene that when expressed in pollen produces a protein that will inhibit pollen germination or pollen tube elongation. Examples of genes that can be used as pollen inhibition include, but are not limited to, the maize alpha-amylase gene (Albertsen et al., 1999. U.S. Pat. No. 5,962,769), the barnase gene from *Bacillus amyloliquefaciens* (Mariani et al., 1990, Nature 347:737-741) and the KID gene from *Escherichia coli* (de al Cueva-Mendez et al., 2003, EMBO J. 22:246-251). Other pollen-inhibitor genes are well known in the art (see van Melderen & de Bast, 2009, PIOS Genetics 5:1-6 and Yamaguchi et al., 2001, Ann Rev Genetics 45:61-79 and Leplae et al., 2001, Nuc Acids Res 1-13).

A conditional pollen-inhibitor gene includes a gene that when expressed to encode a protein in pollen grains is not inhibitory until the protein cognate substrate is supplied to the pollen. At this point, the non-inhibitory substrate is converted to an inhibitory molecule. Conditional inhibitory genes include, but are not limited to, the codA gene (Danielsen et al., 1993, Mol. Microbiol. 6:1335-1344), the dhlA gene (Naested et al., Plant J. 18:571-576), the tms2 gene (Sundaresan et al., 1995, genes Dev. 9:1797-1810), or the CYP105A gene (O'Keefe et al., Plant Physiol. 105:473-482). When expressed in plants, the encoded gene products are themselves neutral. However, when a non-inhibitory substrate is supplied, the encoded protein converts this compound to an inhibitory compound or inhibitory derivative. The coda encoded protein converts 5-fluorocytosine (5-FC) to cytotoxic 5-fluorouracil (5-FU), the dhlA-encoded protein hydrolyzes haloalkanes such as 1,2 dichloroethane to the cytotoxic halogenated alcohol, the tms2-encoded protein converts indole-3 acetamide to the auxin indole-3-acetic acid, and the P450-monooxygenase gene CYP105A encodes a protein that converts the non-herbicidal sufonylurea R7402 into a potent herbicide.

Promoters useful for expressing pollen-inhibitor genes include included promoters that are expressed after tetrad formation within the maturing pollen grain, the mature pollen grain or during pollen germination, for example, the maize Zm13 promoter (Hamilton et al., 1998. Plant Mol Biol. 38:663-669), the tomato LAT52 promoter (Twell et al., 1990. Development 109:705-713), the *Brassica* Bp19 promoter (Albani et al., 1991. PMB 16:501-513), the tobacco NTP303 promoter (Weterings et al., 1995. Plant J. 8:55-63), the wheat TaPSG719 promoter (Chen et al., 2010. Mol Biol. Rep. 37:737-744), maize SEQ ID NO:1 (Allen & Lonsdale, 1995. U.S. Pat. No. 5,412,085), the maize pollen-specific promoter described in Fearing et al (1997: Mol Breeding 3:169-176), the tobacco NTPp13 promoter (Yang et al., 2010. Genetika 46:458-463), and promoters of pollen-specific genes described in Khurana et al. (2012, Critical Rev in Plant Science 31:359-390).

Inducible expression can be driven by a promoter that is activated by a specific ligand or by an environmental stimulus. Examples include, but are not limited to, the tetracyclin-responsive repressor system (Gatz and Quail, 1988, PNAS 85:1394-1397), the ethametsulfuron-responsive repressor system (DuPont Patent Applications, McBride et al), the safener-inducible In2 promoter from maize (DeVelder et al., 1997, Plant Cell Physiol 38:568-577) the copper-inducible ACE1 system (McKenzie et al., 1998), the ethanol-inducible AlcA system (Cadick et al., 1988, Nat. Biotechnol. 16:177-180); Runzhi et al., 2005, Plant Sci. 169:463-469), the glucocorticoid GVG inducible expression system (Aoyama and Chua, 1997, Plant J. 11:605-612), estradiol-inducible expression system (Bruce et al., 2000, Plant Cell 12:65-79); Zuo et al., 2000, Plant J. 24:265-273), and the methoxyfenozide-inducible VGE system (Koo et al., 2004, Plant J. 37:439-448; Padidum et al., 2003, Curr. Opin. Plant Biol. 6:87-91)

As described herein, color markers can be useful for screening kernels for the presence of a specific locus. Seed color markers represent an alternative method to the pollen-inhibitor screen described herein, to screen for progeny that have broken the linkage between the trait and the seed-color locus.

A color marker gene can be expressed by a color marker expression cassette. A color marker expression cassette refers to a recombinant DNA construct comprising a promoter operably linked to a gene encoding a color maker. Color maker genes include genes whose expression result in anthocyanin accumulation including ZM-R (X15806, see Perrot and Cone, 1989, Nucl. Acids Res 17:8003), ZM-C1 (NCBI Locus NM_001158182, see Alexandrov et al., 2009, Plant Mol. Boil 69:179-194) monocot orthologs of the maize R and C1, genes and the fusion of these two genes as CRC (The C1 DNA-Binding domain, the R gene and the C1 activation domain, fused together in that order). Color markers that could be useful also include genes that encode fluorescent proteins such as Am-CYAN1, AcGFP1, ZS-GREEN, ZS-YELLOW1, DS-RED2, DS-RED-EXPRESS (Clontech).

A color marker locus refers to a genomic location defined by a genetic and physical position, where a color marker gene is located, or into which color marker expression cassette has integrated. The genomic location defined by a genetic and physical position, into which a color marker expression cassette has integrated is referred to as a "color marker locus".

Promoters to control expression of color markers in the seed include, but are not limited to, outer endosperm promoters or aleurone promoters such as the barley LTP1 promoter (Skriver et al., 1992, Plant Mol. Biol. 18:585-589), the barley LTP2 promoter (Kalla et al., 1994, Plant J. 6:849-860), the barley GAmyb and High-pI Alpha amylase promoters (Gubler et al., 1995, Plant Cell 7:1879-1891), the wheat Early Methionine promoter (Furtado and Henry, 2005, Plant Biotechnol. J. 3:421-434), the rice Chi26 and LTP2 promoters (Hwang et al., 2001, Plant Cell Rep. 20:647-654), the maize BETL1 promoter (Hueros et al., 1999, Plant Physiol. 121:1143-1152), the maize cystatin (CC7) promoter (U.S. Pat. No. 8,481,811, published Jul. 9, 2013), the maize LEG1A promoter (US patent application US20110271405 A1, published Nov. 3, 2011), maize End 2 promoter (US patent application U.S. Pat. No. 6,903,205, published Mar. 4, 2003), and monocot orthologs or paralogs of the above promoters. Provided herein are plants, plant parts, plant cells or seeds having in its genome a genomic window. A genomic window refers to a segment of a chromosome in the genome of a plant that is desirable for producing at least one trait locus, or the segment of a chromosome comprising at least one trait locus that was produced by the methods provided herein.

The genomic window can be about 1, 2, 3, 4, 5, 6, 7, 8, 9, 10, 11, 12, 13, 14, 15 or more centimorgans (cM) in length. In one embodiment, the genomic window can be about 1-2 cM, about 1-3 cM, about 1-4 cM, about 1-5 cM, about 1-6 cM, about 1-7 cM, about 1-8 cM, about 1-9 cM, about 1-10 cM, about 2-3 cM, about 2-4 cM, about 2-5 cM, about 2-6 cM, about 2-7 cM, about 2-8 cM, about 2-9 cM, about 2-10 cM, about 3-4 cM, about 3-5 cM, about 3-6 cM, about 3-7 cM, about 3-8 cM, about 3-9 cM, about 3-10 cM, about 4-5 cM, about 4-6 cM, about 4-7 cM, about 4-8 cM, about 4-9 cM, about 4-10 cM, about 5-6 cM, about 5-7 cM, about 5-8 cM, about 5-9 cM, about 5-10 cM, about 6-7 cM, about 6-8 cM, about 6-9 cM, about 6-10 cM, about 7-8 cM, about 7-9 cM, about 7-10 cM, about 8-9 cM, or about 8-10 cM in length.

A "centimorgan" (cM) or "map unit" is the distance between two linked genes, markers, target sites, genomic loci of interest, loci, or any pair thereof, wherein 1% of the products of meiosis are recombinant. Thus, a centimorgan is equivalent to a distance equal to a 1% average recombination frequency between the two linked genes, markers, target sites, loci, genomic loci of interest or any pair thereof.

The genomic window can be located proximal to a telomere of a chromosome or in a non-telomeric (internal) region of a chromosome. The location of the genomic window proximal to a telomere can be about 0.1 to 1 cM, 0.1 to 10 cM, 1-10 cM, 5-15 cM or 20-25 cM distant from telomeric end of the chromosome. The genomic window can comprise various components. Such components can include, for example, but not limited to, recombination target sites, target sites for site-specific integration (such as, but not limited to, transgenic SSI target sites), single-strand break target sites, double-strand break target sites, genomic loci of interest, native genes, mutated genes, edited genes, trait loci of interest, pollen-inhibitor genes, and polynucleotides of interest. The genomic window can comprise at least 1, 2, 3, 4, 5 or more target sites for a recombinase, a single-strand-break-inducing agent (such as but not limited to a nickase, a Cas endonuclease), a double-strand-break-target site (such as but not limited to a Cas endonuclease, a Zinc finger nuclease, a TALEN, a meganuclease and/or an engineered endonuclease) such that each target site has a different genomic insertion site within the genomic window. In addition, the genomic window can comprise at least 1, 2, 3, 4, 5, 6, 7, 8, 9, 10 or more trait loci of interest each having a different genomic insertion site. By a "different genomic insertion site" is meant that each component of the genomic window (such as for example target sites and trait loci of interest) is inserted into the genome at a different location and as such each component can segregate independently from one another. For example, the genomic window can comprise a combination of target sites and/or trait loci of interest such that each target site or trait loci of interest has a different genomic insertion site within the genomic window.

The components of the genomic windows provided herein have different genomic insertion sites and as such can segregate independently from one another. As used herein, "segregate independently", is used to refer to the genetic separation of any two or more genes, transgenes, native genes, mutated genes, target sites, genomic loci of interest, markers and the like from one another during meiosis. Assays to measure whether two genetic elements segregate independently are known in the art. As such, any two or more genes, transgenes, native genes, mutated genes, target sites, genomic loci of interest, markers and the like within a genomic window provided herein, have genomic insertion sites located at an appropriate distance from one another so that they generally segregate independently at a rate of about 10% or less. Thus, the components of the genomic windows provided herein can segregate independently from one another at a rate of about 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or 0.05%. Alternatively, the components of the genomic windows provided herein can segregate independently from one another at a rate of about 10-0.1%, about 10-0.5%, about 10-1%, about 10-5%, about 9-0.1%, about 9-0.5%, about 9-1%, about 9-5%, about 8-0.1%, about 8-0.5%, about 8-1%, about 8-4%, about 7-0.1%, about 7-0.5%, about 7-1%, about 7-4%, about 6-0.1%, about 6-1%, about 6-0.5%, about 6-3%, about 5-0.1%, about 5-1%, about 5-0.5%, about 4-0.1%, about 4-1%, about 4-0.5%, about 3-0.1%, about 3-1%, about 3-0.5%, about 2-0.1%, about 2-0.5%, about 1-0.1%, about 1-0.5%, or less than 0.1%. For example, if the genomic window comprises a target site and a trait locus of interest that are about 5 cM from each other, the target site and the trait locus trait locus of interest would segregate independently at a rate of about 5%.

As used herein, a "genomic locus of interest" (plural "genomic loci of interest") comprises a collection of specific polymorphisms that are inherited together. The terms "trait locus" and "trait locus of interest" (plural "trait loci of interest") are used interchangeably herein and refer to a genomic locus of interest that comprises a trait of interest. A given trait locus of interest can include but is not limited to, a modified or edited native gene, a transgene, an altered double-strand-break target site, a native gene, or a transgenic SSI target site.

As used herein, a "trait" refers to the phenotype conferred from a particular gene or grouping of genes. A trait gene of interest includes any one gene or grouping of genes that encodes a trait. Any desired trait (also referred to as trait of interest) can be introduced into the genome at a given trait locus of interest. Such traits include, but are not limited to, traits conferring insect resistance, disease resistance, herbicide tolerance, male sterility, abiotic stress tolerance, altered phosphorus, altered antioxidants, altered fatty acids, altered essential amino acids, altered carbohydrates, or sequences involved in site-specific recombination. In terms of relative position of two loci on a chromosome, a locus is more "proximal" if it is closer to the centromere (and farther from the telomere) of that chromosome, and a locus is more "distal" if it is closer to the telomere (and farther from the centromere.

The trait locus of interest can include, for example, any modification that confers a trait, such as a transgene or a native trait. The trait locus of interest can also include a native trait or a selectable marker. Selectable markers are described in more detail further herein and include DNA segments that encode products which provide resistance against otherwise toxic compounds. As used herein, a "native trait" refers to a trait found in nature. In another embodiment, the trait locus of interest comprises a transgene.

A given trait locus of interest has its own genomic insertion site within the genomic window. For example, a trait locus of interest and a target site (for a recombinase, a single-strand-break-inducing agent, a double-strand-break-target site, or others) within the genomic window will have different genomic insertion sites within the genome. A given target site can be found within about 10 cM, 9 cM, 8 cM, 7 cM, 6 cM, 5 cM, 4 cM, 3 cM, 2 cM, 1 cM, 0.9 cM, 0.8 cM, 0.7 cM, 0.6 cM, 0.5 cM, 0.4 cM, 0.3 cM, 0.2 cM, 0.1 cM or 0.05 cM from the trait locus of interest such that the target site and trait locus of interest have different genomic insertion sites.

Compositions and methods are provided for introducing a pollen-inhibitor gene and/or a color marker gene in close proximity to a trait locus of interest in the genome of a progeny plant. In one embodiment of the disclosure, the method comprises: a) providing a first plant having within a genomic window at least one trait gene of interest integrated into a first target site located proximal to a telomere, wherein said genomic window is about 10 cM in length, wherein said first plant does not comprise a pollen-inhibitor gene; b) breeding to said first plant a second plant, wherein said second plant comprises in said genomic window a pollen-inhibitor gene integrated into a second target site located proximal to both the telomere and said trait gene of interest; and, c) selecting a progeny plant from step (b) comprising said trait gene of interest and said pollen-inhibitor gene, wherein said trait gene of interest and said pollen-inhibitor gene are genetically linked.

In one embodiment of the disclosure, the method comprises: (a) providing a first plant having within a genomic window a first pollen-inhibitor gene integrated into a first target site, wherein said genomic window is about 10 cM in length; (b) breeding to said first plant a second plant having a trait gene of interest integrated into a second target site within said genomic window; (c) selecting a progeny plant from step (b) comprising said first pollen-inhibitor gene and said trait gene of interest in said genomic widow; (d) providing a third plant having a second pollen-inhibitor gene integrated into a third target site within said genomic window; (e) breeding to said third plant a fourth plant, wherein said fourth plant comprises a pollen-inhibitor maintainer (PIM) gene within said genomic window; (f) selecting a progeny plant from step (e) comprising said second pollen-inhibitor gene and said pollen-inhibitor maintainer (PIM) gene; and, (g) cross pollinating the progeny plant of (c) with the progeny plant of (f) and selecting for a progeny plant that comprises, genetically linked to each other. Optionally, the PIM gene is segregated away from said first pollen-inhibitor gene, said trait gene of interest, and said second pollen-inhibitor gene.

As used herein, by "target site" is intended a polynucleotide comprising a nucleotide sequence comprising at least one recognition sequence for an agent such as, but not limited to, a recombinase, a single-strand-break-inducing agent (such as but not limited to a nickase or a Cas endonuclease) or a double-strand-break-inducing target site (such as but not limited to a Cas endonuclease, a Zinc finger nuclease, a TALEN, a meganuclease, an engineered endonuclease, or any one combination thereof).

By "transgenic target site" is meant a target site that is non-native in sequence and/or in genomic location to the plant genome. In some embodiments, the transgenic target site can comprise at least 1, 2, 3, 4, 5 or more recombination sites for site-specific recombination (also referred to as transgenic SSI target site). Site-specific recombination system employ various components which are described herein and in U.S. Pat. Nos. 6,187,994, 6,262,341, 6,331,661 and 6,300,545, each of which is herein incorporated by reference.

The terms "transgenic SSI target site", "transgenic target site for site specific integration (SSI)", and "transgenic target site for SSI" are used interchangeably herein and refer to a polynucleotide comprising a nucleotide sequence flanked by at least two recombination sites (See, for example, US Patent Application US2013-0198888 A1, published on Aug. 1, 2013, and US Patent Application US2014-0338070 A1, published on Nov. 13, 2014, each of which is herein incorporated by reference. In some embodiments, the recombination sites of the transgenic SSI target site are dissimilar and non-recombinogenic with respect to one another. One or more intervening sequences may be present between the recombination sites of the transgenic SSI target site. Intervening sequences of particular interest would include linkers, adapters, selectable markers, pollen-inhibitor genes, polynucleotides of interest, promoters and/or other sites that aid in vector construction or analysis. In addition, the recombination sites of the transgenic SSI target site can be located in various positions, including, for example, within intronic sequences, coding sequences, or untranslated regions.

The transgenic SSI target site can comprise 1, 2, 3, 4, 5, 6 or more recombination sites. In one embodiment, the target site comprises a first recombination site and a second recombination site wherein the first and the second recombination site are dissimilar and non-recombinogenic to each other. In a further embodiment, the target site comprises a third recombination site between the first recombination site and the second recombination site. In such embodiments, the first, second and third recombination sites may be dissimilar and non-recombinogenic with respect to one another. Such first, second and third recombination sites are able to recombine with their corresponding or identical recombination site when provided with the appropriate recombinase.

Pollen-inhibitor genes, color marker genes, or trait loci employed in the methods and compositions provided herein can be integrated into recombination sites that are "corresponding" sites or "dissimilar" sites. By "corresponding recombination sites" or a "set of corresponding recombination sites" is intended that the recombination sites have the same or corresponding nucleotide sequence. A set of corresponding recombination sites, in the presence of the appropriate recombinase, will efficiently recombine with one another (i.e., the corresponding recombination sites are recombinogenic). The recombination sites can also be dissimilar. By "dissimilar recombination sites" or a "set of dissimilar recombination sites" is intended that the recombination sites are distinct (i.e., have at least one nucleotide difference). The recombination sites within "a set of dissimilar recombination sites" can be either recombinogenic or non-recombinogenic with respect to one other. By "recombinogenic" is intended that the set of recombination sites are capable of recombining with one another. Thus, suitable sets of "recombinogenic" recombination sites for use in the methods and compositions provided herein include those sites where the relative excision efficiency of recombination between the recombinogenic sites is above the detectable limit under standard conditions in an excision assay, typically, greater than 2%, 5%, 10%, 20%, 50%, 100%, or greater. By "non-recombinogenic" is intended the set of recombination sites, in the presence of the appropriate recombinase, will not recombine with one another or recombination between the sites is minimal. Thus, suitable "non-recombinogenic" recombination sites for use in the methods and compositions provided herein include those sites that recombine (or excise) with one another at a frequency lower than the detectable limit under standard conditions in an excision assay, typically, lower than 2%, 1.5%, 1%, 0.75%, 0.5%, 0.25%, 0.1%, 0.075, 0.005%, 0.001%.

Each recombination site within the "set of non-recombinogenic sites" is biologically active and therefore can recombine with an identical site. Accordingly, it is recognized that any suitable non-recombinogenic recombination sites may be utilized, including a FRT site or an active variant thereof, a LOX site or active variant thereof, any combination thereof, or any other combination of non-recombinogenic recombination sites known in the art. FRT sites that can be employed in the methods and compositions disclosed herein can be found, for example, in U.S. Pat. No. 8,586,361 issued on Nov. 19, 2013, herein incorporated by reference.

By "recombination site" is intended a recombination site and active variants thereof. Many recombination systems are known in the art and one of skill will recognize the appropriate recombination site to be used with the recombination system of interest. Any suitable recombination site or set of recombination sites may be utilized herein, including a FRT site, a biologically active variant of a FRT site (i.e. a mutant FRT site), a LOX site, a biologically active variant of a LOX site (i.e. a mutant LOX site), any combination thereof, or any other combination of recombination sites known in the art. Examples of FRT sites include, for example, the wild type FRT site (FRT1) (SEQ ID NO: 1), and various mutant FRT sites, including but not limited to, FRT5 (SEQ ID NO: 120), FRT6 (SEQ ID NO: 121), FRT12 (SEQ ID NO: 122) and FRT87 (SEQ ID NO: 2). See, for example, U.S. Pat. No. 6,187,994 issued on Jan. 13, 2001, U.S. Pat. No. 8,586,361 issued on Nov. 19, 2013, and US patent application US2013-0198888A1, published on Aug. 1, 2013, each of which are herein incorporated by reference.

Recombination sites from the Cre/Lox site-specific recombination system can also be used. Such recombination sites include, for example, wild type LOX sites and mutant LOX sites. An analysis of the recombination activity of mutant LOX sites is presented in Lee et al. (1998) Gene 216:55-65, herein incorporated by reference. Also, see for example, Schlake and Bode (1994) Biochemistry 33:12746-12751; Huang et al. (1991) Nucleic Acids Research 19:443-448; Sadowski (1995) In Progress in Nucleic Acid Research and Molecular Biology Vol. 51, pp. 53-91; Cox (1989) In Mobile DNA, Berg and Howe (eds) American Society of Microbiology, Washington D.C., pp. 116-670; Dixon et al. (1995) Mol. Microbiol. 18:449-458; Umlauf and Cox (1988) EMBO 7:1845-1852; Buchholz et al. (1996) Nucleic Acids Research 24:3118-3119; Kilby et al. (1993) Trends Genet. 9:413-421; Rossant and Geagy (1995) Nat. Med. 1: 592-594; Albert et al. (1995) The Plant J. 7:649-659; Bayley et al. (1992) Plant Mol. Biol. 18:353-361; Odell et al. (1990) Mol. Gen. Genet. 223:369-378; Dale and Ow (1991) Proc. Natl. Acad. Sci. USA 88:10558-10562; Qui et al. (1994) Proc. Natl. Acad. Sci. USA 91:1706-1710; Stuurman et al. (1996) Plant Mol. Biol. 32:901-913; Dale et al. (1990) Gene 91:79-85; Albert et al. (1995) The Plant J. 7:649-659 and WO 01/00158; all of which are herein incorporated by reference.

Active variants and fragments of recombination sites are also encompassed by the compositions and methods provided herein. Fragments of a recombination site retain the biological activity of the recombination site and hence facilitate a recombination event in the presence of the appropriate recombinase. Thus, fragments of a recombination site may range from at least about 5, 10, 15, 20, 25, 30, 35, 40 nucleotides, and up to the full-length of a recombination site. Active variants can comprise at least 65%, 70%, 75%, 80%, 85%, 90%, 91%, 92%, 93%, 94%, 95%, 96%, 97%, 98%, 99% or more sequence identity to the native recombination site, wherein the active variants retain biological activity and hence facilitate a recombination event in the presence of the appropriate recombinase. Assays to measure the biological activity of recombination sites are known in the art. See, for example, Senecoll et al. (1988) J. Mol. Biol. 201:406-421; Voziyanov et al. (2002) Nucleic Acid Research 30:7, U.S. Pat. No. 6,187,994, WO/01/00158, and Albert et al. (1995) The Plant Journal 7:649-659.

By "recombinase" is intended a polypeptide that catalyzes site-specific recombination between compatible recombination sites. For reviews of site-specific recombinases, see Sauer (1994) Current Opinion in Biotechnology 5:521-527; and Sadowski (1993) FASEB 7:760-767; the contents of which are incorporated herein by reference. The recombinase can be a naturally occurring recombinase or a biologically active fragment or variant of the recombinase. Recombinases include recombinases from the Integrase and Resolvase families, biologically active variants and fragments thereof, and any other naturally occurring or recombinantly produced enzyme or variant thereof that catalyzes conservative site-specific recombination between specified DNA recombination sites.

The Integrase family of recombinases has over one hundred members and includes, for example, FLP, Cre, Int, and R. For other members of the Integrase family, see for example, Esposito et al. (1997) Nucleic Acid Research 25:3605-3614 and Abremski et al. (1992) Protein Engineering 5:87-91, both of which are herein incorporated by reference. Other recombination systems include, for example, the streptomycete bacteriophage phi C31 (Kuhstoss et al. (1991) J. Mol. Biol. 20:897-908); the SSV1 site-specific recombination system from *Sulfolobus shibatae* (Maskhelishvili et al. (1993) Mol. Gen. Genet. 237:334-342); and a retroviral integrase-based integration system (Tanaka et al. (1998) Gene 17:67-76). Some recombinase do not require cofactors or a supercoiled substrate. Such recombinases include Cre recombinase, FLP recombinase, or active variants or fragments thereof (See for example U.S. Pat. No. 8,586,361, issued on Nov. 19, 2013, which is herein incorporated by reference).

The FLP recombinase is a protein that catalyzes a site-specific reaction that is involved in amplifying the copy number of the two-micron plasmid of *S. cerevisiae* during DNA replication. As used herein, FLP recombinase refers to a recombinase that catalyzes site-specific recombination between two FRT sites. The FLP protein has been cloned and expressed. See, for example, Cox (1993) Proc. Natl. Acad. Sci. U.S.A. 80:4223-4227. The FLP recombinase for use in the methods and with the compositions may be derived from the genus *Saccharomyces*. One can also synthesize a polynucleotide comprising the recombinase using plant-preferred codons for optimal expression in a plant of interest. A recombinant FLP enzyme encoded by a nucleotide sequence comprising maize preferred codons (FLPm) (SEQ ID NO: 119) that catalyzes site-specific recombination events is known. See, for example, U.S. Pat. No. 5,929,301, herein incorporated by reference. Additional functional variants and fragments of FLP are known. See, for example, Buchholz et al. (1998) Nat. Biotechnol. 16:617-618, Hartung et al. (1998) J. Biol. Chem. 273:22884-22891, Saxena et al.

(1997) Biochim Biophys Acta 1340(2):187-204, and Hartley et al. (1980) Nature 286:860-864, all of which are herein incorporated by reference.

The bacteriophage recombinase Cre catalyzes site-specific recombination between two lox sites. The Cre recombinase is known in the art. See, for example, Guo et al. (1997) Nature 389:40-46; Abremski et al. (1984) J. Biol. Chem. 259:1509-1514; Chen et al. (1996) Somat. Cell Mol. Genet. 22:477-488; Shaikh et al. (1977) J. Biol. Chem. 272:5695-5702; and, Buchholz et al. (1998) Nat. Biotechnol. 16:617-618, all of which are herein incorporated by reference. The Cre polynucleotide sequences may also be synthesized using plant-preferred codons. Such sequences (moCre) are described in WO 99/25840, herein incorporated by reference. It is further recognized that a chimeric recombinase can be used in the methods. By "chimeric recombinase" is intended a recombinant fusion protein which is capable of catalyzing site-specific recombination between recombination sites that originate from different recombination systems. That is, if a set of functional recombination sites, characterized as being dissimilar with respect to one another, is utilized in the methods and compositions and comprises a FRT site and a LoxP site, a chimeric FLP/Cre recombinase or active variant or fragment thereof will be needed or, alternatively, both recombinases may be separately provided. Methods for the production and use of such chimeric recombinases or active variants or fragments thereof are described in WO 99/25840, herein incorporated by reference.

As used herein, the terms "double-strand-break target site", "DSB target site", "DSB target sequence", "double-strand-break—inducing-agent target site", and "target site for a double-strand-break-inducing-agent" are used interchangeably and refer to a polynucleotide sequence in the genome of a plant cell (including choloroplastic and mitochondrial DNA) that comprises a recognition sequence for a double-strand-break-inducing agent at which a double-strand-break is induced in the cell genome by a double-strand-break-inducing-agent.

As used herein, the terms "single-strand-break—inducing-agent target site", "single-strand-break target site", "SSB target site", "SSB target sequence", and "target site for a single-strand-break-inducing-agent" are used interchangeably and refer to a polynucleotide sequence in the genome of a plant cell (including choloroplastic and mitochondrial DNA) that comprises a recognition sequence for an agent (such as but not limited to a nickage, a nuclease) at which a single-strand-break is induced in the cell genome.

As used herein, the terms "altered double-strand-break target site", "altered DSB target site", "aDSB target site", and "altered target site for a double-strand-break-inducing-agent" are used interchangeably and refer to a DSB target sequence comprising at least one alteration when compared to a non-altered DSB target sequence. "Alterations" can include, for example: (i) replacement of at least one nucleotide, (ii) a deletion of at least one nucleotide, (iii) an insertion of at least one nucleotide, or (iv) any combination of (i)-(iii).

The DSB target site can be an endogenous site in the plant genome, or alternatively, the DSB target site can be heterologous to the plant and thereby not be naturally occurring in the genome, or the DSB target site can be found in a heterologous genomic location compared to where it occurs in nature. As used herein, the term "endogenous DSB target site" refers to an DSB target site that is endogenous or native to the genome of a plant and is located at the endogenous or native position of that DSB target site in the genome of the plant.

The length of the SSB or DSB target site can vary, and includes, for example, DSB target sites that are at least 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length. It is further possible that the DSB target site could be palindromic, that is, the sequence on one strand reads the same in the opposite direction on the complementary strand. The nick/cleavage site could be within the recognition sequence or the nick/cleavage site could be outside of the recognition sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs.

Pollen-inhibitor genes, color marker genes, or trait loci employed in the methods and compositions provided herein can be integrated into a double-strand-break target site by a double-strand-break-inducing-agent.

A "double-strand-break-inducing agent" (also referred to as "DSB-inducing-agent") refers to any nuclease which produces a double-strand break in the target sequence. The double-strand break target site can be, but is not limited to a zinc finger endonuclease target site, an engineered endonuclease target site, a meganuclease target site, a TALENs target site and a Cas endonuclease target site.

Any nuclease that induces a single or double-strand break into a desired target site can be used in the methods and compositions disclosed herein. A naturally-occurring or native endonuclease can be employed so long as the endonuclease induces a single or double-strand break in a desired target site. Alternatively, a modified or engineered endonuclease can be employed. An "engineered endonuclease" refers to an endonuclease that is engineered (modified or derived) from its native form to specifically recognize and induce a single or double-strand break in the desired target site. Thus, an engineered endonuclease can be derived from a native, naturally-occurring endonuclease or it could be artificially created or synthesized. The modification of the endonuclease can be as little as one nucleotide. Producing a single or double-strand break in a target site or other DNA can be referred to herein as "cutting" or "cleaving" the DSB target site or other DNA.

Active variants and fragments of the SSB or DSB target sites can comprise at least 65%, 70%, 75%, 80%, 85%, 90%, 91%, 92%, 93%, 94%, 95%, 96%, 97%, 98%, 99% or more sequence identity to the given DSB target site, wherein the active variants retain biological activity and hence are capable of being recognized and cleaved by an DSB-inducing-agent. Assays to measure the double-strand break of a DSB target site by an endonuclease are known in the art and generally measure the ability of an endonuclease to cut the DSB target site.

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Restriction enzymes are further described and classified, for example in the REBASE database (Roberts et al., (2003) *Nucleic Acids Res* 31:418-20), Roberts et al., (2003) *Nucleic Acids Res* 31:1805-12, and Belfort et al., (2002) in *Mobile DNA II*, pp. 761-783, Eds. Craigie et al., (ASM Press, Washington, D.C.).

Endonucleases also include meganucleases, also known as homing endonucleases (HEases), which like restriction endonucleases, bind and cut at a specific DSB target site, however the DSB target sites for meganucleases are typically longer, about 18 bp or more. Meganuclease domains, structure and function are known, see for example, Guhan and Muniyappa (2003) *Crit Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples a naturally occurring variant, and/or engineered derivative meganuclease is used. Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

TAL effector nucleases (also referred to as TALENs) can be used to make double-strand breaks at specific target sequences in the genome of a plant or other organism. TAL effector nucleases can be created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res*. (2010) doi:10.1093/nar/gkq704; and Miller et al. (2011) *Nature Biotechnology* 29:143-148; all of which are herein incorporated by reference.

CRISPR (clustered regularly interspaced short palindromic repeats) loci refers to certain genetic loci encoding factors of DNA cleavage systems, for example, used by bacterial and archaeal cells to destroy foreign DNA (Horvath and Barrangou, 2010, Science 327:167-170). A CRISPR locus can consist of a CRISPR array, comprising short direct repeats separated by short variable DNA sequences (called 'spacers'), which can be flanked by diverse Cas (CRISPR-associated) genes. Multiple CRISPR-Cas systems have been described including Class 1 systems, with multisubunit effector complexes, and Class 2 systems, with single protein effectors (such as but not limiting to Cas9, Cpf1, C2c1, C2c2, C2c3). (Zetsche et al., 2015, Cell 163, 1-13; Shmakov et al., 2015, *Molecular Cell* 60, 1-13; Makarova et al. 2015, Nature Reviews Microbiology Vol. 13:1-15). The type II CRISPR/Cas system from bacteria employs a crRNA (CRISPR RNA) and tracrRNA (trans-activating CRISPR RNA) to guide a Cas9 endonuclease to its DNA target. The crRNA contains a region complementary to one strand of the double strand DNA target and a region that base pairs with the tracrRNA (trans-activating CRISPR RNA) forming a RNA duplex that directs the Cas9 endonuclease to cleave the DNA target. CRISPR systems belong to different classes, with different repeat patterns, sets of genes, and species ranges. The number of CRISPR-associated genes at a given CRISPR locus can vary between species (Haft et al., 2005, Computational Biology, PLoS Comput Biol 1(6): e60. doi: 10.1371/journal.pcbi.0010060; Makarova et al. 2015, Nature Reviews Microbiology Vol. 13:1-15).

The term "Cas gene" herein refers to a gene that is generally coupled, associated or close to, or in the vicinity of flanking CRISPR loci. The terms "Cas gene", "CRISPR-associated (Cas) gene" are used interchangeably herein.

The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick).

As used herein, the term "guide polynucleotide", relates to a polynucleotide sequence that can form a complex with a Cas endonuclease (such as but not limited to a Cas9 endonuclease) and enables the Cas endonuclease to recognize and optionally cleave a DNA target site (U.S. Provisional Application No. 62/023,239, filed Jul. 11, 2014). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises of ribonucleic acids is also referred to as a "guide RNA". A guide RNA can include a fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides In one embodiment, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a cRNA or cRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a loop sequence, such as, but not limiting to a GAAA loop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

Polynucleotides of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for gene editing or transformation will change accordingly. Polynucleotides/polypeptides of interest include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition. More specific polynucleotides of interest include, but are not limited to, genes that improve crop yield, genes encoding polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms.

An herbicide resistance protein or a protein resulting from expression of an herbicide resistance-encoding nucleic acid molecule includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, 6,867,293, each of which is herein incorporated by reference.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) Eur. J. Biochem. 165:99-106, the disclosures of which are herein incorporated by reference.

Commercial traits can also be encoded on a polynucleotide of interest that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) J. Bacteriol. 170:5837-5847) facilitate expression of polyhyroxyalkanoates (PHAs).

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other agronomically important genes encode latex, Floury 2, growth factors, seed storage factors, and transcription factors. Polynucleotides that improve crop yield include dwarfing genes, such as Rht1 and Rht2 (Peng et al. (1999) Nature 400:256-261), and those that increase plant growth, such as ammonium-inducible glutamate dehydrogenase. Polynucleotides that improve desirability of crops include, for example, those that allow plants to have reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Polynucleotides/polypeptides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506, herein incorporated by reference. Additional sequences of interest include Chorismate Pyruvate Lyase (CPL) which refers to a gene encoding an enzyme which catalyzes the conversion of chorismate to pyruvate and pHBA. The most well characterized CPL gene has been isolated from E. coli and bears the GenBank accession number M96268. See, U.S. Pat. No. 7,361,811, herein incorporated by reference.

These polynucleotide sequences of interest may encode proteins involved in providing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or Bacillus thuringiensis endotoxins, protease inhibitors, collagenases, lectins, or glycosidases for controlling nematodes or insects are all examples of useful gene products. Genes encoding disease resistance traits include detoxification genes, such as against fumonosin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like.

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker. A phenotypic marker is a screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise inhibitory compounds including antibiotics, such as, spectinomycin, ampicillin, kanamycin, TET-repressor, acycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D).

Methods are provided herein for introducing a pollen-inhibitor gene in close proximity to a trait locus of interest in the genome of a progeny plant.

A trait locus of interest can be integrated into a target site by use of a double-strand-break (DSB) inducing agent. The DSB-inducing agent may be provided by any means known in the art. For example, the DSB-inducing agent can be provided via a polynucleotide encoding the nuclease. Such a polynucleotide encoding a nuclease can be modified to substitute codons having a higher frequency of usage in a plant, as compared to the naturally occurring polynucleotide sequence. The polynucleotide encoding the DSB-inducing agent can be modified to substitute codons having a higher frequency of usage in a maize or soybean plant, as compared to the naturally occurring polynucleotide sequence. A plant having the DSB target site in its genome can also be provided. The DSB-inducing agent may be transiently expressed or the polypeptide itself can be directly provided to the cell. Alternatively, a nucleotide sequence capable of expressing the DSB-inducing agent may be stably integrated into the genome of the plant. In the presence of the corresponding DSB target site and the DSB-inducing agent, a donor DNA comprising the trait of interest can be inserted into the plant's genome. Alternatively, the components of the system (double strand break inducing agent, DSB target site and donor DNA) may be brought together by sexually crossing transformed plants. Thus a sequence encoding the DSB-inducing agent and/or target site (and optionally a donor DNA comprising a trait of interest) can be sexually crossed to one another to allow each component of the system to be present in a single plant. The DSB-inducing agent may be under the control of a constitutive or inducible promoter. Such promoters of interest are discussed in further detail elsewhere herein. Examples of such double-strand-break inducing systems can be guide polynucleotide/Cas endonuclease systems described herein. See also U.S. patent application Ser. No. 14/463,687, filed Aug. 20, 2014, which is hereby incorporated in its entirety by reference.

As used herein, a "genomic region" is a segment of a chromosome in the genome of a plant cell that is present on either side of a target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the plant genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination.

The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

Homologous recombination includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events, the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) *Cell* 31:25-33; Shen and Huang, (1986) *Genetics* 112:441-57; Watt et al., (1985) *Proc. Natl. Acad. Sci. USA* 82:4768-72, Sugawara and Haber, (1992) *Mol Cell Biol* 12:563-75, Rubnitz and Subramani, (1984) *Mol Cell Biol* 4:2253-8; Ayares et al., (1986) *Proc. Natl. Acad. Sci. USA* 83:5199-203; Liskay et al., (1987) *Genetics* 115:161-7.

Once a single or double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) *DNA Repair* 5:1-12). The structural integrity of chromosomes is typically preserved by the repair, but deletions, insertions, or other rearrangements are possible (Siebert and Puchta, (2002) *Plant Cell* 14:1121-31; Pacher et al., (2007) *Genetics* 175:21-9).

Alternatively, the single or double-strand break can be repaired by homologous recombination between homologous DNA sequences. Once the sequence around the double-strand break is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) *Plant Cell* 16:342-52). Ectopic and/or epigenic DNA sequences may also serve as a DNA repair template for homologous recombination (Puchta, (1999) *Genetics* 152:1173-81).

DNA double-strand breaks appear to be an effective factor to stimulate homologous recombination pathways (Puchta et al., (1995) *Plant Mol Biol* 28:281-92; Tzfira and White, (2005) *Trends Biotechnol* 23:567-9; Puchta, (2005) *J Exp Bot* 56:1-14). Using DNA-breaking agents, a two- to nine-fold increase of homologous recombination was observed between artificially constructed homologous DNA repeats in plants (Puchta et al., (1995) *Plant Mol Biol* 28:281-92). In maize protoplasts, experiments with linear DNA molecules demonstrated enhanced homologous recombination between plasmids (Lyznik et al., (1991) *Mol Gen Genet* 230:209-18).

Once a double-strand break is introduced in the DSB target site by the DSB inducing agent, the first and second regions of homology of the donor DNA can undergo homologous recombination with their corresponding genomic regions of homology resulting in exchange of DNA between the donor and the genome. As such, the provided method results in the integration of the donor DNA (comprising for example a trait of interest or a polynucleotide of interest) into the double-strand break in the DSB target site in the plant genome (as described in U.S. patent application Ser. No. 14/463,687, filed Aug. 20, 2014, which is hereby incorporated in its entirety by reference.

The donor DNA may be introduced by any means known in the art. For example, the donor DNA may be provided transiently to a plant or plant cell by any method known in the art. The donor DNA may be provided by any transformation method known in the art including, for example, *Agrobacterium*-mediated transformation or biolistic particle bombardment. The donor DNA may be present transiently in the cell or it could be introduced via a viral replicon. In the presence of a DBS inducing agent and the DSB target site, the donor DNA can be inserted into the transformed plant's genome.

A trait locus of interest can also be integrated (introduced; inserted) into a target site (located proximal or distal to a telomere) by use of a site-specific integration (SSI) system discussed in further detail elsewhere herein. The site-specific recombination system employs various components which are described in detail below and in U.S. Pat. Nos. 6,187,994, 6,262,341, 6,331,661 and 6,300,545, each of which is herein incorporated by reference. A recombinase is provided that recognizes and implements recombination at the recombination sites of the transgenic SSI target site and the transfer cassette. The recombinase can be provided by any means known in the art and is described in detail elsewhere herein. The coding region of a transfer cassette can encode a recombinase that facilitates recombination between the first and the second recombination sites of the transfer cassette and the transgenic SSI target site, the second and the third recombination sites of the transfer cassette and the transgenic SSI target site, or the first and the third recombination sites of the transfer cassette and the transgenic SSI target site.

Methods for selecting plant cells with integration at the target site, such as selecting for cells expressing a trait of interest, a polynucleotide of interest, or a selectable marker, are known in the art.

As discussed above, various methods can be used to introduce a trait gene of interest and/or pollen-inhibitor genes into the genome of a plant or plant cell, thereby creating a plant having within a genomic window at least one trait locus of interest and/or a pollen-inhibitor gene integrated into a target site.

Non-limiting examples of various DNA constructs, transgenic SSI target sites, and transfer cassettes that can be used to insert a polynucleotide of interest into a plant or plant cell are described in PCT/US12/47202 application filed Jul. 18, 2012, incorporated by reference in its entirety herein. In short, once the trait gene of interest has integrated into the target site or once the pollen-inhibitor cassette has integrated into the target site, the appropriate selective agent can be employed to identify the plant cell having the desired DNA construct. Once a target site has been established within the genome, additional target sites may be introduced by incorporating such sites within the nucleotide sequence of the transfer cassette. Thus, once a SSI target site has been established, it is possible to subsequently add or alter sites through recombination or DSB technology. Such methods are described in detail in WO 99/25821, herein incorporated by reference.

Transformation protocols as well as protocols for introducing polypeptides or polynucleotide sequences into plants may vary depending on the type of plant or plant cell, i.e., monocot or dicot, targeted for transformation. By "stably incorporated" or "stably introduced" is intended the introduction of a polynucleotide into the plant such that the nucleotide sequence integrates into the genome of the plant and is capable of being inherited by progeny thereof. Any protocol may be used for the stable incorporation of the DNA constructs or the various components of the pollen-inhibitor system employed herein.

Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (*Longman*, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In other embodiments, any of the polynucleotides employed herein may be introduced into plants by contacting plants with a virus or viral nucleic acids. Generally, such methods involve incorporating a desired polynucleotide within a viral DNA or RNA molecule. It is recognized that a sequence employed in the methods or compositions provided herein may be initially synthesized as part of a viral polyprotein, which later may be processed by proteolysis in vivo or in vitro to produce the desired recombinant protein. Further, it is recognized that promoters employed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

The trait gene(s) of interest, color marker genes, and/or pollen-inhibitor gene(s) can be provided to a plant using a variety of transient transformation methods. "Transient transformation" is intended to mean that a polynucleotide is introduced into the host (i.e., a plant) and expressed temporally. Such transient transformation methods include, but are not limited to, the introduction of any of the components of the pollen-inhibitor system or active fragments or variants thereof directly into the plant or the introduction of the transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma #P3143).

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, transformed seed having the recited DNA construct stably incorporated into their genome is provided.

In specific embodiments, the transgenic SSI target site of the plant cell, plant, plant part and seed further comprises a third recombination site between the first and the second recombination site, wherein the third recombination site is dissimilar and non-recombinogenic to the first and the second recombination sites. The first, second, and third recombination sites can comprise, for example, FRT1, FRT5, FRT6, FRT12, FRT62 (described in US patent U.S. Pat. No. 8,318,493 issued on Nov. 27, 2012, herein incorporated by reference), or FRT87. Also, provided is a plant cell, plant, or seed wherein the first recombination site is FRT1, the second recombination site is FRT12 and the third recombination site is FRT87.

Plants, plant cells, or seeds having in their genome a genomic window comprising at least one trait locus and at least one pollen-inhibitor gene or a color marker gene provided herein are also encompassed.

Plants described herein include plants that comprise a trait locus that is flanked by a pollen-inhibitor gene on each side; plants that comprise a trait locus that is flanked by a color marker gene on each side, or plants that comprise a trait locus that is flanked by a color marker gene on one side and a pollen-inhibitor gene on the opposite side of the trait locus. The proximity of the pollen-inhibitor gene or color marker gene to the trait locus of interest can be about at least 0.05 cM, 0.1 cM, 0.2 cM, 0.3 cM, 0.4 cM, 0.5 cM, 0.6 cM, 0.7 cM, 0.8 cM, 0.9 cM, 1.0 cM, 1.1 cM, 1.2 cM, 1.3 cM, 1.4 cM, 1.5 cM, 1.6 cM, 1.7 cM, 1.8 cM, 1.9 cM, 2.0 cM, 2.1 cM, 2.2 cM, 2.3 cM, 2.4 cM, 2.5 cM, 2.6 cM, 2.7 cM, 2.8 cM, 2.9 cM, 3.0 cM, 3.1 cM, 3.2 cM, 3.3 cM, 3.4 cM, 3.5 cM, 3.6 cM, 3.7 cM, 3.8 cM, 3.9 cM, 4.0 cM or 5.0 cM.

In one embodiment the composition comprises a plant comprising at least one trait gene of interest, a first recombinant DNA construct comprising a color marker gene, and a second recombinant DNA construct comprising a second color marker gene, wherein said first recombinant DNA construct and said second recombinant DNA construct are genetically linked and flank said trait gene of interest.

In one embodiment the composition comprises a plant comprising at least one trait locus of interest and a recombinant DNA construct comprising a color marker gene, wherein said trait locus of interest and said color marker gene segregate independently from one another at a rate of about 10% to about 0.1%.

In one embodiment the composition comprises a plant comprising at least one trait locus of interest and a recombinant DNA construct comprising a pollen-inhibitor gene, wherein said trait locus of interest and said a pollen-inhibitor gene segregate independently from one another at a rate of about 10% to about 0.1%.

Compositions as described herein include plants wherein the first pollen-inhibitor gene (or color maker gene), the second pollen-inhibitor gene (or color maker gene) and the trait gene of interest are located within 0.05 cM, 0.1 cM, 0.2 cM, 0.3 cM, 0.4 cM, 0.5 cM, 0.6 cM, 0.7 cM, 0.8 cM, 0.9 cM, 1.0 cM, 1.1 cM, 1.2 cM, 1.3 cM, 1.4 cM, 1.5 cM, 1.6 cM, 1.7 cM, 1.8 cM, 1.9 cM, 2.0 cM, 2.1 cM, 2.2 cM, 2.3 cM, 2.4 cM, 2.5 cM, 2.6 cM, 2.7 cM, 2.8 cM, 2.9 cM, 3.0 cM, 3.1 cM, 3.2 cM, 3.3 cM, 3.4 cM, 3.5 cM, 3.6 cM, 3.7 cM, 3.8 cM, 3.9 cM, 4.0 cM or 5.0 cM of each other.

Compositions as described herein include plants wherein the first pollen-inhibitor gene and the second pollen-inhibitor is selected from the group consisting of barnase, alpha amylase, KID, or any combination thereof. Compositions as described herein include plants wherein the second pollen-inhibitor gene is selected from the group consisting a non-conditional gene, a conditional gene and an inducible gene.

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included herein, provided that these parts comprise the recited DNA construct.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

In certain embodiments of the disclosure, a fertile plant is a plant that produces viable male and female gametes and is self-fertile. Such a self-fertile plant can produce a progeny plant without the contribution from any other plant of a gamete and the genetic material contained therein. Other embodiments of the disclosure can involve the use of a plant that is not self-fertile because the plant does not produce male gametes, or female gametes, or both, that are viable or otherwise capable of fertilization. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male-fertile, respectively. It is further recognized that a male fertile (but female sterile) plant can produce viable progeny when crossed with a female fertile plant and that a female fertile (but male sterile) plant can produce viable progeny when crossed with a male fertile plant.

In one embodiment, the plant is a soybean or maize plant, wherein the genomic window described herein is not more than 0.1, 0.2, 0.3, 0.4, 0.5, 1, 2, 5, 10 cM in length.

In one embodiment the plant is a plant comprising at least one trait gene of interest, a first recombinant DNA construct comprising a first pollen-inhibitor gene, and a second recombinant DNA construct comprising a second pollen-inhibitor gene, wherein said first recombinant DNA construct and said second recombinant DNA construct are genetically linked and flank said trait gene of interest. The first pollen-inhibitor gene and the second pollen-inhibitor can be selected from the group consisting of barnase, alpha amylase, KID, coda or CYP105A, or any combination thereof. The second pollen-inhibitor gene can be, a non-conditional gene, a conditional gene and an inducible gene.

In one embodiment the plant is a plant comprising at least one trait locus of interest and a recombinant DNA construct comprising a pollen-inhibitor gene, wherein said trait locus of interest and said a pollen-inhibitor gene segregate independently from one another at a rate of about 10% to about 0.1%.

In one embodiment, the plant is a soybean or maize plant, wherein the genomic window comprises at least one transgene and at least one pollen-inhibitor gene, wherein the transgene confers a trait selected from the group consisting of herbicide tolerance, insect resistance, disease resistance, male sterility, site-specific recombination, abiotic stress tolerance, altered phosphorus, altered antioxidants, altered fatty acids, altered essential amino acids, altered carbohydrates, herbicide tolerance, insect resistance and disease resistance.

The trait gene(s) of interest, color marker gene(s), and/or pollen-inhibitor gene(s) described herein can be of used in any plant species, including, but not limited to, monocots and dicots. Examples of plant species of interest include, but are not limited to, corn (maize) (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tufipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed include, for example, pines such as loblolly pine (*Pinus taeda*), slash pine (*Pinus elliothi*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true first such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides provided herein also encompass all forms of sequences including, but not limited to, single-stranded forms, double-stranded forms, hairpins, stem-and-loop structures, and the like.

The compositions provided herein can comprise an isolated or substantially purified polynucleotide. An "isolated" or "purified" polynucleotide is substantially or essentially free from components that normally accompany or interact with the polynucleotide as found in its naturally occurring environment. Thus, an isolated or purified polynucleotide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

The terms "recombinant polynucleotide" and "recombinant DNA construct" are used interchangeably herein. A recombinant construct can comprise an artificial or heterologous combination of nucleic acid sequences, e.g., regulatory and coding sequences that are not found together in nature. For example, a transfer cassette can comprise restriction sites and a heterologous polynucleotide of interest. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments provided herein. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The trait gene(s) of interest, color marker gens, and/or pollen-inhibitor gene(s) described herein can be provided in an expression cassette for expression in a plant or other organism or cell type of interest. The cassette can include 5' and 3' regulatory sequences operably linked to a polynucleotide provided herein. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of a recombinant polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in plants. The regulatory regions (i.e., promoters, transcriptional regulatory regions, and translational termination regions) and/or a polynucleotide provided herein may be native/analogous to the host cell or to each other. Alternatively, the regulatory regions and/or a polynucleotide provided herein may be heterologous to the host cell or to each other. As used herein, "heterologous" in reference to a sequence is a sequence that originates from a foreign species, or, if from the same species, is substantially modified from its native form in composition and/or trait locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide, may be native with the plant host, or may be derived from another source (i.e., foreign or heterologous) to the promoter, the recombinant polynucleotide, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the expression cassettes provided herein. The promoters can be selected based on the desired outcome. It is recognized that different applications can be enhanced by the use of different promoters in the expression cassettes to modulate the timing, location and/or level of expression of the polynucleotide of interest. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

In some embodiments, an expression cassette provided herein can be combined with constitutive, tissue-preferred, or other promoters for expression in plants. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures for each of these are incorporated herein by reference in their entirety.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and TET repressoracycline-inducible and TET repressoracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of a polynucleotide of interest within a particular plant tissue. Tissue-preferred promoters are known in the art. See, for example, Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, for example, Simpson et al. (1958) *EMBO J* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing non-legume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see Plant Science (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. The phaseolin gene (Murai et al. (1983) *Science* 23:476-482 and Sengopta-Gopalen et al. (1988) *PNAS* 82:3320-3324.

The expression cassette containing the polynucleotides provided herein can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D) and sulfonylureas. Additional selectable markers include phenotypic markers such as beta-galactosidase and fluorescent proteins such as green fluorescent protein (GFP) (Su et al. (2004) *Biotechnol. Bioeng.* 85:610-9 and Fetter et al. (2004) *Plant Cell* 16:215-28), cyan fluorescent protein (CYP) (Bolte et al. (2004) *J. Cell Science* 117:943-54 and Kato et al. (2002) *Plant Physiol.* 129:913-42), and yellow fluorescent protein (PhiYFP™ from Evrogen; see, Bolte et al. (2004) *J. Cell Science* 117:943-54). Such disclosures are herein incorporated by reference. The above list of selectable marker genes is not meant to be limiting. Any selectable marker gene can be used in the compositions presented herein.

Where appropriate, the sequences employed in the methods and compositions (i.e., the polynucleotide of interest, the recombinase, the endonuclease, etc.) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Fragments and variants of the various components of the DSB-inducing-agent system, such as for example the guide polynucleotide/Cas endonuclease system and the site-specific integration system (transgenic SSI target site, a donor DNA, a transfer cassette, various site-specific recombination sites, site-specific recombinases, polynucleotides of interest or any active variants or fragments thereof) are also encompassed herein. By "fragment" is intended a portion of the polynucleotide or a portion of the amino acid sequence and hence protein encoded thereby. Fragments of a polynucleotide may encode protein fragments that retain the biological activity of the native protein (i.e., a fragment of a recombinase implements a recombination event). As used herein, a "native" polynucleotide or polypeptide comprises a naturally occurring nucleotide sequence or amino acid sequence, respectively. Thus, fragments of a polynucleotide may range from at least about 20 nucleotides, about 50 nucleotides, about 100 nucleotides, and up to the full-length polynucleotide. A fragment of a polynucleotide that encodes a biologically active portion of a protein employed in the methods or compositions will encode at least 15, 25, 30, 50, 100, 150, 200, or 250 contiguous amino acids, or up to the total number of amino acids present in a full-length protein. Alternatively, fragments of a polynucleotide that are useful as a hybridization probe generally do not encode fragment proteins retaining biological activity. Thus, fragments of a nucleotide sequence may range from at least about 10, 20, 30, 40, 50, 60, 70, 80 nucleotides or up to the full length sequence.

A biologically active portion of a polypeptide can be prepared by isolating a portion of one of the polynucleotides encoding the portion of the polypeptide of interest and expressing the encoded portion of the protein (e.g., by recombinant expression in vitro), and assessing the activity of the portion of the polypeptide. For example, polynucleotides that encode fragments of a recombinase polypeptide can comprise nucleotide sequence comprising at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a nucleotide sequence employed in the methods and compositions provided herein.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. For polynucleotides, conservative variants include those sequences that, because of the degeneracy of the genetic code, encode the amino acid sequence of one of the polypeptides employed in the compositions and methods provided herein. Naturally occurring allelic variants such as these, or naturally occurring allelic variants of polynucleotides can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis. Generally, variants of a particular polynucleotide employed in the methods and compositions provided herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide employed in the methods and compositions provided herein (trait gene(s) of interest and/or pollen-inhibitor gene(s), recombinases, nucleases) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide are disclosed. Percent sequence identity between any two polypeptides can be calculated using sequence alignment programs and parameters described elsewhere herein. Where any given pair of polynucleotides provided herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins employed in the methods and compositions provided herein are biologically active, that is they continue to possess the desired biological activity of the native protein. Such variants may result from, for example, genetic polymorphism or from human manipulation. Biologically active variants of a native protein provided herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein provided herein may differ from that protein by as few as 1-15 amino acid residues, as few as 1-10, such as 6-10, as few as 5, as few as 4, 3, 2, or even 1 amino acid residue.

Proteins may be altered in various ways including amino acid substitutions, deletions, truncations, and insertions. Methods for such manipulations are generally known in the art. For example, amino acid sequence variants of the recombinase proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the polynucleotides used herein can include the naturally occurring sequences, the "native" sequences, as well as mutant forms. Likewise, the proteins used in the methods provided herein encompass both naturally occurring proteins as well as variations and modified forms thereof. Obviously, the mutations that will be made in the polynucleotide encoding the variant polypeptide must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

Variant polynucleotides and proteins also encompass sequences and proteins derived from a mutagenic and recombinogenic procedure such as DNA shuffling. With such a procedure, for example, one or more different recombinase coding sequences can be manipulated to create a new recombinase protein possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347;

Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The following terms are used to describe the sequence relationships between two or more nucleic acids or polynucleotides. As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Sequence relationships can be analyzed and described using computer-implemented algorithms. The sequence relationship between two or more polynucleotides, or two or more polypeptides can be determined by determining the best alignment of the sequences, and scoring the matches and the gaps in the alignment, which yields the percent sequence identity, and the percent sequence similarity. Polynucleotide relationships can also be described based on a comparison of the polypeptides each encodes. Many programs and algorithms for the comparison and analysis of sequences are well-known in the art.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79, 80%, 81%, 82%, 83%, 84%, 85%, 86%, 87%, 88%, 89%, 90%, 91%, 92%, 93%, 94%, 95%, 96%, 97%, 98% or 99%.

Sequence identity/similarity values can also be obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff (1989) *Proc. Natl. Acad. Sci USA* 89:10915); or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold.

As used herein, "breeding" is the genetic manipulation of living organisms. Plants are bred through techniques that take advantage of the plant's method of pollination. A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. In a breeding application, a breeder initially selects and crosses two or more parental plants. As used herein, "crossing" can refer to a simple X by Y cross, or the process of backcrossing, depending on the context.

The introduction of transgenes (transgenic trait of interest) into many major crops is typically performed in a single plant variety that is most amenable to the transformation, tissue culture and regeneration processes. For example, in corn, the readily transformable genotype referred to Hi-II (Armstrong and Green, 1985, 1985, Planta 164(2): 207-214) has been used for many years across the industry for genetic transformation. However, the agronomic characteristics of this genotype are not commercially desirable, so once a transgenic trait locus (genomic locus where transgene has integrated into the plant genome) has been created, the transgenic trait locus must be introgressed from Hi-II into commercially relevant inbreds. Introgression, also known as introgressive hybridization, refers to The movement of a gene (gene flow) from one species into the gene pool of another, which can be accomplished by repeated backcrossing of an interspecific hybrid with one of its parent species.

A transgenic inbred (A) can be crossed to a non-transgenic inbred (B) in order to introgress (or transfer) the transgenic trait into the new germplasm by repeated backcrossing to the recurrent parent (B). The result of the first cross between inbred A and inbred B is the F1 hybrid. The F1 hybrid can then be used as the pollen donor to again cross with the recurrent parent (inbred B) to produce the first backcross generation (the BC1 generation). Successive backcrosses can be performed until the majority of genetic material from the original inbred A has been lost through meiotic recombination and segregation, leaving the transgenic locus in the new inbred background.

Commercial corn seed companies typically work with hundreds of inbreds in different heterotic groups, and thus the transgenic trait locus must be introgressed into numerous inbreds for further efficacy testing—a process that can take up to many successive generations to completely eliminate as much of the undesired germplasm (such as for example the Hi-II germplasm in maize) as possible. A major impediment in the introgression process is identifying progeny in successive crosses in which meiotic recombination has occurred in close proximity on either side of the transgenic locus, replacing as much of the flanking undesired germplasm chromosome with the new inbred chromosome. To identify progeny where closely-spaced (such as but not limited to less than 0-1 cM, 0-2 cM, 0-3 cM, 0-4 cM, 0-5 cM, 0-6 cM, 0-7 cM, 0-8 cM, 0-9 cM, 0-10 cM, 1-1 cM, 1-2 cM, 1-3 cM, 1-4 cM, 1-5 cM, 1-6 cM, 1-7 cM, 1-8 cM, 1-9 cM, 1-10 cM) meiotic recombination on either side of a transgenic locus has occurred a molecular screening using genetic markers can be used thereby adding more work and cost to each generation of screening. In addition, for certain crop species which naturally self-pollinate such as soybean, making crosses through emasculation and hand-pollination on the scale needed in order to identify low-frequency recombination events is extremely labor intensive.

In order to accelerate the introgression process (also referred to as "Accelerated Trait Introgression" and greatly reduce the labor involved, a (screening) method that selects for recombination in the gametes would be of great benefit. One method of accomplishing such as screen is to position a gamete-specific inhibitor gene (or gamete inhibitor gene) in close proximity to the transgenic locus of interest. One can also position at least one color marker gene in close proximity of a trait locus of interest, in combination with or without a pollen-inhibitor gen as described herein. Described herein are compositions and methods to position a pollen-inhibitor gene and/or a color marker in close proximity to a trait locus of interest in the genome of a progeny plant. As described herein the trait locus can be flanked by a pollen-inhibitor gene on each side, a color maker gene on each side, or a combination of a color marker gene and a pollen-inhibitor gene. The proximity of the pollen-inhibitor gene or color marker gene to the trait locus of interest can be about at least 0.05 cM, 0.1 cM, 0.2 cM, 0.3 cM, 0.4 cM, 0.5 cM, 0.6 cM, 0.7 cM, 0.8 cM, 0.9 cM, 1.0 cM, 1.1 cM, 1.2 cM, 1.3 cM, 1.4 cM, 1.5 cM, 1.6 cM, 1.7 cM, 1.8 cM, 1.9 cM, 2.0 cM, 2.1 cM, 2.2 cM, 2.3 cM, 2.4 cM, 2.5 cM, 2.6 cM, 2.7 cM, 2.8 cM, 2.9 cM, 3.0 cM, 3.1 cM, 3.2 cM, 3.3 cM, 3.4 cM, 3.5 cM, 3.6 cM, 3.7 cM, 3.8 cM, 3.9 cM, 4.0 cM or 5.0 cM Compositions and methods are provided herein for the use of pollen-inhibitor genes and/or color maker genes in accelerated trait introgression.

In one embodiment, the method comprises a method of accelerated trait introgression in the genome of a plant, the method comprising: (a) providing a first plant having within a genomic window at least one trait of interest located proximal to a telomere, and at least one pollen-inhibitor gene located proximal to both the telomere and the trait of interest, wherein said trait of interest and said pollen-inhibitor gene are genetically linked in said genomic window, wherein said genomic window is about 5 cM in length and located within 10 cM of the telomere; (b) cross pollinating the first plant of (a) with pollen from a second plant; and, (c) selecting a progeny plant from step (b) comprising said trait of interest and said pollen-inhibitor gene; and, (d) optionally, backcrossing the progeny plant of (c) as the pollen donor onto a recurrent parent plant and selecting progeny plants comprising the trait of interest.

In one embodiment, the method comprises a method of accelerated trait introgression in the genome of a plant, the method comprising: (a) providing a first plant having within a genomic window at least one trait of interest located proximal to a telomere, and at least one color marker gene located proximal to both the telomere and the trait of interest, wherein said trait of interest and said color marker gene are genetically linked in said genomic window, wherein said genomic window is about 5 cM in length and located within 10 cM of the telomere; (b) cross pollinating the first plant of (a) with pollen from a second plant; and, (c) selecting a progeny plant from step (b) comprising said trait of interest site and said color marker gene; and, (d) optionally, backcrossing the progeny plant of (c) as the pollen donor onto a recurrent parent plant and selecting progeny plants comprising the trait of interest.

In one embodiment, the method comprises a method of accelerated trait introgression in the genome of a plant comprising: (a) providing a first plant having within a genomic window at least one trait of interest, a first pollen-inhibitor gene, and a second pollen-inhibitor gene wherein said genomic window is about 5 cM in length, and wherein said trait of interest is flanked by said first and second pollen-inhibitor gene; (b) cross-pollinating the first plant of (a) with pollen from a second plant; and, (c) selecting a progeny plant from step (b) comprising said first pollen-inhibitor gene, said trait of interest, and said second pollen-inhibitor gene; and, (d) optionally, cross pollinating the progeny plant from step (c) to a recurrent parent plant and selecting progeny plants comprising the trait of interest.

In one embodiment, the method comprises a method of accelerated trait introgression in the genome of a plant comprising: (a) providing a first plant having within a genomic window at least one trait of interest, a pollen-inhibitor gene and a color marker gene, wherein said genomic window is about 5 cM in length, and wherein trait of interest is flanked by said first and second pollen-inhibitor gene; (b) cross-pollinating the first plant of (a) with pollen from a second plant; and, (c) selecting a progeny plant from step (b) comprising said first pollen-inhibitor gene, said trait of interest, and said second pollen-inhibitor gene; and, (d) optionally, cross pollinating the progeny plant from step (c) to a recurrent parent plant and selecting progeny plants comprising the trait of interest.

In one embodiment, the method comprises a method accelerated trait introgression in the genome of a plant comprising: (a) providing a first plant having within a genomic window at least one trait of interest and at least a first color marker gene integrated into a first target site, a second color marker gene integrated into a second target site for, wherein said genomic window is about 5 cM in length, and wherein trait of interest is flanked by said first and second pollen-inhibitor gene; (b) cross-pollinating the first plant of (a) with pollen from a second plant; and, (c) selecting a progeny plant from step (b) comprising said first pollen-inhibitor gene, said trait of interest, and said second pollen-inhibitor gene; and, (d) optionally, cross pollinating the progeny plant from step (c) to a recurrent parent plant and selecting progeny plants comprising the trait of interest.

The location of the trait locus can determine how many pollen-inhibitor loci (or color marker loci) are introduced and where the pollen-inhibitor or color marker loci are positioned. If the trait locus is in close proximity (such as but not limited to less than 0-1 cM, 0-2 cM, 0-3 cM, 0-4 cM, 0-5 cM, 0-6 cM, 0-7 cM, 0-8 cM, 0-9 cM, 0-10 cM, 1-1 cM, 1-2 cM, 1-3 cM, 1-4 cM, 1-5 cM, 1-6 cM, 1-7 cM, 1-8 cM, 1-9 cM, 1-10 cM) to a telomere (near the end of the chromosome), only a single pollen-inhibitor locus, located just proximal to the trait locus of interest (i.e. 0.5 to 1.0 cM closer to the centromere) is required. As described in Example 1 and illustrated in FIG. 1, expression cassettes comprising a pollen-inhibitor gene (such as, but not limited to, barnase or alpha amylase) can be introduced just proximal to a trait locus near the telomere. By propagating the pollen-inhibitor locus through the female during sexual crosses, linkage between the trait and the AA1-inhibitor can be established. These plants (labeled "A") containing the linked loci can now be crossed to any inbred "B" to create an F1 hybrid. F1 seed are planted and the F1 plants are now used as the pollen source back to the recurrent inbred parent "B". After taking advantage of the herbicide resistance expression cassette within the trait locus to select against any progeny that were derived from wild-type pollen, only progeny in which the linkage has been broken during meiosis will be viable and all viable progeny will contain just the telomeric segment with the trait locus from the original inbred (A) while the majority of the chromosome is all from parent B. In this manner, selection for accelerated introgression of a trait locus from inbred A into the new chromosome from inbred B has been successfully accomplished.

For trait loci in internal (for example, in non-telomeric locations (more toward the centromere of the chromosome), two flanking pollen-inhibitor loci located one on either side of the trait locus can be used (as described in Example 2). As described in Example 2 and illustrated in FIG. 2, when the transgenic plants carrying the pollen-inhibitor gene are produced, these two loci must be linked through conventional crossing to the trait locus requiring that at least one of the pollen-inhibitor loci must be able to produce pollen in order to make the 3-way linkage. During this time, either expression of the inhibitor gene must be off or the inhibitor must be inactivated by another protein (a maintainer). After the triple-linked inbred line is crossed to the 100 inbreds of interest (producing 100 F1 populations) the pollen-inhibitor must now be on. Various technical approaches can be used to accomplish this, including the use of a bacterial inhibitor/anti-inhibitor combination (for example barnase/barstar), using an inducible inhibitor, use of a repressor protein (with no chemical induction), use of inteins to switch on the pollen screen, and use of a double haploid step with all of the above strategies. Inhibitor/anti inhibitor systems useful for gamete inhibition include, but are not limited to barnase/barstar, kid/kis and numerous other well-characterized bacterial inhibitors (Finbarr Hayes, 2003, Science 301:1496-1499; Yamaguchi et al., 2011, Ann. Rev. Gent. 45:61-79). Conditionally-lethal genes such as the codA gene can also be used.

Another alternative for setting up three linked loci without the use of a maintainer, while also obviating the need for conventional breeding methods to establish the linkage, is to use CRISPR-mediated introduction of the pollen-inhibitors directly into the flanking sites in a chromosome that already contains the trait locus. For pollen inhibition, the alpha-amylase gene can be particularly useful, since the breakdown of starch by the expressed protein renders the pollen incapable of forming a pollen tube.

Methods are provided for introducing a pollen-inhibitor gene in close proximity to a trait locus of interest in the genome of a progeny plant using breeding techniques. For example, a first plant having within a genomic window at least one trait locus of interest integrated into a first target site located proximal to a telomere, wherein said genomic window is about 10 cM in length and located within 10 cM of the telomere, wherein said first plant does not comprise a pollen-inhibitor gene; can be crossed with a second plant, wherein said second plant comprises in said genomic window a pollen-inhibitor gene integrated into a second target site located distal to the telomere, wherein said second plant does not comprise said first target site. A progeny plant in then selected comprising said trait locus of interest and said pollen-inhibitor gene, wherein said trait locus of interest and said pollen-inhibitor gene are genetically linked. Selecting a progeny plant comprising both the trait locus of interest and the pollen-inhibitor gene can be done through various methods. For example, a phenotypic analysis can be performed whereby the activity of the trait of interest or said pollen-inhibitor is detected in the progeny plant. Alternative methods that assay for the presence of said trait locus of interest and said pollen-inhibitor gene which are specific to the said trait locus of interest and said pollen-inhibitor gene include techniques such as PCR, hybridization, Isozyme electrophoresis, Restriction Fragment Length Polymorphisms (RFLPs), Randomly Amplified Polymorphic DNAs (RAPDs), Arbitrarily Primed PCR (AP-PCR), DNA Amplification Fingerprinting (DAF), Sequence Characterized Amplified Regions (SCARs), Amplified Fragment length Polymorphisms (AFLPs), Simple Sequence Repeats (SSRs), and Single Nucleotide Polymorphisms (SNPs).

The meaning of abbreviations is as follows: "sec" means second(s), "min" means minute(s), "h" means hour(s), "d" means day(s), "A" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

Non-limiting examples of compositions and methods disclosed herein are as follows:

1. A method for introducing a pollen-inhibitor gene in close proximity to a trait locus of interest in the genome of a progeny plant, said method comprising:
   (a) providing a first plant having within a genomic window at least one trait gene of interest integrated into a first target site located proximal to a telomere, wherein said genomic window is about 10 cM in length, wherein said first plant does not comprise a pollen-inhibitor gene;
   (b) breeding to said first plant a second plant, wherein said second plant comprises in said genomic window a pollen-inhibitor gene integrated into a second target site located proximal to both the telomere and the trait gene of interest of (a); and,
   (c) selecting a progeny plant from step (b) comprising said trait gene of interest and said pollen-inhibitor gene, wherein said trait gene of interest and said pollen-inhibitor gene are genetically linked.

2. A method for introducing two pollen-inhibitor genes in close proximity to a trait locus of interest in the genome of a progeny plant, said method comprising:
   (a) providing a first plant having within a genomic window a first pollen-inhibitor gene integrated into a first target site, wherein said genomic window is about 10 cM in length;
   (b) breeding to said first plant a second plant having a trait gene of interest integrated into a second target site within said genomic window;
   (c) selecting a progeny plant from step (b) comprising said first pollen-inhibitor gene and said trait gene of interest in said genomic widow;
   (d) providing a third plant having a second pollen-inhibitor gene integrated into a third target site within said genomic window;
   (e) breeding to said third plant a fourth plant, wherein said fourth plant comprises a pollen-inhibitor maintainer (PIM) gene;
   (f) selecting a progeny plant from step (e) comprising said second pollen-inhibitor gene and said pollen-inhibitor maintainer (PIM) gene; and,
   (g) cross pollinating the progeny plant of (c) with the progeny plant of (f) and selecting for a progeny plant that comprises said first pollen-inhibitor gene said trait gene of interest and said second pollen-inhibitor gene, wherein said first pollen-inhibitor gene, said trait gene of interest and said second pollen-inhibitor gene are genetically linked.

3. The method of embodiments 1-2, wherein the first target site and the second target site is selected from the group consisting of a recombinase target site, a transgenic SSI target site, a single-strand-break-inducing-agent target site, and a double-strand-break-inducing-agent target site, or any one combination thereof.

4. The method of embodiments 1-2, wherein the double-strand-break-inducing-agent target site is a target site for an agent selected from the group of a Cas9 endonuclease, a zinc-finger nuclease, a Tal Effector nuclease (TALEN), a meganuclease, and an engineered endonuclease.

5. A method for introducing a pollen-inhibitor gene and a color marker gene in close proximity to a trait locus of interest in the genome of a plant, said method comprising:
   (a) providing a first plant having a trait of interest located within a genomic window, wherein said genomic window is about 10 cM in length;
   (b) introducing into said genomic window of the plant of (a) a color marker gene;
   (c) breeding to the plant of (b) a second plant, wherein said second plant is a haploid inducer line capable of producing haploid embryos;
   (d) selecting haploid embryos from the plant of (c) and introducing into said haploid embryos, a pollen-inhibitor gene; and,
   (e) producing a double haploid plant from the haploid embryo of (d).

6. A method for introducing two color marker genes in close proximity to a trait locus of interest in the genome of a plant, said method comprising:
   (a) providing a first plant having a trait of interest located within a genomic window, wherein said genomic window is about 10 cM in length;

(b) introducing into said genomic window of the plant of (a) a color marker gene;

(c) breeding to the plant of (b) a second plant, wherein said second plant is a haploid inducer line capable of producing haploid embryos;

(d) selecting haploid embryos from the plant of (c) and introducing into said haploid embryos, a second color marker gene; and, (e) producing a double haploid plant from the haploid embryo of (d).

7. The method of embodiments 5-6, wherein color marker or the pollen-inhibitor gene are introduced into a target site of a double-strand-break-inducing-agent target site.

8. A method of accelerated trait introgression in the genome of a plant, the method comprising:
   (a) providing a first plant having within a genomic window at least one trait of interest located proximal to a telomere, and at least one pollen-inhibitor gene located proximal to both the telomere and the trait of interest, wherein said trait of interest and said pollen-inhibitor gene are genetically linked in said genomic window, wherein said genomic window is about 5 cM in length and located within 10 cM of the telomere;
   (b) cross pollinating the first plant of (a) with pollen from a second plant; and,
   (c) selecting a progeny plant from step (b) comprising said trait of interest and said pollen-inhibitor gene; and,
   (d) optionally, backcrossing the progeny plant of (c) as the pollen donor onto a recurrent parent plant and selecting progeny plants comprising the trait of interest.

9. A method of accelerated trait introgression in the genome of a plant, the method comprising:
   (a) providing a first plant having within a genomic window at least one trait of interest located proximal to a telomere, and at least one color marker gene located proximal to both the telomere and the trait of interest, wherein said trait of interest and said color marker gene are genetically linked in said genomic window, wherein said genomic window is about 5 cM in length and located within 10 cM of the telomere;
   (b) cross pollinating the first plant of (a) with pollen from a second plant; and,
   (c) selecting a progeny plant from step (b) comprising said trait of interest site and said color marker gene; and,
   (d) optionally, backcrossing the progeny plant of (c) as the pollen donor onto a recurrent parent plant and selecting progeny plants comprising the trait of interest.

10. A method of accelerated trait introgression in the genome of a plant comprising:
    (a) providing a first plant having within a genomic window at least one trait of interest, a first pollen-inhibitor gene, and a second pollen-inhibitor gene wherein said genomic window is about 5 cM in length, and wherein said trait of interest is flanked by said first and second pollen-inhibitor gene;
    (b) cross-pollinating the first plant of (a) with pollen from a second plant; and,
    (c) selecting a progeny plant from step (b) comprising said first pollen-inhibitor gene, said trait of interest, and said second pollen-inhibitor gene; and,
    (d) optionally, cross pollinating the progeny plant from step (c) to a recurrent parent plant and selecting progeny plants comprising the trait of interest.

11. A method of accelerated trait introgression in the genome of a plant comprising:
    (a) providing a first plant having within a genomic window at least one trait of interest, a pollen-inhibitor gene and a color marker gene, wherein said genomic window is about 5 cM in length, and wherein trait of interest is flanked by said first and second pollen-inhibitor gene;
    (b) cross-pollinating the first plant of (a) with pollen from a second plant; and,
    (c) selecting a progeny plant from step (b) comprising said first pollen-inhibitor gene, said trait of interest, and said second pollen-inhibitor gene; and,
    (d) optionally, cross pollinating the progeny plant from step (c) to a recurrent parent plant and selecting progeny plants comprising the trait of interest.

12. A method of accelerated trait introgression in the genome of a plant comprising:
    (a) providing a first plant having within a genomic window at least one trait of interest and at least a first color marker gene integrated into a first target site, a second color marker gene integrated into a second target site for, wherein said genomic window is about 5 cM in length, and wherein trait of interest is flanked by said first and second pollen-inhibitor gene;
    (b) cross-pollinating the first plant of (a) with pollen from a second plant; and,
    (c) selecting a progeny plant from step (b) comprising said first pollen-inhibitor gene, said trait of interest, and said second pollen-inhibitor gene; and,
    (d) optionally, cross pollinating the progeny plant from step (c) to a recurrent parent plant and selecting progeny plants comprising the trait of interest.

13. A method for introducing a pollen-inhibitor gene in close proximity to a trait locus of interest in the genome of a progeny plant, said method comprising:
    (a) providing a first plant having within a genomic window at least a first transgenic SSI target site located proximal to a telomere, wherein said first transgenic SSI target site comprises at least one trait gene of interest, wherein said genomic window is about 5 cM in length and located within 0.1 cM to 100 cM of the telomere, and wherein said first plant does not comprise a pollen-inhibitor gene;
    (b) breeding to said first plant a second plant, wherein said second plant comprises in said genomic window a second transgenic SSI target site located proximal to both the telomere and the trait gene of interest, wherein said second transgenic SSI target site comprises a pollen-inhibitor gene, wherein said second plant does not comprise said first transgenic target site; and,
    (c) selecting a progeny plant from step (b) comprising said trait gene of interest and said pollen-inhibitor gene, wherein said trait gene of interest and said pollen-inhibitor gene are genetically linked in said genomic window.

14. A method of accelerated trait introgression in the genome of a plant, the method comprising:
    (a) providing a first progeny plant having within a genomic window at least a first transgenic SSI target site located proximal to a telomere and a second transgenic SSI target site located proximal to both the telomere and the trait gene of interest, wherein said first transgenic SSI target site comprises at least one trait gene of interest, wherein said second transgenic SSI target site comprises a pollen-inhibitor gene, wherein said first transgenic target site and said pollen-inhibitor gene are genetically linked in said genomic window, wherein said genomic window is about 5 cM in length and located within 10 cM of the telomere;
(b) cross pollinating the first plant of (a) with pollen from a second plant (elite inbred); and,
(c) selecting a progeny plant from step (b) comprising said first transgenic target site and said pollen-inhibitor gene;

15. The method of embodiment 8, further comprising:
(d) backcrossing the progeny plant of (c) as the pollen donor onto a recurrent parent plant and selecting progeny plants comprising the trait gene of interest.

16. The method of any one of embodiments 13-14, wherein the pollen-inhibitor gene is selected from the group consisting of barnase, alpha amylase and KID.

17. The method of anyone of embodiments 13-14 wherein the trait gene of interest is selected from the group consisting of a selectable marker, a modified or edited native gene, a transgene, an altered double-strand-break target site, a native gene, or a transgenic SSI target site.

18. The method of anyone of embodiments 13-14, wherein the trait gene of interest and the pollen-inhibitor gene are genetically linked and located within 0.5 cM to 1 cM from each other.

19. A method for introducing two pollen-inhibitor genes in close proximity to a trait locus of interest in the genome of a progeny plant, said method comprising:
(a) providing a first plant having within a genomic window at least a first transgenic SSI target site, wherein said first transgenic SSI target site comprises a first pollen-inhibitor gene, wherein said genomic window is about 5 cM in length;
(b) breeding to said first plant a second plant, wherein said second plant comprises in said genomic window a second transgenic SSI target site, wherein said second transgenic SSI target site comprises at least one trait gene of interest wherein said second plant does not comprise said first transgenic target site;
(c) selecting a progeny plant from step (b) comprising said first transgenic target site and said second transgenic target site genetically linked in said genomic widow;
(d) providing a third plant having within said genomic window at least a third transgenic SSI target site and a pollen-inhibitor maintainer (PIM), wherein said third transgenic SSI target site comprises a second pollen-inhibitor gene; and,
(e) using the third plant of step (d) to pollinate the plant of step (c) and selecting a progeny plant wherein said first transgenic SSI target site, said second transgenic SSI target site, and said third transgenic SSI target site are genetically linked to each other 20. A method of accelerated trait introgression in the genome of a plant comprising:
(a) providing a first plant having a pollen-inhibitor maintainer gene and a genomic window, wherein said genomic window is about 5 cM in length and wherein said genomic window comprises at least a first transgenic SSI target site, a second transgenic SSI target site and a third transgenic SSI target site, wherein said first transgenic SSI target site comprises a first pollen-inhibitor gene, wherein said second transgenic SSI target site comprises at least one trait gene of interest, wherein said third transgenic SSI target site comprises a second pollen-inhibitor gene, wherein said second transgenic target site is flanked by said first transgenic SSI target site and said third transgenic SSI target site;
(b) cross-pollinating the first plant of (a) with pollen from a second plant; and,
(c) selecting a progeny plant from step (b) comprising said first transgenic target site, said second transgenic target site and said third transgenic target site.

21. The method of embodiment 20, further comprising cross pollinating the progeny plant from step (c) to a recurrent parent plant and selecting progeny plants by exposing germinating seedlings to said selectable marker.

22. A method of accelerated trait introgression in the genome of a plant comprising:
(a) providing a first plant having within a genomic window a trait of interest and at least a first pollen-inhibitor gene integrated into a first target site for a Cas9 endonuclease, a second pollen-inhibitor gene integrated into a second target site for a Cas9 endonuclease, wherein said genomic window is about 5 cM in length, and wherein trait of interest is flanked by said first and second pollen-inhibitor gene;
(b) cross-pollinating the first plant of (a) with pollen from a second plant; and,
(c) selecting a progeny plant from step (b) comprising said first pollen-inhibitor gene, said trait of interest, and said second pollen-inhibitor gene;

23. The method of embodiment 22, further comprising cross pollinating the progeny plant from step (c) to a recurrent parent plant and selecting progeny plants by exposing germinating seedlings to said selectable marker.

24. A method for introducing two pollen-inhibitor genes in close proximity to a trait gene of interest in the genome of a progeny plant, said method comprising:
(a) providing a first plant having within a genomic window at least a first transgenic SSI target site, wherein said first transgenic SSI target site comprises at least one trait gene of interest, wherein said genomic window is about 5 cM in length;
(b) introducing into the plant of (a) a first pollen-inhibitor gene, wherein said first pollen-inhibitor gene is genetically linked to said trait gene of interest
(c) selecting a progeny plant from (b) comprising the pollen-inhibitor gene genetically linked to the trait gene of interest.
(d) breeding to said progeny plant of (c) a haploid-inducer plant and producing haploid immature embryos.
(e) introducing into the haploid immature embryos of (d) a second pollen-inhibitor gene linked to said trait gene of interest and said first pollen-inhibitor gene, wherein the trait gene of interest is flanked by the first and second pollen-inhibitor gene; and,
(f) producing a homozygous plant from the haploid immature embryo of (e);

25. A method of accelerated trait introgression in the genome of a plant comprising
(a) providing a first plant having a genomic window comprising a trait gene of interest flanked by and genetically linked to a first pollen-inhibitor gene and a second pollen-inhibitor gene, wherein said genomic window is about 5 cM in length;
(b) cross pollinating the first plant of (a) with pollen from a second plant; and,
(c) selecting a progeny plant from step (b) comprising said trait gene of interest flanked by and genetically linked to said first pollen-inhibitor gene and said second pollen-inhibitor gene.

26. The method of embodiment 25 further comprising cross-pollinating the progeny plant from step (c) to a recurrent parent plant and selecting progeny plants by exposing germinating seedlings to said selectable marker.
27. A plant comprising at least one trait gene of interest, a first recombinant DNA construct comprising a first pollen-inhibitor gene, and a second recombinant DNA construct comprising a second pollen-inhibitor gene, wherein said first recombinant DNA construct and said second recombinant DNA construct are genetically linked and flank said trait gene of interest.
28. A plant comprising at least one trait locus of interest and a recombinant DNA construct comprising a pollen-inhibitor gene, wherein said trait locus of interest and said a pollen-inhibitor gene segregate independently from one another at a rate of about 10% to about 0.1%.
29. The plant of embodiment 27, wherein the first pollen-inhibitor gene, the second pollen-inhibitor gene and the trait gene of interest are located within 5 cM of each other.
30. The plant of embodiment 27, wherein the first pollen-inhibitor gene and the second pollen-inhibitor is selected from the group consisting of barnase, alpha amylase, KID, or any combination thereof
31. The plant of embodiment 27, wherein the second pollen-inhibitor gene is selected from the group consisting a non-conditional gene, a conditional gene and an inducible gene.
32. A plant comprising at least one trait gene of interest, a first recombinant DNA construct comprising a color marker gene, and a second recombinant DNA construct comprising a second color marker gene, wherein said first recombinant DNA construct and said second recombinant DNA construct are genetically linked and flank said trait gene of interest.
33. A plant comprising at least one trait locus of interest and a recombinant DNA construct comprising a color marker gene, wherein said trait locus of interest and said color marker gene segregate independently from one another at a rate of about 10% to about 0.1%.
34. The plant of embodiment 33, wherein the first color marker gene, the second color marker gene and the trait gene of interest are located within 5 cM of each other.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1

Figure 1:
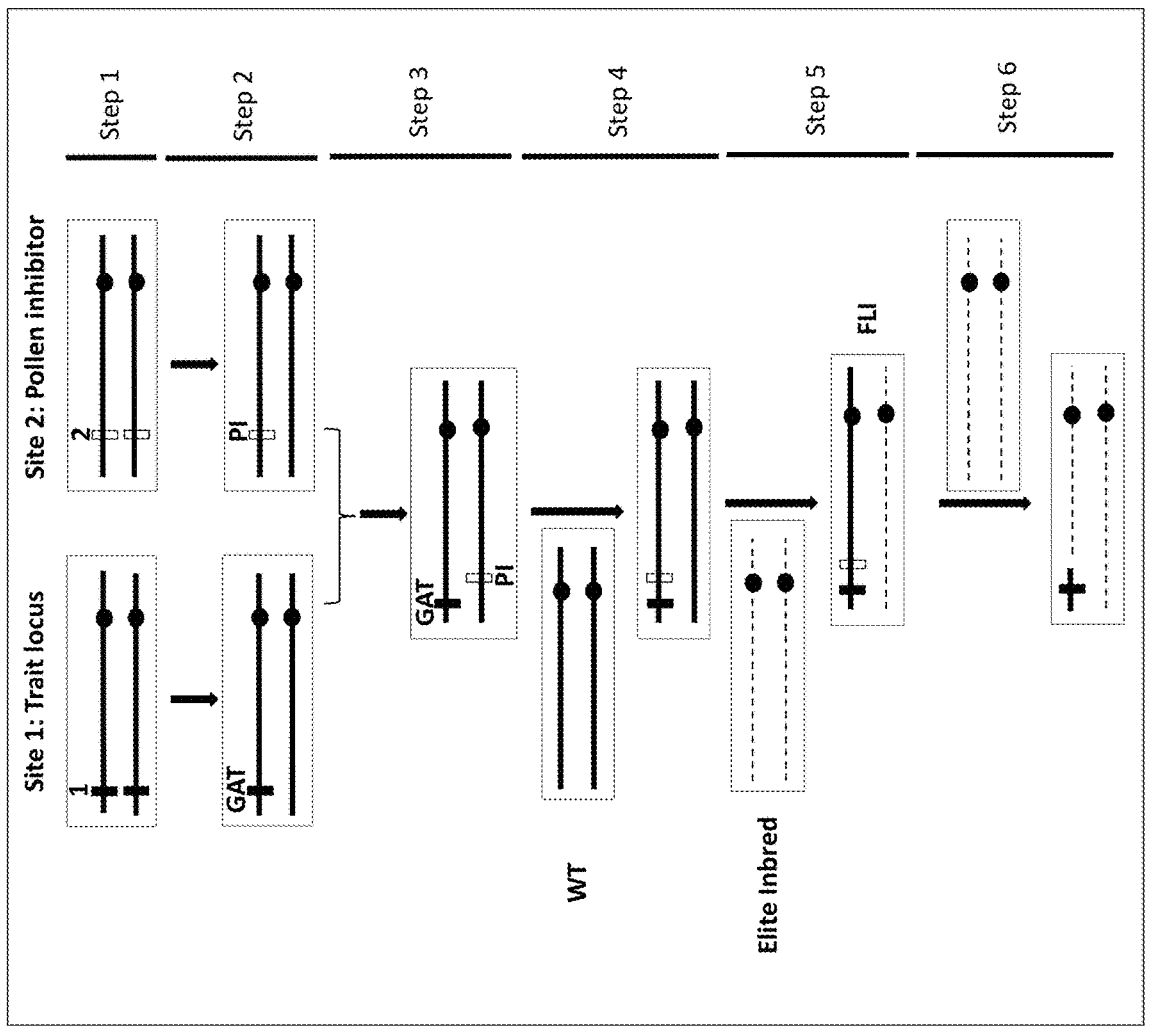
FIG. 1 shows a schematic of a crossing scheme used to establish and perform accelerated introgression for a telomeric trait locus.

Using a Single Pollen-Inhibitor Locus to Screen for Accelerated Trait Introgression of a Telomeric Trait Locus Illustrated in FIG. 1 and described below is an example of how a single pollen-inhibitor gene can be located near a trait of interest, and its use for accelerated trait introgression of a telomeric trait locus of maize.
FIG. 1 shows a schematic of a crossing scheme used to establish and perform accelerated introgression for a telomeric trait locus. Step 1: Choose an inbred amenable to transformation, identify accessions that contain two SSI target sites, the first at a position close to the telomere (labeled as "1") and the second SSI site being distal (closer to the centromere, labeled as "2"), the distance between Site 1 and Site 2 being within a close genetic distance, for example 1 cM. Step 2: In two separate transformation experiments, use the SSI transformation method to introduce a trait gene (for example, UBI::GAT:pinII, abbreviated as GAT in the figure, which confers resistance to glyphosate) into Site 1, and a Pollen-inhibitor gene (for example PG47:: ZmAA1::pinII, abbreviated as PI in the figure) into Site 2. Step 3: Carry pollen from the GAT-containing plant to PI-containing plant and screen the progeny by molecular markers in order to identify plants containing both GAT and PI. Step 4: Carry pollen from the Wild Type inbred plant to the plants containing both GAT and PI to establish the linkage between Site 1 and Site 2. Use molecular markers to screen the progeny in order to identify plants in which GAT and PI are genetically linked (1% of the progeny at a genetic distance of 1 cM). Step 5: Carry pollen from different Elite inbred (into which you wish to introgress the GAT trait) onto ears of plants containing the linked GAT and PI. Use molecular markers to identify F1 progeny that contain the linked GAT and PI. Step 6: Carry pollen from the F1 progeny containing linked GAT and PI back to the Recurrent Parent (i.e. the Elite inbred of step 5) to generate a progeny pool.
   a. If the linkage between GAT and PI is broken during meiosis then the pollen is viable and GAT can be transmitted to progeny.
   b. Spray with glyphosate to eliminate any progeny derived from wild-type pollen grains.
   c. The surviving plants will have GAT gene with a minimal linkage drag from the transformation inbred.
A. Introducing the Pollen-Inhibitor Gene—Barnase-in Close Proximity to a Trait Locus of Interest (GAT, Glyphosate Resistance Trait) in the Genome of a Maize Plant.

A donor sequence for site specific integration (SSI) (SEQ ID NO: 44) was introduced into a pre-existing transgenic SSI target site containing a first expression cassette comprising a ubiquitin promoter driving a phosphomannose isomerase (PMI) and a pin II terminator, wherein the PMI was preceded by a FRT1 recombination site (UBI PRO:: FRT1::PMI::pinII) linked to a second expression cassette comprising an actin promoter driving a moPAT selectable marker and a pin II terminator, followed by a FRT87 recombination site (ACTIN PRO:: moPAT::pinII-FRT87) located on chromosome 3 at genetic position 0.9 cM (close to the end of the short arm of the chromosome), replacing the PMI and moPAT genes with FRT1-NPTII:PINII TERM, 3×35S ENH:UBI PRO:UBI INTRON:GAT891G3:UBQ3 TERM AND LTP2:GZ-W64A TERM-FRT87 (SEQ ID NO: 44). In a second independent transformation experiment, the pollen-inhibitor cassette PG47::barnase (comprising a PG47 [a maize promoter from a polygalacturonase gene] promoter driving the pollen-inhibitor gene barnase and a pinII terminator; bp 4438 to bp 8039 in PHP70154, SEQ ID NO: 43) was introduced into a pre-existing SSI target site also containing FRT1-PMI+Actin::moPAT-FRT87) located on chromosome 3 at genetic position 3.2 cM, replacing PMI and moPAT with PG47::Barnase.

These two transgenic events were crossed together, creating an F1 generation. Progeny in the F2 generation were then screened for linkage and a progeny plant (maize Pioneer inbred line 1, such as for example PHN46) is selected comprising the linked GAT (glyphosate resistant trait locus of interest) and barnase (pollen-inhibitor gene loci B. Use of a Pollen-Inhibitor Gene Barnase to Break Linkage with a Glyphosate Resistance Trait (GAT) on Chromosome Three of Maize for Accelerated Trait Introgression.

The maize Pioneer inbred line 1 carrying the linked GAT (glyphosate resistant trait locus of interest) and barnase (pollen-inhibitor gene) described above, can be used as the female in a cross with an (elite) inbred into which GAT will be introgressed. The resultant F1 plants can then be used as pollen-donors back onto the recurrent parent. Pollen that carries both the GAT locus and the pollen-specific barnase expression cassette are non-viable. Progeny of this cross can be screened by exposing the germinating seedlings to glyphosate which eliminates any progeny not carrying the trait locus. In viable progeny that pass this screen (i.e. progeny that contains the GAT trait and is resistant to the herbicide), the linkage between GAT and the pollen-specific barnase inhibitor would have been broken during meiosis. The resultant progeny now carry only the terminal end of the original Pioneer inbred line 1 chromosome 3 carrying the GAT locus, and the remainder of chromosome 3 has been replaced by chromosome 3 from the recurrent parent inbred (FIG. 1).

C. Introducing the Pollen-Inhibitor Gene-Alpha Amylase-in Close Proximity to a Trait Locus of Interest (GAT, Glyphosate Resistance Trait) in the Genome of a Maize Plant.

A Pioneer inbred Line 1 (PHN46) was identified that comprised a pre-existing transgenic SSI target site located at 152 cM on chromosome 10 containing a first expression cassette comprising a ubiquitin promoter driving a phosphomannose isomerase (PMI) and a pin II terminator, wherein the PMI was preceded by a FRT1 recombination site (UBI PRO::FRT1::PMI::pinII) linked to a second expression cassette comprising an actin promoter driving a moPAT selectable marker and a pin II terminator, followed by a FRT87 recombination site (ACTIN PRO:: moPAT::pinII-FRT87). That Pioneer inbred line 1 was then used as the transformation target for particle-gun-mediated delivery and introduction of a GAT-resistance expression cassette between two dissimilar FLP-recombinase sites (FRT sites FRT1-NPTII::PINII TERM+3X(35S ENH): UBI1ZM PRO:UBI1ZM INTRON::GAT891G3::UBQ3 TERM+LTP2 PRO::DS-RED2::GZ-W64a TERM-FRT87(SEQ ID NO:44), along with a separate plasmid cassette (comprising a ubiquitin promoter driving a FLP recombinase terminated by a pinII terminator, UBI1ZM PRO:UBI1ZM INTRON:FLPM:: PINII TERM (bp 411 to bp 4012 of PHP5096, SEQ ID NO:50), resulting in RMCE and the replacement of PMI & moPAT by GAT in the pre-existing transgenic SSI target site located at 152 cM on chromosome 10. At a position 2 cM proximal (150 cM on chromosome 10), an SSI donor sequence (SEQ ID NO:46) containing FRT1-NPT-II:pinII+ 35S ENH:LTP2 PRO::TAGBFP::GZ-W64A TERM+ZM-PG47-PRO::Zm-AA1::IN2-1 TERM-FRT87 (comprising a PG47 promoter driving the Zea mays alpha amylase (Zm-AA1) gene) was also introduced via particle-gun-mediated RMCE in a separate transformation experiment with Pioneer inbred line 1. The expression of alpha amylase in maize plant comprising the expression cassette PG47-PRO::Zm-AA1::pinII inhibits pollen tube growth and these plants must therefore be crossed with plants containing the GAT locus through the female ear in order to establish linkage.

D. Use of a Pollen-Inhibitor Gene—Alpha Amylase- to Break Linkage with a Glyphosate Resistance Trait (GAT) on Chromosome Three of Maize for Accelerated Trait Introgression.

The maize Pioneer inbred line 1 carrying the linked GAT (glyphosate resistant trait locus of interest) and alpha-amylase (pollen-inhibitor gene) described above, can be used as the female in a cross with an (elite) inbred into which GAT will be introgressed. The resultant F1 plants can then be used as pollen-donors back onto the recurrent parent. Pollen that carries both the GAT locus and the pollen-specific alpha-amylase expression cassette are non-viable. Progeny of this cross can be screened by exposing the germinating seedlings to glyphosate which eliminates any progeny not carrying the trait locus. In viable progeny that pass this screen (i.e. progeny that contains the GAT trait and is resistant to the herbicide), the linkage between GAT and the pollen-specific alpha-amylase inhibitor would have been broken during meiosis. The resultant progeny now carry only the terminal end of the original Pioneer inbred line 1 chromosome 10 carrying the GAT locus, and the remainder of chromosome 10 has been replaced by chromosome 3 from the recurrent parent inbred (FIG. 1).

In a fashion similar to Example 1 A-D described above, a trait locus of interest located at position of 0.9 cM on chromosome 1 containing the trait expression cassette ACTIN PRO::moPAT::pinII and the PG47 PRO::ZmAA1:: pinII cassette can be introduced into on chromosome 1, at position 3.2 cM of the Pioneer Proprietary genomic map (PHD 3.2 cM). Establishing linkage (between the pollen-inhibitor genes such as ZM-AA1 and the trait loci of interest such as GAT891G3) and using this linked pair to cross to many different commercially important inbreds, can create a population of F1 hybrids. Each of the F1 hybrids can be used as a pollen donor back onto the same commercially-important inbred and progeny can be screened for accelerated introgression of the trait into each of the commercially-important inbreds.

Example 2

Using Two Pollen-Specific Inhibitor Loci Flanking a Trait of Interest for Accelerated Trait Introgression of a Non-Telomeric Trait Locus Illustrated in FIG. 2 and described below is an example of how two pollen-specific inhibitor loci can be located such that they flank a trait of interest, and its use for accelerated trait introgression of a non-telomeric trait locus of maize.

Figure 2:
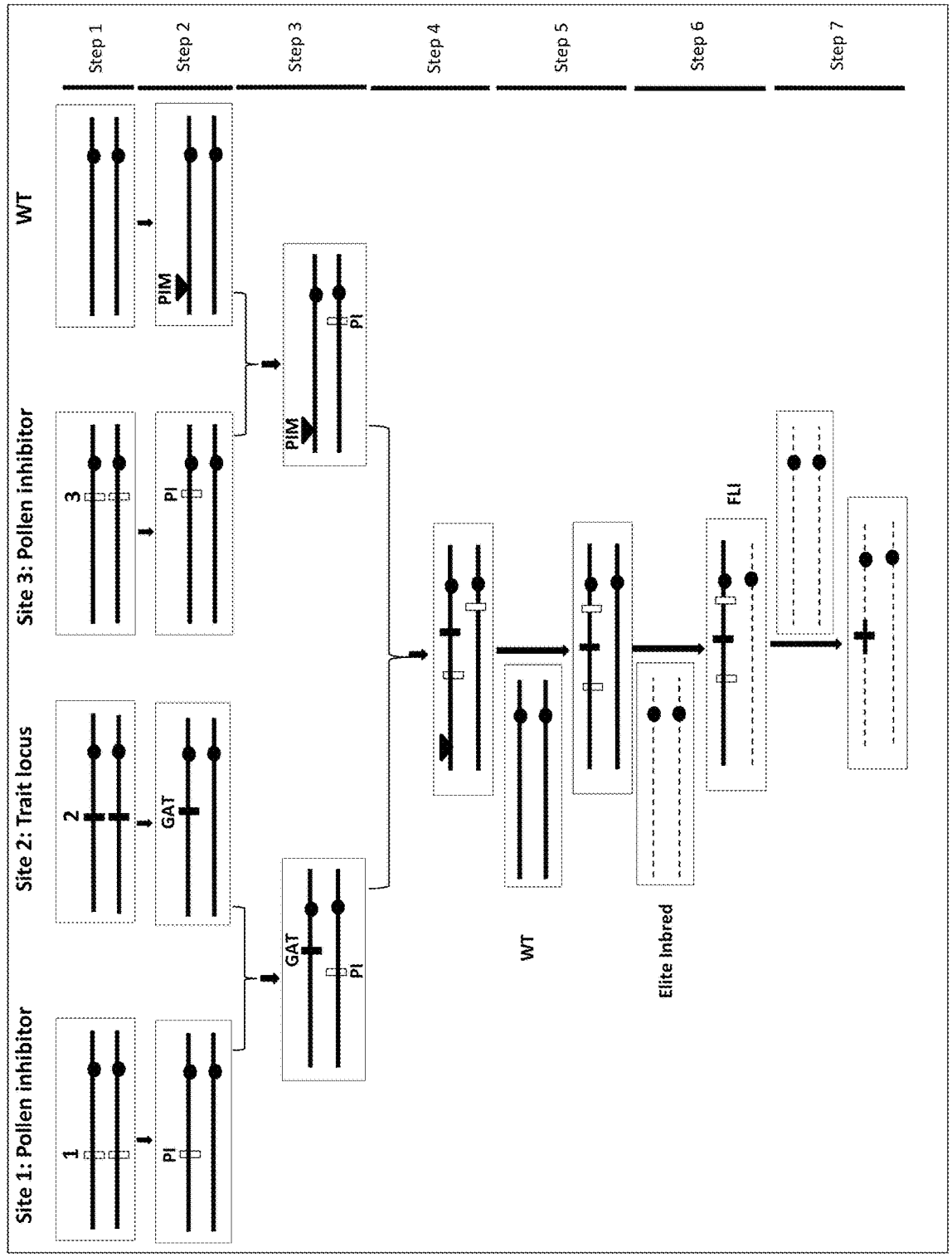
FIG. 2 shows a schematic of introducing flanking pollen-inhibitor loci around an internal chromosome location containing a trait, and using the triple-linked site to rapidly introgress the trait into other inbreds.

FIG. 2 shows a schematic of introducing flanking pollen-inhibitor loci around an internal chromosome location containing a trait, and using the triple-linked site to rapidly introgress the trait into other inbreds. Step 1: Choose a transformable inbred that contains three SSI target sites, the first site for introduction of the trait (i.e. GAT at site 2) and two flanking sites (Sites 1 & 3), each a close genetic distance from the trait locus (for example, 1 cM), into which a pollen-inhibitor cassette (P1) will be introduced. In a fourth transformation, *Agrobacterium* is used to randomly integrate a Pollen-inhibitor maintainer (PIM). Step 2: Use three separate SSI transformation experiments to introduce PI (for example, PG47::barnase::pinII) into Sites 1 and 3 and and GAT (UBI::GAT::pinII) into Site 2. Use *Agrobacterium* to randomly integrate PIM (for example, UBI::barstar::pinII) into the same inbred background. Identify the PIM transgenic line that expresses the highest level of PIM to use as a maintainer (of male fertility) in crosses performed in steps 3 & 4 below. Step 3: Carry pollen from the GAT-containing plant to a PI-containing plant (Site 1) and screen the progeny using molecular markers to identify plants containing both GAT and PI. Meanwhile, carry pollen from PIM-containing plant to PI-containing plant (Site 3) and screen progeny with molecular markers find plants containing both PIM and PI.

Step 4: Carry pollen from plants containing both PIM/PI to plants containing GAT/PI generate progeny having all four genes. During this step, the first linkage between Site 1 (P1) and Site 2 (GAT) has been established. Step 5: Carry pollen from a Wild-type inbred plant to the plants containing all four genes and use molecular markers to screen progeny in order to identify plants that contain Site1(P1), Site2(GAT) and SITE3(PI) with no PIM. Linkage has now been established in these plants for sites 1,2 and 3. Step 6: Carry pollen from a different Elite inbred to Linked WT plants and use molecular markers to screen for F1 progeny that contain the triple-linked PI-GAT-PI. Step 7: Carry pollen from PI-GAT-PI F1 progeny back to the Recurrent Parent (the elite inbred) to generate a progeny pool. Screen progeny for glyphosate resistance by spraying with the herbicide. The surviving plants will contain the GAT gene with a minimal linkage drag the transformation inbred (i.e. less than 1 cM of flanking chromosome remains from this inbred).

A. Introducing Two Pollen-Inhibitor Genes in Close Proximity to a Trait Locus of Interest (GAT, Glyphosate Resistance Trait) in the Genome of a Maize Plant.

A transgenic trait locus containing the GAT expression locus (GAT, FIG. 2) can be introduced using SSI to introduce the expression cassettes between FRT1 and FRT878 of PHP69519 (SEQ ID NO: 44) into chromosome six (6) at a genetic position of 23.7 centimorgans (cM) in the maize Pioneer inbred line 1(such as for example PHN46). This will be abbreviated in the remainder of this example as the GAT trait locus. Two flanking transgenic SSI target sites at genetic positions 22.7 cM and 24.7 cM can be used to set up the recombination screen (i.e. screening for two recombinations in one generation), setting up the screen to function during pollen germination (as illustrated in FIG. 2). Before introducing the pollen-inhibitor expression cassette (PI, FIG. 2), the transgenic line containing the GAT trait locus can also be transformed using *Agrobacterium* with T-DNA to create a randomly-integrated maintainer locus. In a male sterile line, a maintainer locus modulates or antidotes the pollen-inhibitor locus so that the pollen is viable when the maintainer is present and the plant can be used as a pollen donor. For example, if a pollen-expressed barnase is used in the pollen-inhibitor locus, its cognate antidote protein barstar expressed by a similar pollen-specific promoter would be used as the maintainer. When barstar segregates away from barnase, pollen-inhibitor effect is restored. In this example, we use a variation on this theme, with a pollen-specific promoter with TET repressor operator sequences surrounding the TATA box controlling expression of the ZM-AA1 gene that confers pollen sterility, and a pollen-expressed TET repressor gene at another genomic locus to prevent expression of the pollen-inhibitor, thus acting as a maintainer. To create the maintainer germplasm containing TET repressor, a separate *Agrobacterium*-mediated transformation is performed to introduce the T-DNA shown in PHP01 (FIG. 9-H, SEQ ID NO: 51) which introduces the following expression cassettes: RB-35S-Enhancer::PG47 PRO::TET repressor (MOD 1)::SB-SAG12 TERM+UBI1ZM PRO: UBI1ZM INTRON::PMI::pinII-LB (RB=right border, PG47=PG47 promoter, TETR=TET repressor, which is a maize-optimized gene that encoded the *E. coli* TET repressor protein, pinII terminator, UBI=ubiquitin promoter, PMI=phosphomannoase isomerase, LB=left border of T-DNA). In this construct the 35S-enhancer element can be used to enhance expression of the PG47-driven TET repressor (TET repressor) gene. The expressed TET repressor is capable of binding to the TET operator (OpT) sequence placed between the PG47 promoter and the ZM-AA1 pollen-inhibitor gene.

Pollen inhibition can be accomplished by using a pollen-specific promoter driving the alpha-amylase gene (AA) which is introduced both at positions 22.7 cM and 24.7 cM on chromosome six using SSI-mediated integration of the seed-specific DS-RED2 and PG47:Top3:ZM-AA1 contained in PHP02 (FIG. 9-I, SEQ ID NO: 52) at position 22.7 cM, and the seed-specific YFP and PG47:Top3:ZM-AA1 contained in PHP03 (FIG. 9-J, SEQ ID NO: 53) at position 24.7 cM. By crossing the TET repressor (TETR) germplasm expressing TETRrepressorwith germplasm containing PG47:Top3:ZM-AA1 and identifying progeny that now contain both loci, expression of the ZM-AA1 pollen-inhibitor is repressed and these progeny plants can be used as the pollen donor for further crossing, eventually bringing all three transgenic loci (DS-RED/ZM-AA1 at position 22.7, GAT at position 23.7, and YFP/ZM-AA1 at position 24.7, all three forming a linkage group on the same chromosome. Progeny plants confirmed to contain all three linked loci can be used to outcross to another inbred (referred to as the recurrent parent in backcross breading), beginning the introgression process (see section B below).

B. Use of Two Pollen-Inhibitor Genes Flanking a Trait Locus on Interest (ZMAA1-GAT-ZMAA1) to Break Linkage with a Glyphosate Resistance Trait (GAT) for Accelerated Trait Introgression in Maize.

Once all three loci are physically linked (ZMAA1—GAT—ZMAA1), this material can then be used to cross with other inbreds (for example, Pioneer Inbred Line 3, FIG. 2) to begin the introgression process. The resultant F1 hybrid contains one copy of chromosome 6 that contains the three linked loci, and the other copy of chromosome 6 with no transgenes (from the recurrent parent). F1 hybrids are screened for the presence of TET repressor using PCR, and individuals in which the TET repressor locus has segregated away are identified for the next cross. For the next cross, the F1 hybrid is used as the male for pollination of ears on wild-type recurrent parent plants. In pollen grains in which no meiotic recombination occurs between the three linked loci, expression of alpha amylase depletes the pollen grain of starch and pollen tube growth is inhibited. In pollen grains in which a single cross-over occurs between GAT and one of the flanking ZMAA1 loci, there is still an active ZMAA1 expression cassette linked to GAT on the side where the cross-over did not occur and the pollen does not germinate. However, in pollen grains in which recombination occurred between GAT and each of the flanking ZZAA1 loci, the pollen grains contain no pollen-inhibitor and can successfully germinate to deliver the sperm cells to the ovule resulting in successful fertilization and embryo development. Progeny seedlings can be screened for GAT by spraying with glyphosate, eliminating any progeny resulting from wild-type pollen. The remaining viable plants now contain the GAT gene and only a small surrounding segment of the original Pioneer inbred line 1 chromosome 6 (i.e. less than 1 cM on either side of GAT) in a Pioneer Inbred Line 3 chromosome 6. To further confirm that the two pollen-inhibitor loci were lost, progeny seed exhibit no red or yellow fluorescence. Using inbred-specific markers provides the final confirmation that less than 1 cM on either side of the GAT locus is from the original transformed inbred and the remainder of chromosome 6 is from the recurrent parent Pioneer Inbred Line 3.

Using marker-assisted background selection methods has been widely used in agriculture since the 1990's (for example, see Frisch et al., 1999. Crop Science 39(5):1295-1301). However, the difficulty in introgressing a single trait is actually identifying meiotic recombination events that have occurred close the trait of interest. Out method provides a genetic selection at the gamete level (pollen) that identifies cells and progeny in which this has occurred. Once the chromosome that contains the trait has been substantially converted to the new inbred background, marker-assisted background selection can be used to more rapidly convert the remaining nine chromosomes.

C. Use of One Flanking Pollen-Inhibitor and a Seed Color Marker on the Other Flank of an Internal Trait Locus for Accelerated Trait Introgression in Maize.

FIG. 15 shows a schematic of identifying an internal trait locus (referred to as PAT, Step 1) and then selfing to produce a homozygous trait locus (Step 2). In Step 3, an aleurone-specific anthocyanin cassette (RK for Red Kernel phenotype, also referred to as a seed color marker) is introduced into a locus on one side of an internal chromosome location containing a trait through targeted integration into the trait-containing chromosome. This line, now containing the linked RK and Trait loci is pollinated by a haploid inducer line (RWS) to produce haploid immature embryos (Step 4), and then the haploid embryos are used for targeted integration of the pollen-inhibitor (PI) cassette (Step 4). The haploid embryos are treated with a doubling agent such as colchicine to produce a double-haploid plant (Step 5). The triple-linked inbred is now ready for rapid introgression of the trait into other inbreds.

In Step 6, pollen is carried from a different Elite inbred (the recurrent parent into which the trait will be introgressed) onto the triple-linked plants (containing RK—Trait—PI) and use molecular markers to screen for F1 progeny that contain the triple-linked RK-GAT-PI. In Step 7, pollen is carried from the RK-Trait-PI F1 progeny back to the Recurrent Parent (the elite inbred) to generate a progeny pool. Kernels are screened for red color. If the kernel is red, it is discarded or set aside for another round of crossing. Yellow kernels were produced by pollen that had lost the pollen-inhibitor through breaking the linkage between the Trait and the PI locus, and had also lost the Red Kernel phenotype by breaking the linkage between the Trait and RK. Yellow kernels are then germinated in herbicide (or germinated and then sprayed with herbicide) to eliminate wild-type progeny, and the surviving seedlings contain the trait locus that has been rapidly introgressed into the trait-carrier chromosome.

D. Use of Two Flanking Seed Color Markers for Accelerated Trait Introgression in Maize.

FIG. 16 shows a schematic of identifying an internal trait locus (referred to as PAT, Step 1) and then selfing to produce a homozygous trait locus (Step 2). In Step 3, an aleurone-specific anthocyanin cassette (RK for Red Kernel phenotype) is introduced into a locus on one side of an internal chromosome location containing a trait through targeted integration into the trait-containing chromosome. This line, now containing the linked RK and Trait loci is pollinated by a haploid inducer line (RWS) to produce haploid immature embryos (Step 4), and then the haploid embryos are used for targeted integration of the same aleurone-specific anthocyanin cassette (Step 4). The haploid embryos are treated with a doubling agent such as colchicine to produce a double-haploid plant (Step 5). The triple-linked inbred is now ready for rapid introgression of the trait into other inbreds. In Step 6, pollen is carried from a different Elite inbred (the recurrent parent into which the trait will bge introgressed) onto the triple-linked plants (containing RK—Trait— RK) and use molecular markers to screen for F1 progeny that contain the triple-linked RK-GAT-RK. In Step 7, pollen is carried from the RK-Trait-RK F1 progeny back to the Recurrent Parent (the elite inbred) to generate a progeny pool. Kernels are screened for red color. If the kernel is red, it is discarded or set aside for another round of crossing. Yellow kernels are produced by pollen that had lost the Red Kernel phenotype by breaking the linkage between the Trait both RK loci. Yellow kernels are then germinated in herbicide (or germinated and then sprayed with herbicide) to eliminate wild-type progeny, and the surviving seedlings contain the trait locus that has been rapidly introgressed into the trait-carrier chromosome.

E. Use of One Flanking Seed Color Marker Expressed in the Crown of the Kernel and a Second Seed Color Marker Expressed in the Base of the Kernel on the Other Flank of an Internal Trait Locus for Accelerated Trait Introgression in Maize.

FIG. 17 shows a schematic of identifying an internal trait locus (referred to as PAT, Step 1) and then selfing to produce a homozygous trait locus (Step 2). In Step 3, a crown-specific anthocyanin cassette (RC for Red Crown phenotype) is introduced into a locus on one side of an internal chromosome location containing a trait through targeted integration into the trait-containing chromosome. This line, now containing the linked RC and Trait loci is pollinated by a haploid inducer line (RWS) to produce haploid immature embryos (Step 4), and then the haploid embryos are used for targeted integration of base-specific anthocyanin cassette (referred to in Step 4 as RP for red basel expression in the endosperm or aleurone underneath the pedicel). The haploid embryos are treated with a doubling agent such as colchicine to produce a double-haploid plant (Step 5). The triple-linked inbred is now ready for rapid introgression of the trait into other inbreds.

In Step 6, pollen is carried from a different Elite inbred (the recurrent parent into which the trait will be introgressed) onto the triple-linked plants (containing RK—Trait—RP) and use molecular markers to screen for F1 progeny that contain the triple-linked RK-GAT-RP. In Step 7, pollen is carried from the RK-Trait-RP F1 progeny back to the Recurrent Parent (the elite inbred) to generate a progeny pool. Kernels are screened for red color. If the kernel has a red crown or a red base, or both, it is discarded or set aside for another round of crossing (with the expression pattern being an indication or which side broke linkage). Yellow kernels are produced by pollen that had lost the both the RC and RP phenotypes by breaking the linkage between the Trait both flanking loci. Yellow kernels are then germinated in herbicide (or germinated and then sprayed with herbicide) to eliminate wild-type progeny, and the surviving seedlings contain the trait locus that has been rapidly introgressed into the trait-carrier chromosome.

Example 3

Using Guide Polynucleotide/Cas Endonuclease Mediated Integration to Introduce Two Pollen-Specific Inhibitor Loci Flanking a Trait Locus for Accelerated Introgression of a Non-Telomeric Trait Locus Illustrated in FIG. 4 and described below is an example of how a guide polynucleotide/Cas endonuclease system can be used to mediate integration to introduce two pollen-specific inhibitor loci flanking a trait locus for accelerated introgression of a non-telomeric trait locus.

Figure 4:
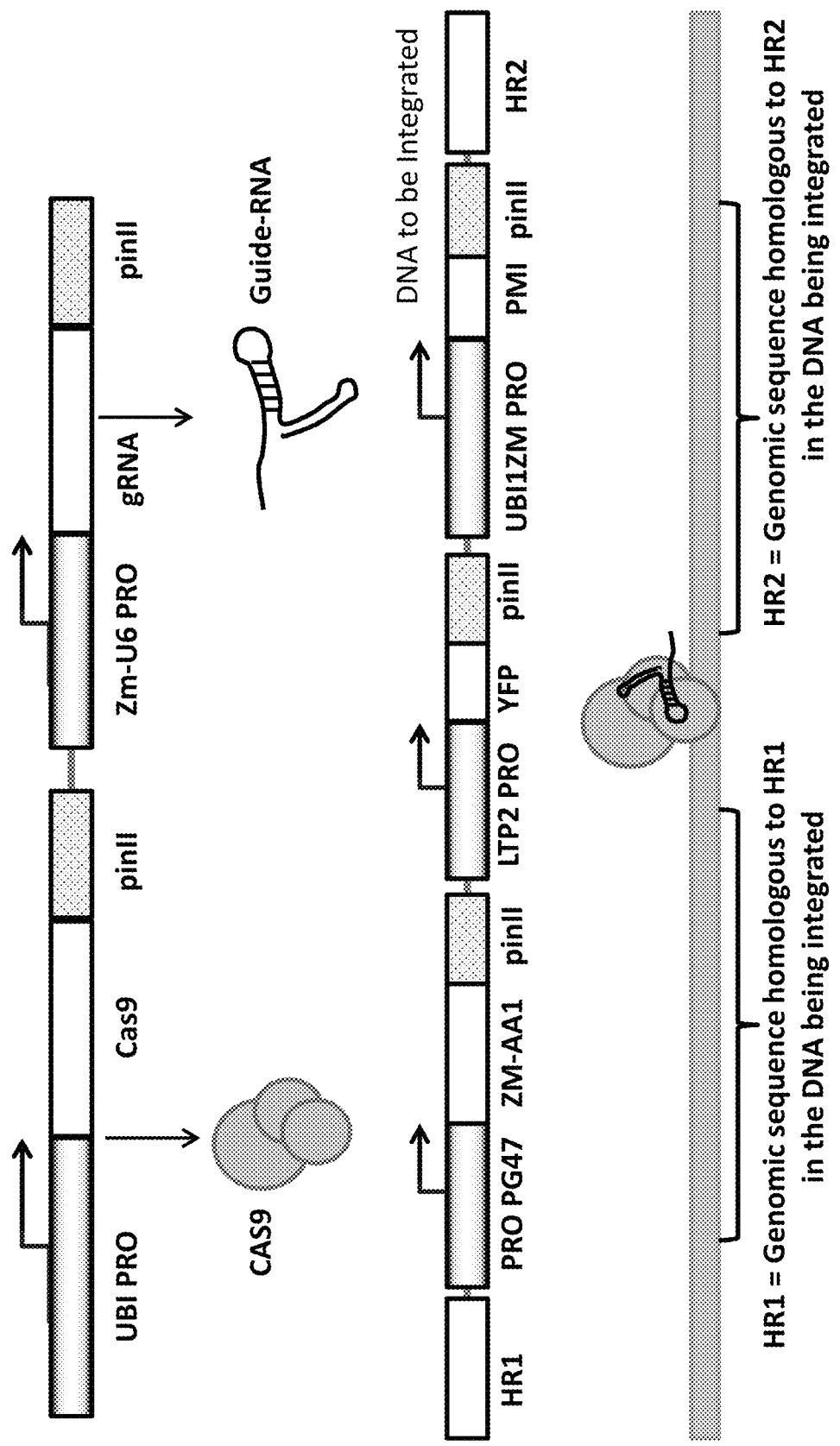
FIG. 4 shows a schematic of the use of a guide polynucleotide/Cas endonuclease system to integrate a pollen-inhibitor cassette.

FIG. 4 shows a schematic of the use of the guide polynucleotide/Cas endonuclease system to integrate a pollen-inhibitor cassette. Two expression cassettes are introduced along with the DNA to be integrated, using an equimolar amount of the three DNAs to attach to 0.6 uM gold particles for particle bombardment. The first expression cassette contains the UIB1ZM PRO & INTRON::CAS9 and a PINII TERM. The second expression cassette contains the maize U6 PolIII Chr8 promoter driving expression of the guide RNA and a terminator in the form of ZM-U6 PRO::gRNA:: PINII TERM. The DNA to be integrated contains two flanking sequences that are homologous to the inbred genomic sequence at the target site (HR1 at the 5' end and HR2 at the 3' end) with the following three expression cassettes in between HR1 and HR2; PG47 PRO::ZM-AA1:: PINII TERM+LTP2 PRO::ZS-YELLOW1 N1::PINII AND UBI1ZM PRO & INTRON::PMI::PINII. Upon particle gun-mediated delivery of all three DNA molecules, CAS9 protein is encoded and guide-RNA is transcribed. The guide RNA associates with the CAS9 protein and guides the complex to a genomic sequence (complementary to the guide-RNA) in between the genomic sequences that correspond to the HR1 and HR2 sequences in the DNA to be integrated. CAS9 creates a double-stranded break at the target site, stimulating homologous recombination between the HR sequences and their corresponding genomic sequences, integrating the three expression cassettes containing ZM-AA1, ZS-YELLOW1 N1 and PMI. Transgenic events that have successfully integrated these genes at this specific genomic site are selected by culturing on medium containing mannose and confirmed through yellow fluorescence, PCR and sequencing.

In this example, the trait locus can be a GAT expression cassette (UBI::GAT::pinII) integrated into chromosome 1 at genetic position 53.14 cM. A pollen-inhibitor expression cassette (PG47-PRO::ZM-AA1::pinII) can be introduced at positions 52.56 cM and 54.56 cM on chromosome 1 using guide polynucleotide/Cas endonuclease mediated integration of the a sequence containing three expression cassettes, an expression cassette with PG47 PRO::ZM-AA1::PINII TERM, a cassette with the LTP2 PRO::YFP::PINII TERM (or with DS-RED2 in place of YFP), and a cassette with UBI1ZM PRO: UBI1ZM INTRON::PMI::PINII TERM (FIG. 4). The contiguous sequence containing all three expression cassettes is also flanked by maize genomic sequences that are homologous to the genomic sequence to which the guide-RNA will direct CAS9 for targeted double stranded breakage. Using the inbred line that is homozygous for the GAT expression cassette for transformation, UBI:: CAS9::pinII and a guide RNA that directs the CAS9 protein to position 52.56 cM or 54.56 cM can be introduced into immature embryo cells via particle bombardment along with the Zea mays alpha amylase (Zm-AA1) expression cassette flanked by genomic regions for homologous recombination from the inbred (HR regions, see FIG. 4). The inbred HR sequences can be about 1-2 kb sequences that are homologous to the endogenous inbred chromosome sequences flanking the Cas9 recognition sequence (a DNA sequence that is recognized and optionally cleaved by the polynucleotide-guided Cas endonuclease). For position 52.56 cM, the three expression cassettes shown in FIG. 4 are integrated using HR sequences that correspond to flanking sequences at 52.56 cM. For position 54.56 cM, a similar integration construct is integrated except that DS-RED2 is the fluorescence gene in the first expression cassette (between LTP2 PRO and PINII TERM) and the HR sequences correspond to flanking sequences at this position. Transgenic events containing the targeted integration can be recovered by selecting on medium containing 5 g/l maltose and 12.5 g/l mannose. Transgenic plants can be regenerated and used as the female parent for pollination with RWS homozygous for a LEC1:: GFP::pinII cassette. The resulting immature embryos can be screened first for lack of green fluorescence (indicating diploid embryos which are discarded), then for DsRED (containing the ZM-AA1 locus), can be re-transformed using the guide polynucleotide/Cas endonuclease system, but this time integrating the ZM-AA1 expression cassette along with UBI::NPT-II::pinII at PDH 54.56 cM on chromosome 1. After re-transformation, the immature embryos can be exposed to 0.06% colchicine for 8 hours in culture and can be then moved onto kanamycin to select events that have integrated AA1 and NPT-II at position 54.56 cM on chromosome 1. The resultant plants that are regenerated are homozygous for the triple-linked loci (AA—GAT-AA). This material can now be used as a female to bulk up seed. The resultant hemizygous progeny can then be used to cross with other inbreds (for example, Pioneer Inbred Line 3) to begin the introgression process. The resulting F1 plants can then be used as the male crossing once again to the recurrent parent (Pioneer Inbred Line 3). In pollen grains in which no meiotic recombination occurs, expression of alpha amylase depletes the pollen grain of starch and pollen tube growth is inhibited. In pollen grains in which a single cross-over occurs between GAT and one of the flanking AA loci, there can still be an active AA expression cassette linked to GAT and the pollen does not germinate. However, in pollen grains in which recombination occurred between GAT and each of the flanking AA loci, the pollen grains can successfully germinate and deliver the sperm cells to the ovule resulting in successful fertilization and embryo development. Progeny seedlings can be screened for GAT by spraying with glyphosate, eliminating any progeny resulting from wild-type pollen. The remaining viable plants now contain the GAT gene and only a small surrounding segment of the original Pioneer inbred line 1 chromosome 1 (for example, but not limited to, less than 2 cM on either side of GAT) in an otherwise complete Pioneer Inbred Line 3 chromosome 1.

Example 4

Creating a Pre-Existing Precision Accelerated Trait Integration Site (PATI Site)

Figure 6:
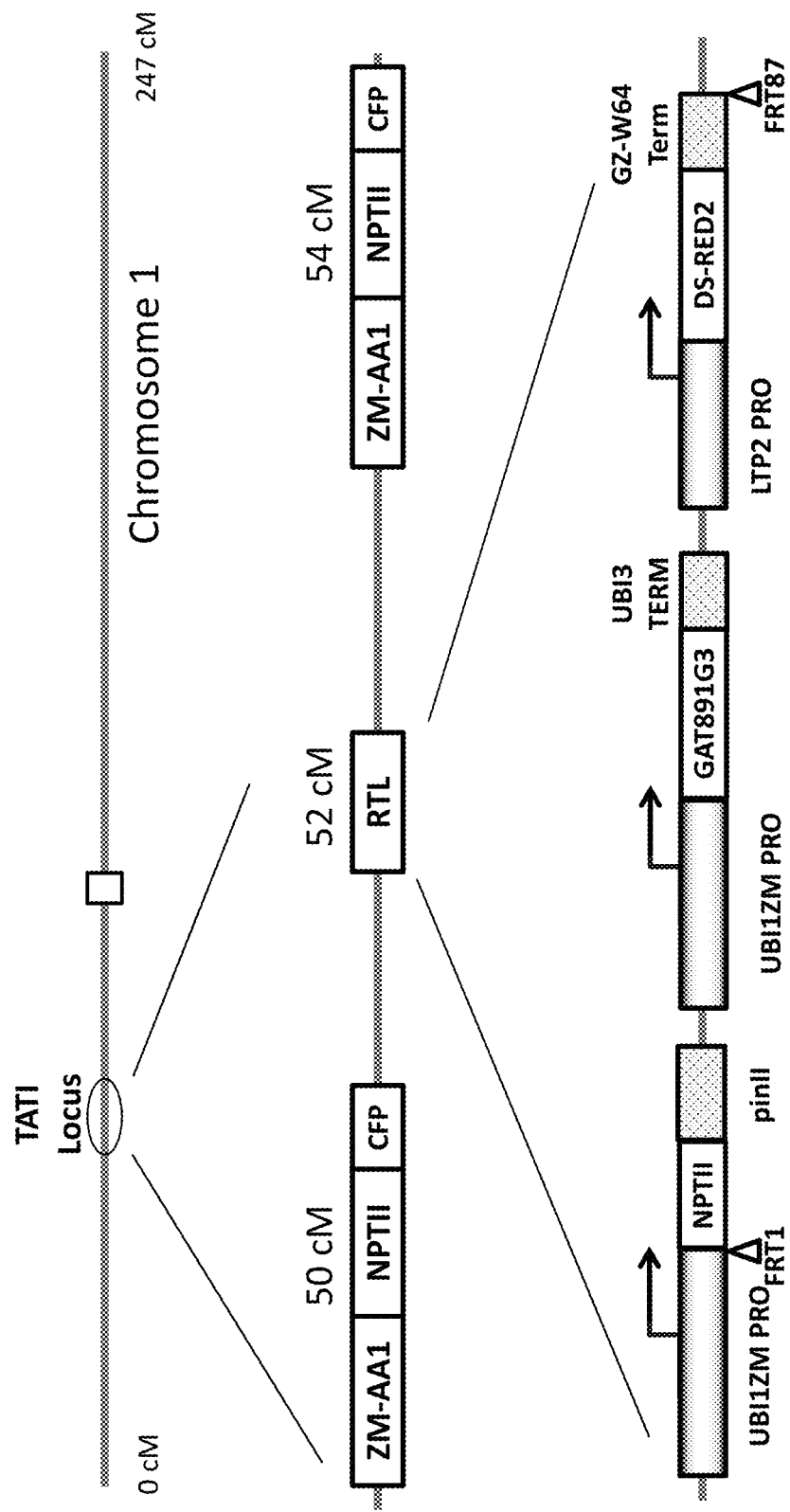
FIG. 6 shows a schematic of a pre-established Targeted Accelerated Trait Integration locus.

Illustrated in FIG. 6 and described below is an example of how a pre-existing Precision Accelerated Trait Integration Site (PATI Site) can be created.

A SSI-generated trait locus can be established at a chromosomal location that is confirmed to be agronomically neutral, have no deleterious impacts on expression patterns of surrounding endogenous genes, and that supports good transgene expression levels. For example, as shown in FIG. 6, a SSI target site (RTL) can be introduced into position 52 cM on maize Pioneer Inbred Line 3 chromosome 1, using Site-Specific Integration. This event can contain three expression cassettes; UBI1ZM PRO & INTRON:FRT1: NPTII::PINII+UBI1ZM PRO & INTRON::GAT891G3:: UBI3 TERM+LTP2::DS-RED2::GZ-W64 TERM-FRT87, with the sequence and features from FRT1 to FRT87 being shown in FIG. 9-B, (SEQ ID NO: 44) which were found to support expression of NPTII at consistently high levels across multiple generations. In immature embryos homozygous for the NPTII-containing locus, guide polynucleotide/ Cas endonuclease-mediated targeted integration (see also FIG. 4) of PG47 PRO::ZM-AA1::pinII+LOXP-UBI PRO &

INTRON::PMI::pinII-LOXP+UBI PRO & INTRON::CYA-N::pinII can be performed to introduce these expression cassettes at chromosomal position 50 cM on chromosome 1, and in a successive transformation, guide polynucleotide/Cas endonuclease systems can be used again to integrate a third combination of expression cassettes (PG47 PRO::ZM-AA1::pinII+LOX2272-OS-ACTIN PRO:: MOPAT::35S TERM-LOX2272+UBI PRO & INTRON::ZS-GREEN::pinII) at position 54 cM on chromosome one. Once the final integration event (on 3 mg/l bialaphos) and plants are regenerated, the T0 plants can be crossed to another transgenic line containing RAB17 PRO::MO-CRE::PINII (SEQ ID NO: 75), which expresses CRE recombinase in response to desiccation (i.e. during late embryogenesis) or cold temperatures. In cells containing the triple-linked PATI locus and expression CRE recombinase, both the PMI and MOPAT expression cassettes are excised, leaving PG47 PRO::ZM-AA1::pinII+LOX2272+UBI PRO & INTRON::CYAN::pinII at both flanking positions in the PATI locus. This germplasm, now containing the three linked loci (trait locus and the two flanking pollen-inhibition loci, FIG. 6) can be used for subsequent testing of new trait constructs and for rapid product development. Using either guide polynucleotide/Cas endonuclease systems or RMCE, new trait cassettes can be introduced into the trait locus (replacing NPTII with an herbicide resistance gene for selection along with new traits (or trait-stacks). When efficacious events are identified, the T1 plants can be crossed to new inbreds producing the F1 hybrid for introgression. The F1 can be used as the male to cross back to the same recurrent inbred parent and the BC1-progeny can be screened for the new trait. At this point, the only remnant of Pioneer Inbred Line 3 chromosome 1 will be a fragment somewhere between 50 and 54 cM (the exact junctions depending on precisely where the meiotic recombinations occurred) containing the trait, while the remainder of chromosome 1 (from somewhere between about 50-54 centimorgans from the new inbred)

Any proven PATI site with a trait locus linked to a pollen-inhibition locus (for a telomeric trait locus) or to two pollen-inhibition loci (for an internal or non-telomeric trait locus) that has been demonstrated to support appropriate transgene expression and not be deleterious to plant growth and productivity can be used in this fashion, as a pre-established site for transgene introduction and accelerated trait introgression. Pre-existing Targeted Accelerated Integration Sites such as these can be used to introduce the trait gene, and can be used to introduce either single genes or molecular stacks and then rapidly introgressed these into many new inbreds for testing.

Example 5

Two Flanking Pollen-Inhibitor Intein Halves Used in Two-Stage Screening for Two Sequential Recombinations This experiment utilizes a bacterial endoribonuclease from *Escherichia coli* referred to as KID (Ruiz-Echevarria et al., 1991, Mol. Microbiol. 5:2685-2693. This gene was split into two fragments and then the sequences encoding the amino-(KID-N, SEQ ID NO: 67) and carboxy- (KID-C, SEQ ID NO: 69) fragments were fused to the amino (NP-INTE-N, SEQ ID NO: 65) and the carboxy (NP-INTE-C, SEQ ID NO: 63) intein halves, respectively. These intein halves (from *Nostoc, puncteforma*, see Iwai et al., 2006, FEBS Lett. 580:1853-1858) encode two cognate intein, that when expressed in the same cell when fused to two cognate protein fragments peptides (fusing KID-N with NP-INTE-N in that order, and fusing NP-INTE-C with KID-C in that order) will bind with each other and catalyze their own excision, effectively splicing the two protein fragments (i.e. KID-N AND KIDC) together to form a fully functional protein (i.e. KID).

Figure 7:
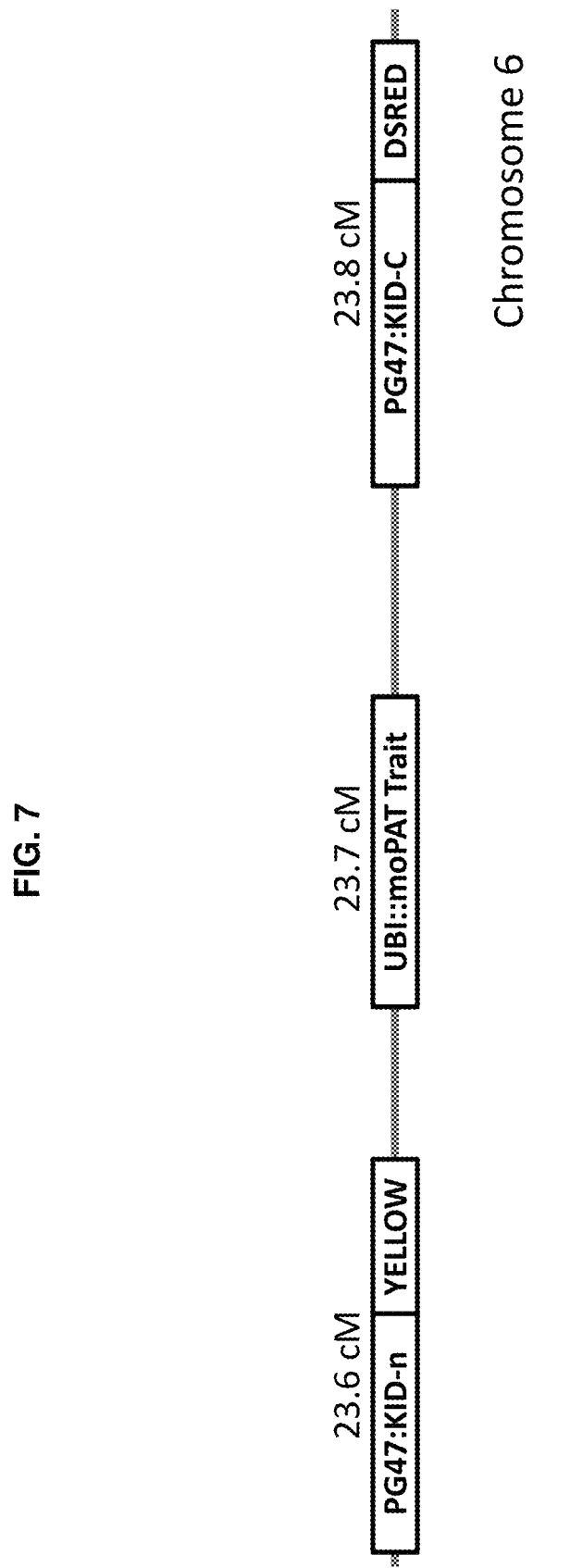
FIG. 7 shows a schematic of a SATI configuration using intein splicing, allowing two-step screening (i.e. over two generations) for breakage of linkage on both sides of an internal genomic locus.

An internal trait locus such as the RMCE locus at position 23.7 cM on chromosome 6 (FIG. 7) containing UBI1ZM PRO:: UBI1ZM INTRON::moPAT::PINII (SEQ ID NO: 19, SEQ ID NO: 20, SEQ ID NO: 35, and SEQ ID NO: 8, respectively) can be flanked by PG47 PRO::::NP-INTE-C-KID-C::PINII (SEQ ID NOs: 13, 63, 69 and 8, respectively)+LTP2 PRO::MO-CYAN::PINII (SEQ ID NOs: 9, 71 and 8, respectively) at position 23.8 cM and by PG47 PRO::KID-N~NP-INT-N::PINII (SEQ ID NOs: 13, 67, 65 and 8, respectively)+LTP2 PRO::MO-CYAN::PINII at position 23.6 cM (shown in FIG. 7). When both i) the carboxy-half of the KID protein fused to the carboxy-half of the *Nostoc* intein pair, and ii) the amino-half of the intein pair fused to the amino-half of alpha-amylase are expressed in the same pollen grain, the intein pair splices the two halves of the KID protein together resulting in full enzyme function and concomitant pollen inhibition. Seed containing both KID-INTE also fluoresce blue. Pioneer inbred line 1 containing the trait locus linked to both of the KID-intein loci (hemizygous) can be crossed to other inbreds for introgression of the trait, producing F1 populations. The F1 progeny can then be used as the pollen donor back onto the recurrent inbred. In pollen in which a double crossover occurs breaking the linkage on both sides of the trait locus, the pollen can be viable and produces seed with just the trait locus introgressed into the new inbred chromosome 6. However, if recombination to break linkage occurs on only one side of the trait (removing either the carboxy- or amino-half of KID) the pollen can also be viable leaving behind a non-functional KID-intein half and blue fluorescence. This blue seed can then be grown and used as the pollen donor and the resultant progeny are germinated in the presence of glufosinate (eliminating progeny that came from wild-type pollen). Plants that are herbicide resistant and also produce no blue seed have the UBI::moPAT trait locus that has been introgressed with less than 0.1 cM of Pioneer inbred line 1 chromosome remaining on either side of the locus.

As an alternative to the fluorescent proteins used in the second screening step (to monitor the second recombination and breakage of the linkage), a conditional negative selection marker such as the coda gene, the dhIA gene or the CYP105A gene can be used. When these genes are expressed in plant cells there is no adverse effect until their cognate substrates (5-fluorocytosine, dihaloalkanes or sulfonylurea R4702, respectively) are provided to the plant cell at which point these non-inhibitory substrates are converted to an inhibitor. Using such as marker, fluorescent microscopy is not needed to identify plant cells or tissues in which the genetic linkage has been broken and there is also no need for a maintainer line to render the inhibitor (coda, dhIA or CYP105A) inactive when not needed.

A trait such as resistance to the glufosinate herbicides such as Basta and Liberty (OS-ACTIN PRO & INTRON::MOPAT::35S TERM (SEQ ID NO: 95) can be integrated at Chromosome 6, 23.7 cM in inbred Pioneer inbred line 1 (FIG. 7) which can represent the internal trait locus to be introgressed into other inbreds. At position Chr6-23.8 cM the following can be introduced; FRT1-NPTII-PINII TERM+LTP2 PRO-DSRED-GZ-W64A TERM+PG47 PRO-NPINTEC-KIDC-PINII TERM (PHP04, FIG. 9-K and SEQ ID NO: 54). At position Chr6-23.6 Cm the following can be introduced; FRT1-NPTII-PINII TERM+LTP2 PRO-ZSYELLOW1N1-GZ-W64A TERM+PG47 PRO-KIDN-NPINTEN-PINII TERM (PHPO4 in FIG. 9-K). Thus, expression of the cassettes at 23.6 cM encode a pollen-specific KID-N (the amino-fragment of the KID protein fused to the *Nostoc puntiforma* DnaE amino-intein half) and a seed-specific yellow fluorescent protein. Expression of the cassettes at 23.8 cM encode a pollen-specific KID-C (the carboxy-fragment of the KID protein fused to the *Nostoc puntiforma* DnaE carboxy-intein half) and a seed-specific red fluorescent protein. When both intein halves are expressed in the same pollen grain, the intein-halves undergo self-catalyzed cleavage resulting in perfect reconstitution of the full-length, active KID toxin protein, and the pollen are non-viable. However, if linkage on either side of the trait gene occurs between the trait and the intein/fluorescent locus on that side, only one half of the intein-pair is expressed in the pollen grain and the pollen grain is viable. In this manner, breaking the linkage on either side of the trait can readily be determined because the pollen grain is viable and only one color of fluorescence is passed on to the BC1 ($1^{st}$ generation of backcrossing) progeny. These progeny can then be used for a subsequent round of pollination back to the recurrent parent, and BC2 progeny screened for lack of any fluorescence. At this point, successful introgression of the trait into chromosome 6 has been accomplished.

Example 6

Figure 3:
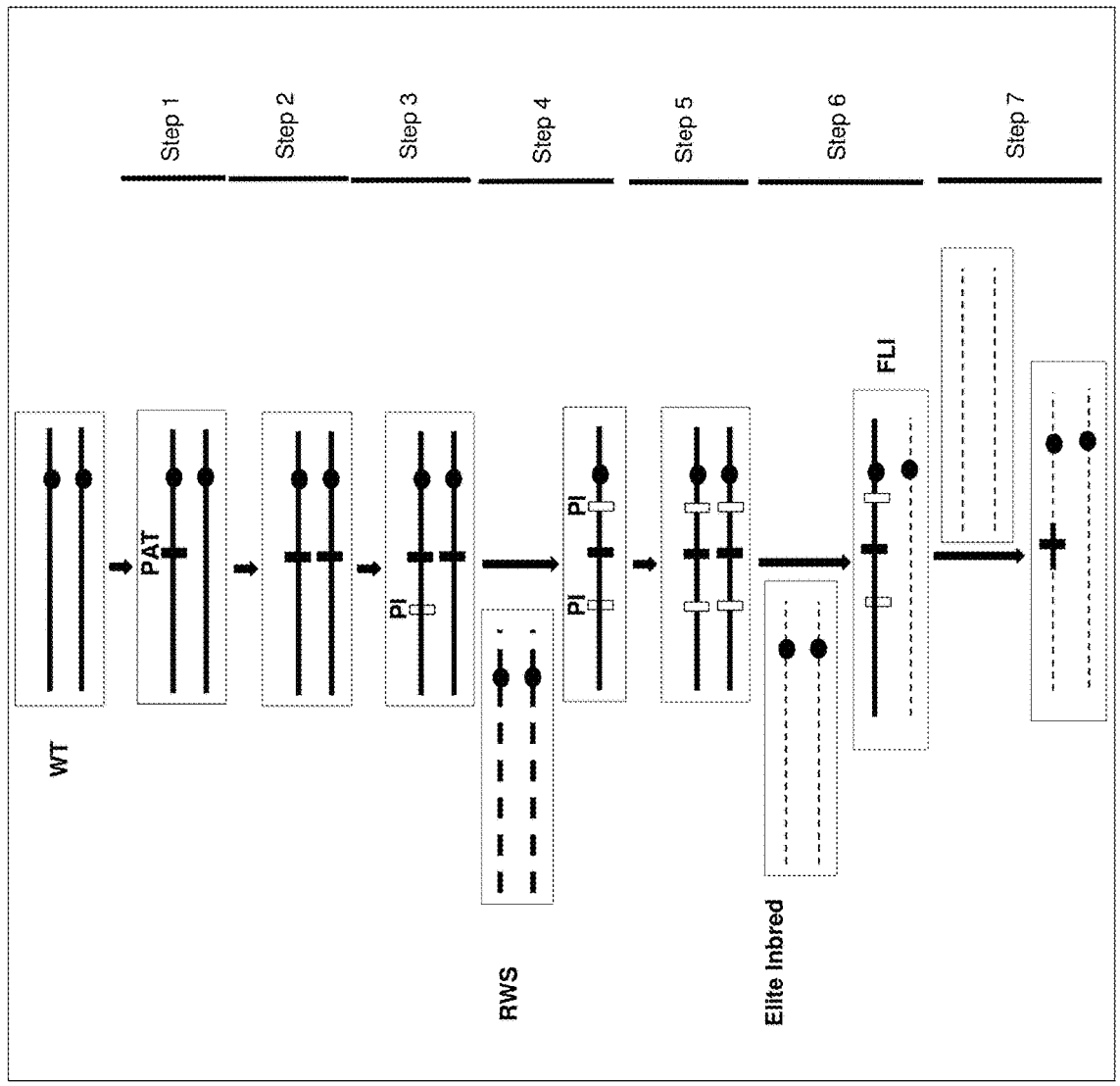
FIG. 3 shows a schematic of the use of sequential targeting into haploid embryos to rapidly create linkage between a trait locus and two flanking pollen-inhibitor loci.

Rapid Creation of Two Pollen-Specific Inhibitor Loci Flanking a Trait of Interest for Accelerated Trait Introgression In this example we describe the use of sequential guide polynucleotide/Cas endonuclease system mediated integration to introduce a first flanking pollen-inhibitor cassette, followed by SSI-mediated targeting along with haploid embryo transformation to produce two flanking pollen-specific inhibitor loci linked to an intervening trait locus (illustrated in FIG. 3).

FIG. 3 shows a schematic of the use of sequential targeting into haploid embryos to rapidly create linkage between a triat locus and two flanking pollen-inhibitor loci. Step 1: The Pioneer inbred Line 3 containing a 35S::PAT expression cassette at position 53.1 cM on Chromosome 1 (conferring the trait of bialophos-resistance) is used as the starting germplasm in this strategy. Step 2: The hemizygous PAT-containing plants are self-pollinated to create homozygous PAT/PAT progeny. Step 3: The CAS/CRISPR system is used to target a PI (PG47::ZmAA1::pinII+UBI::DsRED::pinII+UBI::PMI::pinII) with into 51.56 cM and establish the first linkage between PI and GAT. Transgenic events are selected on mannose and hemizygous T0 plants are regenerated. Step 4: T0 plants containing PI(51.56) and PAT(53.1) are pollinated by a DuPont/Pioneer RWS-derived haploid-inducer line (Big Kahuna) progeny immature embryos are screened by color to discard diploid embryos and harvest DsRED-expressing embryos for re-transformation. The haploid embryos containing PI(52.3) linked to PAT(53.1) are used for a second round of CAS/CRISPR transformation in order to introduce a second PI (PG47::barnase::pinII+UBI::CYAN::pinII+UBI::NPTII::pinII) at position 54.56 cM, establishing linkage between all three transgenic loci. Transgenic events are selected on G418. Step 5: The embryos are treated briefly with colchicine to double the chromosome number and homozygous plants containing the three linked loci on both copies of chromosome 1 are produced. Step 6: Pollen from the Elite inbred into which PAT is being introgressed (for example, Pioneer Inbred Line 2) is carried to the triple-linked Pioneer Inbred Line 3 ears to produce F1 progeny. Step 7: Pollen from the F1 progeny is used to pollinate the recurrent parent (Pioneer Inbred Line 2) to generate progeny. Progeny are sprayed with bialaphos herbicide which eliminates progeny derived from wild-type pollen. The surviving plants will have GAT gene with a minimal linkage drag from donor inbred.

The Pioneer inbred Line 3 homozygous for a specific trait locus referred to as TRAIT1 located at 53.1 cM (Pioneer Proprietary genomic map) on chromosome 1 can be transformed using particle bombardment of immature embryos to introduce via guide polynucleotide/Cas endonuclease systems (FIG. 4). A donor DNA sequence containing UBI1ZM PRO::UBI1ZM INTRON::PMI::PINII+UBI1ZM PRO::UBI1ZM INTRON::ZS-YELLOW N1::GZ-W64 TERM+35S ENH:PG47 PRO::BT1 TP::ZM-AA1::IN2-1 TERM (FIG. 9-O and SEQ ID NO: 116) can be integrated at position 51.6 cM on chromosome one. Successful targeted integration events can be selected on medium containing mannose. Plants can be regenerated from these events and grown in a greenhouse. Perfect homologous recombination at position 51.6 cM can be confirmed by PCR reactions specific for the recombination product. When plants are mature and the ears have produced silks, these plants can be pollinated using RWS haploid inducer line (see Rober et al., 2005, Maydica 50:275-283). In progeny immature embryos, diploid embryos expressing an anthocyanin marker can be discarded. Haploid embryos that fluoresce yellow (indicating that they contain SEQ ID NO: 117 at position 51.6 cM) can be used for a second round of targeting, using particle gun delivery of UBI::moFLP::pinII, OS-ACTIN::WUS::PIN, UBI PRO & INTRON::ODP2::PINII plus an SSI-donor DNA containing a second pollen-inhibitor cassette, a second selectable marker and a second fluorescent marker (FRT1::NPTII::pinII+35S ENH:UBI1ZM PRO::UBI1ZM INTRON::DS-RED2::PINII+35S ENH:PG47 PRO::ZM-AA1::IN2-1 TERM-FRT87 (FIG. 9-M and SEQ ID NO: 76) at position 54.56 cM on chromosome one. Successful RMCE into this recombinant trait locus (RTL) can activate NPTII gene expression which permits primary selection of the RMCE events on kanamycin- or G418-containing medium with a secondary selection for red fluorescence, that can target integration into a RTL at 54.56 cM on chromosome 1 that can contain the same two dissimilar IFRTb sites (FRT1 and FRT87). Events can be briefly exposed to colchicine early in tissue culture to double the chromosome number. Events can be selected for NPTII expression using the selective agent G418 and can further be confirmed by visually selecting for red fluorescence. Events can be screened using PCR for the correct RMCE into the Pioneer Inbred Line 3 RTL located at 54.56 cM on chromosome 1. These events can be regenerated into plants and grown in a greenhouse, and upon further characterization using PCR analysis, can be confirmed to be homozygous for the DsRED locus at 51.56 cM, homozygous for the DP4114 trait locus at 53.1 cM and homozygous for the ZS-YELLOW N1 locus at 54.56 cM. These plants can be grown alongside an inbred into which the TRAIT1 will be introgressed, for example Pioneer Inbred Line 2. Pollen from Pioneer Inbred Line 2 can be used to pollinate the PH2HT plants containing the triple-linked loci to produce an F1 hybrid. The F1 seed can then be planted and the resulting F1 plants can be used to pollinate the recurrent parent Pioneer Inbred Line 2. Only pollen grains in which the linkage has been broken will i) be viable successfully fertilizing the wild-type Pioneer Inbred Line 2 egg cells to produce kernels, and ii) produce bialaphos-resistant plants (conferred by the TRAIT1 locus)—resulting in rapid introgression of this trait into the Pioneer Inbred Line 2 chromosome 1.

Performing Two Sequential Targeted Integrations to Introduce Two Screening Markers on Either Flank of a Transgenic Trait Locus (without a Haploid Step).

A trait locus located on Chr1-50.5 cM in Pioneer inbred line 1 has been demonstrated to be efficacious and is to be introgressed into many new inbreds for testing. Cas9-mediated targeted integration using immature embryo transformation can be used to introduce a pollen-specific promoter driving expression the pollen-tube inhibitor AA1 at Chr1-49.5 cM, and single-copy targeted-integration T0 plants can be identified using PCR. These plants can then be pollinated using wild-type pollen of Pioneer inbred line 1, and the T1 immature embryos can be isolated for a second round of CAS9-mediated integration of a second AA1 Marker at Chr1-51.5 cM. Using two back-to-back transformations of immature embryos permits rapid creation of the triple-linked AA1—Trait—AA1 that can then be used for rapid introgression.

Example 7

Flanking an Internal Trait Locus with a Non-Conditional Pollen-Inhibitor Gene on One Side and a Conditional Lethal Gene on the Other, for Two-Step Screening for an Introgressed Trait Locus This example describes a method for flanking an internal (non-telomeric) trait locus with a non-conditional pollen-inhibitor gene on one side and a conditional lethal gene on the other. This can be used for traits where breaking the linkage on both sides of the trait simultaneously (using back-crossing for introgression) occurs at too low a frequency (for example, due to very short genetic distances (between the trait locus and the flanking pollen-inhibitor loci on both sides) or due to meiotic recombinational-interference), The two pollen-inhibitor flanking loci can be as follows: one flanking locus can contain a non-conditional pollen-inhibitor such as PG47 PRO::ZM-BT1 TP-ZM-AA1::IN2-1 TERM (SEQ ID NO: 77) or PG47 PRO::BA-BARNASE::PINII TERM (SEQ ID NO: 78), and the opposite flanking locus can contain a conditional pollen-inhibitor expression cassette. Examples of a conditional expression cassette can be PG47 PRO::CODAcodA::PINII TERMpinII (Ffor CODA gene, see SEQ ID NO: 81, and for encoded protein see SEQ ID NO: 82). The encoded CODA protein has been shown to be non-inhibitory when expressed in plant cells, until a non-inhibitory substrate is added (5-fluorocytosine, see Koprek et al., 1999, Plant Journal 6:719-726). Upon addition of the substrate, 5-fluorocytosine is converted by the encoded protein into the inhibitory product 5-fluorouracil (see Koprek et al., 1999, Plant Journal 6:719-726).

Expressing a non-conditional pollen-inhibitor such as AA on one side can indicate that this locus can be crossed through the female to establish linkage, while the conditional codA locus does not inhibit pollen in the absence of 5-FC and can be crossed through the male to establish the three-way linkage and can be made homozygous. The Triple-linked plant (AA—GAT—codA) can be crossed to the inbred-of-interest to create the F1. At this juncture, the F1 can be crossed back to the recurrent parent with no 5-FC application. Of the pollen-grains containing the triple-stacked locus, only those that have lost AA will be viable. The progeny can be sprayed with glyphosate to recover the GAT—codA progeny. These can again be crossed back to the recurrent parent but this time the plants can be sprayed with the non-toxic 5-FC immediately before pollen-shed. Of the pollen grains containing codA before meiosis, only those pollen grains in which the linkage was broken will be viable.

This strategy can be used in the following, non-limiting examples:

1) when the genetic distances on either side are very small (and thus the frequency of a double cross-over can be very small)

2) when recominbinational-interference makes it impractical to screen for two simultaneous cross-overs 3) in crops where the number of pollen grains is not as great as in maize.

Example 8

Creating a Cas9 Mediated System for Pollen Inhibition

Figure 5A:
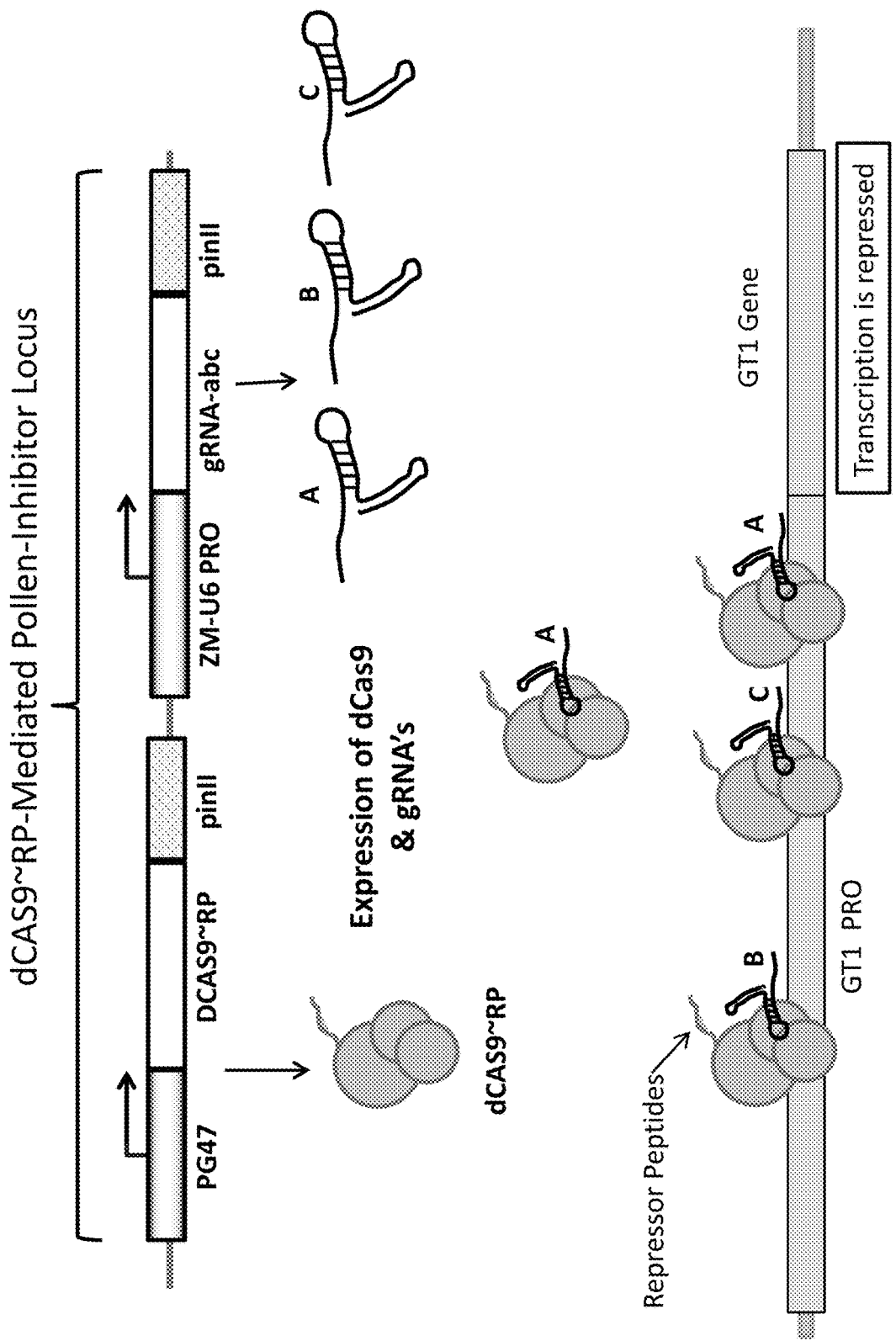
FIG. 5A shows a schematic of the expression of dCAS9 fused to repressor peptides along with three guide-RNAs complementary to different sequences in the maize GT1 promoter.
Figure 5B:
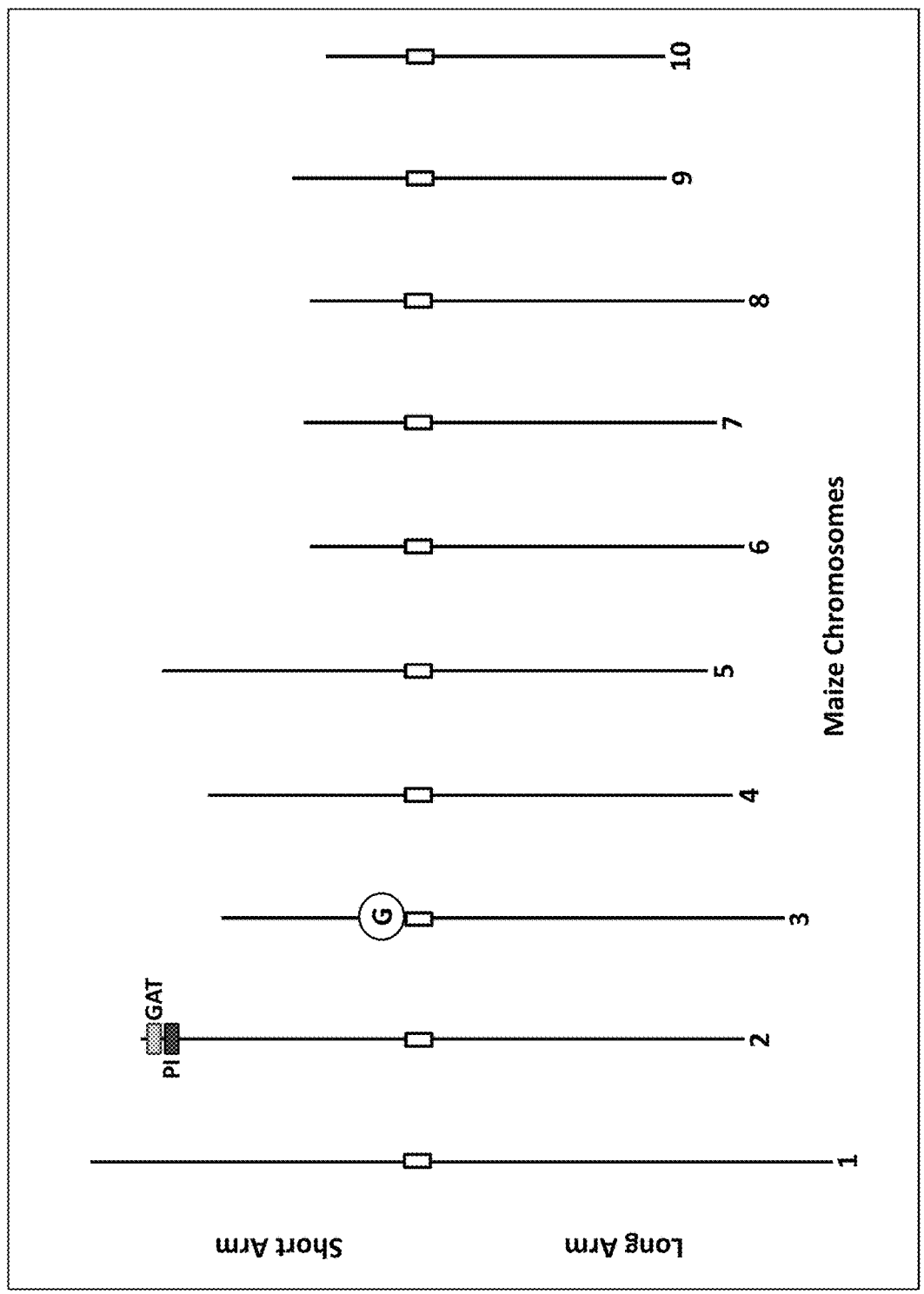
FIG. 5B shows a schematic of the use of dCAS9-RP as the pollen-inhibitor for accelerated trait introgression.
Figure 5C:
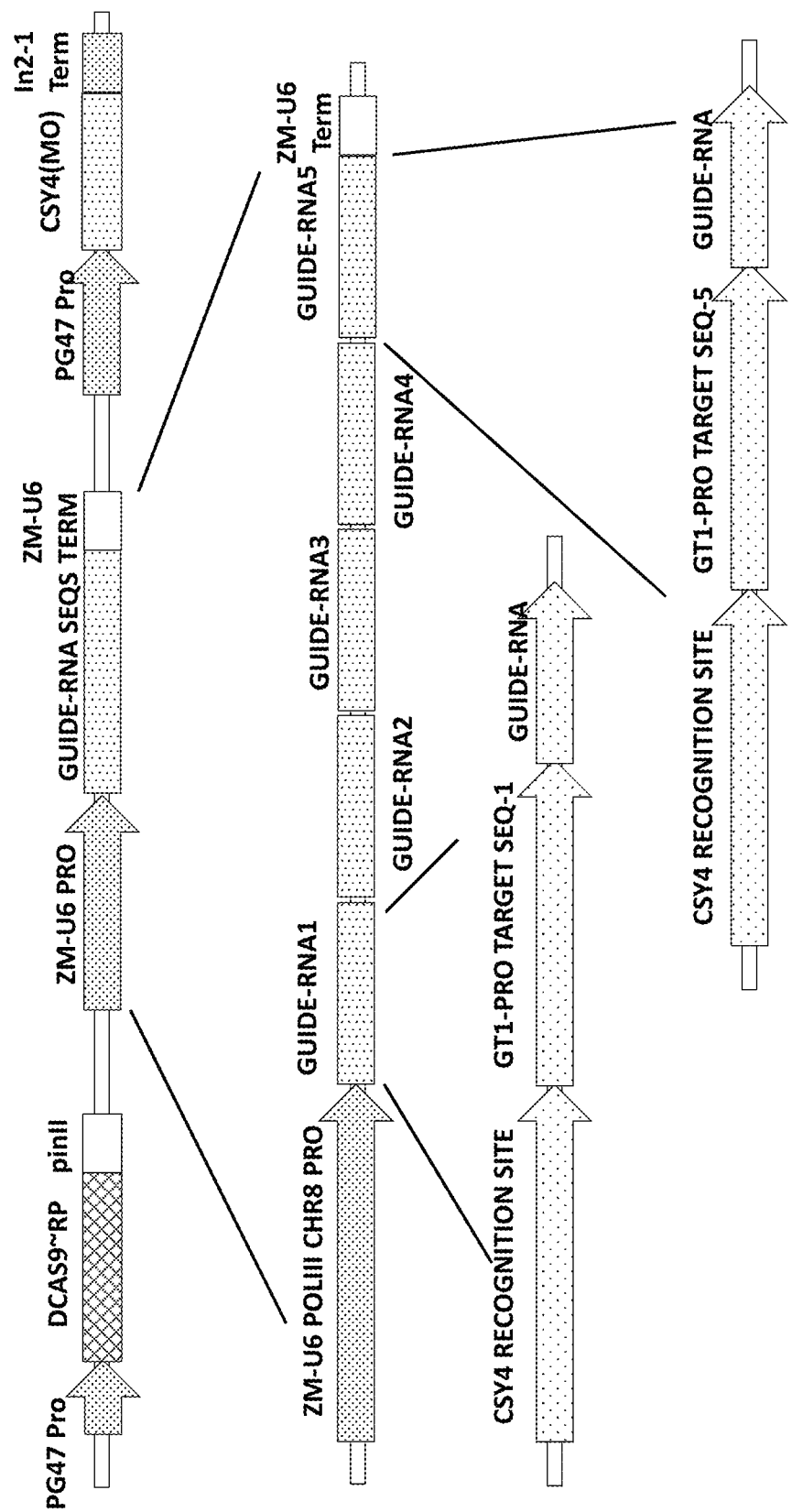
FIG. 5C shows a schematic of the expression cassettes comprising the DCAS9-RP-mediated Pollen-inhibitor locus.

In this example we describe how one can create a Cas9 mediated system for pollen inhibition useful for providing an alternative for accomplishing pollen inhibition for use in accelerated trait introgression (see FIGS. 5a, 5b and 5c).

FIG. 5-A shows a diagram of the expression of a modified Cas endonuclease protein fused to repressor peptides along with three guide-RNAs complementary to different sequences in the maize GT1 promoter. The modified Cas9 gene (dCAS9) has been modified to encode two altered amino acids in the protein, changing aspartic acid at position-10 to alanine and changing histidine at position 840 to alanine. These two amino acid changes inactivate the CAS9 nuclease activity while maintaining the Cas9 DNA-binding function with the mutated version being referred to as dCAS9. The guide-RNAs (labeled A, B and C) associate with the dCAS9 protein fused to ear-motif repressor peptides and guide the fusion-protein to the GT1 promoter, where the repressor motifs block transcription, effectively silencing the gene while the dCAS9-RP fusion is being expressed along with the guide-RNAs.

FIG. 5-B shows a diagram of the use of dCAS9-RP as the pollen-inhibitor for accelerated trait introgression. An expression cassette conferring resistance to glufosinate herbicides such as Basta and Liberty, containing RB-LOXP-OS-ACTIN PRO::OS-ACTIN INTRON:: MO-PAT::35S TERM-LOXP-LB (SEQ ID NO: 89) is integrated on Chromosome 2 at genetic position of 5 cM in the inbred Pioneer inbred line 1, while a second DNA containing the dCAS9-RP-mediated pollen-inhibitor locus is integrated using SSI at a distance of one centimorgan proximal (toward the centromere, at 6 cM). When dCAS9-RP and the guide RNAs for the endogenous glycosyltransferase 1 gene (labeled as "G" on chromosome 3 are expressed (see FIG. 5-A), the dCAS9-RP/gRNA complexes can bind to their cognate sequences in the GT1 promoter, thereby silencing the gene and resulting in non-viable pollen grains.

FIG. 5-C shows a diagram of expression cassettes comprising the DCAS9~RP-mediated Pollen-inhibitor locus. Three expression cassettes can be used; i) the pollen-specific promoter PG47 PRO can be used to drive expression of the fusion protein DCAS9-RP, ii) the maize constitutive promoter ZM-U6 POLIII CHR PRO driving expression of five complexes consisting of a CYS4 recognition site, a GT1-PRO TARGET SEQUENCE (1-5) and a guide-RNA sequence (expanded cartoons for target sequence 1 and target sequence 5 are shown, but all five have the same general composition, varying only in the specific target sequences corresponding to five distinct sequences in the GT1 endogenous promoter sequence), and iii) the pollen-specific promoter PG47 PRO driving expression of a maize-optimized CYS4 gene.

There are Three Components to the Cas9 Mediated Pollen-Inhibitor System:

First, expressing a catalytically inactive double mutant of CAS9 (referred to as dCas9 and containing mutations in the RuvC1 and HNH nuclease domains) which can still associated with a guide-RNA and bind to a specific genomic sequence but without inducing a double strand break. While it's been demonstrated in E. coli that simple binding of dCas9 protein to a promoter can interfere with transcription (see Qi et al., 2013, Cell 152:1173-1183), the transcriptional interference can be enhanced, as described herein, namely by fusing a second component of the system to dCas9. The second component of the system comprises at least one repressor peptide that can be fused to dCas9. These repressor peptides comprise highly conserved motifs, such as "EAR-motifs" (with consensus signatures such as LxLxL or LxLxPP) that actively repress transcription (see Kagale & Rozwadowski 2011, Epigenetics 6:141-146). By fusing the repressor to dCas9, and expressing the protein behind a pollen-specific promoter, and using the third component, namely at least one expressed guide-RNA that direct the dCas9-LxLxPP fusion protein to an endogenous promoter (or multiple endogenous promoters) whose encoded protein(s) is(are) required for either pollen development or pollen tube growth, the result will be non-viable pollen.

Examples of genes that can be targeted to produce non-viable pollen;

a) A GT1 (glycosyltransferase gene) gene. It has been demonstrated in rice that knocking out the GT1 gene results in non-viable pollen. The maize ortholog of the rice GT1 gene (glycosyltransferase 1) is located on the short arm of chromosome 3 relatively near the centromere. FIGS. 5-A and 5-B show how dCAS9-RP can be directed to bind the maize GT1 promoter and inhibit pollen function. This specific example is for a single gene that when transcriptionally-repressed will result in pollen inhibition. The next two examples (described in "b" and "c" below) describe how using a single locus which contains the pollen-specific dCAS9-RP and an expression cassette producing multiple guide RNAs directed at multiple promoters in a gene family ("b") or duplicated genes ("c") can result in non-viable pollen.

b) It has been documented that in the triple-mutant oas-tLABC (in which the A, B and C family members for the gene encoding O-acetylserine(thiol)lyase are knocked out, pollen germination does not occur or is so impaired as to be non-functional (see Birke et al., 2013, Plant Physiol 163: 959-972). However, trying to create a triple-mutant and have all three mutant isoforms segregate together is impractical. By using a pollen-specific promoter to express dcas9~LxLxPP and the guide-RNA's that will target dcas9-LxLxPP to the promoters of oar-tIA, oar-tIB and oar-tIC—pollen tube growth in that pollen grain is blocked, and because these are expressed only in the pollen, there are no whole-plant pleiotropic effects.

c) This system can be used for any gene whose encoded product is essential for pollen viability and function. Another example of maize genes whose down-regulation will result in non-viable pollen are the maize chalcone synthase genes Whp (white pollen) and C2 which both encode a chalcone synthase protein necessary for pollen viability [Coe et al., 1981. J Heredity 72:318-320; Franken et al., 1991. EMBO J. 10(9):2605-2612].

Example 9

Use of a Two-Component Expression System to Control Pollen-Inhibition in the First of a Two-Step Screening Process, and a Conditional Negative Marker as the Second Screen to Rapidly Identify Introgressed Trait Loci in Two Generations Two component transactivation expression systems have been used for many years in plants, for example, see Schwechheiner et al., 1998, Plant Mol. Biol. 36:195-204) in which a fusion protein consisting of the GAL4 DNA-binding domain and the herpes simplex virus PV16 activation domain is expressed behind a promoter such as CaMV 35S, which binds to upstream activation sequences (UAS) in front of a minimal −45 CaMV promoter and the reporter gene beta-glucuronidase. However, it is also known that the GAL4 UAS is methylated in plants which inhibits binding (Gälweiler et al., 2000, Plant J. 23:143-157). As an alternative to GAL4~VP16, the use of alternative DNA-binding domains such as LEXA (REF) fused to plant activation domains and the cognate UAS sequence for LEXA make a good alternative for two component expression in plants (Boddepalli et al., US2013/055791). One such plant transcriptional activation domain comes from the Arabidopsis CBF1A protein (Stockinger et al., 1997, PNAS 94:1035-1040; Wang et al., 2005, Plant Mol. Biol. 58:543-559).

A two-step (two-generations) method comprising a two-component transactivation system to drive expression of a pollen-inhibitor gene (step one), along with a pollen-specific conditional-inhibitor gene (step two) can be used to break linkage on both sides of an internal trait locus in two successive crosses. In the constructs described herein, moLEXA is a maize-optimized gene (SEQ ID NO: 97) which encodes the DNA binding domain of the Esherichia coli LEXA protein (LEXA described in Brent & Ptashne, 1985, Cell 43:729-736; see SEQ ID NO: 98), UAS is the upstream activation sequence to which the LEXA fragment binds (SEQ ID NO: 99), and CBF1A is the polynucleotide sequences encoding the activation domain from the Arabidopsis CBF1A transcription factor (SEQ ID NO: 100).

Figure 8:
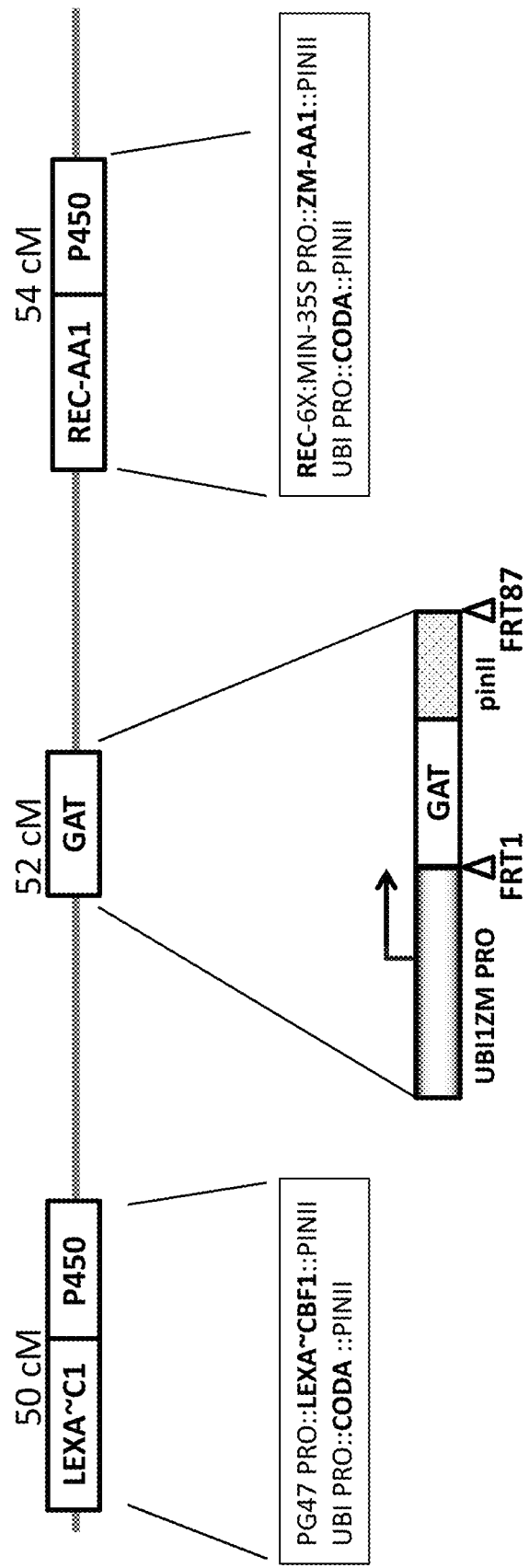
FIG. 8 shows a schematic of a SATI configuration using a two component expression system, allowing two step screening (i.e. over two generations) for breakage of linkage on both sides of an internal genomic locus.
Figure 9A:
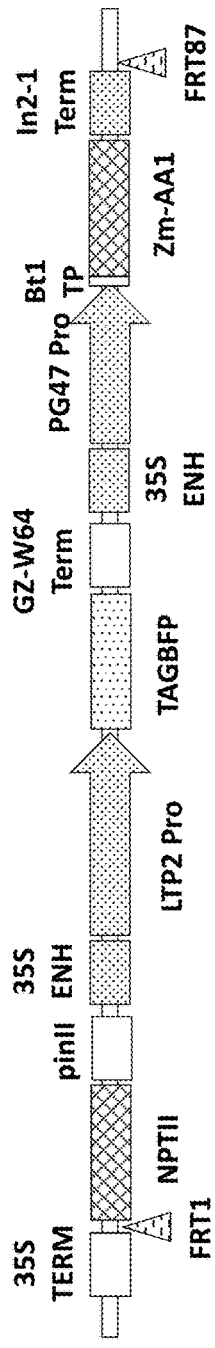
FIG. 9A shows a schematic of the components located between the right border (RB) and left border (LB) of the TDNA in PHP68884.
Figure 9B:
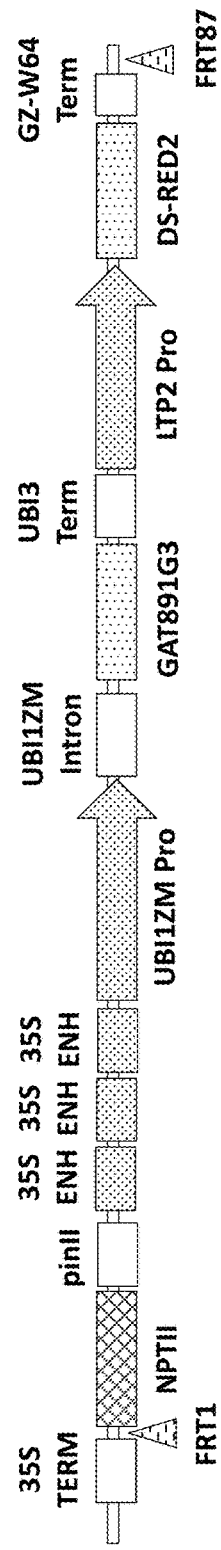
FIG. 9B shows a schematic of the components located between the right border (RB) and left border (LB) of the TDNA in of PHP69519.
Figure 9C:
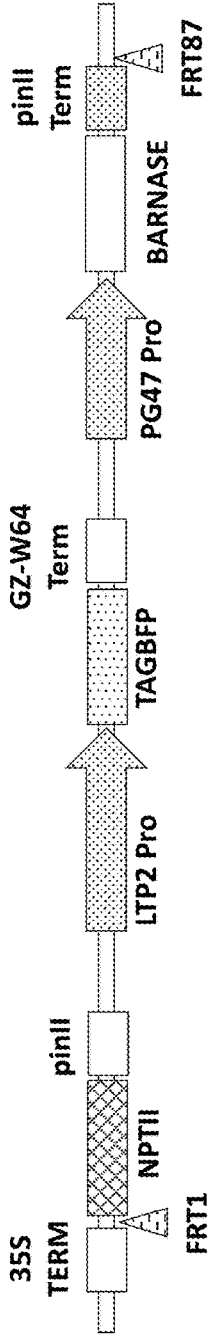
FIG. 9C shows a schematic of the components located between the right border (RB) and left border (LB) of the TDNA in PHP70154.
Figure 9D:
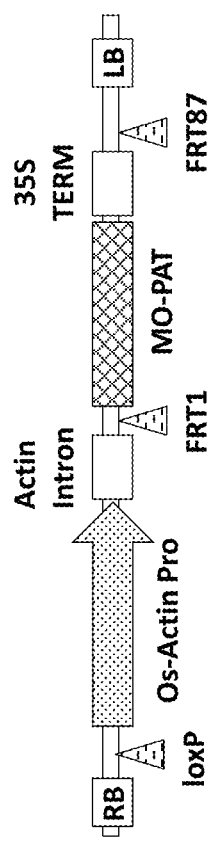
FIG. 9D shows a schematic of the components located between the right border (RB) and left border (LB) of the TDNA in PHP46070.
Figure 9E:
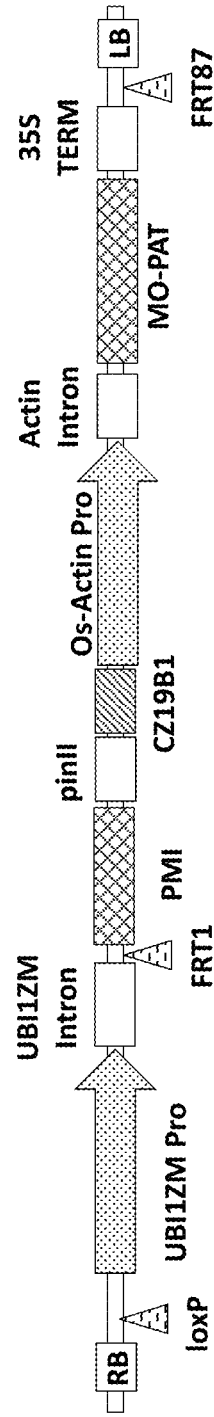
FIG. 9E shows a schematic of the components located between the right border (RB) and left border (LB) of the TDNA in PHP53203.
Figure 9F:
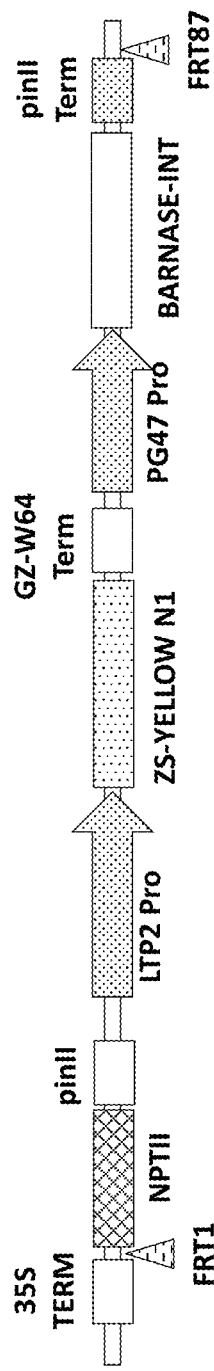
FIG. 9F shows a schematic of the components located between the right border (RB) and left border (LB) of the TDNA in PHP71464
Figure 9G:
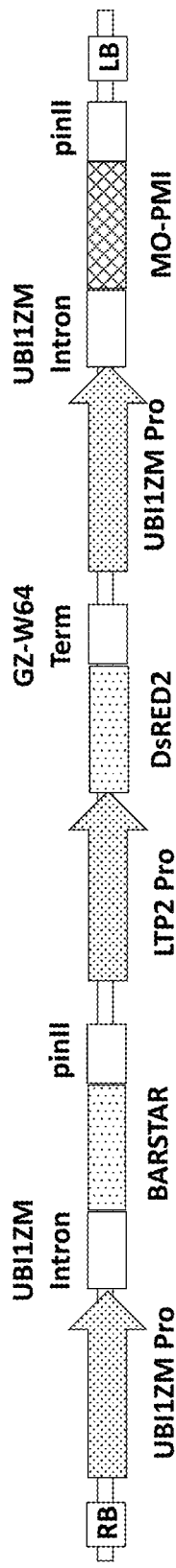
FIG. 9G shows a schematic of the components located between the right border (RB) and left border (LB) of the TDNA in PHP66566
Figure 9H:
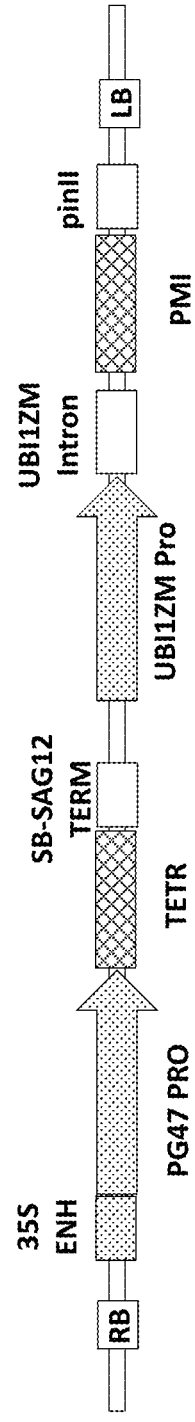
FIG. 9H shows a schematic of the components located between the right border (RB) and left border (LB) of the TDNA in PHP01.
Figure 9I:
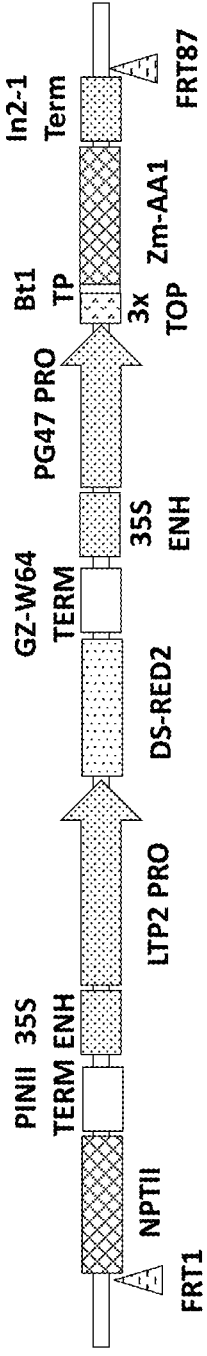
FIG. 9I shows a schematic of the components located between the right border (RB) and left border (LB) of PHP02.
Figure 9J:
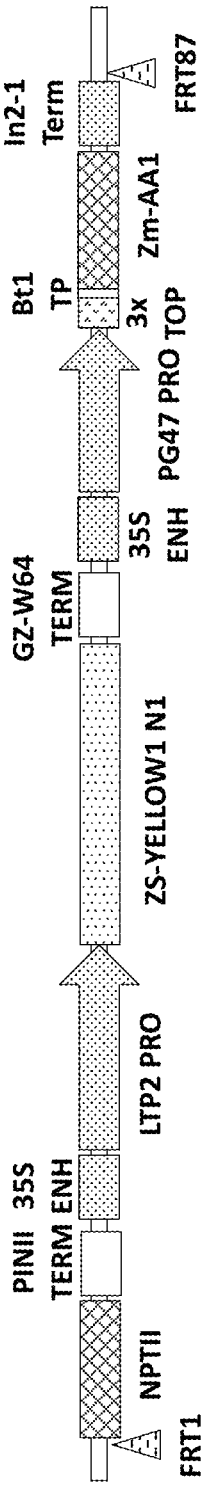
FIG. 9J shows a schematic of the components located between the right border (RB) and left border (LB) of PHP03.
Figure 9K:
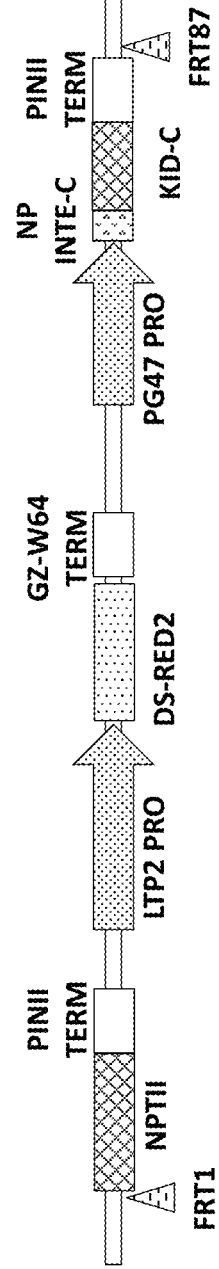
FIG. 9K shows a schematic of the components located between the right border (RB) and left border (LB) of PHP04.
Figure 9L:
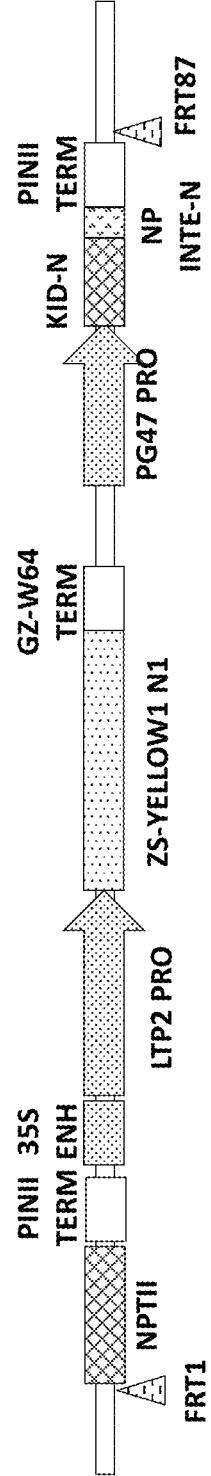
FIG. 9L shows a schematic of the components located between the right border (RB) and left border (LB) of PHP05.
Figure 9O:
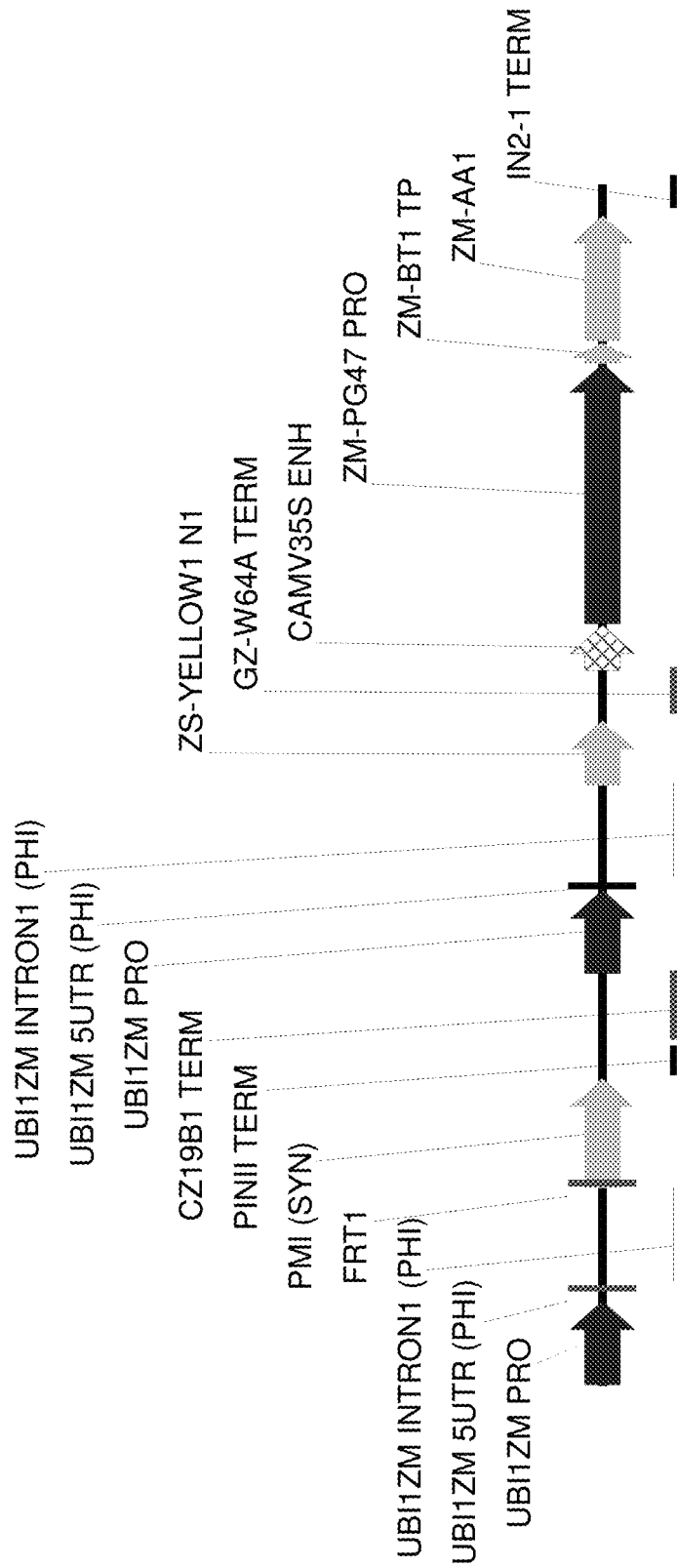
FIG. 9O shows a schematic of the components located between the right border (RB) and left border (LB) of PHP08.
Figure 9P:
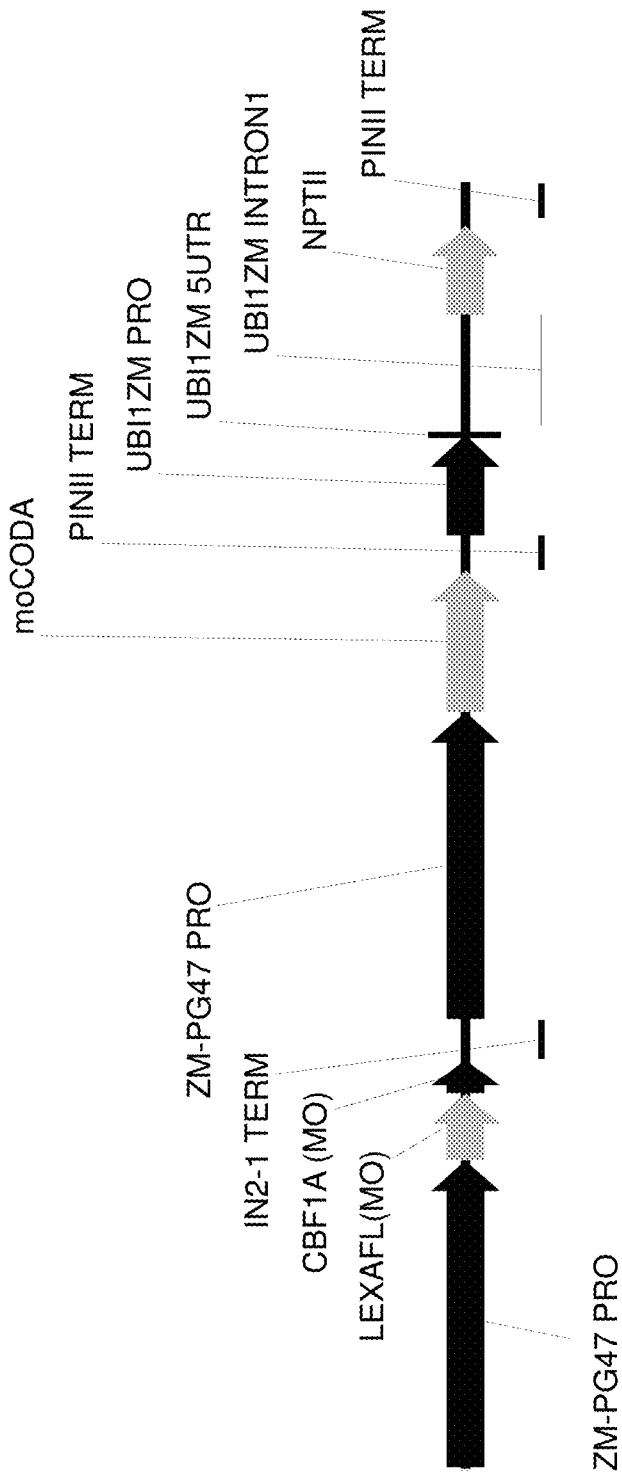
FIG. 9P shows a schematic of the components located between the right border (RB) and left border (LB) of PHP09.

An RTL exists at Chr1-52 cM in Pioneer Inbred Line 3 is used to introduce a trait expression cassette (labeled "GAT" in FIG. 8) such as UBI1ZM PRO (SEQ ID NO: 19), UBI1ZM INTRON (SEQ ID NO: 20), GAT891G3 (SEQ ID NO: 26) and the PINII TERM (SEQ ID NO: 8) and events are selected on medium containing glyphosate. In a second transformation, CAS/CRISPR-mediated integration is used (See Example 3) to introduce three expression cassettes at Chr1-50 cM; PG47 PRO::moLEXA-CBF1A::IN2-1 TERM+UBI1ZM PRO:UBI1ZM INTRON::CODA::PINII TERM+UBI1ZM PRO:UBI1ZM INTRON::NPTII::PINII (SEQ ID NO: 102) and events are selected on medium containing G418. In a third transformation, CAS/CRISPR-mediated integration is again used to introduce three expression cassettes at Chr1-54 cM; 5x(UAS):-45 35s PRO::ZM-AA1::PINII TERM+UBI1ZM PRO:UBI1ZM INTRON::CODA::PINII TERM+UBI1ZM PRO:UBI1ZM INTRON::PMI::PINII (SEQ ID NO: 103) and transgenic events are selected on medium containing mannose. The resultant 3-way linkage is shown in FIG. 8. Once this linkage has been generated in Pioneer Inbred Line 3, inbreds into which the GAT trait will be introgressed (for example, Pioneer Inbred Line 2) are used as pollen donors onto silks of the PH2HT germplasm containing the 3-way linkage. The resultant F1 hybrid is then used as the pollen donor back onto the recurrent parent (Pioneer Inbred Line 2). Pollen grains containing both the transgenic locus at 50 cM (expressing the LEXA-CBF1A transactivator) and the transgenic locus at 54 cM containing the 5xUAS::ZM-AA1 expression cassette will be inhibited and will not transmit to the next generation. However in pollen grains in which either flanking transgenic locus (50 or 54 cM) was lost due to meiotic recombination, the pollen will be viable and transmit to the next generation (at a frequency of about 1/50 progeny). The progeny that lost either flanking transgenic locus (and that are still glyphosate resistant) are grown to maturity and again used again as the pollen donor back onto the recurrent parent (back onto Pioneer Inbred Line 2). Progeny seed are germinated in water containing both glyphosate and 5-fluorocytosine and only progeny which contain the glyphosate trait but have lost both flanking loci will be viable. As an alternative to using a conditional negative marker such as coda, a seed specific promoter such at LTP2 PRO can be used to drive expression of a fluorescent protein (i.e. DS-RED2 or ZS-YELLOW1 N1) and progeny seed expressing the fluorescent protein can be discarded before germinating seed in the presence of glyphosate. Seed with no fluorescence that produce glyphosate-resistant seedlings contain the trait without either flanking locus.

Example 10

Using a Single Pollen-Inhibitor Locus to Screen for Accelerated Trait Introgression of a Telomeric Trait Locus Illustrated in FIG. 1 and described below is an example of how a single pollen-inhibitor gene can be located near a trait of interest, and its use for accelerated trait introgression of a telomeric trait locus of maize.

FIG. 1 shows a schematic of a crossing scheme used to establish and perform accelerated introgression for a telomeric trait locus, the trait locus being created through for example, but not limited to, either random integration or through targeted integration (for example, but not limited to, through targeted integration using Site Specific Integration, targeted meganucleases, or CAS/CRISPR technologies). Step 1: Choose an inbred amenable to transformation, and identify accessions that contain a trait locus and a "targeted-integration site", the trait locus being located at a position close to the telomere (labeled as "1") and the targeted-integration site being proximal (closer to the centromere, labeled as "2"), the distance between the target site 1 and Site 2 being within a close genetic distance, for example 1 cM. Step 2: In two separate transformation experiments, introduce a trait gene (for example, UBI::GAT:pinII, abbreviated as GAT in the figure, which confers resistance to glyphosate) into the trait locus (Site 1), and using targeted integration, introduce a Pollen-inhibitor gene (for example PG47::ZmAA1::pinII, abbreviated as PI in the figure) into Site 2. Step 3: Carry pollen from the GAT-containing plant to PI-containing plant and screen the progeny by molecular markers in order to identify plants containing both GAT and PI. Step 4: Carry pollen from the Wild Type inbred plant to the plants containing both GAT and PI to establish the linkage between Site 1 and Site 2. Use molecular markers to screen the progeny in order to identify plants in which GAT and PI are genetically linked (1% of the progeny at a genetic distance of 1 cM). Step 5: Carry pollen from different Elite inbreds (into which you wish to introgress the GAT trait) onto ears of plants containing the linked GAT and PI. Use molecular markers to identify F1 progeny that contain the linked GAT and PI. Step 6: Carry pollen from the F1 progeny containing linked GAT and PI back to the Recurrent Parent (i.e. the Elite inbred of step 5) to generate a progeny pool.
  a. If the linkage between GAT and PI is broken during meiosis then the pollen is viable and GAT can be transmitted to progeny.
  b. Spray with glyphosate to eliminate any progeny derived from wild-type pollen grains.
  c. The surviving plants will contain the GAT locus with minimal linkage drag from the transformation (donor) inbred.

A. Introducing the Pollen-Inhibitor Gene—Alpha Amylase—in Close Proximity to a Trait Locus of Interest (GAT, Glyphosate Resistance Trait) in the Genome of a Maize Plant.

A Pioneer Inbred Line1 (PHN46) (the target line) was identified that comprised a pre-existing transgenic SSI target site located at 150.7 cM on chromosome 10 containing a first expression cassette comprising a ubiquitin promoter driving a phosphomannose isomerase (PMI) and a pin II terminator, wherein the PMI was preceded by a FRT1 recombination site (UBI PRO::FRT1::PMI::pinII) linked to a second expression cassette comprising an actin promoter driving a moPAT selectable marker and a pin II terminator, followed by a FRT87 recombination site (ACTIN PRO:: moPAT:: pinII-FRT87). The target line was then used as the transformation target for particle-gun-mediated delivery and introduction of a GAT-resistance expression cassette between two dissimilar FLP-recombinase sites (FRT sites FRT1-NPTII::PINII TERM+3X(35S ENH):UBI1ZM PRO: UBI1ZM INTRON::GAT891G3::UBQ3 TERM+LTP2 PRO::DS-RED2::GZ-W64a TERM-FRT87(SEQ ID NO:44), along with a separate plasmid cassette (comprising a ubiquitin promoter driving a FLP recombinase terminated by a pinII terminator, UBI1ZM PRO:UBI1ZM INTRON: FLPM::PINII TERM (bp 411 to bp 4012 of PHP5096, SEQ ID NO:50), which resulted in RMCE and the replacement of PMI & moPAT by GAT in the pre-existing transgenic SSI target site located at 150.7 cM on chromosome 10. At a position 0.5 cM proximal (150 cM on chromosome 10), an SSI donor sequence (SEQ ID NO:46) containing FRT1-NPT-II:pinII+35S ENH:LTP2 PRO::TAGBFP::GZ-W64A TERM+ZM-PG47-PRO::Zm-AA1::IN2-1 TERM-FRT87 (comprising a PG47 promoter driving the Zea mays alpha amylase (Zm-AA1) gene) was also introduced via particle-gun-mediated RMCE in a separate transformation experiment with Pioneer Inbred Line 1.

Figure 10:
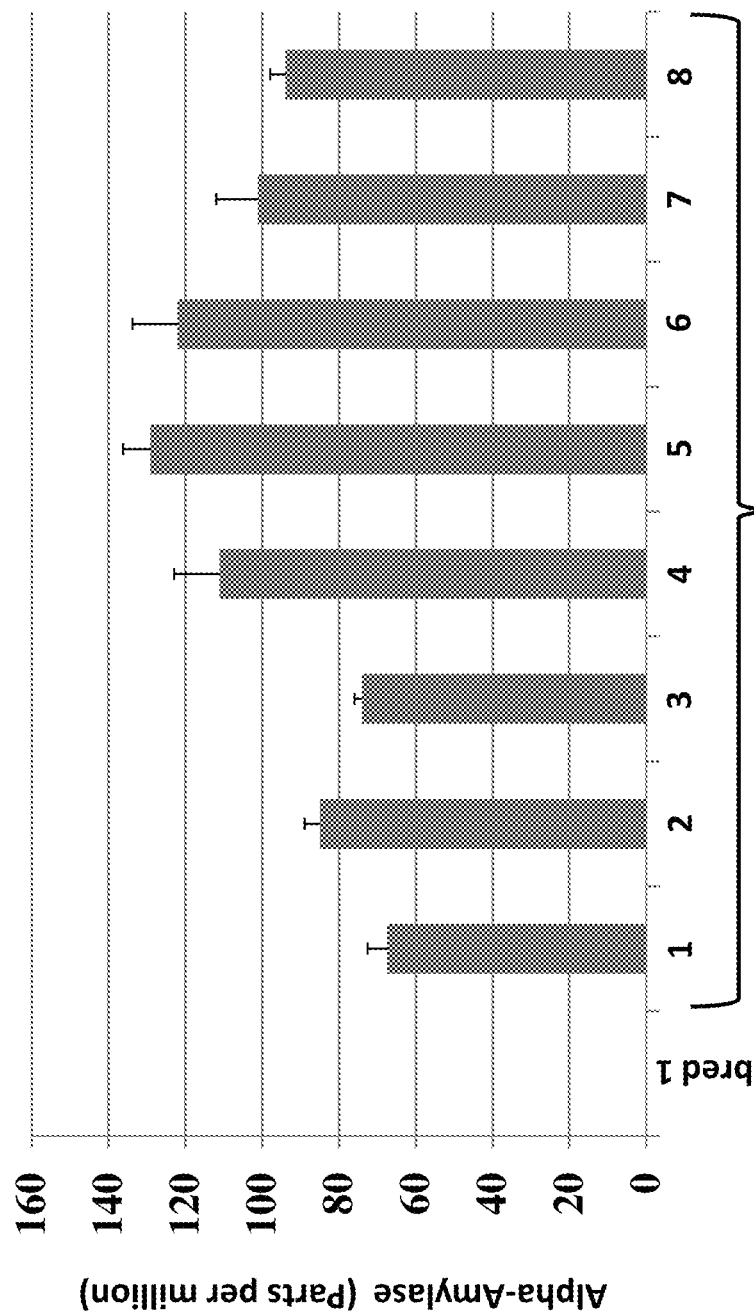
FIG. 10 shows alpha amylase (parts per million) activities of wild type Pioneer Inbred Line 1 (Inbred 1) (negative control) and eight transgenic events (1-8) containing the PG47::AA1 expression cassette.

To confirm that the PG47::AA1::pinII expression cassette targeted to Chr10-150 cM resulted in pollen tube inhibition, we first verified that AA1 protein was being produced and then assessed the efficacy to inhibit pollen tube growth. For the first step (assessing expression), protein extracted from segregating pollen produced by eight SSI-targeted events (all at this same location) was analyzed by ELISA to assess AA1 protein levels. In these assays, wild-type Pioneer Inbred Line 1 pollen was used as the negative control and no AA1 protein was detected (labeled "Inbred 1" in FIG. 10). However, for the eight transgenic events containing the PG47:: AA1::pinII, AA1 protein was detected at levels between 66 and 128 PPM (labeled 1-8 in FIG. 10). The transgenic events that were determined by PCR to be clean single-copy "Recombinase-mediated cassette exchange" events were tested for efficacy of the AA1 expression cassette to inhibit pollen tube growth and fertilization. This was assessed by using these AA1 events as the pollinators back onto wild-type Pioneer Inbred Line 1 silks and analyzing progeny for the transmission of the AA1 locus (FIG. 11). In this experiment, 1688 F1 progeny plants were analyzed by PCR for the presence or absence of the ZmAA1 and NPTII genes. Of the 1688 DNA samples analyzed, the DNA concentration was too low to perform the NPTII assay in 32 samples, was too low for the ZmAA1 assay in 14 samples, and was too low for both assays in 4 samples. Excluding samples for which the DNA concentration was too low to insure a reliable PCR reaction, of the 1588 F1 progeny that provided adequate DNA levels, all were null for AA1 and NPTII (see FIG. 11). Thus, the expression of alpha amylase in maize plant comprising the expression cassette PG47-PRO::Zm-AA1::pinII inhibited pollen tube growth as expected (with a low escape rate) and plants from these events were subsequently used as the female in crosses with plants containing the GAT locus in order to establish linkage. The targeted-integration event containing GAT+DsRED (at genetic position Chr10-250.5 cM) was also evaluated for proper Mendelian inheritance and when outcrossed to wild-type Pioneer Inbred Line 1 exhibited the expected 1:1 segregation ratio.

B. Use of a Pollen-Inhibitor Gene Alpha Amylase (AA1) to Break Linkage with a Glyphosate Resistance Trait (GAT) on Chromosome Ten of Maize for Accelerated Trait Introgression.

An efficacious event containing AA1+BFP at Chr10-250 cM (referred to as PI in FIG. 1) and the event containing GAT+DsRED at Chr10-250.5 (referred to as GAT in FIG. 1) were crossed together (FIG. 1, Step 2), and progeny were identified using PCR that contained both transgenic loci (FIG. 1, Step 3). The progeny plants containing both loci were then pollinated with wild-type Pioneer Inbred Line 1 (such as PHN46) pollen, and the next generation of progeny were again analyzed by PCR for both loci (FIG. 1, Step 4); of 1146 plants screened for the AA1 and GAT loci, 5 plants were found to contain both (contained both loci linked on the same chromosome). Based on this data for Pioneer Inbred Line 1 (PHN46), it appeared that the genetic distance between the two loci was 0.4 cM. All the steps up to this point were necessary to first create the two independent targeted-integration events containing either AA1/BFP or GAT/DsRED, and then using conventional breeding methods to link the two loci, which represented the required preparatory work before actually conducting the evaluation as to whether this configuration would aid in accelerating the introgression process.

The next step of the experiment was the first step in testing whether this closely linked pollen-inhibitor locus would facilitate more rapid and more precise introgression into another inbred. First, Pioneer Inbred line 1 plants containing the linked AA1 and GAT loci were crossed to Pioneer inbred Line 2 (such as inbred line PHHSG, the inbred into which the trait would be introgressed), using Pioneer inbred Line 2 as the pollen donor and producing the first filial generation (more commonly called the F1 hybrid) in the first step of the introgression process (Step 5 in FIG. 1). The resultant F1 hybrid plants were then used as the recurrent parent to pollinate wild-type Pioneer Inbred line 2 (PHHSG) (Step 6) to produce BC1 F1 progeny (BackCross1 after the filial generation). These BC1 F1 progeny were then analyzed for inheritance and introgression of the trait locus into the Pioneer Inbred Line 2 Chr10. This analysis consisted of three steps, each providing a progressively greater level of resolution. First, 4800 BC1 F1 progeny were screened by PCR and 28 progeny were found to contain the GAT/DsRED locus at Chr10-150.7 cM with no AA1/BFP locus, providing a first indication that meiotic recombination had occurred during pollen formation between Chr10-150.5 and Chr10-150 cM, producing the type of BC1 F1 offspring indicated at the bottom of Step 6 (FIG. 1) in which the progeny plant now carried a copy of chromosome 10 in which only the telomeric segment containing the GAT trait was from the original Pioneer Inbred Line 1 donor and the remainder of this chromosome had a high likelihood of being entirely Pioneer Inbred Line 2. In the second analytical step, the frequency of converting the remainder of chromosome ten to Pioneer Inbred Line 2 (i.e. from position 150.7 cM to 0 cM at the other end of the chromosome) was determined using 2 restriction-enzyme Genotype-by-Sequencing (GbS) on all 28 progeny that had lost the GAT/DsRED locus. Three replicates were run for each progeny plant to validate the consistency of the results, and for all 28 progeny the three replicates corroborated each other. For the 28 progeny, 22 events contained more than 80% of Pioneer Inbred Line 2 Chr10 (except for both telomeric ends where recombination appeared to be more frequent and remnant Pioneer Inbred Line 1 chromosome persisted), and 13 plants contained more than 90% Pioneer Inbred Line 2 chromosome. An examples of GbS results for a progeny plant carrying the GAT/DsRED locus within a small segment of Pioneer Inbred Line 1 chromosome on the end of the long arm of Chr10, followed by a small segment of Pioneer Inbred Line 2 chromosome, and the remainder of Chr10 being Pioneer Inbred Line 1 (FIG. 12) represents one of the 6 progeny plants that were discarded due to the high percentage of Pioneer Inbred Line 1 Chr10 that remained. In contrast, FIG. 13 shows the GbS results from one of the desirable plants in which the majority of Chr 10 has been successfully converted to Pioneer Inbred Line 2 in just one generation. Finally, in the third analytical step, haplotype analysis was performed, using nine pairs of diagnostic SNPs between 132 cM and 155.0 cM surrounding the trait locus at 150.7 cM. As seen in FIG. 14, for each of the 28 BC1 F1 plants analyzed, the Pioneer Inbred Line 1 haplotypes are depicted as black bars and and the Pioneer Inbred Line 2 haplotypes are depicted in grey. Genomic DNA from wild-type Pioneer Inbred Line 2 and Pioneer Inbred Line 1 contained only the expected wild-type SNPs for each inbred (grey or black bars, respectively). Of the transgenic BC1 F1 plants analyzed, 25 contained Pioneer Inbred Line 1 chromosome at the distal end of the chromosome including the GAT/DsRED trait locus at 150.7 cM, with recombination occurring somewhere between the trait locus and the first proximal haplotype marker at approximately 149.3 cM, at which point the chromosome converts to Pioneer Inbred Line 2. Surprisingly, three plants contained chromosome 10 that was predominantly Pioneer Inbred Line 2 and where a double recombination had occurred on either side flanking the trait locus, with Progeny Number 1 showing evidence of a proximal cross-over within 0.7 cM of the trait and a distal cross-over within 1.5 cM on the other side, and Progeny 2 and 15 in which two crossovers occurred within 0.7 cM on the proximal side and somewhere between 1.5 and 4.0 cM away from the trait on the distal side.

These results demonstrated that using a closely-located pollen-inhibitor locus next to a trait of interest could be effectively used to rapidly (with one generation from the F1 hybrid) screen and identify progeny that had converted the transgene-carrier chromosome (Chr10) to the recurrent parent Pioneer Inbred Line 2.

C. Use of the AA1 Pollen-Inhibitor Locus for Accelerated Trait Introgression of a Telomeric Trait Located at 0.9 cM on the Short Arm of Chromosome One.

A trait locus on Chr 1 of Pioneer Inbred Line 1 (PHN46) at genetic position 0.9 cM contained both a moPAT (maize-optimized phosphinithricin acetyl transferase) and PMI (phosphomannose isomerase) (illustrated as GAT on FIG. 1, step 2). Using Site-Specific Integration, a pollen-inhibitor locus (illustrated as PI on FIG. 1, step 2) was introduced into Pioneer Inbred Line 1 at a genetic position of 2.3 cM on Chr1 (UBI::NPTII::pinII and PG47 PRO::ZM-AA1::pinII) and the two loci were genetically-linked using conventional breeding methods (FIG. 1, Steps 3 and 4).

Pollen from wild-type Pioneer Inbred Line 2 (PHH5G) was used to pollinate ears of the doubly-linked (Traits+AA1) Pioneer Inbred Line 1 to produce the F1 hybrid (FIG. 1, Step 5). The F1 hybrid was then used to pollinate the recurrent parent (RP) Pioneer Inbred Line 2 (FIG. 1, Step 6). Of 3587 progeny screened by PCR, 42 contained the trait locus but no longer contained the AA1, again demonstrating that the pollen-inhibitor could be effectively used to rapidly screen for progeny in which Chr1 had undergone a meiotic recombination, potentially creating a predominantly Pioneer Inbred Line 2 Chr1 with <2.3 cM of telomeric Chr1 from Pioneer Inbred Line 1 containing the transgenic trait locus.

Both of the above examples on the long arm of Chr10 and the short arm of Chr1 demonstrated the ability to use pollen-inhibitor loci to rapidly and precisely introgress a transgenic trait locus into a new inbred with a minimum of yield drag (unwanted flaking donor inbred chromosome segments remaining next to the introgressed trait).

Example 11

Use of Two Sequential Screenings Using a Pollen-Inhibitor Locus on One Side of the Trait Locus and a Locus Encoding a Visible Kernel Phenotype on the Other Side, in Order to Rapidly Identify Progeny in which the Linkage had been Broken on Both Sides of the Trait An internal trait locus containing at least one trait gene of interest in the Pioneer Inbred Line 1 (such as PHN46) is located at Chr1-51.8 cM. Using Cas9-mediated targeted integration, a pollen tube inhibitor expression cassette (PG47::Zm-AA1::pinII) is positioned at Chr1-50.8 cM, and in a second round of CAS9-medaited targeted integration, a seed-specific color marker (LTP2 PRO::CRC::pinII) is introduced at Chr1-52.8 cM. The seed is bulked up by pollinating with the wild-type Pioneer Inbred Line 1.

To begin the introgression process, ears of the triple-linked transgenic inbred are pollinated with pollen from the various inbreds (for example, Pioneer Inbred Line 2, such as PHHSG) into which trait of interest will be introgressed to produce F1 hybrids. The F1 hybrids are then used as the male to pollinate the recurrent parent (i.e. Pioneer Inbred Line 2) and the BC1 F1 seed are examined. Kernels are separated into two pools; the red-kernel phenotype imparted by the anthocyanin fusion-gene CRC and yellow kernels (non-red). Because of the pollen-inhibitor locus that was originally on the distal flank of the trait, any F1 pollen grains containing this locus would not form pollen tubes, and only wild-type pollen grains or transgenic pollen grains that had lost the AA1 locus due to meiotic recombination would produce a pollen tube and hence BC1F1 progeny. Non-red kernels are germinated in the presence of herbicide (which kills all the progeny derived from wild-type pollen) and only the non-red kernels (that had lost the color marker due to meiotic recombination) will survive.

If no surviving progeny are recovered in the first BC1 F1 screening, the red BC1 F1 seeds can be germinated and used to again pollinate the wild-type recurrent parent (i.e. Pioneer Inbred Line 2). The resultant BC2 seed are again separated into red and non-red kernels and the yellow kernels are germinated in herbicide. Resultant plants that germinate in the presence of herbicide have broken linkage on both sided of the trait and the trait has been introgressed in the RP with <1.0 cM of remaining Pioneer Inbred Line 1 chromosome on either side of the trait.

Example 12

Using a Flanking Pollen-Inhibitor Proximal to a Telomeric Trait Along with a Meiotically-Expressed Targeted Nuclease Between the Pollen-Inhibitor and the Trait Locus to Simulate Targeted Recombination and Chromosome Exchange A trait locus in Pioneer Inbred line 1 (such as PHN46) containing a moPAT and PMI at Chr1-0.9 cM is produced, and a T-DNA containing a pollen-inhibitor expression cassette is positioned at Chr1-1.0 cM (0.1 cM proximal to the trait) using Cas9/CRISPR systems. In addition to the pollen-inhibitor expression cassette (PI), the T-DNA contains a 2 kb spacer sequence, an expression cassette containing a meiosis-specific promoter such as the SPO11 PRO in front of Cas9 (CAS9 locus) and an expression cassette driving expression of a guide-RNA that will target a Double-Stranded Break in between the T-DNA and the trait locus.

After establishing these two linked loci (the trait locus and the PI/CAS9 locus) on the same chromosome, pollen from various inbreds (for example Pioneer Inbred Line 1) is used to pollinate the ears of Pioneer Inbred Line 1 comprising the Trait-PI/CAS9 to produce the F1 hybrid. The F1 hybrids are grown to maturity and then used to pollinate the recurrent parent, Pioneer Inbred Line 2. BC1 F1 progeny are screened for introgression of the Trait Locus into the Pioneer Inbred Line2Chromosome 1, which normally is predicted to occur in 1/1000 progeny, based on a genetic distance between the two loci of 0.1 cM. However, because of the targeted cutting activity of the CAS9 protein during meiosis, targeted meiotic recombination between the trait and the pollen-inhibitor is stimulated resulting in a higher frequency of progeny that have introgressed the trait into the Pioneer Inbred Line 1 chromosome 1 at very close genetic distance (i.e. <0.1 cM).

In addition to using Cas9, other double strand break inducing systems can be used in the methods described herein, One can express a fusion between a well-established DNA-binding-domain (DBD) such as GAL4 or LEXA and a nuclease (or meganuclease; abbreviated MN) such I-SceI, I-CreI, I-DmoI, PI-SceI, PI-PfuI, Fok1, One can also use the DBD fused to Spoil in this type of a scenario, One can include the pollen-inhibitor (or the red-aleurone marker) in the T-DNA followed by a meiosis-specific promoter driving expression of fusion protein (comprising a DNA-binding domain and a meganuclease (or a topoisomerase), a 2-3 kb spacer and then the DNA sequence that is bound by the DNA-binding-domain), which positions the MN at this cleavage site. This provides the pollen-inhibitor (or the seed color marker) to be used as the screening method(s) to identify the progeny in which the linkage has been broken within a specified nearby genetic interval, a meiosis-specific catalyst to create double-strand breaks, and the cutting target site provided by the target sequence of the DNA-binding domain. Targeted double-strand breaks in this region during meiosis will stimulate localized homologous recombination (crossovers) and the pollen and/or seed screening tools will permit rapid identification.

That what is claimed:

1. A method for introgressing a trait of interest into the genome of a plant, said method comprising:
   (a) providing a first plant having the trait of interest located within a genomic window, wherein said genomic window is about 10 cM in length;
   (b) introducing into said genomic window of the first plant a color marker gene such that the color marker gene is linked to the trait of interest within the genomic window;
   (c) crossing the first plant with a second plant, wherein said second plant is a haploid inducer line capable of producing haploid embryos;
   (d) selecting haploid embryos from the crossing of the first plant with the second plant and introducing into said haploid embryos, a pollen-inhibitor gene such that the pollen-inhibitor gene is linked to the trait of interest within the genomic window;
   (e) producing a double haploid plant from the haploid embryo; and
   (f) backcrossing the double haploid plant to a recurrent parent plant to introduce the trait of interest to a progeny plant, wherein the progeny plant have broken the linkage between the trait of interest and the pollen-inhibitor gene and the color marker gene.

2. A method for introducing two color marker genes in close proximity to a trait locus of interest in the genome of a plant, said method comprising:
   (a) providing a first plant having a trait of interest located within a genomic window, wherein said genomic window is about 10 cM in length;
   (b) introducing into said genomic window of the first plant a color marker gene;
   (c) crossing the first plant with a second plant, wherein said second plant is a haploid inducer line capable of producing haploid embryos;
   (d) selecting haploid embryos from the crossing of the first plant with the second plant and introducing into said haploid embryos, a second color marker gene such that the second color marker gene is linked to the trait of interest within the genomic window;
   (e) producing a double haploid plant from the haploid embryo, wherein the double haploid plant comprises the color marker gene and the second color mark gene; and
   (f) backcrossing the double haploid plant to a recurrent parent plant to introduce the trait of interest to a progeny plant, wherein the progeny plants have broken the linkage between the trait of interest and the and the color marker genes.

3. The method of claim 1, wherein the color marker gene or the pollen-inhibitor gene are introduced into a target site of a double-strand-break-inducing-agent.

* * * * *